US012622895B2

(12) United States Patent
Chase et al.

(10) Patent No.: US 12,622,895 B2
(45) Date of Patent: May 12, 2026

(54) ANTI-NEURODEGENERATIVE COMBINATIONS AND USE FOR TREATMENT OF NEURODEGENERATIVE DISEASES

(71) Applicant: ALTO NEUROSCIENCE, INC., Mountain View, CA (US)

(72) Inventors: Thomas N. Chase, Washington, DC (US); Kathleen E. Clarence-Smith, Washington, DC (US)

(73) Assignee: ALTO NEUROSCIENCE, INC., Mountain View, CA (US)

( * ) Notice: Subject to any disclaimer, the term of this patent is extended or adjusted under 35 U.S.C. 154(b) by 834 days.

(21) Appl. No.: 17/279,705

(22) PCT Filed: Sep. 25, 2019

(86) PCT No.: PCT/US2019/052849

§ 371 (c)(1),
(2) Date: Mar. 25, 2021

(87) PCT Pub. No.: WO2020/068913

PCT Pub. Date: Apr. 2, 2020

(65) Prior Publication Data

US 2021/0393595 A1 Dec. 23, 2021

Related U.S. Application Data

(60) Provisional application No. 62/896,088, filed on Sep. 5, 2019, provisional application No. 62/884,311, filed on Aug. 8, 2019, provisional application No. 62/884,314, filed on Aug. 8, 2019, provisional application No. 62/785,990, filed on Dec. 28, 2018, provisional application No. 62/785,996, filed on Dec. 28, 2018, provisional application No. 62/770,234, filed on Nov. 21, 2018, provisional application No. 62/770,245, filed on Nov. 21, 2018, provisional application No. 62/743,690, filed on Oct. 10, 2018, provisional application No. 62/743,800, filed on Oct. 10, 2018, provisional application No. 62/736,190, filed on Sep. 25, 2018, provisional application No. 62/736,137, filed on Sep. 25, 2018, provisional application No. 62/735,959, filed on Sep. 25, 2018, provisional application No. 62/735,947, filed on Sep. 25, 2018.

(51) Int. Cl.

| | |
|---|---|
| ***A61K 31/428*** | (2006.01) |
| ***A61K 31/138*** | (2006.01) |
| ***A61K 31/4178*** | (2006.01) |
| ***A61K 31/423*** | (2006.01) |
| ***A61K 31/438*** | (2006.01) |
| ***A61K 31/439*** | (2006.01) |
| ***A61K 31/496*** | (2006.01) |
| ***A61K 31/505*** | (2006.01) |
| ***A61K 31/5377*** | (2006.01) |
| ***A61P 25/16*** | (2006.01) |
| ***A61P 25/28*** | (2006.01) |

(52) U.S. Cl.

CPC .......... *A61K 31/428* (2013.01); *A61K 31/138* (2013.01); *A61K 31/4178* (2013.01); *A61K 31/423* (2013.01); *A61K 31/438* (2013.01); *A61K 31/439* (2013.01); *A61K 31/496* (2013.01); *A61K 31/505* (2013.01); *A61K 31/5377* (2013.01); *A61P 25/16* (2018.01); *A61P 25/28* (2018.01)

(58) Field of Classification Search

CPC ........................................................ A61P 25/28

See application file for complete search history.

(56) References Cited

U.S. PATENT DOCUMENTS

| | | | |
|---|---|---|---|
| 6,667,329 | B1 | 12/2003 | Maj |
| 9,303,045 | B2 | 4/2016 | Hitchcock et al. |
| 2009/0042956 | A1 | 2/2009 | Bozik et al. |
| 2011/0207776 | A1 | 8/2011 | Buntinx |
| 2013/0116215 | A1 | 5/2013 | Coma et al. |

OTHER PUBLICATIONS

Pramipexole in patients with early Parkinson's disease (PROUD): a randomised delayed-start trial Schapira et al. Lancet Neurol 2013; 12: 747-55 (Year: 2013).*

Does Fluoxetine Aggravate Parkinson's Disease? A Pilot Prospective Study Montastruc et al. Movement Disorders, Val. 10, No. 3, 1995 (Year: 1995).*

The 5-HT 3antagonist ondansetron reduces gastrointestinal side effects induced by a specific serotonin re-uptake inhibitor in man Bailey et al. Journal of Psychopharmacology 9(2) (1995) 137-141 (Year: 1995).*

Psychosis in advanced Parkinson's disease: Treatment with ondansetron, a 5-HT3 receptor antagonist Zoldan et al. Neurology 1995;45: 1305-1308 (Year: 1995).*

Once-Weekly Fluoxetine Wagstaff et al. File Drugs 2001; 61 (15): 2221 (Year: 2001).*

(Continued)

*Primary Examiner* — Jeffrey S Lundgren
*Assistant Examiner* — Eric Tran
(74) *Attorney, Agent, or Firm* — COOLEY LLP

(57) ABSTRACT

The present invention provides a combination of a 5HT3-antagonist and/or a NK-1 antagonist with 6-propylamino-4,5,6,7-tetrahydro-1,3-benzothiazole-2-amine and with fluoxetine or a pharmaceutically acceptable salt or solvate thereof, zonisamide or a pharmaceutically acceptable salt or solvate thereof, or a statin or a pharmaceutically acceptable salt or solvate thereof, for use for treating a protein misfolding neurodegenerative disease such as Alzheimer's disease, Lewy body disease, Parkinson's disease, or Huntington's disease.

17 Claims, No Drawings

(56) References Cited

OTHER PUBLICATIONS

Added ondansetron for stable schizophrenia: A double blind, placebo controlled trial Akhondzadeh et al. Schizophrenia Research 107 (2009) 206-212 (Year: 2009).*
Written opinion for PCT/US2019/052849, dated Feb. 4, 2020.
International search report for PCT/US2019/052849, dated Feb. 4, 2020.

* cited by examiner

ANTI-NEURODEGENERATIVE COMBINATIONS AND USE FOR TREATMENT OF NEURODEGENERATIVE DISEASES

CROSS-REFERENCE TO RELATED APPLICATIONS

This application is a National Stage of International Application No. PCT/US2019/052849, filed Sep. 25, 2019, which claims the benefit of U.S. Provisional Patent Application Ser. No. 62/736,190, filed Sep. 25, 2018, U.S. Provisional Patent Application Ser. No. 62/735,947, filed Sep. 25, 2018, U.S. Provisional Patent Application Ser. No. 62/736,137, filed Sep. 25, 2018, U.S. Provisional Patent Application Ser. No. 62/735,959, filed Sep. 25, 2018, U.S. Provisional Patent Application Ser. No. 62/743,690, filed Oct. 10, 2018, U.S. Provisional Patent Application Ser. No. 62/743,800, filed Oct. 10, 2018, U.S. Provisional Patent Application Ser. No. 62/770,234, filed Nov. 21, 2018, U.S. Provisional Patent Application Ser. No. 62/770,245, filed Nov. 21, 2018, U.S. Provisional Patent Application Ser. No. 62/785,996, filed Dec. 28, 2018, U.S. Provisional Patent Application Ser. No. 62/785,990, filed Dec. 28, 2018, U.S. Provisional Patent Application Ser. No. 62/884,314, filed Aug. 8, 2019, U.S. Provisional Patent Application Ser. No. 62/884,311, filed Aug. 8, 2019, and U.S. Provisional Patent Application Ser. No. 62/896,088, filed Sep. 5, 2019, the disclosures of which are incorporated herein in their entirety by reference.

FIELD OF THE INVENTION

The present invention pertains to the field of the treatment of neurodegenerative diseases, and in particular, of the treatment of neurotoxic processes due to protein misfolding in neurodegenerative diseases.

OBJECT OF THE INVENTION

The present invention concerns a pharmaceutical combination comprising a 5HT3-antagonist and/or NK-1 antagonist, 6-propylamino-4,5,6,7-tetrahydro-1,3-benzothiazole-2-amine, and fluoxetine, zonisamide or a statin, and its use for the treatment of protein misfolding neurodegenerative diseases (or disorders) in humans. A preferred embodiment of the present invention includes the use of a 5HT3-antagonist and/or NK-1 antagonist and fluoxetine, zonisamide or a statin combination for augmenting the synucleinopathy-modifying potential of pramipexole in humans, thus allowing at least a slowing of disease progression at doses that are both safe and tolerable.

Definitions

"CNS": Central Nervous System.

"IR": Immediate Release of the active ingredient from a composition.

"ER": Extended Release of the active ingredient from a composition.

"GI": Gastro-Intestinal.

"AE(s)": Adverse Effect(s).

"SNCA gene": Synuclein-alpha or alpha-synuclein gene.

"α-Syn": α-Synuclein or alpha-synuclein.

"A-β". Amyloid-β.

"TauP": Tau protein.

"PMND": Protein Misfolding Neurodegenerative Disease.

"AD": Alzheimer's Disease.

"PD": Parkinson's Disease.

"LBD": Lewy Body Dementia.

"DLB": Dementia with Lewy Bodies.

"HD": Huntington's Disease.

"CBD": Corticobasal degeneration.

"FTD-PD17": frontotemporal dementia with parkinsonism-linked to chromosome 17.

"FTLD": Frontotemporal Lobe Dementia.

"PSP": Progressive Supranuclear Palsy.

"PickD": Pick's Disease.

"GBA": Mutations in the glucocerebrosidase gene.

"MSA": Multiple System Atrophy.

"MT": Multiple Tauopathies.

"ALS": Amyotrophic Lateral Sclerosis.

"SEP": Spongiform encephalopathies.

"FAP": Familial amyloidotic polyneuropathy.

"TDDS": Transdermal Drug Delivery System.

"mers": this term, preceded by a number-range, is a neologism indicating the number of protein monomers in an oligomer formed in the oligomerization of said protein, as described in the Sengupta et al. 2016 reference, which is incorporated herein by reference in its entirety.

"Dyslipidemia": a disorder of lipoprotein metabolism, including lipoprotein overproduction or deficiency, as may be manifested by elevation of the total cholesterol, the low-density lipoprotein (LDL) cholesterol and the triglyceride concentrations, and a decrease in the high-density lipoprotein (HDL) cholesterol concentration in the blood, and other blood disorders the statins are indicated for.

"Effective daily dose of 5HT3-antagonist": This expression, as used herein, refers to a dose of said 5HT3-antagonist that is at least as high as that for preventing or treating nausea and vomiting in pediatric or adult patients under cancer chemotherapy according to the current protocols for said treatment. Said dose normally is from 1 μg to 600 mg per unit form and from 1 μg to 600 mg daily; preferably, from 1 μg to 300 mg per unit form and from 1 μg to 300 mg daily.

"Effective daily dose of NK1-antagonist": This expression, as used herein, refers to a dose of said NK1-antagonist that is at least as high as that for preventing or treating nausea and vomiting in pediatric or adult patients under cancer chemotherapy according to the current protocols for said treatment. Said daily dose normally is from 1 μg to 600 mg.

"6-propylamino-4,5,6,7-tetrahydro-1,3-benzothiazole-2-amine": A chiral chemical compound that is available as racemate, chemically (R,S)-6-propylamino-4,5,6,7-tetrahydro-1,3-benzothiazole-2-amine, as (R)-stereoisomer, chemically (R)-6-propylamino-4,5,6,7-tetrahydro-1,3-benzothiazole-2-amine ("dexpramipexole", INN), and as (S)-stereoisomer, chemically (S)-6-propylamino-4,5,6,7-tetrahydro-1,3-benzothiazole-2-amine ("pramipexole", INN). These three chemical entities are basic substances that may be isolated each as an acid addition salt and solvate thereof. Pramipexole dihydrochloride monohydrate is also known with its USAN "pramipexole hydrochloride". As used herein, "6-propylamino-4,5,6,7-tetrahydro-1,3-benzothiazole-2-amine" is a general term that, unless otherwise specified, designates a member selected from the group consisting of pramipexole, the racemate, and a pramipexole/dexpramipexole mixture.

"(R)/(S)-mixture": This term designates a dexpramipexole/pramipexole physical mixture used as an active ingredient according to the present invention.

"(S)-enantiomer": This term, as used herein with reference to 6-propylamino-4,5,6,7-tetrahydro-1,3-benzothiazole-2-amine doses (daily or per unit form) designates the (S)-stereoisomer, included in said doses that, in said 6-propylamino-4,5,6,7-tetrahydro-1,3-benzothiazole-2-amine, are primarily responsible for its dopaminergic action, with such dopaminergic action counteracted by the 5HT3-antagonist as described herein. More specifically, S-enantiomer is herein used to designate the S-stereoisomer that is present in the racemate or pharmaceutically acceptable salt thereof, and similarly, to designate the pramipexole or pharmaceutically acceptable salt thereof that is present, as (S)-constituent, in a (R)/(S)-mixture, in order to distinguish it from pramipexole used alone.

The terms "6-propylamino-4,5,6,7-tetrahydro-1,3-benzothiazole-2-amine", "(R)-6-propylamino-4,5,6,7-tetrahydro-1,3-benzothiazole-2-amine", "dexpramipexole", "pramipexole", "(S)-6-propylamino-4,5,6,7-tetrahydro-1,3-benzothiazole-2-amine", "(S)-enantiomer", "racemate" and "(R)/(S)-mixture" include the free bases and pharmaceutically acceptable salts and solvates thereof (unless otherwise specified); and the relative doses (daily or per unit form) are given in equivalents of pramipexole dihydrochloride monohydrate.

"Effective daily dose of pramipexole" or "effective daily dose of (S)-enantiomer": An effective pediatric or adult daily (S)-6-propylamino-4,5,6,7-tetrahydro-1,3-benzothiazole-2-amine or pharmaceutically acceptable salts and solvates thereof dose equivalent to at least the pramipexole dihydrochloride monohydrate approved daily dose for the treatment of PD.

"Effective pramipexole amount (or dose) per unit form" or "effective amount (or dose) per unit form of (S)-enantiomer": An amount per unit form of pramipexole or pharmaceutically acceptable salt or solvate thereof that is equivalent to at least a pramipexole dihydrochloride monohydrate amount per unit form approved for the treatment of PD. More specifically said amount per unit form is equivalent to from 0.125 mg to 45 mg of pramipexole dihydrochloride monohydrate. As noted above and as used herein, "pramipexole" and "(S)-enantiomer" refer to the same chemical entity, but the term "(S)-enantiomer" is generally used when describing the composition of the racemate and of (R)/(S)-mixtures.

Unless otherwise specified, the terms designating the 5HT3-antagonist active principles, in particular "ondansetron", "dolasetron", "palonosetron"; and the SSRI active principle "fluoxetine", with their INN include the free base and salts and solvates thereof.

"Statin": a class of chemical compounds with a 3,5-dihydroxyheptane or 3,5-dihydroxyhept-6-ene carboxylic acid structure linked, via its 7-position, to a carbocyclic or heterocyclic structure, in some cases in form of 5-lactone thereof, used as medicaments for treating dyslipidemia.

"Effective statin dose per unit form (or dose per unit form)" and "Effective statin daily dose": a statin dose per unit form or daily dose of from 0.5 mg to 80 mg. According to the structure of each statin, said dose-range refers to an equivalent of the free acid, to an equivalent of a specific salt, or, in case of a lactone, to the lactone itself.

"Zonisamide": benzo[d]isoxazol-3-ylmethanesulfonamide. Unless otherwise specified, the term zonisamide (INN) designates zonisamide acidic form and alkaline metal salts thereof, in particular, its sodium salt.

The terms "comprise," "comprises," "comprising" "include," "includes," and "including" are interchangeable and not intended to be limiting. It is to be further understood that where descriptions of various embodiments use the term "comprising," those skilled in the art would understand that the present disclosure also contemplates such embodiments alternatively described using the language "consisting essentially of" or "consisting of". It is to be further understood that where descriptions of various embodiments use the term "comprising," those skilled in the art would understand that the present disclosure also contemplates such embodiments alternatively described using the language "consisting essentially of" or "consisting of".

BACKGROUND OF THE INVENTION

Neurodegenerative disorders cause progressive injury and death to nerve cells in the central nervous system. They include Parkinson's disease, Alzheimer's disease, Huntington's disease, and amyotrophic lateral sclerosis. All are incurable, resulting in an inexorable loss of neurologic and psychiatric function. Although the clinical features of these disorders differ, they all share one similar characteristic—pathogenesis involves a prion-like misprocessing of a normal brain protein into an aggregated form that is capable of replication, propagation and neurotoxicity. In PD for example the protein is alpha-synuclein.

As research progresses, many similarities appear that relate these diseases to one another on a cellular and sub-cellular level. Discovering these similarities offers hope for therapeutic advances that could ameliorate many diseases simultaneously. There are many known similarities between different neurodegenerative disorders including atypical protein assemblies as well as induced cell death. Neurodegeneration can be found in many different levels of neuronal circuitry ranging from the molecular to the systemic.

The synthesis and misfolding of oligomeric/aggregated species of such proteins as amyloid-β, tau and alpha-synuclein now appear to be the predominant pathology underlying most, if not all, neurodegenerative disorders, including Alzheimer's and Parkinson's disease. Whilst end stage insoluble products of aggregation have been well characterized in human and animal models of disease, increasing evidence from in vitro and in vivo studies indicates that soluble intermediates of aggregation, i.e. oligomers, especially those in the 4 to 20 mers range, may be the key species that mediate toxicity and underlie seeding and spreading in disease (Choi and Gandhi 2018).

A-β is a 38 to 43 amino acid peptide generated by the sequential proteolytic cleavage of amyloid precursor protein ("APP") by β- and γ-secretases (Chow et al. 2010). It is thought that the over-production of A-β generated from APP plays a role in AD development. Soluble A-β oligomers, on the other hand, have been shown to produce cognitive deficits in the absence of plaques (Gandy et al. 2010). The larger aggregates are not essential to cognitive impairment (Petersen et al. 2013) nor responsible for neurodegeneration and the smaller soluble oligomers are presumed to be the toxic species of A-β. The toxic soluble oligomers are spherical in shape ranging from about 3 to 10 nm. These spheroidal structures come together forming strings of beads, termed protofibrils, which reportedly also possess toxic effects (Glabe, 2006).

Alpha-synuclein, a protein composed of 140 amino acids encoded by the SNCA (Synuclein-Alpha) gene, is abundantly expressed in the human brain and to a lesser extent in various other organs. In brain, alpha-synuclein (hereafter also referred to as simply "synuclein") is mainly found in neuronal terminals, especially in the cortex, hippocampus, substantia nigra and cerebellum, where it contributes to the regulation of neurotransmitter release, and passes into the peripheral blood stream (Marques and Outeiro, 2012), in part packaged within exosomal vesicles originating from the CNS (Shi et al. 2014).

Many amyloidogenic proteins, such as tau and amyloid-beta (A-β) species, may also be aberrantly converted from their normal monomeric form into soluble intermediates of aggregation, i.e., oligomeric species, that can become neurotoxic. For A-β, toxic oligomers are now thought to range from 8-24 mers while α-synuclein oligomers are 6-18 mers and tau oligomers are 3-15 mers (Sengupta et al 2016), suggesting a universal mechanism of toxicity for amyloid proteins such as tau (Gerson and Kayed, 2013, cited in Sengupta et al. 2016), α-Synuclein (Sengupta et al. 2016), and TAR DNA-binding protein 43 (TDP-43) (Choksi et al. 2014, Fang et al. 2014, both cited in Sengupta et al. 2016).

Under normal circumstances, these proteins appear to form stably folded oligomers that resists aggregation. But, in certain pathological conditions, for unknown reasons, they misfold, oligomerize and aggregate (with the eventual formation of fibrils). Somewhere along this aberrant pathway, toxic misfolded protein species are believed to be formed which may also pass into the peripheral (systemic) circulation.

Aberrant protein oligomerization and aggregation are now thought to be the cause of PMNDs, notably PD, LBD, DLB, Parkinsonian disorders associated with glucocerebrosidase (GBA) mutations, MSA, AD, HD, multiple tauopathies, and several other disorders, which are collectively referred to as "synucleinopathies". Alpha-synuclein is a ubiquitous protein that is especially abundant in the brain and has been postulated to play a central role in the pathogenesis of Parkinson's disease (PD), some cases of Alzheimer's disease, and other neurodegenerative disorders (Kim et al. 2004; Sweeney et al 2017).

Synucleinopathies are generally defined as a group of neurodegenerative disorders characterized in part by the intracellular accumulation of abnormal synuclein aggregates, some of which are toxic and contribute to the pathogenesis of the aforementioned disorders.

An abnormal ratio of monomeric to oligomeric synuclein species, or more specifically of particular oligomeric species, in brain-derived exosomes in peripheral blood of a patient, is postulated to be a diagnostic hallmark of a synucleinopathy and thus, for example, of one of the aforementioned neurodegenerative disorders of the human CNS.

PD is a common neurodegenerative disorder of the human CNS (Poewe et al. 2017) typically presenting with three major clinical signs: resting tremor, bradykinesia, and muscular rigidity. In addition, postural instability and various neurobehavioral disabilities may occur. In the US alone it is now estimated that well over one million individuals are afflicted by this inexorably progressive disorder. Along with the aging of the American population, prevalence rates and societal costs are expected to rise exponentially. Parkinsonian signs largely reflect a loss of dopamine-containing neurons in the basal ganglia. Drugs now used to relieve symptoms generally act by restoring brain dopaminergic function (Connolly and Lang. 2014). None are known to alter the basic parkinsonian disease process. Indeed, notwithstanding prodigious investigative efforts over the past half-century, the cause and cure of these fatal disorders remain elusive.

LBD is one of the most common types of progressive dementia. The central features of LBD include progressive cognitive decline, visual hallucinations, and parkinsonian motor symptoms, such as slowness of movement, difficulty walking, and muscular rigidity. Some may also suffer from depression. The symptoms of LBD are caused by the selective loss of nerve cells, presumably a result of synuclein misprocessing and associated with the build-up of Lewy bodies, spherical synuclein accumulations inside many of the degenerating neurons. Researchers do not know precisely why alpha-synuclein accumulates into Lewy bodies or how synuclein species can cause the symptoms of LBD. The formation of Lewy bodies have been considered to be a marker for PD; however, Lewy bodies have also been observed in approximately 60% of both sporadic and familial cases of Alzheimer's disease (AD) (Al-Mansoor et al. 2013). Accordingly, the aggregation of α-synuclein has been strongly implicated as a critical step in the development of neurodegenerative diseases (Al-Mansoor et al. 2013).

Sporadic PD or brainstem-predominant type LBD, and dementia with Lewy bodies (DLB) are the two most frequent α-synucleinopathies, and are progressive multisystem neurodegenerative disorders with widespread occurrence of α-synuclein deposits in the central, peripheral, and autonomic nervous system (Jellinger 2008a). Reportedly, there is considerable clinical and pathologic overlap between PD (with or without dementia) and DLB, corresponding to Braak LB stages 5 and 6 (Braak et al. 2003), both frequently associated with variable Alzheimer-type pathology (Jellinger 2008a). Dementia often does not correlate with progressed stages of LB pathology, but may also be related to concomitant Alzheimer lesions or mixed pathologies (Jellinger 2008a).

Alzheimer disease (AD) is characterized by deposition of β-amyloid peptides, phosphorylated tau protein (3- and 4-repeat tau) and frequent α-synuclein (aSyn, as abbreviated by the authors) deposits (Jellinger 2008b). Lewy body diseases, such as sporadic Parkinson disease (PD) and dementia with Lewy bodies (DLB), show a-Synuclein-positive deposits in neurons, neurites, glia, and presynaptic terminals, while frontotemporal dementias present tau-positive and tau-negative, ubiquitin- and TDP-43-positive neuronal and glial inclusions (Jellinger 2008b). Molecular interactions between major proteins, which may occur within the same brain in various distribution patterns, cause variable phenotypes and mixed pathologies, e.g. AD with a-Synuclein pathology in the brainstem and amygdala, PD and DLB with AD lesions, and frontotemporal dementia with a mixture of various deposits, while others are featured by one principal pathology without other lesions (e.g. tangle-predominant type of dementia, pure PD, brainstem-predominant LBD) (Jellinger 2008b). In Alzheimer's disease, amyloid-β and tau proteins become oligomerized and accumulate in brain tissue where they appear to cause neuronal injury and loss; indeed, some aver that such soluble intermediates of aggregation, or oligomers, are the key species that mediate toxicity and underlie seeding and spreading in disease (Cline et al. 2018, Choi and Gandhi 2018).

The aforementioned Transactive Response DNA-binding protein 43 (TDP-43) is a 43 kDa protein encoded in humans by the TAR DBP gene. In Frontotemporal lobe dementia, a mutation of TAR DBP gene forms highly phosphorylated toxic amyloid TDP-43 oligomers that accumulate in frontal brain region of patient suffering from this disease (Fang at al. 2014).

In ALS, fibrils and oligomers have also been regarded as the aggregated protein agents of neuronal dysfunction. More specifically, a corkscrew-like structure in oligomerized superoxide dismutase 1 (SOD1) reportedly can serve as the cytotoxic segment in certain individuals with ALS. Mutations that prevent formation of this structure eliminate cytotoxicity of the segment in isolation as well as cytotoxicity of the ALS-linked mutants of SOD-1, in primary motor neurons and in a *Danio rerio* (zebrafish) model of ALS (Sangwan et al. 2017).

α-Synuclein and tau aggregates can co-exist in several neurodegenerative disorders, including Parkinson's disease, Alzheimer's disease, and progressive supranuclear palsy (PSP) and indeed there is evidence that α-synuclein enhances the harmful effects of tau, thus contributing to disease progression (Castillo-Carranza et al. 2018; Erro Aguirre et al. 2015). Tau oligomers in biological fluids, in particular in CSF, can be measured by ELISA and Western blot analysis using anti-tau oligomer antibodies (Sengupta et al. 2017).

MSA with orthostatic hypotension is the current term for a neurological disorder that was once called Shy-Drager syndrome. A progressive disorder of the central and autonomic nervous systems, it is characterized by orthostatic hypotension (an excessive drop in blood pressure when standing up), which causes dizziness and fainting. Multiple system atrophy can occur without orthostatic hypotension, but instead have urinary tract involvement (urgency/incontinence). Neurologists classify the disorder into 3 types: the Parkinsonian-type includes symptoms of Parkinson's disease such as slow movement, stiff muscles, and tremor; the cerebellar-type, which causes problems with coordination and speech; and the combined-type, which includes symptoms of both parkinsonism and cerebellar dysfunction. Problems with urinary incontinence, constipation, and sexual impotence may happen early in the course of the disease. Other symptoms include generalized weakness, double vision or other vision disturbances, difficulty breathing and swallowing, sleep disturbances, and decreased sweating. Because the disease resembles others, a correct diagnosis may take years.

Mutations in the glucocerebrosidase gene (GBA) can result in the autosomal recessive disorder Gaucher disease, Different lines of evidence suggest that mutant GBA can be a risk factor for some cases of Parkinson's disease. Indeed, GBA mutations are now thought to be the single largest risk factor for development of idiopathic PD. Clinically, on imaging and pharmacologically, GBA PD is nearly identical to idiopathic PD (O'Regan et al. 2017). The molecular mechanisms which lead to this increased PD risk in GBA mutation carriers are not fully elucidated, but have been shown to be associated with the accumulation of synuclein (Soria et al. 2017).

Corticobasal Degeneration ("CBD"), pathologically classified as tauopathy, presents with various phenotypes some of which include parkinsonian features, especially rigidity and akinesia (Reich and Grill 2009). Only in a few do these manifestations benefit from standard dose dopaminergic therapy, usually only to a moderate degree and with short-lived duration, notwithstanding evidence of neuronal loss in the substantia nigra and a reduction in presynaptic dopamine transporter binding in the striatum.

In Huntington's disease (HD), cleavage of the full-length mutant huntingtin (mhtt) protein into smaller, soluble aggregation-prone mhtt fragments appears to be a key process in the neuropathophysiology of this disorder. Indeed, aggregation and cytotoxicity of mutant proteins containing an expanded number of polyglutamine (polyQ) repeats is a hallmark of several diseases, in addition to HD. Within cells, mutant Huntingtin (mHtt) and other polyglutamine expansion mutant proteins exist as monomers, soluble oligomers, and insoluble inclusion bodies (Mitchell Sontag et al. 2012).

Several other PMNDs have also, albeit less frequently, been considered synucleinopathies. These include Hallevorden-Spatz syndrome, neuronal axonal dystrophy, and some cases of traumatic brain injury. In the case of Hallevorden-Spatz, symptoms include parkinsonism, dystonia, dysphagia/dysarthria, rigidity or stiffness of the limbs, dementia and spasticity.

Many now believe that processes leading to protein oligomerization and aggregation may be central to the cellular injury and destruction occurring in these disorders.

The mechanism of alpha-synuclein aggregation in these PMNDs remains poorly understood. Current evidence suggests the conversion of a soluble alpha helical structure into a beta pleated conformation with subsequent oligomer formation leads to the aggregation, fibrillization and ultimately deposition of synuclein. Certain of the oligomeric forms of synuclein appear highly neurotoxic and could contribute to the neurodegenerative process characterizing PD and related disorders. These characteristics are similar to the aberrant processing of prion proteins that also can become highly neurotoxic. In addition, phosphorylation of alpha-synuclein at the serine-129 residue has been implicated as a contributory factor (Chen et al. 2016). According to Prusiner et al. 2015, a prion form of alpha-synuclein could be a causal agent, especially for multiple system atrophy. Prions are small proteins that also can misfold, oligomerize, aggregate and propagate to other cells. The result in brain is a profound and spreading neurodegenerative process.

Accordingly, inhibiting the initial misfolding, oligomerization and aggregation of certain brain proteins may be beneficial in slowing or even arresting the progression of PMNDs.

Current evidence further suggests that this aberrant misfolding, oligomerization, fibrilization process also involves other brain proteins such as beta-amyloid, tau, and huntingtin proteins and that certain of these abnormal species thus formed may play a role in the pathogenesis of disorders such as AD, various tauopathies including PSP, and of HD (Choi and Ghandi, 2018; Nilson et al, 2017; Hoffner and Djian, 2014). Accordingly, drugs that block the formation and/or neurotoxic action of these aberrant species may confer therapeutic benefit to patients suffering from these disorders (Choi and Ghandi 2018; Nilson et al. 2017; Sengupta et al, 2017).

As mentioned above, alpha-synuclein, as well as others of the aforementioned oligomerized species, readily pass into extracellular spaces and have been identified in cerebrospinal fluid, blood, urine, and saliva (Marques and Outeiro 2012). The mechanisms of alpha-synuclein excretion are not fully understood, but studies have demonstrated that at least a fraction of alpha-synuclein is excreted within exosomes, the 40 nm to 100 nm vesicles of endocytic origin (reviewed in Shi et al. 2014). The ratio of monomeric to oligomeric species within exosomes in peripheral blood originating from the CNS could thus reflect disease transient intensity and/or cumulative severity (Shi et al. 2014), thus suggesting that peripheral blood exosomal alpha-synuclein and related species can help monitor the clinical state of a neurodegenerative disease and response to therapy. Similarly, alpha-synuclein levels in brain-derived exosomes have been reported to correlate with severity of impairment in cross-sectional samples from patients with LBD (Stuendl et al. 2016).

Based on the above, drugs that normalize the ratio of monomeric to oligomeric alpha-synuclein species in peripheral blood exosomes deriving from brain should slow or even arrest the neurodegenerative process associated with the synucleinopathies.

Various compositions for the treatment of PD and related disorders that target the aggregation of brain proteins such as synuclein have been proposed. The discovery process primarily involves cellular and animal models of prion- and synuclein-induced neurodegeneration (Prusiner et al. 2015; Visanji et al. 2016). Unfortunately, none of these models has been validated and all are currently regarded uncertain predictors of effects in humans. Nevertheless, these models continue to be widely used in the absence of better discovery techniques.

Pharmaceutical agents currently proposed for consideration in the present invention include, for instance, such small molecules as (S)-6-propylamino-4,5,6,7-tetrahydro-1,3-benzothiazole-2-amine (pramipexole) and fluoxetine, (S)-6-propylamino-4,5,6,7-tetrahydro-1,3-benzothiazole-2-amine (pramipexole) and zonisamide, or (S)-6-propylamino-4,5,6,7-tetrahydro-1,3-benzothiazole-2-amine (pramipexole) and a statin.

Pramipexole and its analogs, alone or in combination with various drugs have also been considered for the treatment of PD and related disorders.

Pramipexole is a synthetic aminothiazole derivative described in U.S. Pat. No. 4,886,812, the content of which is incorporated herein in their entirety by reference. It is a dopamine agonist of the non-ergoline class (Schneider and Mierau 1987) that has been approved since the late 1990s for the symptomatic treatment of Parkinson's disease (PD) in doses ranging from 0.375 mg/day to 4.5 mg/day, given in 3 equally divided doses (Mirapex® Prescribing Information, July 2016). Pramipexole is supplied in tablets for immediate release containing 0.125 mg, 0.25 mg, 0.5 mg, 1 mg and 1.5 mg of pramipexole dihydrochloride monohydrate; and in tablets for extended release containing 4.5 mg of pramipexole dihydrochloride monohydrate.

Although pramipexole is widely used for the relief of Parkinsonian symptoms, its potential as a disease modifying agent has made it the object of considerable investigative attention.

Pramipexole reportedly diminishes synuclein oligomer formation in vitro (Ono et al. 2013). Related studies suggest that pramipexole inhibits the toxic effects of rotenone on dopaminergic neurons in a mouse PD model while reducing immunoreactivity for alpha-synuclein; additionally, pramipexole decreases the in vitro oligomerization of human wild-type alpha-synuclein by $H_2O_2$ plus cytochrome c (Inden et al. 2009). Pramipexole has also been observed to inhibit the aggregation of alpha-synuclein in human neuroblastoma SH-SY5Y cells (Kakimura et al. 2001). Importantly, the relative expression of α-synuclein in peripheral blood exosomes has been reported to decline during pramipexole treatment of PD-type patients, especially those manifesting acute symptomatic benefit (Luo et al. 2016); an observation of considerable interest since animal model studies have indicated that changes in peripheral blood exosomal synuclein species correlate with changes in the CNS (Shi et al. 2014).

In addition, it began to be reported that pramipexole can exert neuroprotective effects in various in vitro cellular and in vivo animal models of PD. Mechanisms by which these protective effects may occur remain uncertain. Unfortunately, the protective effects of pramipexole in animal models are generally small and require higher doses than are considered safe and tolerable for human administration. It is thus hardly surprising that pramipexole, in doses approved for the treatment of motor symptoms of PD failed to evidence neuroprotective (i.e., disease modifying) activity in a randomized, controlled, clinical trial involving 535 PD patients (Schapira et al. 2013).

(R)/(S)-mixtures, consisting of pharmaceutical compositions comprising a therapeutically effective amount of dexpramipexole or pharmaceutically acceptable salts and solvates thereof and a therapeutically effective amount of pramipexole or pharmaceutically acceptable salts and solvates thereof, useful for the treatment of PD, are disclosed in US 2008/0014259, the contents of which are incorporated herein in their entirety by reference.

According to US 2008/0014259, both enantiomers are able to confer neuroprotective effects by their ability to accumulate in brain cells, the spinal cord and mitochondria where they exert a positive effect on neurological function that is independent of the dopamine agonist activity of pramipexole. In particular, said document proposes said composition as a neuroprotective agent and a therapeutically effective amount of from about 0.0625 mg to about 6 mg of pramipexole in combination with up to 5000 mg of dexpramipexole. However, this document emphasizes the pramipexole adverse effects due to its dopaminergic action and tends to privilege pramipexole low doses, as also confirmed by the same applicant in the almost concurrent WO 2008/113003 document, the contents of both of which are incorporated herein in their entirety by reference.

According to US 2013/0116292, the contents of which are incorporated herein in their entirety by reference, dexpramipexole, or pharmaceutically acceptable salts and solvates thereof, acts by slowing the progression of neuronal degeneration and/or by preventing neuronal cell death, even though no further evidence of this possible noteworthy action of dexpramipexole appeared in the literature.

A synthesis of dexpramipexole and of pharmaceutically acceptable salts thereof, in particular dexpramipexole dihydrochloride monohydrate, is described in US 2012/0253047, the contents of which are incorporated herein in their entirety by reference.

Unfortunately, limitations associated with the administration of pramipexole to for example parkinsonian patients limit its use at the potentially higher neuroprotective doses predicted by some animal models. First, mechanisms to explain its putatively beneficial effects on synuclein-related neurotoxicity continue to elude full understanding. Second, effect sizes in animal model studies tend to be small and occur only at relatively high drug doses. Both situations were also observed in the above mentioned report of pramipexole-induced changes in exosomal synuclein in PD patients, which were associated with the administration of the highest—4.5 mg/day—recommended/approved dose of pramipexole (Mirapex® Package Insert; Revised July 2016).

In the aforementioned report of the Luo et al. 2016 reference, although treatment of Parkinson patients with pramipexole at approved therapeutic doses significantly lowered the relative expression of alpha-synuclein (compared with pre-treatment values) in peripheral blood, the magnitude of the effect was small. Higher doses of pramipexole could have been more efficacious, but side effects such as vomiting and severe nausea preclude the use of higher doses. For example, in Corrigan et al. 2000, the authors report that doses of 5 mg/day of pramipexole, hardly higher than the maximum recommended dose of 4.5 mg/day (Pramipexole FDA-approved package Insert) caused nausea in 76% of patients and vomiting in 39% of patients. Furthermore, 36% of patients were not able to complete the study, presumably because of intolerable GI adverse events.

In addition, there is no clinical demonstration of a neuroprotective effect of pramipexole, or of any disease modifying action by pramipexole, at the recommended doses, in patients suffering from a PMND such as PD.

The US 2003/0032661 patent document, the content of which is incorporated herein in its entirety by reference, discloses the use of pramipexole therapeutically effective doses for the prevention and/or treatment of generalized seizures (absences, also atypical absences, myoclonic, clonic, tonic, and tonic-clonic seizures), focal (simple and complex focal) and secondary generalized seizures; and affirms that pramipexole can be used in therapeutically effective doses as an anticonvulsant for treating said cerebral seizures. According to this document, pramipexole may be used in doses of about 0.05 mg to 7.5 mg, preferably 0.1 mg to 5 mg per day, at maximum doses of about 5 mg to 7.5 mg of pramipexole per day. In addition, this document affirms that pramipexole may be used to treat the abovementioned conditions in conjunction, for example, with one or more, preferably one of the following substances: carbamazepine, oxcarbamazepine, valproic acid, diphenylhydantoin, ethosuximide, mesuximide, phenobarbital, primidone, benzodiazepines (preferably diazepam, clonazepam or clobazam), corticotrophin, corticoids, bromides (such as potassium bromide), sultiam, acetazolamide, felbamate, gabapentin, lamotrigine, topiramate, vigabatrin, levetiracetam, and zonisamide. This document, however, does not give any information about how said pramipexole and, a fortiori, any combination thereof with other drugs would have been used for treating said seizures, and limits the description of the pramipexole unit forms to a maximum 1 mg strength.

In a case report (Kataoka and Ueno 2014), pramipexole (4.5 mg/day), in combination with levodopa (250-500 mg/day), entcapone (200 mg/day), selegiline (5 mg/day) and zonisamide (25-50 mg/day), was reported to induce hallucinations in one moderate Parkinsonian patient, when administered in extended-release formulation, but not when administered in immediate release formulation.

Fluoxetine

Fluoxetine, 1-methylamino-3-phenyl-3-[4-(trifluoromethyl)phenoxy]propane, is a selective serotonin reuptake inhibitor (SSRI) antidepressant, available in preparations comprising fluoxetine hydrochloride, in an amount per IR-unit form equivalent to 10 mg, 20 mg or 40 mg of fluoxetine base, to be administered once or twice per day (typically as Prozac®). Fluoxetine hydrochloride is also available in a specific preparation (Prozac® Weekly™), in capsules comprising fluoxetine hydrochloride, in an amount per ER-unit form equivalent to 90 mg of fluoxetine base, to be administered once a week (herein below referred to as "90 mg ER-weekly preparation"). Fluoxetine is currently used in the treatment of major depressive disorder, obsessive-compulsive disorder (OCD), bulimia nervosa, panic disorder, and premenstrual dysphoric disorder. When taken by mouth at recommended maintenance IR-doses (20 mg to 80 mg daily in 1 to 2 divided doses), or in the specific 90 mg ER-weekly preparation by patients with these disorders, fluoxetine typically evinces a high degree of efficacy.

The mechanism by which fluoxetine benefits patients with psycho-affective disorders is generally considered to be linked to the drug's ability to augment CNS serotonin-mediated transmission. In addition, however, large fluoxetine doses in rodents have been shown to induce a significant increase in extracellular concentrations of norepinephrine and dopamine after acute systemic administration (Bymaster et al. 2002).

Fluoxetine augments levels of neurotrophic factors such as glial-derived neurotrophic factor (GDNF) and brain-derived neurotrophic factor (BDNF) and, in addition, the effects of fluoxetine in in vivo transgenic models of alpha-synucleinopathy have received careful investigative attention.

It has also been extensively reported to exhibit neuroprotective activity in various cellular and animal models of neurodegenerative disease (Ubhi et al. 2012).

For example, a laboratory study examined the effect of fluoxetine in the MBP1-hα-syntg mice, a model of MSA (Shults et al. 2005).

Fluoxetine can protect against 6-OHDA (6-hydroxydopamine) (Suzuki et al. 2010) and MPTP (1-methyl-4-phenyl-1,2,3,6-tetrahydropyridine) (Chung et al. 2011) induced damage in toxin-induced models of PD.

Fluoxetine was also disclosed to significantly delay amyloid-β-induced paralysis in the *Caenorhabditis elegans* model of amyloid-β toxicity by reducing amyloid-β oligomers and to increase thermal stress resistance and extend life span, thus suggesting that fluoxetine may have benefit for the treatment of AD by the reduction of proteotoxicity (Keowkase et al. 2010).

Interestingly, fluoxetine has been reported to enhance the activity of pramipexole in a rodent forced swimming test model of depression by a mechanism yet to be precisely elucidated (Rogóz and Skuza 2006).

The document U.S. Pat. No. 6,667,329 (see also WO00/06162), the contents of which are incorporated herewith in their entirety by reference, discloses a combination of pramipexole with another antidepressant for the treatment of depression. Said other antidepressant may be alprazolam, fluoxetine, opipramol, amitriptyline, fluvoxamine, paroxetine, amitriptyline oxide, imipramine, sertraline, chlordiazepoxide, lofepramine, sulpiride, citalopram, maprotiline, tranylcypromine, clomipramine, mianserin, trazodone, quinpirole, mirtazapine, trimipramine, dibenzepin, moclobemide, tryptophan, doxepin, nefazodone, venlafaxine, nortriptyline or viloxazine. According to U.S. Pat. No. 6,667,329, pramipexole combined with another antidepressant has a significantly greater antidepressant activity than either of the two individual components taken alone, the improvement in the effect of pramipexole by the simultaneous administration of another antidepressant having been discovered in tests on rats using the forced swimming test. Said combination may be a fixed-dose combination.

The document U.S. Pat. No. 6,319,953 (see also WO 98/15277), the contents of which are incorporated herewith in their entirety by reference, discloses a method for the treatment or prevention of depression and/or anxiety, which method comprises administration to a patient in need of such treatment an amount of a CNS-penetrant NK-1 receptor antagonist and an amount of an antidepressant or anti-anxiety agent, such that together they give effective relief Among a series of antidepressants' classes, including selective serotonin reuptake inhibitors, and within a list of antidepressants, said document cites fluoxetine.

Nevertheless, no evidence has been reported showing that fluoxetine exerts disease modifying effects in humans with a neurodegenerative disease such as PD, or even positively influences the misfolding of neuronal proteins causing a PMND.

In conclusion, notwithstanding the extensive studies on the effects of fluoxetine and pramipexole, separately, on alpha-synuclein processing over the past ten years, the massive existing literature, and the disclosures of US 2008/0014259, U.S. Pat. Nos. 6,319,953, and 6,667,329, no-one has succeeded in safely increasing pramipexole efficacy, because pramipexole currently provides only marginal activity in the treatment of or prevention of progression of Parkinson's disease or related disorders.

The problem of providing effective treatment to patients suffering from a PMND remains unresolved. In fact, during the last seventeen years no-one has disclosed or suggested a combination of a 5HT3-antagonist with both pramipexole and fluoxetine, or a combination of a NK1-antagonist with both pramipexole and fluoxetine, which could be used to provide an effective means for treating PMNDs.

Zonisamide

Zonisamide (1,2-benzisoxazole-3-methanesulfonamide) is a sulfonamide anticonvulsant approved for use in the adjunctive therapy of adults with partial-onset seizures ("antiseizure indication"); including infantile spasm, mixed seizure types of Lennox-Gastaut syndrome, myoclonic, and generalized tonic clonic seizure.

This drug is commercially available (Zonegran®) and is supplied for oral administration as capsules containing 25 mg or 100 mg zonisamide. In the treatment of epilepsy, oral zonisamide is generally used in daily doses of 200 mg to 600 mg per day, divided in 2 daily doses, and adjusted to maintain serum levels of 15 to 40 micrograms/milliliter.

The drug, unrelated to other anticonvulsants, is believed to act, at least in part, by blocking voltage dependent sodium and T-type calcium channels. It is also a weak carbonic anhydrase inhibitor and a modulator of brain GABAergic and glutamatergic neurotransmission.

Zonisamide has also been reported to exhibit protective activity in various neurotoxin-based cellular and animal models of PD.

U.S. Pat. No. 6,342,515 (Masuda and Ochi, see also WO 99/33465), the contents of which are incorporated herein in their entirety by reference, claims the use of zonisamide for treating neurodegenerative diseases such as primary or secondary Parkinson's disease, Huntington's disease, choric syndrome and dystonic syndrome in mammals (including human). This claim is supported by pharmacological experiments carried out in mice intraperitoneally treated with 1-methyl-4-phenyl-1,2,3,6-tetrahydropyridine (MPTP) 30 mg/kg, once a day for 8 days repetitively.

In MPTP-treated mice, zonisamide administration (20 mg/kg) also reduced the loss of nigral TH-positive neurons while attenuating the associated striatal dopamine depletion (Yokoyama H et al. 2010). In mice that received 6-hydroxydopamine (6-OHDA) to induce hemiparkinsonism, the injection of zonisamide (30 mg/kg) prevented the loss of nigral dopamine neurons.

In an in vitro neurotoxic model obtained by acutely exposing rat corticostriatal slices to rotenone, a selective inhibitor of mitochondrial complex, low concentrations of zonisamide (0.3, 1, 3 and 10 μM) significantly reduced the rotenone-induced toxicity protecting striatal slices from the irreversible loss of corticostriatal field potential amplitude via a GABA-mediated mechanism (Costa et al. 2010).

In more direct relation to neurodegeneration due to the misfolding of proteins such as α-Synuclein, zonisamide inhibits the in vitro oligomerization and aggregation of alpha-synuclein, a key event in the pathogenesis of PD and related disorders (Ono et al. 2013) and exerts protective effects against A53T α-synuclein-induced neurodegeneration in a manner that may be independent of synuclein aggregation in an in vivo rat model (Arawaka et al. 2014). In the latter study, orally administered zonisamide (40 mg/kg/day) significantly delayed the pace of degeneration four weeks after injection of the viral vector for the A53T α-synuclein gene as compared with the control group. This effect lasted at least eight weeks after transgene injection, but appeared to have no impact on the survival of nigrostriatal dopamine neurons. The chronic administration of zonisamide to Engrailed mutant mice, another genetic model of PD, improved the survival of nigrostriatal dopaminergic neurons as well as their striatal dopaminergic terminals and motor function as compared with saline treatment (Sano et al 2015). The mechanism of these protective effects remains uncertain, although brain-derived neurotrophic factor content reportedly increased in the striatum and ventral midbrain of the zonisamide-treated mice compared to saline-treated controls.

Zonisamide, given at relatively low doses (25 mg-50 mg) either alone or with levodopa, has been observed to improve motor symptoms in patients with PD (Grover et al. 2013). However, there are no clinical reports documenting that zonisamide exerts disease modifying effects in humans with a neurodegenerative disease such as PD, or modifies synuclein species in blood exosomes from patients with PD type disorders.

Thus, notwithstanding the disclosures of the aforementioned U.S. Pat. No. 6,342,515/WO 99/33465 and US 2003/0032661 documents, zonisamide has not been used, nor suggested for use, in combination with pramipexole and/or with a 5HT3-antagonist for treating PD or any other PMND. Similarly, zonisamide has not been used, nor suggested for use, in combination with pramipexole and/or with a NK1-antagonist for treating PD or any other PMND.

Statins

Statins constitute a class of widely marketed drugs approved since the late 1980s for the treatment of hyperlipidemia. All act to inhibit the enzyme HMG-CoA reductase, which plays a critical role in the synthesis of cholesterol. Evidence from large randomized trials shows that statin therapy reduces the risk of major vascular events such as myocardial infarction, strokes, and coronary revascularization procedures (Collins et al. 2016).

For nearly three decades, statins have been regarded as safe and effective in the primary and secondary prevention of cardiovascular disease, especially for reducing the risk of heart attacks, stroke, and certain arterial revascularization procedures.

Studies in cultured human cells as well as in animal models have shown that drugs of this class are copiously yet selectively taken up by the liver, the target organ for cholesterol lowering drugs. Within the liver, it is currently believed that the lipid-modifying effects of statins such as rosuvastatin occur as a result of increasing the number of hepatic LDL receptors on cell-surfaces to enhance the uptake and catabolism of LDL as well as by inhibiting the hepatic synthesis of very low-density lipoproteins (VLDL).

Statins act selectively as competitive inhibitors of HMG-CoA reductase, the rate-limiting enzyme that converts 3-hydroxy3methylglutaryl coenzyme A to mevalonate, a precursor in the synthesis of cholesterol.

Some statins are also reported to have a favorable effect on other disorders including dementia, lung and prostate cancer, and hypertension.

Evidence accumulated over the past two decades also suggests that statins' class drug may be useful in the treatment of CNS diseases (Willey and Elkind 2010). In vitro studies, suggest that drugs of this class, for example simvastatin, could also be used in the treatment of PD and related disorders because they have been reported in animals to protect against the deleterious consequences of dopaminergic neurotoxin MPTP (Roy and Pahan 2011), even though this beneficial action is still controversial (Carrrol J A et al. 2017).

Statins such as atorvastatin (Kumar et al 2012), lovastatin (Lin et al. 2015, Yan et al. 2015), and simvastatin (Kumar et al 2012, Xu et al. 2013) have been reported to protect against the deleterious consequences of the dopaminergic neurotoxin 6-hydroxydopamine (6-OHDA) in brain cell systems. Similarly, in a 6-OHDA-lesioned cell model, simvastatin provides robust neuroprotection against dopaminergic neurodegeneration, possibly in part via antiinflammatory mechanisms and the PI3K/Akt/caspase 3 pathway (Xu et al. 2013).

Statin class drugs also appear to protect against synuclein related neurotoxicity in PD model using rotenone (Kang et al. 2017).

Statin treatment has also been reported to modify the concentration of alpha-synuclein species contained within exosomes collected from the peripheral blood of PD patients (Bar-On et al. 2008).

In a phase 2 clinical trial on 140 patients aged 18-65 years with secondary progressive multiple sclerosis, high-dose simvastatin reduced the annualised rate of whole-brain atrophy compared with placebo, and was well tolerated and safe (Chataway et al 2014).

These results suggested that simvastatin could also possess disease modifying activity in PD and prompted a clinical investigation on 198 patients as part of a clinical trial (PD-STAT), begun in 2015 in the UK as a 24-months Phase-2 that, if successful, would be followed by a Phase-3 clinical trial (Carrol G B et al. 2017). To date, no other information about this study seems to be available to the public.

As mentioned above, (S)-6-propylamino-4,5,6,7-tetrahydro-1,3-benzothiazole-2-amine (pramipexole) and its analogues, alone or in combination with various drugs have also been considered for the treatment of PD and related disorders.

However, notwithstanding the massive existing literature, in particular in particular Corrigan et al. 2000, and the disclosures of US 2008/0014259 and US 2011/0071135, no-one has succeeded in safely increasing pramipexole efficacy, and pramipexole currently provides only marginal activity in the treatment of or prevention of progression of Parkinson's disease or related disorders.

There is no clinical demonstration of a neuroprotective effect of pramipexole, or of any disease modifying action by pramipexole, in patients suffering from a PMND such as PD.

Practical limitations associated with the safety and tolerability of administering pramipexole to synucleinopathic patients at the high, neuroprotective doses generally predicted by animal models pose a significant challenge. The effects of pramipexole in animal model studies tend to be small and occur only at relatively high doses. As with most pharmaceuticals, higher doses of pramipexole generally produce more frequent and severe adverse effects along with improved therapeutic efficacy. Side effects of the approved doses, often dose-limiting, include nausea, vomiting, somnolence, confusion, postural hypotension, and hallucinations as well as gastrointestinal disturbances (Mirapex Package Insert, Revised July 2016).

In conclusion, the state of the art shows (a) that the efficacy of pramipexole in the treatment of PD is insufficient, (b) the fact that pramipexole possesses a disease modifying ability in patients suffering from a PMND has not been clinically proven; and (c) that, as set forth above, said efficacy is limited by the adverse effects of this drug.

Thus, more than twenty years after the approval of Mirapex®, nineteen years after the disclosure of Masuda-Ochio WO 99/33465, eighteen years after the approval of Zonegran®, and fifteen years after the publication of US 2003/0032661, the problem of providing safe, chronic, effective treatment of a patient suffering from a PMND with pramipexole remains unresolved.

SUMMARY OF THE INVENTION

The present invention increases the therapeutic window for pramipexole, thus safely enabling its full neuroprotective efficacy to a degree that delays onset and/or slows symptom progression to a clinically significant extent in patients suffering from a PMND, such as those with PD-like disorders.

The present inventors have discovered that the effects of (S)-6-propylamino-4,5,6,7-tetrahydro-1,3-benzothiazole-2-amine (pramipexole) on the exosomal biomarker in the peripheral blood of patients with synucleinopathic disorders like PD of the aberrant processing of synuclein is substantially and unexpectedly improved by the co-administration of a 5HT-3 antagonist and/or NK1-antagonist and a fluoxetine, zonisamide, or a statin. Not only does the effect size become clinically significant but the dose requirement for both pramipexole and fluoxetine, zonisamide, or a statin now falls into the range considered safe and tolerable for human subjects. In the present invention, the combination of pramipexole plus fluoxetine, zonisamide, or a statin and 5HT-3 antagonist and/or NK1-antagonist safely interdicts the basic degenerative disease process in such patients to a clinically meaningful degree.

Not less surprisingly, it has been discovered that a further combination with a 5HT3-antagonist and/or NK-1 antagonist increases the efficacy of pramipexole and, in addition, allows the administration of pramipexole daily doses as high as up to 45 mg, in particular from more than 20 mg to 45 mg, more particularly from 20.25 mg to 45 mg (in pramipexole dihydrochloride monohydrate).

One approach to this end is to administer to a patient a drug that acts synergistically with pramipexole, for instance, to reduce the minimum effective dose for pramipexole and/or increase the efficacy of pramipexole without diminishing its minimum toxic dose.

The antidepressant fluoxetine exhibits these properties when combined with with 6-propylamino-4,5,6,7-tetrahydro-1,3-benzothiazole-2-amine or pharmaceutically acceptable salt thereof, preferably pramipexole.

Zonisamide exhibits these properties when combined with 6-propylamino-4,5,6,7-tetrahydro-1,3-benzothiazole-2-amine or pharmaceutically acceptable salt thereof, preferably pramipexole.

Statins also exhibit these properties when combined with 6-propylamino-4,5,6,7-tetrahydro-1,3-benzothiazole-2-amine or pharmaceutically acceptable salt thereof, preferably pramipexole.

According to a a first aspect of the invention, it has been found that fluoxetine acts by augmenting the PMND-modifying potential of pramipexole in humans, thus allowing at least a slowing of the disease progression at doses that are both safe and tolerable.

In addition, it has been found that fluoxetine allows for the safe administration of 6-propylamino-4,5,6,7-tetrahydro-1,3-benzothiazole-2-amine at a daily dose comprising a (S)-enantiomer dose that may be higher, and even much higher, than the pramipexole maximum daily dose recommended for the relief of the symptomatic treatment of Parkinson's disease. Consequently, an improvement of the conditions of a patient suffering from a PMND can be attained.

For example, the combination of fluoxetine or of a pharmaceutically acceptable salt or solvate thereof with a 6-propylamino-4,5,6,7-tetrahydro-1,3-benzothiazole-2-amine or a pharmaceutically acceptable salt or solvate thereof, acts to normalize levels of synuclein species within the brain-derived exosomes in peripheral blood of patients suffering from a synucleinopathy, in particular by diminishing the concentration of abnormal synuclein species (congeners) in the patient's exosomal vesicles found therein, to a clinically significant degree at doses that are safe and tolerable thus evidencing that said patients will enjoy neuroprotective benefit.

This observation is unexpected since neither drug has been found clinically to possess any disease modifying ability in patients with a synuclein related disorder. Moreover, nowhere has it even been suggested that the combination of these drugs might confer such significant benefit to such individuals since the antiparkinson drug and the antidepressant drug primarily act by very different mechanisms.

In addition, it has been found that the combination (including fixed-dose combinations) of a 5HT3-antagonist and/or a NK1 receptor antagonist and of fluoxetine allows for the safe administration of a pramipexole dose that may be higher, and even much higher, than the pramipexole maximum daily dose recommended for the symptomatic treatment of Parkinson's disease. Consequently, an improvement in the condition of a patient suffering from a PMND is attained.

The present invention is based on the discovery that

- fluoxetine potentiates (augments) the ability of pramipexole to alter misfolded protein species in ways indicating the activation of a central neuroprotective mechanism, i.e. reducing oligomerization of said proteins;
- these changes occur at safe and tolerable doses of both drugs;
- these changes are indicative of CNS changes that will confer disease clinical improvement in a way and to a degree that will provide practical and significant disease modifying benefit to sufferers; and
- the addition of a 5HT3-antagonist and/or NK-1 antagonist unexpectedly allows a better response at relatively low pramipexole doses and also the safe administration of high pramipexole doses, with a consequent possibility of safely improving the conditions of patients suffering from a PMND.

In spite of numerous publications on pramipexole and on fluoxetine and their combination, no observations on this possibility were reported, mentioned or suggested, and no speculation on its consequences were found. Moreover, it is unexpected since the two drugs act on different targets, by different mechanisms, to produce different clinical effects, and thus would hardly be expected to have synergistic effects in the manner disclosed herein in the treatment of a PMND.

In addition, it has also surprisingly been found that fluoxetine

- attenuates the GI adverse effects of pramipexole, thus allowing the safe administration of pramipexole within the whole pramipexole recommended daily dose range (0.375 mg-4.5 mg);
- acts synergistically, by potentiating the pramipexole effect within the above whole pramipexole recommended daily dose range; and
- allows the administration of pramipexole at doses higher than the maximum recommended daily dose, for example from 4.5 mg to 6 mg, from more than 6 mg to 10 mg, from 6.5 mg to 10 mg and even from 6.5 mg to 15 mg or from 6.5 mg to 20 mg.

In particular, the addition of a 5HT3-antagonist and/or NK-1 antagonist to 6-propylamino-4,5,6,7-tetrahydro-1,3-benzothiazole-2-amine and fluoxetine allows the administration of, for example, pramipexole at doses (per unit form and daily) much higher than the maximum recommended pramipexole doses. Thus, for example, in a combination of a 5HT3-antagonist and/or NK-1 antagonist with pramipexole and fluoxetine the pramipexole doses per unit form or daily doses, including pediatric daily doses and doses used in the titration period, may be in a range equivalent to from 0.375 mg to 45 mg of pramipexole dihydrochloride monohydrate. In an adult patient, the pramipexole dihydrochloride monohydrate daily dose may be from more than 4.5 mg to 45 mg, from 6 mg to 45, from more than 10 mg to 45 mg; from 14.5 mg to 45 mg, or from 20.25 mg to 45 mg, normally from 15 mg to 35 mg, from 15 mg to 30 mg or from 15 mg to 25 mg.

These findings provide safe treatment for disabling diseases such as PD, LBD, mutations in the glucocerebrosidase (GBA) gene, AD, the Lewy body variant of AD and PD, neurodegeneration with brain iron accumulation, MSA, HD, MT, ALS, SEP, FAP, and other PMNDs.

Thus, the present invention provides a 5HT3-antagonist and/or NK-1 antagonist, for use for the treatment of a PMND in patients in need of said treatment, in combination with pramipexole and fluoxetine; and the use of a 5HT3-antagonist and/or NK-1 antagonist, for the preparation of a medicament for the treatment of a PMND in combination with pramipexole and fluoxetine.

The invention further provides a method for treating a patient suffering from a PMND, which comprises administering to said patient in need of said treatment a 5HT3-antagonist and/or NK-1 antagonist, in combination with a 6-propylamino-4,5,6,7-tetrahydro-1,3-benzothiazole-2-amine and with fluoxetine.

Pharmaceutically acceptable acid addition salts and solvates of the 5HT3-antagonist and/or a NK1 receptor antagonist and of the 6-propylamino-4,5,6,7-tetrahydro-1,3-benzothiazole-2-amine, as well as pharmaceutically acceptable salts, in particular alkaline and alkaline-earth metal salts of the acidic 5HT3-antagonist and pharmaceutically acceptable salts, in particular alkaline and alkaline-earth metal salts of the statin are also included in the method (or use) of the present invention.

In the method (or use) according to the present invention, said 6-propylamino-4,5,6,7-tetrahydro-1,3-benzothiazole-2-amine and said fluoxetine, zonisamide, or statin combination is administered to said patient in a fixed-dose combination wherein said fluoxetine and said 6-propylamino-4,5,6,7- tetrahydro-1,3-benzothiazole-2-amine are mixed together, and with a pharmaceutical carrier or vehicle.

In certain embodiments of the method (or use) according to the present invention, said 6-propylamino-4,5,6,7-tetrahydro-1,3-benzothiazole-2-amine and said fluoxetine combination is administered to said patient in a fixed-dose combination wherein said 6-propylamino-4,5,6,7-tetrahydro-1,3-benzothiazole-2-amine and said fluoxetine are mixed together, and with a pharmaceutical carrier or vehicle.

Pharmaceutically acceptable salts and solvates of the 5HT3-antagonist and/or NK-1 antagonist, the 6-propylamino-4,5,6,7-tetrahydro-1,3-benzothiazole-2-amine, and fluoxetine are also included in the method (or use) of the present invention.

Preferably, 6-propylamino-4,5,6,7-tetrahydro-1,3-benzothiazole-2-amine is pramipexole base or pramipexole dihydrochloride monohydrate.

Preferably, said 5HT3-antagonist is ondansetron or dolasetron, and said 6-propylamino-4,5,6,7-tetrahydro-1,3-benzothiazole-2-amine is pramipexole.

Preferably, said NK1-antagonist is aprepitant or rolapitant, and said 6-propylamino-4,5,6,7-tetrahydro-1,3-benzothiazole-2-amine is pramipexole.

Preferably, fluoxetine is used as fluoxetine hydrochloride and the 6-propylamino-4,5,6,7-tetrahydro-1,3-benzothiazole-2-amine is used as pramipexole dihydrochloride monohydrate.

In said compositions,

- said 5HT3-antagonist is present in an amount per unit form of from 1 μg to 300 mg and/or said NK1-antagonist in said pharmaceutical composition is administered to said patient at a daily dose of from 1 μg to 600 mg, and
- said fluoxetine is present in an amount per unit form equivalent to from 2 mg to 90 mg of fluoxetine base, and
- said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate.

Preferably, in said compositions,

- said 5HT3-antagonist is ondansetron, in an amount per unit form (in ondansetron base) of from 2 mg to 32 mg or dolasetron in an amount per unit form (in dolasetron mesylate) of from 25 mg to 200 mg,
- said 6-propylamino-4,5,6,7-tetrahydro-1,3-benzothiazole-2-amine is pramipexole, in an amount per unit form equivalent to from 0.125 mg to 45 mg of pramipexole dihydrochloride monohydrate; and
- said fluoxetine is fluoxetine hydrochloride, in an amount per unit form equivalent to from 2 mg to 90 mg of fluoxetine base.

Alternatively, in said compositions, said NK1-antagonist is present in an amount per unit form of from 1 μg to 600 mg, said fluoxetine is present in an amount per unit form equivalent to from 2 mg to 90 mg of fluoxetine base, and said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate.

Preferably, in said compositions,

- said NK1-antagonist is aprepitant, in an amount per unit form of from 10 mg to 250 mg; or rolapitant, in an amount per unit form of from 15 mg to 270 mg,
- said 6-propylamino-4,5,6,7-tetrahydro-1,3-benzothiazole-2-amine is pramipexole, in an amount per unit form equivalent to from 0.125 mg to 45 mg of pramipexole dihydrochloride monohydrate, and
- said fluoxetine is fluoxetine hydrochloride, in an amount per unit form equivalent to from 2 mg to 90 mg of fluoxetine base.

In particular, the present invention provides a pharmaceutical unit form comprising a medicament selected from the group consisting of

- a 5HT3-antagonist, in a pharmaceutical composition comprising said 5HT3-antagonist in an amount of from 1 μg to 300 mg and/or a NK-1 antagonist, in a pharmaceutical composition comprising said NK-1 antagonist in an amount of from 1 μg to 600 mg, in admixture with a pharmaceutical carrier or vehicle; and fluoxetine, in an amount of from 2 mg to 90 mg, in admixture with a pharmaceutical carrier or vehicle; and
- a 5HT3-antagonist, in an amount of from 1 μg to 300 mg and/or a NK-1 antagonist, in an amount of from 1 μg to 600 mg, and fluoxetine, in an amount of from 2 mg to 90 mg, in admixture with a pharmaceutical carrier or vehicle.

This unit form is to be administered to a patient suffering from a PMND in combination with 6-propylamino-4,5,6,7-tetrahydro-1,3-benzothiazole-2-amine, preferably pramipexole.

For the treatment of a PMND, according to the above method (or use), the 5HT3-antagonist and/or a NK1 receptor antagonist, pramipexole and fluoxetine are each formulated in a pharmaceutical composition in admixture with a pharmaceutical carrier and concurrently or sequentially administered to a patient in need of said treatment.

In addition, the 5HT3-antagonist and/or a NK1 receptor antagonist and pramipexole may be mixed together and formulated in a pharmaceutical composition (fixed-dose combination) in admixture with a pharmaceutical carrier or vehicle. This composition is destined to be concurrently or sequentially administered to a patient suffering from a PMND, in combination with fluoxetine, also formulated in a pharmaceutical composition in admixture with a pharmaceutical carrier or vehicle.

Furthermore, the 5HT3-antagonist and/or a NK1 receptor antagonist and fluoxetine may be mixed together and formulated in a pharmaceutical composition (fixed-dose combination) in admixture with a pharmaceutical carrier, to be administered to a patient suffering from a PMND, in combination with pramipexole.

According to the above method (or use) for the treatment of a PMND,

- said 5HT3-antagonist in said pharmaceutical composition is administered to said patient at a daily dose of from 1 μg to 300 mg and/or said NK1-antagonist in said pharmaceutical composition is administered to said patient at a daily dose of from 1 μg to 600 mg;
- said 6-propylamino-4,5,6,7-tetrahydro-1,3-benzothiazole-2-amine in said composition is administered to said patient in need of said treatment at a daily dose that is equivalent to from 0.375 mg to 3000 mg of pramipexole dihydrochloride monohydrate, said daily dose including an (S)-enantiomer daily dose equivalent to from 0.375 mg to 45 mg of pramipexole dihydrochloride monohydrate; and
- said fluoxetine in said pharmaceutical composition is administered to a patient in need of said treatment at a daily dose that is equivalent to from 4 mg to 90 mg of fluoxetine base.

In particular, the method (or use) for treating a patient suffering from a PMND according to the present invention comprises treating said patient with an effective daily dose of a 5HT3-antagonist and/or NK-1 antagonist combined with an effective daily dose of 6-propylamino-4,5,6,7-tetrahydro-1,3-benzothiazole-2-amine and an effective daily dose of fluoxetine. Normally, said effective 5HT3-antagonist and/or NK-1 antagonist daily dose is from 1 μg to 600 mg.

Preferably, in said method (or use), the 5HT3-antagonist and/or NK-1 antagonist is administered at a daily dose at least as high as that approved for the prevention or treatment of postoperative nausea and vomiting or for the prevention of chemotherapy-induced nausea and vomiting, in combination with an effective daily dose of 6-propylamino-4,5,6,7-tetrahydro-1,3-benzothiazole-2-amine and with an effective daily dose of fluoxetine.

According to the invention, said effective daily dose of 6-propylamino-4,5,6,7-tetrahydro-1,3-benzothiazole-2-amine, including low doses used in the titration period, is equivalent to from 0.375 mg to 3000 mg of pramipexole dihydrochloride monohydrate, including a (S)-enantiomer daily dose of from 0.375 mg to 45 mg of pramipexole dihydrochloride monohydrate.

In said method (or use) described above, said 5HT3-antagonist and/or NK1 receptor antagonist/pramipexole/fluoxetine combination is administered to said patient in a fixed-dose combination wherein said pramipexole and said zonisamide are mixed together, and with a pharmaceutical carrier or vehicle.

For this treatment, the 5HT3-antagonist and/or NK-1 antagonist, the 6-propylamino-4,5,6,7-tetrahydro-1,3-benzothiazole-2-amine, and fluoxetine are each formulated in a pharmaceutical composition (fixed-dose combination) in admixture with a pharmaceutical carrier and concurrently or sequentially administered to a patient suffering from a PMND.

In addition, the 5HT3-antagonist and/or NK-1 antagonist and the 6-propylamino-4,5,6,7-tetrahydro-1,3-benzothiazole-2-amine may be mixed together and formulated in a pharmaceutical composition (fixed-dose combination) in admixture with a pharmaceutical carrier or vehicle. This composition is concurrently or sequentially administered to a patient suffering from a PMND, in combination with fluoxetine, also formulated in a pharmaceutical composition in admixture with a pharmaceutical carrier or vehicle.

Furthermore, the 5HT3-antagonist and/or NK-1 antagonist and fluoxetine may be mixed together and formulated in a pharmaceutical composition (fixed-dose combination) in admixture with a pharmaceutical carrier, to be administered to a patient suffering from a PMND, in combination with 6-propylamino-4,5,6,7-tetrahydro-1,3-benzothiazole-2-amine.

Moreover, the 5HT3-antagonist and/or NK-1 antagonist may be formulated in a pharmaceutical composition in admixture with a pharmaceutical carrier, to be administered to a patient suffering from a PMND, in combination with 6-propylamino-4,5,6,7-tetrahydro-1,3-benzothiazole-2-amine and with fluoxetine, mixed together and formulated in a pharmaceutical composition (fixed-dose combination) in admixture with a pharmaceutical carrier.

Finally, the 5HT3-antagonist and/or NK-1 antagonist, the 6-propylamino-4,5,6,7-tetrahydro-1,3-benzothiazole-2-amine and fluoxetine are mixed together and formulated in a pharmaceutical composition (fixed-dose combination) in admixture with a pharmaceutical carrier, to be administered to a patient suffering from a PMND.

Preferably, said 5HT3-antagonist is ondansetron or dolasetron, and said 6-propylamino-4,5,6,7-tetrahydro-1,3-benzothiazole-2-amine is pramipexole.

In said compositions, said 5HT3-antagonist is present in an amount per unit form of from 1 μg to 300 mg, said fluoxetine is present in an amount per unit form equivalent to from 2 mg to 80 mg of fluoxetine base, and said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate.

Preferably, in said compositions,

- said 5HT3-antagonist is ondansetron, in an amount per unit form of from 2 mg 32 mg, or dolasetron, in an amount per unit form (in dolasetron mesylate) of from 25 mg to 200 mg,
- said fluoxetine is fluoxetine hydrochloride, in an amount per unit form equivalent to from 2 mg to 80 mg, and
- said 6-propylamino-4,5,6,7-tetrahydro-1,3-benzothiazole-2-amine is pramipexole, in an amount per unit form equivalent to from 0.125 mg to 45 mg of pramipexole dihydrochloride monohydrate.

According to each of the above alternatives, in the method (or use) for the treatment of a PMND, said 6-propylamino-4,5,6,7-tetrahydro-1,3-benzothiazole-2-amine is pramipexole or a pharmaceutically acceptable salt or solvate thereof.

In particular, according to the above alternatives, in the method (or use) for the treatment of a PMND,

- said 5HT3-antagonist in said pharmaceutical composition is administered to said patient at a daily dose of from 1 μg to 300 mg;
- said 6-propylamino-4,5,6,7-tetrahydro-1,3-benzothiazole-2-amine in said composition is administered to said patient in need of said treatment at a daily dose that is equivalent to from 0.375 mg to 3000 mg of pramipexole dihydrochloride monohydrate, said daily dose including an (S)-enantiomer daily dose equivalent to from 0.375 mg to 45 mg of pramipexole dihydrochloride monohydrate; and
- said fluoxetine in said pharmaceutical composition is administered to a patient in need of said treatment at a daily dose that is equivalent to from 4 mg to 80 mg of fluoxetine base.

In said method (or use), said 6-propylamino-4,5,6,7-tetrahydro-1,3-benzothiazole-2-amine and said fluoxetine combination is administered to said patient in a fixed-dose combination wherein said fluoxetine and said 6-propylamino-4,5,6,7-tetrahydro-1,3-benzothiazole-2-amine are mixed together, and with a pharmaceutical carrier or vehicle.

Preferably, fluoxetine is used as fluoxetine hydrochloride and the 6-propylamino-4,5,6,7-tetrahydro-1,3-benzothiazole-2-amine is used as pramipexole dihydrochloride monohydrate.

Preferably, according to above methods for treating a patient suffering from a PMND said 5HT3-antagonist is ondansetron or dolasetron.

Preferably, according to each of the above alternatives, in the method for treating a patient suffering from a PMND said 5HT3-antagonist is selected from the group consisting of ondansetron and pharmaceutically acceptable salts and solvates thereof and dolasetron and pharmaceutically acceptable salts and solvates thereof. If the 5HT3-antagonist is ondansetron, said ondansetron is administered to said patient, as ondansetron hydrochloride dihydrate, at a daily dose that is equivalent to from 4 mg to 32 mg of ondansetron base. If the 5HT3-antagonist is dolasetron, said dolasetron is administered to said patient at a daily dose that is equivalent to from 25 mg to 200 mg of dolasetron mesylate.

Preferably, according to each of the above alternatives, in the method (or use) for the treatment of a PMND, said 5HT3-antagonist in said pharmaceutical composition is ondansetron, administered at a daily dose of from 4 mg to 32 mg or from 6 mg to 32 mg;

said 6-propylamino-4,5,6,7-tetrahydro-1,3-benzothiazole-2-amine in said composition is pramipexole or a pharmaceutically acceptable salt or solvate thereof, at a daily dose, including pediatric daily doses and daily doses used in the titration period, equivalent to from 0.375 mg to 45 mg of pramipexole dihydrochloride monohydrate; and said fluoxetine in said pharmaceutical composition is administered to a patient in need of said treatment at a daily dose that is equivalent to from 4 mg to 90 mg of fluoxetine base, or Preferably and more particularly, according to each of the above method (or use) for the treatment of a PMND, said 5HT3-antagonist in said pharmaceutical composition is ondansetron, administered at a daily dose of from 4 mg to 32 mg or from 6 mg to 32 mg;

said 6-propylamino-4,5,6,7-tetrahydro-1,3-benzothiazole-2-amine in said composition is pramipexole or a pharmaceutically acceptable salt or solvate thereof, at a daily dose, including doses used in the titration period, equivalent to from 0.375 mg to 45 mg of pramipexole dihydrochloride monohydrate; and said fluoxetine in said pharmaceutical composition is administered to a patient in need of said treatment at a daily dose that is equivalent to from 4 mg to 80 mg of fluoxetine base.

Preferably, according to each of the above alternatives, in the method for treating a patient suffering from a PMND, said NK1-antagonist is selected from the group consisting of aprepitant and pharmaceutically acceptable salts and solvates and prodrugs thereof, and rolapitant and pharmaceutically acceptable salts and solvates and prodrugs thereof. If the NK1-antagonist is aprepitant or fosaprepitant, said NK1-antagonist is administered to said patient at a daily dose, in aprepitant, of from 10 mg to 250 mg, or in some embodiments of from 10 mg to 125 mg. If the NK1-antagonist is rolapitant, said rolapitant is administered to said patient at a daily dose of from 15 mg to 270 mg.

Preferably and more particularly, according to the above method (or use) for the treatment of a PMND, said NK1-antagonist in said pharmaceutical composition is aprepitant, administered at a daily dose of from 15 mg to 250 mg;

said 6-propylamino-4,5,6,7-tetrahydro-1,3-benzothiazole-2-amine in said composition is pramipexole or a pharmaceutically acceptable salt or solvate thereof, at a daily dose, including doses used in the titration period, equivalent to from 0.375 mg to 45 mg of pramipexole dihydrochloride monohydrate; and said fluoxetine in said pharmaceutical composition is administered to a patient in need of said treatment at a daily dose that is equivalent to from 4 mg to 90 mg of fluoxetine base.

According to a specific alternative, the invention provides a pharmaceutical composition for the treatment of protein misfolding neurodegenerative disorders in a patient, in combination with a pramipexole daily dose equivalent to from 0.375 mg to 45 mg, up to from 14.5 mg to 45 mg or from more than 20 mg to 45 mg, normally from 15 mg to 25 mg, of pramipexole dihydrochloride monohydrate, comprising a pharmaceutical carrier or vehicle and a fixed-dose combination of a 5HT3-antagonist, in an amount per unit form of from 1 μg to 300 mg and/or a NK1-antagonist, in an amount per unit form of from 1 μg to 600 mg, and fluoxetine or a pharmaceutically acceptable salt or solvate thereof, in an amount per unit form equivalent to from 2 mg to 90 mg of fluoxetine base.

In said composition said 5HT3-antagonist advantageously is ondansetron hydrochloride dihydrate, in an amount per unit form of from 0.5 mg to 32 mg of ondansetron base, and said fluoxetine is fluoxetine hydrochloride, in an amount per unit form equivalent to from 2 mg to 90 mg of fluoxetine base.

In said composition said 5HT3-antagonist advantageously may also be dolasetron mesylate, in an amount per unit form of from 25 mg to 200 mg, and said fluoxetine is fluoxetine hydrochloride, in an amount per unit form equivalent to from 2 mg to 90 mg of fluoxetine base.

In said composition said 5HT3-antagonist advantageously may also be dolasetron mesylate, in an amount per unit form of from 25 mg to 200 mg, and said zonisamide is zonisamide free acid, in an amount per unit form of from 25 mg to 600 mg. In combination with said 5HT3-antagonist and/or said NK-1 antagonist and said zonisamide in said fixed dose combination Component (ac), said pramipexole Component (b) is advantageously administered at a daily dose equivalent to from more than 4.5 mg to 45 mg, from more than 6 mg to 45 mg, from 6.5 mg to 45 mg, up to from 14.5 mg to 45 mg or from more than 20 mg to 45 mg, normally from 15 mg to 25 mg, of pramipexole dihydrochloride monohydrate.

In said composition said NK1-antagonist advantageously is aprepitant, in an amount per unit form of from 10 mg to 250 mg, and said fluoxetine is fluoxetine hydrochloride, in an amount per unit form equivalent to from 2 mg to 90 mg of fluoxetine base. Preferably, said composition is in an unit form to be administered once a day, wherein said aprepitant is present in an amount of from 10 mg to 250 mg in an IR-form, and said fluoxetine is present in an amount equivalent to from 4 mg to 90 mg in an ER-form.

In said composition said NK1-antagonist advantageously may also be rolapitant, in an amount per unit form of from 15 mg to 270 mg, and said fluoxetine is fluoxetine hydrochloride, in an amount per unit form equivalent to from 2 mg to 90 mg of fluoxetine base.

Preferably, said composition is in an unit form, to be administered once a day, wherein said rolapitant is present in an amount of from 15 mg to 270 mg in an IR-form, and said fluoxetine is present in an amount equivalent to from 4 mg to 90 mg in an ER-form.

A specific combination of a NK1-antagonist and of a 5HT3-antagonist is selected from the group consisting of the fixed-dose combinations netupitant-300/palonosetron-0.5 and fosnetupitant-235/palonosetron-0.25.

In combination with said 5HT3-antagonist and/or said NK1-antagonist and with said fluoxetine in said fixed dose combination Component (ac), said pramipexole Component (b) is advantageously administered at a daily dose equivalent to from more than 4.5 mg to 45 mg, from more than 6 mg to 45 mg, from 6.5 mg to 45 mg, up to from 14.5 mg to 45 mg or from more than 20 mg to 45 mg, normally from 15 mg to 25 mg, of pramipexole dihydrochloride monohydrate.

The present invention further provides a kit or package comprising a pharmaceutical combination or pharmaceutical compositions as described herein, and instructions for use of the same for treatment of a synucleinopathy in a patient in need thereof.

According to a second aspect of the invention, the present inventors also found that zonisamide synergistically acts by augmenting the PMND-modifying potential of pramipexole in humans, thus allowing at least a slowing of the disease progression at 6-propylamino-4,5,6,7-tetrahydro-1,3-benzothiazole-2-amine, preferably pramipexole, doses that are both safe and tolerable.

It has been found that zonisamide allows for the safe administration of 6-propylamino-4,5,6,7-tetrahydro-1,3-benzothiazole-2-amine at a daily dose comprising a (S)-enantiomer dose that may be higher, and even much higher, than the pramipexole maximum daily dose recommended for the relief of the symptomatic treatment of Parkinson's disease. Consequently, an improvement of the conditions of a patient suffering from a PMND can be attained.

For example, the combination of zonisamide or of a pharmaceutically acceptable salt or solvate thereof with a 6-propylamino-4,5,6,7-tetrahydro-1,3-benzothiazole-2-amine or a pharmaceutically acceptable salt or solvate thereof, acts to normalize levels of synuclein species within the brain-derived exosomes in peripheral blood of patients suffering from a synucleinopathy, in particular by diminishing the concentration of abnormal synuclein species (congeners) in the patient's exosomal vesicles found therein, to a clinically significant degree at doses that are safe and tolerable thus evidencing that said patients will enjoy neuroprotective benefit.

This observation is unexpected since neither drug has been found clinically to possess any disease modifying ability in patients with a synuclein related disorder. Moreover, nowhere has it even been suggested that the combination of these drugs might confer such significant benefit to such individuals since the antiparkinson drug and the anticonvulsant drug primarily act by very different mechanisms.

Finally, it has been found that, a 5HT3-antagonist and/or NK-1 antagonist, in combination with a 6-propylamino-4,5,6,7-tetrahydro-1,3-benzothiazole-2-amine, in particular pramipexole, and with zonisamide dramatically increases the tolerable pramipexole dose to a level heretofore unattainable.

In particular, according to the invention, said patient is treated with (1) a 5HT3-antagonist dose and/or a NK1 receptor antagonist dose, in combination with pramipexole, that enables a heretofore unimaginable increase, including even high increases, of the 6-propylamino-4,5,6,7-tetrahydro-1,3-benzothiazole-2-amine, preferably pramipexole, dose thus providing a stronger dopaminergic action; in further combination with (2) a dose of zonisamide that reduces the minimum effective dose of 6-propylamino-4,5,6,7-tetrahydro-1,3-benzothiazole-2-amine, preferably pramipexole, and/or increases the 6-propylamino-4,5,6,7-tetrahydro-1,3-benzothiazole-2-amine effect magnitude without lowering its minimum toxic dose.

In addition, it has been found that the combination (including fixed-dose combinations) of a 5HT3-antagonist and/or a NK1 receptor antagonist and of zonisamide allows for the safe administration of a pramipexole dose that may be higher, and even much higher, than the pramipexole maximum daily dose recommended for the symptomatic treatment of Parkinson's disease. Consequently, an improvement in the condition of a patient suffering from a PMND is attained.

The present invention is based on the discovery that

- zonisamide potentiates (augments) the ability of pramipexole to alter misfolded protein species in ways indicating the activation of a central neuroprotective mechanism, i.e. reducing oligomerization of said proteins;
- these changes occur at safe and tolerable doses of both drugs;
- these changes are indicative of CNS changes that will confer disease clinical improvement in a way and to a degree that will provide practical and significant disease modifying benefit to sufferers; and
- the addition of a 5HT3-antagonist and/or a NK1 receptor antagonist unexpectedly allows a better response at relatively low pramipexole doses and also the safe administration of high pramipexole doses, with a consequent possibility of safely improving the conditions of patients suffering from a PMND.

In spite of numerous publications on pramipexole and on zonisamide and their combination, no observations on this possibility were reported, mentioned or suggested, and no speculation on its consequences was found. Moreover, it is unexpected since the two drugs act on different targets, by different mechanisms, to produce different clinical effects, and thus would hardly be expected to have synergistic effects in the manner disclosed herein in the treatment of a PMND.

In addition, it has also surprisingly been found that zonisamide, in combination with a 5HT3-antagonist and/or a NK1 receptor antagonist

- attenuates the GI adverse effects of pramipexole, thus allowing the safe administration of pramipexole within the whole pramipexole recommended daily dose range (0.375 mg-4.5 mg);
- acts synergistically, by potentiating the pramipexole effect within the above whole pramipexole recommended daily dose range; and
- allows the administration of pramipexole dihydrochloride monohydrate doses (per unit form and daily) that are higher, and even much higher than the maximum recommended daily dose.

In particular, the addition of a 5HT3-antagonist and/or a NK1 receptor antagonist to pramipexole and zonisamide allows the administration of, for example, pramipexole doses (per unit form and daily) much higher than the maximum recommended pramipexole doses. Thus, for example, in a combination of a 5HT3-antagonist and/or a NK1 receptor antagonist with pramipexole and zonisamide, the pramipexole daily doses, including pediatric daily doses and daily doses used in the titration period, are equivalent to from 0.375 mg to 45 mg of pramipexole dihydrochloride monohydrate. In an adult patient, the pramipexole dihydrochloride monohydrate daily dose may be in a range equivalent to from more than 4.5 mg to 45 mg, from 6 mg to 45, and from more than 10 mg to 45 mg. Normally, said pramipexole dihydrochloride monohydrate daily dose in an adult patient is from 14.5 mg to 45 mg, from 15 mg to 35 mg, from 15 mg to 30 mg or from 15 mg to 25 mg.

These findings provide safe treatment for disabling diseases such as PD, LBD, mutations in the glucocerebrosidase (GBA) gene, AD, the Lewy body variant of AD and PD, neurodegeneration with brain iron accumulation, MSA, HD, MT, ALS, SEP, FAP, and other PMNDs.

Thus, the present invention provides a 5HT3-antagonist and/or a NK1 receptor antagonist, for use for the treatment of a PMND in patients in need of said treatment, in combination with pramipexole and zonisamide; and the use of a 5HT3-antagonist and/or a NK1 receptor antagonist, for the preparation of a medicament for the treatment of a PMND in combination with pramipexole and zonisamide.

The invention further provides a method for treating a patient suffering from a PMND, which comprises treating said patient with a 5HT3-antagonist and/or a NK1 receptor antagonist, in combination with pramipexole and zonisamide.

Preferably, in said method (or use), the 5HT3-antagonist and/or NK-1 antagonist is administered at a daily dose at least as high as that approved for the prevention or treatment of postoperative nausea and vomiting or for the prevention of chemotherapy-induced nausea and vomiting, in combination with an effective daily dose of 6-propylamino-4,5,6,7-tetrahydro-1,3-benzothiazole-2-amine and with an effective daily dose of zonisamide.

Pharmaceutically acceptable acid addition salts and solvates of the 5HT3-antagonist and/or a NK1 receptor antagonist and of the 6-propylamino-4,5,6,7-tetrahydro-1,3-benzothiazole-2-amine, as well as pharmaceutically acceptable salts, in particular alkaline and alkaline-earth metal salts of the acidic 5HT3-antagonist and pharmaceutically acceptable salts, in particular alkaline and alkaline-earth metal salts of the zonisamide are also included in the method (or use) of the present invention.

In certain embodiments of the method (or use) according to the present invention, said 6-propylamino-4,5,6,7-tetrahydro-1,3-benzothiazole-2-amine and said zonisamide combination is administered to said patient in a fixed-dose combination wherein said 6-propylamino-4,5,6,7-tetrahydro-1,3-benzothiazole-2-amine and said fluoxetine are mixed together, and with a pharmaceutical carrier or vehicle.

In particular, the method (or use) for treating a patient suffering from a PMND according to the present invention comprises treating said patient with an effective daily dose of a 5HT3-antagonist and/or a NK1 receptor antagonist in combination with an effective daily dose of pramipexole dihydrochloride monohydrate and an effective daily dose of zonisamide. Normally, said effective 5HT3-antagonist daily dose is from 1 μg to 600 mg.

Preferably, in said method (or use), the 5HT3-antagonist and/or a NK1 receptor antagonist is administered at a daily dose at least as high as that approved for the prevention or treatment of postoperative nausea and vomiting or for the prevention of chemotherapy-induced nausea and vomiting, in combination with an effective daily dose of pramipexole and with an effective daily dose of zonisamide.

According to the invention, said effective daily dose of pramipexole, including pediatric doses and low doses used in the titration period, is equivalent to from 0.375 mg to 45 mg, normally from 0.375 mg to 20 mg of pramipexole dihydrochloride monohydrate.

Said zonisamide daily dose is at least as high as the dose approved for its antiseizure indication. Normally, the zonisamide daily dose, including pediatric doses and low doses used in the titration period, is from 25 mg to 600 mg.

Preferably, 6-propylamino-4,5,6,7-tetrahydro-1,3-benzothiazole-2-amine is pramipexole base or pramipexole dihydrochloride monohydrate.

Preferably, said 5HT3-antagonist is ondansetron or dolasetron, and said 6-propylamino-4,5,6,7-tetrahydro-1,3-benzothiazole-2-amine is pramipexole.

Preferably, said NK1-antagonist is aprepitant or rolapitant, and said 6-propylamino-4,5,6,7-tetrahydro-1,3-benzothiazole-2-amine is pramipexole.

Preferably, zonisamide is used as zonisamide free acid and the 6-propylamino-4,5,6,7-tetrahydro-1,3-benzothiazole-2-amine is used as pramipexole dihydrochloride monohydrate.

In said compositions, said 5HT3-antagonist is present in an amount per unit form of from 1 μg to 300 mg and/or said NK1-antagonist in said pharmaceutical composition is administered to said patient at a daily dose of from 1 μg to 600 mg, and said zonisamide is present in an amount per unit form equivalent to from 25 mg to 600 mg of zonisamide free acid, and said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate.

Preferably, in said compositions, said 5HT3-antagonist is ondansetron, in an amount per unit form (in ondansetron base) of from 2 mg to 32 mg or dolasetron in an amount per unit form (in dolasetron mesylate) of from 25 mg to 200 mg;

said 6-propylamino-4,5,6,7-tetrahydro-1,3-benzothiazole-2-amine is pramipexole, in an amount per unit form equivalent to from 0.125 mg to 45 mg of pramipexole dihydrochloride monohydrate; and said zonisamide is zonisamide free acid, in an amount per unit form of from 25 mg to 600 mg.

Alternatively, in said compositions, said NK1-antagonist is present in an amount per unit form of from 1 μg to 600 mg, said zonisamide is present in an amount per unit form equivalent to from 25 mg to 600 mg of zonisamide free acid, and said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate.

Preferably, in said compositions, said NK1-antagonist is aprepitant, in an amount per unit form of from 10 mg to 250 mg; or rolapitant, in an amount per unit form of from 15 mg to 270 mg;

said 6-propylamino-4,5,6,7-tetrahydro-1,3-benzothiazole-2-amine is pramipexole, in an amount per unit form equivalent to from 0.125 mg to 45 mg of pramipexole dihydrochloride monohydrate; and said zonisamide is zonisamide free acid, in an amount per unit form of from 25 mg to 600 mg.

In particular, the present invention provides a pharmaceutical unit form comprising a medicament selected from the group consisting of a 5HT3-antagonist, in a pharmaceutical composition comprising said 5HT3-antagonist in an amount of from 1 μg to 300 mg and/or a NK-1 antagonist, in a pharmaceutical composition comprising said NK-1 antagonist in an amount of from 1 μg to 600 mg, in admixture with a pharmaceutical carrier or vehicle; and zonisamide, in an amount of from 25 mg to 600 mg, in admixture with a pharmaceutical carrier or vehicle; and a 5HT3-antagonist, in an amount of from 1 μg to 300 mg and/or a NK-1 antagonist, in an amount of from 1 μg to 600 mg, and zonisamide, in an amount of from 25 mg to 600 mg, in admixture with a pharmaceutical carrier or vehicle.

This unit form is to be administered to a patient suffering from a PMND in combination with 6-propylamino-4,5,6,7-tetrahydro-1,3-benzothiazole-2-amine, preferably pramipexole.

For the treatment of a PMND, according to the above method (or use), the 5HT3-antagonist and/or a NK1 receptor antagonist, pramipexole and zonisamide are each formulated in a pharmaceutical composition in admixture with a pharmaceutical carrier and concurrently or sequentially administered to a patient in need of said treatment.

In addition, the 5HT3-antagonist and/or a NK1 receptor antagonist and pramipexole may be mixed together and formulated in a pharmaceutical composition (fixed-dose combination) in admixture with a pharmaceutical carrier or vehicle. This composition is destined to be concurrently or sequentially administered to a patient suffering from a PMND, in combination with zonisamide, also formulated in a pharmaceutical composition in admixture with a pharmaceutical carrier or vehicle.

Furthermore, the 5HT3-antagonist and/or a NK1 receptor antagonist and zonisamide may be mixed together and formulated in a pharmaceutical composition (fixed-dose combination) in admixture with a pharmaceutical carrier, to be administered to a patient suffering from a PMND, in combination with pramipexole.

In particular, the method (or use) for treating a patient suffering from a PMND according to the present invention comprises treating said patient with an effective daily dose of a 5HT3-antagonist and/or NK-1 antagonist combined with an effective daily dose of 6-propylamino-4,5,6,7-tetrahydro-1,3-benzothiazole-2-amine and an effective daily dose of zonisamide. Normally, said effective 5HT3-antagonist and/or NK-1 antagonist daily dose is from 1 μg to 600 mg.

According to the above method (or use) for the treatment of a PMND,

- said 5HT3-antagonist in said pharmaceutical composition is administered to said patient at a daily dose of from 1 μg to 300 mg and/or said and/or NK1 receptor antagonist in said pharmaceutical composition is administered to said patient at a daily dose of from 1 μg to 600 mg;
- said 6-propylamino-4,5,6,7-tetrahydro-1,3-benzothiazole-2-amine in said composition is administered to said patient in need of said treatment at a daily dose that is equivalent to from 0.375 mg to to 3000 mg of pramipexole dihydrochloride monohydrate, said daily dose including an (S)-enantiomer daily dose equivalent to from 0.375 mg to 45 mg of pramipexole dihydrochloride monohydrate; and
- said zonisamide in said pharmaceutical composition is administered to a patient in need of said treatment at a daily dose that is equivalent to from 25 mg to 600 mg.

According to the invention, said effective daily dose of 6-propylamino-4,5,6,7-tetrahydro-1,3-benzothiazole-2-amine, including low doses used in the titration period, is equivalent to from 0.375 mg to 3000 mg of pramipexole dihydrochloride monohydrate, including a (S)-enantiomer daily dose of from 0.375 mg to 45 mg of pramipexole dihydrochloride monohydrate.

In said method (or use) described above, said 5HT3-antagonist and/or NK1 receptor antagonist/pramipexole/zonisamide combination is administered to said patient in a fixed-dose combination wherein said pramipexole and said zonisamide are mixed together, and with a pharmaceutical carrier or vehicle.

For this treatment, the 5HT3-antagonist and/or NK-1 antagonist, the 6-propylamino-4,5,6,7-tetrahydro-1,3-benzothiazole-2-amine, and zonisamide are each formulated in a pharmaceutical composition (fixed-dose combination) in admixture with a pharmaceutical carrier and concurrently or sequentially administered to a patient suffering from a PMND.

In addition, the 5HT3-antagonist and/or NK-1 antagonist and the 6-propylamino-4,5,6,7-tetrahydro-1,3-benzothiazole-2-amine may be mixed together and formulated in a pharmaceutical composition (fixed-dose combination) in admixture with a pharmaceutical carrier or vehicle. This composition is concurrently or sequentially administered to a patient suffering from a PMND, in combination with fluoxetine, also formulated in a pharmaceutical composition in admixture with a pharmaceutical carrier or vehicle.

Furthermore, the 5HT3-antagonist and/or NK-1 antagonist and zonisamide may be mixed together and formulated in a pharmaceutical composition (fixed-dose combination) in admixture with a pharmaceutical carrier, to be administered to a patient suffering from a PMND, in combination with 6-propylamino-4,5,6,7-tetrahydro-1,3-benzothiazole-2-amine.

Moreover, the 5HT3-antagonist and/or NK-1 antagonist may be formulated in a pharmaceutical composition in admixture with a pharmaceutical carrier, to be administered to a patient suffering from a PMND, in combination with 6-propylamino-4,5,6,7-tetrahydro-1,3-benzothiazole-2-amine and with zonisamide, mixed together and formulated in a pharmaceutical composition (fixed-dose combination) in admixture with a pharmaceutical carrier.

Finally, the 5HT3-antagonist and/or NK-1 antagonist, the 6-propylamino-4,5,6,7-tetrahydro-1,3-benzothiazole-2-amine and zonisamide are mixed together and formulated in a pharmaceutical composition (fixed-dose combination) in admixture with a pharmaceutical carrier, to be administered to a patient suffering from a PMND.

Preferably, said 5HT3-antagonist is ondansetron or dolasetron, and said 6-propylamino-4,5,6,7-tetrahydro-1,3-benzothiazole-2-amine is pramipexole.

In said compositions, said 5HT3-antagonist is present in an amount per unit form of from 1 μg to 300 mg, said zonisamide is present in an amount per unit form equivalent to from 25 mg to 600 mg of zonisamide free acid, and said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate.

Preferably, in said compositions,

- said 5HT3-antagonist is ondansetron, in an amount per unit form of from 2 mg 32 mg, or dolasetron, in an amount per unit form (in dolasetron mesylate) of from 25 mg to 200 mg,
- said zonisamide is zonisamide free acid, in an amount per unit form equivalent to from 25 mg to 600 mg, and
- said 6-propylamino-4,5,6,7-tetrahydro-1,3-benzothiazole-2-amine is pramipexole, in an amount per unit form equivalent to from 0.125 mg to 45 mg of pramipexole dihydrochloride monohydrate.

According to each of the above alternatives, in the method (or use) for the treatment of a PMND, said 6-propylamino-4,5,6,7-tetrahydro-1,3-benzothiazole-2-amine is pramipexole or a pharmaceutically acceptable salt or solvate thereof.

Preferably, pramipexole is used as pramipexole base or as pramipexole dihydrochloride monohydrate.

Preferably, according to each of the above alternatives, in the method for treating a patient suffering from a PMND, said 5HT3-antagonist is ondansetron.

In particular, according to the above alternatives, in the method (or use) for the treatment of a PMND,

- said 5HT3-antagonist in said pharmaceutical composition is administered to said patient at a daily dose of from 1 μg to 300 mg;
- said 6-propylamino-4,5,6,7-tetrahydro-1,3-benzothiazole-2-amine in said composition is administered to said patient in need of said treatment at a daily dose that is equivalent to from 0.375 mg to 3000 mg of pramipexole dihydrochloride monohydrate, said daily dose including an (S)-enantiomer daily dose equivalent to from 0.375 mg to 45 mg of pramipexole dihydrochloride monohydrate; and said zonisamide in said pharmaceutical composition is administered to a patient in need of said treatment at a daily dose that is equivalent to from 25 mg to 600 mg.

In said method (or use), said 6-propylamino-4,5,6,7-tetrahydro-1,3-benzothiazole-2-amine and said zonisamide combination is administered to said patient in a fixed-dose combination wherein said fluoxetine and said 6-propylamino-4,5,6,7-tetrahydro-1,3-benzothiazole-2-amine are mixed together, and with a pharmaceutical carrier or vehicle.

Preferably, zonisamide is used as zonisamide free acid and the 6-propylamino-4,5,6,7-tetrahydro-1,3-benzothiazole-2-amine is used as pramipexole dihydrochloride monohydrate.

Preferably, according to above methods for treating a patient suffering from a PMND said 5HT3-antagonist is ondansetron or dolasetron.

Preferably, according to each of the above alternatives, in the method for treating a patient suffering from a PMND said 5HT3-antagonist is selected from the group consisting of ondansetron and pharmaceutically acceptable salts and solvates thereof and dolasetron and pharmaceutically acceptable salts and solvates thereof. If the 5HT3-antagonist is ondansetron, said ondansetron is administered to said patient, as ondansetron hydrochloride dihydrate, at a daily dose that is equivalent to from 4 mg to 32 mg of ondansetron base. If the 5HT3-antagonist is dolasetron, said dolasetron is administered to said patient at a daily dose that is equivalent to from 25 mg to 200 mg of dolasetron mesylate.

Preferably, according to each of the above alternatives, in the method (or use) for the treatment of a PMND, said 5HT3-antagonist in said pharmaceutical composition is ondansetron, administered at a daily dose of from 4 mg to 32 mg or from 6 mg to 32 mg;

said 6-propylamino-4,5,6,7-tetrahydro-1,3-benzothiazole-2-amine in said composition is pramipexole or a pharmaceutically acceptable salt or solvate thereof, at a daily dose, including pediatric daily doses and daily doses used in the titration period, equivalent to from 0.375 mg to 45 mg of pramipexole dihydrochloride monohydrate; and said zonisamide is administered at a daily dose of from 25 mg to 600 mg.

Preferably and more particularly, according to each of the above method (or use) for the treatment of a PMND, said 5HT3-antagonist in said pharmaceutical composition is ondansetron, administered at a daily dose of from 4 mg to 32 mg or from 6 mg to 32 mg;

said 6-propylamino-4,5,6,7-tetrahydro-1,3-benzothiazole-2-amine in said composition is pramipexole or a pharmaceutically acceptable salt or solvate thereof, at a daily dose, including doses used in the titration period, equivalent to from 0.375 mg to 45 mg of pramipexole dihydrochloride monohydrate; and said zonisamide in said pharmaceutical composition is administered to a patient in need of said treatment at a daily dose that is equivalent to from 25 mg to 600 mg.

Preferably, according to each of the above alternatives, in the method for treating a patient suffering from a PMND, said NK1-antagonist is selected from the group consisting of aprepitant and pharmaceutically acceptable salts and solvates and prodrugs thereof, and rolapitant and pharmaceutically acceptable salts and solvates and prodrugs thereof. If the NK1-antagonist is aprepitant or fosaprepitant, said NK1-antagonist is administered to said patient at a daily dose, in aprepitant, of from 10 mg to 250 mg, or in some embodiments of from 10 mg to 125 mg. If the NK1-antagonist is rolapitant, said rolapitant is administered to said patient at a daily dose of from 15 mg to 270 mg.

Preferably and more particularly, according to the above method (or use) for the treatment of a PMND, said NK1-antagonist in said pharmaceutical composition is aprepitant, administered at a daily dose of from 15 mg to 250 mg;

said 6-propylamino-4,5,6,7-tetrahydro-1,3-benzothiazole-2-amine in said composition is pramipexole or a pharmaceutically acceptable salt or solvate thereof, at a daily dose, including doses used in the titration period, equivalent to from 0.375 mg to 45 mg of pramipexole dihydrochloride monohydrate; and said zonisamide is administered at a daily dose of from 25 mg to 600 mg.

According to a specific alternative, the invention provides a pharmaceutical composition for the treatment of protein misfolding neurodegenerative disorders in a patient, in combination with a pramipexole daily dose equivalent to from 0.375 mg to 45 mg, up to from 14.5 mg to 45 mg or from more than 20 mg to 45 mg of pramipexole dihydrochloride monohydrate, comprising a pharmaceutical carrier or vehicle and a fixed-dose combination of a 5HT3-antagonist, in an amount per unit form of from 1 μg to 300 mg and/or a NK1-antagonist, in an amount per unit form of from 1 μg to 600 mg, and zonisamide free acid, in an amount per unit form of from 25 mg to 600 mg of zonisamide free acid.

In said composition said 5HT3-antagonist advantageously is ondansetron hydrochloride dihydrate, in an amount per unit form of from 0.5 mg to 32 mg of ondansetron base, and said zonisamide is zonisamide free acid, in an amount per unit form of from 25 mg to 600 mg.

In said composition said 5HT3-antagonist advantageously may also be dolasetron mesylate, in an amount per unit form of from 25 mg to 200 mg, and said zonisamide is zonisamide free acid, in an amount per unit form of from 25 mg to 600 mg. In combination with said 5HT3-antagonist and/or said NK-1 antagonist and said zonisamide in said fixed dose combination Component (ac), said pramipexole Component (b) is advantageously administered at a daily dose equivalent to from more than 4.5 mg to 45 mg, from more than 6 mg to 45 mg, from 6.5 mg to 45 mg, up to from 14.5 mg to 45 mg or from more than 20 mg to 45 mg, normally from 15 mg to 25 mg, of pramipexole dihydrochloride monohydrate.

In said composition said NK1-antagonist advantageously is aprepitant, in an amount per unit form of from 10 mg to 250 mg, and zonisamide is zonisamide free acid, in an amount per unit form of from 25 mg to 600 mg of zonisamide free acid. Preferably, said aprepitant composition is in a unit form to be administered once a day, wherein said aprepitant is present in an amount of from 10 mg to 250 mg of aprepitant in an IR-form, and said zonisamide free acid, present in an amount of from 25 mg to 600 mg of zonisamide free acid is in an ER-form.

In said composition said NK1-antagonist advantageously may also be rolapitant, in an amount per unit form of from 15 mg to 270 mg, and said zonisamide is zonisamide free acid, in an amount of from 25 mg to 600 mg of zonisamide free acid.

Preferably, said composition is in an unit form, to be administered once a day, wherein said rolapitant is present in an amount of from 15 mg to 270 mg in an IR-form, and said zonisamide is present (as zonisamide free acid) in an amount of from 200 mg to 600 mg of zonisamide free acid in an ER-form.

A specific combination of a NK1-antagonist and of a 5HT3-antagonist is selected from the group consisting of the fixed-dose combinations netupitant-300/palonosetron-0.5 and fosnetupitant-235/palonosetron-0.25.

In combination with said 5HT3-antagonist and/or said NK1-antagonist and with said zonisamide in said fixed dose combination Component (ac), said pramipexole Component (b) is advantageously administered at a daily dose equivalent to from more than 4.5 mg to 45 mg, from more than 6 mg to 45 mg, from 6.5 mg to 45 mg, up to from 14.5 mg to 45 mg or from more than 20 mg to 45 mg of pramipexole dihydrochloride monohydrate.

This second aspect of present invention further provides a kit or package comprising a pharmaceutical combination or pharmaceutical compositions as described herein, and instructions for use of the same for treatment of a synucleinopathy in a patient in need thereof.

According to a third aspect of the invention, the present inventors found that a statin synergistically acts by augmenting the PMND-modifying potential of pramipexole in humans, thus allowing at least a slowing of the disease progression at 6-propylamino-4,5,6,7-tetrahydro-1,3-benzothiazole-2-amine, preferably pramipexole, doses that are both safe and tolerable.

It has been found that the effects of (S)-6-propylamino-4,5,6,7-tetrahydro-1,3-benzothiazole-2-amine (pramipexole) on the exosomal biomarker in the peripheral blood of patients with synucleinopathic disorders like PD of the aberrant processing of synuclein is substantially and unexpectedly improved by the co-administration of a statin and 5HT3-antagonist and/or NK1 receptor antagonist. Not only does the effect size become clinically significant but the dose requirement for both pramipexole and statin now falls into the range considered safe and tolerable for human subjects. In the present invention, the combination of pramipexole plus a statin and 5HT3-antagonist and/or NK1 receptor antagonist safely interdicts the basic degenerative disease process in such patients to a clinically meaningful degree.

In particular, the addition of a 5HT3-antagonist and/or NK1 receptor antagonist to a statin allows the administration of, for example, pramipexole at doses (per unit form and daily) much higher than the maximum recommended pramipexole doses. Thus, for example, in combination with a 5HT3-antagonist and/or NK1 receptor antagonist and a statin the pramipexole doses per unit form or daily doses, including pediatric daily doses and doses used in the titration period, may be in the range equivalent to from 0.375 mg to 45 mg of pramipexole dihydrochloride monohydrate. In an adult patient, a pramipexole dihydrochloride monohydrate daily dose may range from more than 4.5 mg to 45 mg, normally from 6 mg to 45, from more than 10 mg to 45 mg; or from 14.5 mg to 45 mg, from 15 mg to 35 mg, from 15 mg to 30 mg or from 15 mg to 25 mg.

In particular, the present invention provides a pharmaceutical composition comprising a 5HT3-antagonist and/or NK1-antagonist, in an amount of from 1 μg to 600 mg and a statin, in an amount of from 0.5 mg to 80 mg, in in admixture with a pharmaceutical carrier or vehicle. According to the present invention, this composition is administered to a patient suffering from a PMND in combination with 6-propylamino-4,5,6,7-tetrahydro-1,3-benzothiazole-2-amine, preferably pramipexole. In particular, in said combination, pramipexole may be administered to said patient at a daily dose (in pramipexole dihydrochloride monohydrate) of from 0.375 mg to 45 mg, preferably from more than 4.5 mg to 45 mg or from 14.5 mg to 45 mg, normally from 15 mg to 25 mg or from 20.25 mg to 25 mg.

Thus, the present invention provides a combination (including fixed-dose combinations) of a 5HT3-antagonist and/or NK1 receptor antagonist and a statin for increasing the therapeutic doses of pramipexole to consequently enable a better neuroprotective response in a patient suffering from a PMND such as PD or related synucleinopathic disorder.

The advantage of this 5HT3-antagonist and/or NK1-antagonist/statin fixed-dose combination is flexibility in the dosage and in the mode of administration of the 6-propylamino-4,5,6,7-tetrahydro-1,3-benzothiazole-2-amine, in particular of pramipexole, in the treatment of a patient suffering from a PMND with the NK1-antagonist/6-propylamino-4,5,6,7-tetrahydro-1,3-benzothiazole-2-amine/statin combination of the present invention.

The origin of the observed synergy in the 6-propylamino-4,5,6,7-tetrahydro-1,3-benzothiazole-2-amine/statin and 5HT3-antagonist and/or NK1 receptor antagonist/6-propylamino-4,5,6,7-tetrahydro-1,3-benzothiazole-2-amine/statin combinations is unknown.

It has been found that a statin allows for the safe administration of 6-propylamino-4,5,6,7-tetrahydro-1,3-benzothiazole-2-amine at a daily dose comprising a (S)-enantiomer dose that may be higher, and even much higher, than the pramipexole maximum daily dose recommended for the relief of the symptomatic treatment of Parkinson's disease. Consequently, an improvement of the conditions of a patient suffering from a PMND can be attained.

Moreover, it has been found that the combination (including fixed-dose combinations) of a 5HT3-antagonist and/or a NK1 receptor antagonist and of a statin allows for the safe administration of a pramipexole dose that may be higher, and even much higher, than the pramipexole maximum daily dose recommended for the symptomatic relief of Parkinson's disease. Consequently, an improvement of the conditions of a patient suffering from a PMND is attained.

It has also been found that, with the co-administration of a 5HT3-antagonist and/or NK1-antagonist/statin combination, not only did the pramipexole effect size become clinically significant but the dose requirement for either drug now fell into the range considered safe and tolerable for human subjects. These observations indicate that the combination of pramipexole, its stereoisomer, and mixtures thereof, plus a NK1-antagonist/statin, safely ameliorates the basic degenerative disease process in synucleinopathic disorders to a clinically meaningful degree.

The combination of pramipexole plus a NK1-antagonist/statin serves as the first neuroprotective treatment for those suffering from a parkinsonian synucleinopathic disorder, a goal long sought but never heretofore achieved.

Finally, it has been found that the combination (including fixed-dose combinations) of a NK1-antagonist and of a statin allows for the safe administration of a pramipexole dose that may be higher, and even much higher, than the pramipexole maximum daily dose recommended for the symptomatic relief of Parkinson's disease. Consequently, an improvement of the conditions of a patient suffering from a PMND is attained.

For example, the combination of a statin or of a pharmaceutically acceptable salt or solvate thereof with a 6-propylamino-4,5,6,7-tetrahydro-1,3-benzothiazole-2-amine or a pharmaceutically acceptable salt or solvate thereof, acts to normalize levels of synuclein species within the brain-derived exosomes in peripheral blood of patients suffering from a synucleinopathy, in particular by diminishing the concentration of abnormal synuclein species (congeners) in the patient's exosomal vesicles found therein, to a clinically significant degree at doses that are safe and tolerable thus evidencing that said patients will enjoy neuroprotective benefit.

This observation is unexpected since neither drug has been found clinically to possess any disease modifying ability in patients with a synuclein related disorder. Moreover, nowhere has it even been suggested that the combination of these drugs might confer such significant benefit to such individuals since the antiparkinson drug and the HMG CoA reductase inhibitor drug primarily act by very different mechanisms.

Finally, it has been found that, a 5HT3-antagonist and/or NK-1 antagonist, in combination with a 6-propylamino-4,5,6,7-tetrahydro-1,3-benzothiazole-2-amine, in particular pramipexole, and with a statin dramatically increases the tolerable pramipexole dose to a level heretofore unattainable.

In particular, according to the invention, said patient is treated with (1) a 5HT3-antagonist dose and/or a NK1 receptor antagonist dose, in combination with pramipexole, that enables a heretofore unimaginable increase, including even high increases, of the 6-propylamino-4,5,6,7-tetrahydro-1,3-benzothiazole-2-amine, preferably pramipexole, dose thus providing a stronger dopaminergic action; in further combination with (2) a dose of a statin that reduces the minimum effective dose of 6-propylamino-4,5,6,7-tetrahydro-1,3-benzothiazole-2-amine, preferably pramipexole, and/or increases the 6-propylamino-4,5,6,7-tetrahydro-1,3-benzothiazole-2-amine effect magnitude without lowering its minimum toxic dose.

In addition, it has been found that the combination (including fixed-dose combinations) of a 5HT3-antagonist and/or a NK1 receptor antagonist and of a statin allows for the safe administration of a pramipexole dose that may be higher, and even much higher, than the pramipexole maximum daily dose recommended for the symptomatic treatment of Parkinson's disease. Consequently, an improvement in the condition of a patient suffering from a PMND is attained.

The present invention is based on the discovery that statins potentiate (augment) the ability of pramipexole to alter misfolded protein species in ways indicating the activation of a central neuroprotective mechanism, i.e. reducing oligomerization of said proteins;

these changes occur at safe and tolerable doses of both drugs;

these changes are indicative of CNS changes that will confer disease clinical improvement in a way and to a degree that will provide practical and significant disease modifying benefit to sufferers; and the addition of a 5HT3-antagonist and/or NK1 receptor antagonist to the statin unexpectedly allows a better response at relatively low pramipexole doses and also the safe administration of high pramipexole doses, with a consequent possibility of safely improving the conditions of patients suffering from a PMND.

The forgoing observations are especially surprising since statins, such as atorvastatin, fluvastatin, lovastatin, pitavastatin, pravastatin, simvastatin and rosuvastatin, were approved beginning in the late 1980s as lipid lowering agents;

the neuroprotective activity in PD models (Orr JD) and the reduction of neuronal alpha-synuclein aggregation (Bar-On et al.) was known since 2008;

no one suspected that a combination of a statin and 6-propylamino-4,5,6,7-tetrahydro-1,3-benzothiazole-2-amine, including pramipexole, could have been disease-modifying when administered to a patient suffering of a synucleinopathy;

notwithstanding controversial claims to the contrary, no statin has been rigorously demonstrated to confer disease modifying benefit to those with PD or a similar synucleinopathic disorder or to affect any peripheral exosomal biomarker of CNS disorders of this type;

6-propylamino-4,5,6,7-tetrahydro-1,3-benzothiazole-2-amine, such as pramipexole, has no known effects on the mevalonate pathway believed to be central to the lipid-lowering effects of the statins; indeed, statins and 6-propylamino-4,5,6,7-tetrahydro-1,3-benzothiazole-2-amine such as pramipexole are taken up, metabolized and excreted by different, essentially non-interactive, ways;

the HMG-CoA reductase inhibitor, as a statin, and the dopamine agonist, as pramipexole, act by different means on different body systems to produce different clinical effects in human subjects;

neither rosuvastatin nor any other drug of the HMG-CoA reductase inhibitor class is known to exert a synergistic effect on any pharmacologic action of pramipexole or of its isomer or of mixtures thereof, and no one has suggested that these two drugs be co-administered to PD-type patients with neuroprotective intent.

In spite of numerous publications on pramipexole and on statins and their combination, no observations on this possibility were reported, mentioned or suggested, and no speculation on its consequences was found. Moreover, it is unexpected since the two drugs act on different targets, by different mechanisms, to produce different clinical effects, and thus would hardly be expected to have synergistic effects in the manner disclosed herein in the treatment of a PMND.

In addition, it has also surprisingly been found that statins, in combination with a 5HT3-antagonist and/or a NK1 receptor antagonist attenuates the GI adverse effects of pramipexole, thus allowing the safe administration of pramipexole within the whole pramipexole recommended daily dose range (0.375 mg-4.5 mg);

acts synergistically, by potentiating the pramipexole effect within the above whole pramipexole recommended daily dose range; and allows the administration of pramipexole dihydrochloride monohydrate doses (per unit form and daily) that are higher, and even much higher than the maximum recommended daily dose.

Not less surprisingly, it has been discovered that a further combination of fluoxetine with a NK1-antagonist increases the efficacy of pramipexole and, in addition, allows the administration of pramipexole daily doses as high as up to 45 mg, in particular from more than 20 mg to 45 mg, more particularly from 20.25 mg to 45 mg (in pramipexole dihydrochloride monohydrate).

In particular, the addition of a 5HT3-antagonist and/or a NK1 receptor antagonist to 6-propylamino-4,5,6,7-tetrahydro-1,3-benzothiazole-2-amine and statin allows the administration of, for example, pramipexole doses (per unit form and daily) much higher than the maximum recommended pramipexole doses. Thus, for example, in a combination of a 5HT3-antagonist and/or a NK1 receptor antagonist with pramipexole and a statin, the pramipexole daily doses, including pediatric daily doses and daily doses used in the titration period, are equivalent to from 0.375 mg to 45 mg of pramipexole dihydrochloride monohydrate. In an adult patient, the pramipexole dihydrochloride monohydrate daily dose may be in a range equivalent to from more than 4.5 mg to 45 mg, from 6 mg to 45, and from more than 10 mg to 45 mg. Normally, said pramipexole dihydrochloride monohydrate daily dose in an adult patient is from 14.5 mg to 45 mg, from 15 mg to 35 mg, from 15 mg to 30 mg or from 15 mg to 25 mg.

These findings provide safe treatment for disabling diseases such as PD, LBD, mutations in the glucocerebrosidase (GBA) gene, AD, the Lewy body variant of AD and PD, neurodegeneration with brain iron accumulation, MSA, HD, MT, ALS, SEP, FAP, and other PMNDs.

The invention further provides the use of a statin for the preparation of a medicament for combating synucleinopathies in a patient, in combination with 6-propylamino-4,5,6,7-tetrahydro-1,3-benzothiazole-2-amine, in particular pramipexole or a pharmaceutically acceptable salt thereof Thus, the present invention provides a 5HT3-antagonist and/or a NK1 receptor antagonist, for use for the treatment of a PMND in patients in need of said treatment, in combination with pramipexole and a statin; and the use of a 5HT3-antagonist and/or a NK1 receptor antagonist, for the preparation of a medicament for the treatment of a PMND in combination with pramipexole and a statin.

The invention also provides the use of a NK1-antagonist for the preparation of a medicament for the treatment of a PMND in a patient, in combination with 6-propylamino-4,5,6,7-tetrahydro-1,3-benzothiazole-2-amine, in particular pramipexole, and a statin; or the use of a NK1-antagonist for the treatment of a PMND in combination with 6-propylamino-4,5,6,7-tetrahydro-1,3-benzothiazole-2-amine, in particular pramipexole or a pharmaceutically acceptable salt thereof, and a statin. Herein below, these two expressions will be merged and referred to as "the use of a NK1-antagonist for the preparation of a medicament (or a NK1-antagonist for use) for the treatment of a PMND in combination with a 6-propylamino-4,5,6,7-tetrahydro-1,3-benzothiazole-2-amine and a statin".

The invention further provides a method for treating a patient suffering from a PMND, which comprises treating said patient with a 5HT3-antagonist and/or a NK1 receptor antagonist, in combination with 6-propylamino-4,5,6,7-tetrahydro-1,3-benzothiazole-2-amine and a statin.

The invention also provides the use of a NK1-antagonist for the preparation of a medicament for the treatment of a PMND in a patient, in combination with 6-propylamino-4,5,6,7-tetrahydro-1,3-benzothiazole-2-amine, in particular pramipexole, and a statin; or the use of a NK1-antagonist for the treatment of a PMND in combination with 6-propylamino-4,5,6,7-tetrahydro-1,3-benzothiazole-2-amine, in particular pramipexole or a pharmaceutically acceptable salt thereof, and a statin. Herein below, these two expressions will be merged and referred to as "the use of a NK1-antagonist for the preparation of a medicament (or a NK1-antagonist for use) for the treatment of a PMND in combination with a 6-propylamino-4,5,6,7-tetrahydro-1,3-benzothiazole-2-amine and a statin".

Preferably, in said method (or use), the 5HT3-antagonist and/or NK-1 antagonist is administered at a daily dose at least as high as that approved for the prevention or treatment of postoperative nausea and vomiting or for the prevention of chemotherapy-induced nausea and vomiting, in combination with an effective daily dose of 6-propylamino-4,5,6,7-tetrahydro-1,3-benzothiazole-2-amine and with an effective daily dose of a statin.

Pharmaceutically acceptable acid addition salts and solvates of the 5HT3-antagonist and/or a NK1 receptor antagonist and of the 6-propylamino-4,5,6,7-tetrahydro-1,3-benzothiazole-2-amine, as well as pharmaceutically acceptable salts, in particular alkaline and alkaline-earth metal salts of the acidic 5HT3-antagonist and pharmaceutically acceptable salts, in particular alkaline and alkaline-earth metal salts of the statin are also included in the method (or use) of the present invention.

In certain embodiments of the method (or use) according to the present invention, said 6-propylamino-4,5,6,7-tetrahydro-1,3-benzothiazole-2-amine and said statin combination is administered to said patient in a fixed-dose combination wherein said 6-propylamino-4,5,6,7-tetrahydro-1,3-benzothiazole-2-amine and said statin are mixed together, and with a pharmaceutical carrier or vehicle.

In particular, the method (or use) for treating a patient suffering from a PMND according to the present invention comprises treating said patient with an effective daily dose of a 5HT3-antagonist and/or a NK1 receptor antagonist in combination with an effective daily dose of pramipexole dihydrochloride monohydrate and an effective daily dose of a statin. Normally, said effective 5HT3-antagonist and/or a NK1 receptor antagonist daily dose is from 1 μg to 600 mg.

Preferably, in said method (or use), the 5HT3-antagonist and/or a NK1 receptor antagonist is administered at a daily dose at least as high as that approved for the prevention or treatment of postoperative nausea and vomiting or for the prevention of chemotherapy-induced nausea and vomiting, in combination with an effective daily dose of pramipexole and with an effective daily dose of a statin.

According to the invention, said effective daily dose of pramipexole, including pediatric doses and low doses used in the titration period, is equivalent to from 0.375 mg to 3000 mg of pramipexole dihydrochloride monohydrate, including a (S)-enantiomer daily dose of from 0.375 mg to 45 mg, normally from 0.375 mg to 20 mg of pramipexole dihydrochloride monohydrate.

Said statin daily dose is at least as high as the dose approved for its dyslipidemia treatment indication. Normally, the statin daily dose, including pediatric doses and low doses used in the titration period, is from 0.5 mg to 80 mg.

Said daily dose of said statin may be lower than the maximum daily dose approved for the treatment of dyslipidemia. Preferably, said statin is selected from the group consisting of lovastatin, at a daily dose of from 5 mg to 80 mg, normally from 5 mg to 60 mg or from 10 mg to 60 mg, and rosuvastatin calcium, at a daily dose of from 2.5 mg to 40 mg, normally from 2.5 mg to 30 mg.

Preferably, said daily dose of said statin is lower than the maximum daily dose approved for the treatment of dyslipidemia.

Preferably, 6-propylamino-4,5,6,7-tetrahydro-1,3-benzothiazole-2-amine is pramipexole base or pramipexole dihydrochloride monohydrate.

Preferably, said 5HT3-antagonist is ondansetron or dolasetron, and said 6-propylamino-4,5,6,7-tetrahydro-1,3-benzothiazole-2-amine is pramipexole.

Preferably, said NK1-antagonist is aprepitant or rolapitant, and said 6-propylamino-4,5,6,7-tetrahydro-1,3-benzothiazole-2-amine is pramipexole.

Preferably, said statin is lovastatin or rosuvastatin, and the 6-propylamino-4,5,6,7-tetrahydro-1,3-benzothiazole-2-amine is used as pramipexole dihydrochloride monohydrate.

Thus, the invention provides a pharmaceutical composition for the treatment of protein misfolding neurodegenerative disorders in combination with propylamino-4,5,6,7-tetrahydro-1,3-benzothiazole-2-amine, in particular pramipexole, comprising a pharmaceutical carrier or vehicle and a fixed-dose combination of a NK1-antagonist and a statin. A pharmaceutical composition in dosage unit form comprising, as active ingredients, aprepitant and lovastatin is particularly advantageous.

In said compositions, said 5HT3-antagonist is present in an amount per unit form of from 1 μg to 300 mg and/or said NK1-antagonist in said pharmaceutical composition is administered to said patient at a daily dose of from 1 μg to 600 mg, and said statin is in an amount per unit form of from 0.5 mg to 80 mg, and said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate.

Preferably, in said compositions, said 5HT3-antagonist is ondansetron, in an amount per unit form (in ondansetron base) of from 2 mg to 32 mg or dolasetron in an amount per unit form (in dolasetron mesylate) of from 25 mg to 200 mg;

said 6-propylamino-4,5,6,7-tetrahydro-1,3-benzothiazole-2-amine is pramipexole, in an amount per unit form equivalent to from 0.125 mg to 45 mg of pramipexole dihydrochloride monohydrate; and said statin is lovastatin, in an amount per unit form of from 0.5 mg to 80 mg, normally from 10 mg to 60 mg.

Alternatively, in said compositions, said NK1-antagonist is present in an amount per unit form of from 1 μg to 600 mg, said said statin is present in an amount per unit form of from 0.5 mg to 80 mg, and said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate.

Preferably, in these compositions said NK1 antagonist is aprepitant or rolapitant, said 6-propylamino-4,5,6,7-tetrahydro-1,3-benzothiazole-2-amine is pramipexole or a pharmaceutically acceptable salt or solvate thereof, and said statin is lovastatin or rosuvastatin.

Preferably, in said compositions, said NK1-antagonist is aprepitant, in an amount per unit form of from 10 mg to 250 mg; or rolapitant, in an amount per unit form of from 15 mg to 270 mg;

said 6-propylamino-4,5,6,7-tetrahydro-1,3-benzothiazole-2-amine is pramipexole, in an amount per unit form equivalent to from 0.125 mg to 45 mg of pramipexole dihydrochloride monohydrate; and said statin is lovastatin, in an amount per unit form of from 5 mg to 80 mg, normally from 10 mg to 60 mg.

In particular, the present invention provides a pharmaceutical unit form comprising a medicament selected from the group consisting of a 5HT3-antagonist, in a pharmaceutical composition comprising said 5HT3-antagonist in an amount of from 1 μg to 300 mg and/or a NK-1 antagonist, in a pharmaceutical composition comprising said NK-1 antagonist in an amount of from 1 μg to 600 mg, in admixture with a pharmaceutical carrier or vehicle; and statin, in an amount of from 0.5 mg to 80 mg, in admixture with a pharmaceutical carrier or vehicle; and a 5HT3-antagonist, in an amount of from 1 μg to 300 mg and/or a NK-1 antagonist, in an amount of from 1 μg to 600 mg, and statin, in an amount of from 0.5 mg to 80 mg, in admixture with a pharmaceutical carrier or vehicle.

This unit form is to be administered to a patient suffering from a PMND in combination with 6-propylamino-4,5,6,7-tetrahydro-1,3-benzothiazole-2-amine, preferably pramipexole.

For the treatment of a PMND, according to the above method (or use), the 5HT3-antagonist and/or a NK1 receptor antagonist, the 6-propylamino-4,5,6,7-tetrahydro-1,3-benzothiazole-2-amine and a statin are each formulated in a pharmaceutical composition in admixture with a pharmaceutical carrier and concurrently or sequentially administered to a patient in need of said treatment.

The 5HT3-antagonist and/or a NK1 receptor antagonist and pramipexole may be mixed together and formulated in a pharmaceutical composition (fixed-dose combination) in admixture with a pharmaceutical carrier or vehicle. This composition is destined to be concurrently or sequentially administered to a patient suffering from a PMND, in combination with a statin, also formulated in a pharmaceutical composition in admixture with a pharmaceutical carrier or vehicle.

Furthermore, the 5HT3-antagonist and/or a NK1 receptor antagonist and a statin may be mixed together and formulated in a pharmaceutical composition (fixed-dose combination) in admixture with a pharmaceutical carrier, to be administered to a patient suffering from a PMND, in combination with 6-propylamino-4,5,6,7-tetrahydro-1,3-benzothiazole-2-amine. A pharmaceutical composition in dosage unit form comprising, as active ingredients, ondansetron and lovastatin is particularly advantageous.

According to an advantageous alternative, in order to allow flexibility in the prescription of 6-propylamino-4,5,6,7-tetrahydro-1,3-benzothiazole-2-amine, preferably pramipexole, the 5HT3-antagonist and/or NK1-antagonist and the statin may be mixed together and formulated in a pharmaceutical composition (fixed-dose combination) in admixture with a pharmaceutical carrier or vehicle, to be administered to a patient suffering from a PMND, in combination with said 6-propylamino-4,5,6,7-tetrahydro-1,3-benzothiazole-2-amine, preferably pramipexole.

In particular, the method (or use) for treating a patient suffering from a PMND according to the present invention comprises treating said patient with an effective daily dose of a 5HT3-antagonist and/or NK-1 antagonist combined with an effective daily dose of 6-propylamino-4,5,6,7-tetrahydro-1,3-benzothiazole-2-amine and an effective daily dose of a statin. Normally, said effective 5HT3-antagonist and/or NK-1 antagonist daily dose is from 1 μg to 600 mg.

According to the above method (or use) for the treatment of a PMND, said 5HT3-antagonist in said pharmaceutical composition is administered to said patient at a daily dose of from 1 μg to 300 mg and/or said and/or NK1 receptor antagonist in said pharmaceutical composition is administered to said patient at a daily dose of from 1 μg to 600 mg;

said 6-propylamino-4,5,6,7-tetrahydro-1,3-benzothiazole-2-amine in said composition is administered to said patient in need of said treatment at a daily dose that is equivalent to from 0.375 mg to to 3000 mg of pramipexole dihydrochloride monohydrate, said daily dose including an (S)-enantiomer daily dose equivalent to from 0.375 mg to 45 mg of pramipexole dihydrochloride monohydrate; and said statin in said pharmaceutical composition is administered to said patient in need of said treatment at a daily dose that is equivalent to from 2.5 mg to 80 mg, preferably, said statin is selected from the group consisting of lovastatin at a daily dose of from 5 mg to 60 mg, or rosuvastatin calcium at the daily dose of from 2.5 mg to 40 mg, normally rom 2.5 mg to 30 mg.

According to the invention, said effective daily dose of 6-propylamino-4,5,6,7-tetrahydro-1,3-benzothiazole-2-amine, including low doses used in the titration period, is equivalent to from 0.375 mg to 3000 mg of pramipexole dihydrochloride monohydrate, including a (S)-enantiomer daily dose of from 0.375 mg to 45 mg of pramipexole dihydrochloride monohydrate.

In said method (or use) described above, said 5HT3-antagonist and/or NK1 receptor antagonist/pramipexole/statin combination is administered to said patient in a fixed-dose combination wherein said pramipexole and said statin are mixed together, and with a pharmaceutical carrier or vehicle.

For this treatment, the 5HT3-antagonist and/or NK-1 antagonist, the 6-propylamino-4,5,6,7-tetrahydro-1,3-benzothiazole-2-amine, and a statin are each formulated in a pharmaceutical composition (fixed-dose combination) in admixture with a pharmaceutical carrier and concurrently or sequentially administered to a patient suffering from a PMND.

In addition, the 5HT3-antagonist and/or NK-1 antagonist and the 6-propylamino-4,5,6,7-tetrahydro-1,3-benzothiazole-2-amine may be mixed together and formulated in a pharmaceutical composition (fixed-dose combination) in admixture with a pharmaceutical carrier or vehicle. This composition is concurrently or sequentially administered to a patient suffering from a PMND, in combination with a statin, also formulated in a pharmaceutical composition in admixture with a pharmaceutical carrier or vehicle.

Furthermore, the 5HT3-antagonist and/or NK-1 antagonist and a statin may be mixed together and formulated in a pharmaceutical composition (fixed-dose combination) in admixture with a pharmaceutical carrier, to be administered to a patient suffering from a PMND, in combination with 6-propylamino-4,5,6,7-tetrahydro-1,3-benzothiazole-2-amine.

Moreover, the 5HT3-antagonist and/or NK-1 antagonist may be formulated in a pharmaceutical composition in admixture with a pharmaceutical carrier, to be administered to a patient suffering from a PMND, in combination with 6-propylamino-4,5,6,7-tetrahydro-1,3-benzothiazole-2-amine and with a statin, mixed together and formulated in a pharmaceutical composition (fixed-dose combination) in admixture with a pharmaceutical carrier.

Finally, the 5HT3-antagonist and/or NK-1 antagonist, the 6-propylamino-4,5,6,7-tetrahydro-1,3-benzothiazole-2-amine and a statin are mixed together and formulated in a pharmaceutical composition (fixed-dose combination) in admixture with a pharmaceutical carrier, to be administered to a patient suffering from a PMND.

The 5HT3-antagonist and/or NK1 receptor antagonist and the 6-propylamino-4,5,6,7-tetrahydro-1,3-benzothiazole-2-amine may be mixed together and formulated in a pharmaceutical composition (fixed-dose combination) in admixture with a pharmaceutical carrier or vehicle. This composition is concurrently or sequentially administered to a patient suffering from a PMND, in combination with a statin, also formulated in a pharmaceutical composition in admixture with a pharmaceutical cater or vehicle.

According to advantageous embodiments, the invention provides a pharmaceutical composition comprising a pharmaceutically acceptable carrier or vehicle and a fixed dose combination of a NK1-antagonist, a 6-propylamino-4,5,6,7-tetrahydro-1,3-benzothiazole-2-amine and a statin.

a pharmaceutical composition for use in treatment of a PMND in a patient, comprising a pharmaceutically acceptable carrier or vehicle and a fixed dose combination of a NK1-antagonist, a 6-propylamino-4,5,6,7-tetrahydro-1,3-benzothiazole-2-amine and a statin; and the use of a NK1-antagonist for the preparation of a medicament (or a NK1-antagonist for use) for the treatment of a PMND in a patient, in a fixed-dose combination of said NK1-antagonist, a 6-propylamino-4,5,6,7-tetrahydro-1,3-benzothiazole-2-amine and a statin.

Preferably, said 5HT3-antagonist is ondansetron or dolasetron, said statin is lovastatin, and said 6-propylamino-4,5,6,7-tetrahydro-1,3-benzothiazole-2-amine is pramipexole.

According to a preferred embodiment, said 5HT3-antagonist is ondansetron and said statin is lovastatin.

In said compositions, said 5HT3-antagonist is present in an amount per unit form of from 1 μg to 300 mg and/or NK1 receptor antagonist is present in an amount per unit form of from 1 μg to 600 mg, said statin is present in an amount per unit form equivalent to from 0.5 mg to 80 mg, and said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate.

Preferably, in said compositions, said 5HT3-antagonist is ondansetron, in an amount per unit form of from 2 mg 32 mg, or dolasetron, in an amount per unit form (in dolasetron mesylate) of from 25 mg to 200 mg, said statin is in an amount per unit form equivalent to from 10 mg to 60 mg, and said 6-propylamino-4,5,6,7-tetrahydro-1,3-benzothiazole-2-amine is pramipexole, in an amount per unit form equivalent to from 0.125 mg to 45 mg of pramipexole dihydrochloride monohydrate.

According to each of the above alternatives, in the method (or use) for the treatment of a PMND, said 6-propylamino-4,5,6,7-tetrahydro-1,3-benzothiazole-2-amine is pramipexole or a pharmaceutically acceptable salt or solvate thereof.

Preferably, pramipexole is used as pramipexole base or as pramipexole dihydrochloride monohydrate.

Preferably, according to each of the above alternatives, in the method for treating a patient suffering from a PMND, said 5HT3-antagonist is ondansetron.

In particular, according to the above alternatives, in the method (or use) for the treatment of a PMND, said 5HT3-antagonist in said pharmaceutical composition is administered to said patient at a daily dose of from 1 μg to 300 mg and/or said NK1 receptor antagonist in said pharmaceutical composition is administered to said patient at a daily dose of from 1 μg to 600 mg;

said 6-propylamino-4,5,6,7-tetrahydro-1,3-benzothiazole-2-amine in said composition is administered to said patient in need of said treatment at a daily dose that is equivalent to from 0.375 mg to 3000 mg of pramipexole dihydrochloride monohydrate, said daily dose including an (S)-enantiomer daily dose equivalent to from 0.375 mg to 45 mg of pramipexole dihydrochloride monohydrate; and said statin in said pharmaceutical composition is administered to a patient in need of said treatment at a daily dose that is equivalent to from 0.5 mg to 80 mg.

In said method (or use), said 6-propylamino-4,5,6,7-tetrahydro-1,3-benzothiazole-2-amine and said statin combination is administered to said patient in a fixed-dose combination wherein said statin and said 6-propylamino-4,5,6,7-tetrahydro-1,3-benzothiazole-2-amine are mixed together, and with a pharmaceutical carrier or vehicle.

Preferably, according to above methods for treating a patient suffering from a PMND said 5HT3-antagonist is ondansetron or dolasetron.

Preferably, according to each of the above alternatives, in the method for treating a patient suffering from a PMND said 5HT3-antagonist is selected from the group consisting of ondansetron and pharmaceutically acceptable salts and solvates thereof and dolasetron and pharmaceutically acceptable salts and solvates thereof. If the 5HT3-antagonist is ondansetron, said ondansetron is administered to said patient, as ondansetron hydrochloride dihydrate, at a daily dose that is equivalent to from 4 mg to 32 mg of ondansetron base. If the 5HT3-antagonist is dolasetron, said dolasetron is administered to said patient at a daily dose that is equivalent to from 25 mg to 200 mg of dolasetron mesylate.

Preferably, according to each of the above alternatives, in the method for treating a patient suffering from a PMND said NK1-antagonist is selected from the group consisting of aprepitant and pharmaceutically acceptable salts and solvates and prodrugs thereof, and rolapitant and pharmaceutically acceptable salts and solvates and prodrugs thereof. If the NK1-antagonist is aprepitant or fosaprepitant, said NK1-antagonist is administered to said patient at a daily dose, in aprepitant, of from 10 mg to 250 mg of aprepitant, or in some embodiments of from 10 mg to 125 mg of aprepitant. If the NK1-antagonist is rolapitant, said rolapitant is administered to said patient at a daily dose of from 15 mg to 270 mg of rolapitant. Said 6-propylamino-4,5,6,7-tetrahydro-1,3-benzothiazole-2-amine is pramipexole and said statin is lovastatin or rosuvastatin.

Preferably, according to each of the above alternatives, in the method (or use) for the treatment of a PMND, said 5HT3-antagonist in said pharmaceutical composition is ondansetron, administered at a daily dose of from 4 mg to 32 mg or from 6 mg to 32 mg;

said 6-propylamino-4,5,6,7-tetrahydro-1,3-benzothiazole-2-amine in said composition is pramipexole or a pharmaceutically acceptable salt or solvate thereof, at a daily dose, including pediatric daily doses and daily doses used in the titration period, equivalent to from 0.375 mg to 45 mg of pramipexole dihydrochloride monohydrate; and said statin is administered at a daily dose of from 0.5 mg to 80 mg.

In particular, according to the above alternatives, in the method (or use) for the treatment of a PMND, said 5HT3-antagonist in said pharmaceutical composition is administered to said patient at a daily dose of from 1 μg to 300 mg and/or said NK1 receptor antagonist in said pharmaceutical composition is administered to said patient at a daily dose of from 1 μg to 600 mg;

said 6-propylamino-4,5,6,7-tetrahydro-1,3-benzothiazole-2-amine in said composition is administered to said patient in need of said treatment at a daily dose that is equivalent to from 1.5 mg to 3000 mg of pramipexole dihydrochloride monohydrate, said daily dose including an (S)-enantiomer daily dose equivalent to from 1.5 mg to 45 mg of pramipexole dihydrochloride monohydrate; and said statin in said pharmaceutical composition is administered to a patient in need of said treatment at a daily dose that is equivalent to from 2.5 mg to 80 mg.

Preferably and more particularly, according to each of the above method (or use) for the treatment of a PMND, said 5HT3-antagonist in said pharmaceutical composition is ondansetron, administered at a daily dose of from 4 mg to 32 mg or from 6 mg to 32 mg;

said 6-propylamino-4,5,6,7-tetrahydro-1,3-benzothiazole-2-amine in said composition is pramipexole or a pharmaceutically acceptable salt or solvate thereof, at a daily dose, including doses used in the titration period, equivalent to from 0.375 mg to 45 mg of pramipexole dihydrochloride monohydrate; and said statin in said pharmaceutical composition is administered to a patient in need of said treatment at a daily dose that is equivalent to from 2.5 mg to 80 mg.

Preferably, according to each of the above alternatives, in the method for treating a patient suffering from a PMND, said NK1-antagonist is selected from the group consisting of aprepitant and pharmaceutically acceptable salts and solvates and prodrugs thereof, and rolapitant and pharmaceutically acceptable salts and solvates and prodrugs thereof. If the NK1-antagonist is aprepitant or fosaprepitant, said NK1-antagonist is administered to said patient at a daily dose, in aprepitant, of from 10 mg to 250 mg, or in some embodiments of from 10 mg to 125 mg. If the NK1-antagonist is rolapitant, said rolapitant is administered to said patient at a daily dose of from 15 mg to 270 mg.

Preferably and more particularly, according to the above method (or use) for the treatment of a PMND, said NK1-antagonist in said pharmaceutical composition is aprepitant, in an amount per unit form of from 10 mg to 250 mg, administered at a daily dose of from 15 mg to 250 mg;

said 6-propylamino-4,5,6,7-tetrahydro-1,3-benzothiazole-2-amine in said composition is pramipexole or a pharmaceutically acceptable salt or solvate thereof, in an amount per unit form of from 0,125 mg to 45 mg (in pramipexole dihydrochloride monohydrate), administered at a daily dose, including doses used in the titration period, equivalent to from 0.375 mg to 45 mg of pramipexole dihydrochloride monohydrate; and said statin in said pharmaceutical composition is administered to said patient in need of said treatment at a daily dose that is equivalent to from 2.5 mg to 80 mg, preferably, said statin is selected from the group consisting of lovastatin at a daily dose of from 5 mg to 60 mg, or rosuvastatin calcium at the daily dose of from 2.5 mg to 40 mg, normally rom 2.5 mg to 30 mg.

According to a specific alternative, the invention provides a pharmaceutical composition for the treatment of protein misfolding neurodegenerative disorders in a patient, in combination with a pramipexole daily dose equivalent to from 0.375 mg to 45 mg, up to from 14.5 mg to 45 mg or from more than 20 mg to 45 mg, normally from 15 mg to 25 mg, of pramipexole dihydrochloride monohydrate, comprising a pharmaceutical carrier or vehicle and a fixed-dose combination of a 5HT3-antagonist, in an amount per unit form of from 1 μg to 300 mg and/or a NK1-antagonist, in an amount per unit form of from 1 μg to 600 mg, and a statin, in an amount per unit form of from 0.5 mg to 80 mg.

According to a specific alternative, the invention provides a 5HT3-antagonist/statin fixed-dose combination comprising or consisting of a pharmaceutical composition comprising a pharmaceutical carrier or vehicle and a fixed-dose combination of the 5HT3-antagonist selected from the group consisting of ondansetron, in an amount per unit form of from 2 mg to 64 mg, normally from 2 mg to 32 mg (in ondansetron base); and dolasetron, in an amount per unit form of from 15 mg to 200 mg (in dolasetron mesylate; and a statin selected from the group consisting of lovastatin, in an amount per unit form of from 5 mg to 80 mg, normally from 5 mg to 60 mg; and rosuvastatin calcium, in an amount per unit form of from 2.5 mg to 40 mg, normally from 2.5 mg to 30 mg. Said pharmaceutical composition is useful or for use for the treatment of a protein misfolding neurodegenerative disorder in a patient, in combination with a pramipexole daily dose equivalent to from 0.375 mg to 45 mg, up to from 14.5 mg to 45 mg or from more than 20 mg to 45 mg, normally from 15 mg to 25 mg or from 20.25 mg to 25 mg, of pramipexole dihydrochloride monohydrate.

According to a specific alternative, the invention provides a NK1-antagonist/statin fixed-dose combination comprising or consisting of a pharmaceutical composition comprising a pharmaceutical carrier or vehicle and a fixed-dose combination of the NK1-antagonist selected from the group consisting of aprepitant, in an amount per unit form of from 10 mg to 250 mg; and rolapitant, in an amount per unit form of from 15 mg to 270 mg; and a statin a selected from the group consisting of lovastatin, in an amount per unit form of from 5 mg to 80 mg, normally from 5 mg to 60 mg; and rosuvastatin calcium, in an amount per unit form of from 2.5 mg to 40 mg, normally from 2.5 mg to 30 mg. Said pharmaceutical composition is useful or for use for the treatment of a protein misfolding neurodegenerative disorder in a patient, in combination with a pramipexole daily dose equivalent to from 0.375 mg to 45 mg, up to from 14.5 mg to 45 mg or from more than 20 mg to 45 mg, normally from 15 mg to 25 mg or from 20.25 mg to 25 mg, of pramipexole dihydrochloride monohydrate.

In said composition said 5HT3-antagonist advantageously is ondansetron hydrochloride dihydrate, in an amount per unit form of from 0.5 mg to 32 mg of ondansetron base, and said statin, in an amount per unit form of from 0.5 mg to 80 mg.

In said composition said 5HT3-antagonist advantageously may also be dolasetron mesylate, in an amount per unit form of from 25 mg to 200 mg, and said statin, in an amount per unit form of from 0.5 mg to 80 mg.

In combination with said 5HT3-antagonist and/or said NK-1 antagonist and said statin in said fixed dose combination Component (ac), said pramipexole Component (b) is advantageously administered at a daily dose equivalent to from more than 4.5 mg to 45 mg, from more than 6 mg to 45 mg, from 6.5 mg to 45 mg, up to from 14.5 mg to 45 mg or from more than 20 mg to 45 mg, normally from 15 mg to 25 mg, of pramipexole dihydrochloride monohydrate.

In said compositions, said NK1-antagonist is present in an amount per unit form of from 1 μg to 600 mg, said 6-propylamino-4,5,6,7-tetrahydro-1,3-benzothiazole-2-amine is present in an amount of from 0.125 mg to 3000 mg, including a (S)-enantiomer amount per unit form equivalent to from 0.125 mg to 45 mg of pramipexole dihydrochloride monohydrate, and said statin is present in an amount per unit form of from 0.5 mg to 80 mg.

In said composition said NK1-antagonist advantageously is aprepitant, in an amount per unit form of from 10 mg to 250 mg, and a statin, in an amount per unit form of from 0.5 mg to 80 mg. Preferably, said aprepitant composition is in a unit form to be administered once a day, wherein said aprepitant is present in an amount of from 10 mg to 250 mg of aprepitant in an IR-form, and said a statin, in an amount per unit form of from 0.5 mg to 80 mg is in an ER-form.

In said composition said NK1-antagonist advantageously may also be rolapitant, in an amount per unit form of from 15 mg to 270 mg, and said a statin, in an amount per unit form of from 0.5 mg to 80 mg.

Preferably, said composition is in an unit form, to be administered once a day, wherein said rolapitant is present in an amount of from 15 mg to 270 mg in an IR-form, and said a statin, in an amount per unit form of from 0.5 mg to 80 mg in an ER-form.

A specific combination of a NK1-antagonist and of a 5HT3-antagonist is selected from the group consisting of the fixed-dose combinations netupitant-300/palonosetron-0.5 and fosnetupitant-235/palonosetron-0.25.

In combination with said 5HT3-antagonist and/or said NK1-antagonist and with said statin in said fixed dose combination Component (ac), said pramipexole Component (b) is advantageously administered at a daily dose equivalent to from more than 4.5 mg to 45 mg, from more than 6 mg to 45 mg, from 6.5 mg to 45 mg, up to from 14.5 mg to 45 mg or from more than 20 mg to 45 mg of pramipexole dihydrochloride monohydrate.

This third aspect of present invention further provides a kit or package comprising a pharmaceutical combination or pharmaceutical compositions as described herein, and instructions for use of the same for treatment of a synucleinopathy in a patient in need thereof.

These findings are surprising because, as discussed above, nothing in the art the last seventeen years has suggested or disclosed that a combination of pramipexole and fluoxetine, zonisamide, or a statin, with a 5HT3-antagonist and/or a NK1 receptor antagonist, would provide an effective means for treating PMND, for example synucleinopathies such as PD. In addition, no one suspected that, at safe and tolerable doses, a NK1-antagonist and/or a 5HT3-antagonist, combined with pramipexole and fluoxetine, zonisamide, or a statin, would result in the modification of α-Syn species in blood exosomes in ways and to degrees indicative of significant disease modifying efficacy.

[Moved to Above]

It has been found that the combination of fluoxetine, zonisamide, or a statin, with a 5HT3 antagonist such as ondansetron, dolasetron or palonosetron, and/or a NK1 receptor antagonist such as aprepitant, netupitant, and rolapitant, by reducing or even abrogating the GI side effects, in particular nausea and vomiting, of high doses of pramipexole enables the synucleinopathy-modifying potential of pramipexole. The combination of a 6-propylamino-4,5,6,7-tetrahydro-1,3-benzothiazole-2-amine with a 5HT3-antagonist, such as ondansetron, dolasetron or palonosetron, and/or a NK1-antagonist, such as aprepitant, rolapitant, or netupitant, acts by normalizing the abnormal ratio of monomeric to oligomeric synuclein species in blood exosomes originating from the CNS of patients suffering from a synucleinopathy.

Hence, the combination (including fixed-dose combinations) of fluoxetine, zonisamide, or a statin with a 5HT3-antagonist and/or a NK1-antagonist, allows for the safe administration of 6-propylamino-4,5,6,7-tetrahydro-1,3-benzothiazole-2-amine at a daily dose comprising a (S)- enantiomer dose that may be higher, and even much higher, than the pramipexole maximum daily dose recommended for the symptomatic treatment of Parkinson's disease. Consequently, an improvement of the conditions of a patient suffering from a PMND can be attained. In particular, it has been found that the protective action of said combination of 5HT3-antagonist and/or NK1-antagonist with fluoxetine, zonisamide, or a statin makes it possible to increase the pramipexole daily dose up to from more than 3.2 times to 10 times the maximum recommended dose, up to from at least four times and 10 times the maximum recommended and approved dose, and even more.

For example, the combination of fluoxetine or of a pharmaceutically acceptable salt or solvate thereof, zonisamide or of a pharmaceutically acceptable salt or solvate thereof, or a statin, with a 5HT3 antagonist or a pharmaceutically acceptable salt or solvate thereof and/or NK1-antagonist or a pharmaceutically acceptable salt or solvate thereof, and a 6-propylamino-4,5,6,7-tetrahydro-1,3-benzothiazole-2-amine or a pharmaceutically acceptable salt or solvate thereof, acts to normalize levels of synuclein species within the brain-derived exosomes in peripheral blood of patients suffering from a synucleinopathy, in particular by diminishing the concentration of abnormal synuclein species (congeners) in the patient's exosomal vesicles found therein, to a significant degree at doses that are safe and tolerable thus evidencing that said patients will enjoy neuroprotective benefit.

This observation is unexpected since a NK1-antagonist and/or a 5HT3 antagonist, in combination with fluoxetine, zonisamide, or a statin has not been found clinically to possess any disease modifying ability in patients with a synuclein related disorder. Moreover, nowhere has it even been suggested that the combination of these drugs might confer such significant benefit to such individuals since each of the antiparkinson drug (pramipexole), the antidepressant drug (fluoxetine), the anticonvulsant (zonisamide), an HMG CoA reductase inhibitor (a statin), and antiemetic drug(s) (5HT3 antagonist and/or NK1-antagonist) primarily act by very different mechanisms.

Finally, it has been found that, a 5HT3-antagonist and/or a NK1-antagonist, in combination with a 6-propylamino-4,5,6,7-tetrahydro-1,3-benzothiazole-2-amine, in particular pramipexole, and with fluoxetine, zonisamide, or a statin, dramatically increases the tolerable pramipexole dose to a level heretofore unattainable.

[moved to above] Not less surprisingly, it has been discovered that a further combination of fluoxetine, zonisamide, or a statin with a 5HT3-antagonist and/or a NK1-antagonist increases the efficacy of pramipexole and, in addition, allows the administration of pramipexole daily doses as high as up to 45 mg, in particular from more than 20 mg to 45 mg, more particularly from 20.25 mg to 45 mg, normally from 15 mg to 25 mg (in pramipexole dihydrochloride monohydrate).

In particular, the addition of a 5HT3-antagonist and/or a NK1-antagonist to 6-propylamino-4,5,6,7-tetrahydro-1,3-benzothiazole-2-amine and fluoxetine, zonisamide, or a statin, allows the administration of, for example, pramipexole at doses (per unit form and daily) much higher than the maximum recommended pramipexole doses or much higher than the approved daily dose of pramipexole dihydrochloride monohydrate for the treatment of PD (such as treatment of the motor symptoms of PD). Thus, for example, in a combination of a 5HT3-antagonist and/or a NK1-antagonist with pramipexole and fluoxetine, zonisamide, or a statin, the pramipexole doses per unit form or daily doses, including pediatric daily doses and doses used in the titration period, may be in a range equivalent to from 0.375 mg to 45 mg, up to 14.5 mg to 45 mg or from more than 20 mg to 45 mg, normally from 15 mg to 25 mg, of pramipexole dihydrochloride monohydrate. In an adult patient, the pramipexole dihydrochloride monohydrate daily dose may be from more than 4.5 mg to 45 mg, from 6 mg to 45 mg, from more than 10 mg to 45 mg; from 14.5 mg to 45 mg or from 20.25 mg to 45 mg, normally, from 15 mg to 35 mg, from 15 mg to 30 mg or from 15 mg to 25 mg.

These findings provide safe treatment for disabling diseases such as PD, LBD, DLB, mutations in the glucocerebrosidase (GBA) gene, AD, the Lewy body variant of AD and PD, neurodegeneration with brain iron accumulation, MSA, HD, MT, ALS, SEP, FAP, and other PMNDs.

Thus, the present invention provides a 5HT3-antagonist and/or a NK1-antagonist, for use for the treatment of a PMND in patients in need of said treatment, in combination with pramipexole and fluoxetine, zonisamide, or a statin; and the use of a 5HT3-antagonist and/or a NK1-antagonist for the preparation of a medicament for the treatment of a PMND in combination with pramipexole and fluoxetine, zonisamide, or a statin.

The invention further provides a method for treating a patient suffering from a PMND, which comprises administering to said patient in need of said treatment a 5HT3-antagonist and/or a NK1-antagonist, in combination with a 6-propylamino-4,5,6,7-tetrahydro-1,3-benzothiazole-2-amine, in particular pramipexole, and with fluoxetine, zonisamide, or a statin.

Pharmaceutically acceptable salts and solvates of the 5HT3-antagonist, the 6-propylamino-4,5,6,7-tetrahydro-1,3-benzothiazole-2-amine and fluoxetine, zonisamide, or a statin are included in the method (or use) of the present invention.

Pharmaceutically acceptable salts and solvates of the NK1-antagonist, the 6-propylamino-4,5,6,7-tetrahydro-1,3-benzothiazole-2-amine, and fluoxetine, zonisamide, or a statin are also included in the method (or use) of the present invention.

In particular, the method (or use) for treating a patient suffering from a PMND according to the present invention comprises treating said patient with an effective daily dose of a 5HT3-antagonist and/or an effective daily dose of a NK1-antagonist in combination with an effective daily dose of 6-propylamino-4,5,6,7-tetrahydro-1,3-benzothiazole-2-amine and an effective daily dose of fluoxetine, an effective daily dose of zonisamide, or an effective daily dose of a statin. Normally, said effective 5HT3-antagonist daily dose is from 1 μg to 300 mg or said effective NK1-antagonist daily dose is from 1 μg to 600 mg. Preferably, in said method (or use), the 5HT3-antagonist or NK1-antagonist is administered at a daily dose at least as high as that approved for the prevention or treatment of postoperative nausea and vomiting or for the prevention of chemotherapy-induced nausea and vomiting, in combination with an effective daily dose of 6-propylamino-4,5,6,7-tetrahydro-1,3-benzothiazole-2-amine, preferably of pramipexole, and with an effective daily dose of fluoxetine, an effective daily dose of zonisamide, or an effective daily dose of a statin. According to the invention, said effective daily dose of 6-propylamino-4,5,6,7-tetrahydro-1,3-benzothiazole-2-amine, including pediatric doses and low doses used in the titration period, is equivalent to from 0.375 mg to 3000 mg of pramipexole dihydrochloride monohydrate, including a (S)-enantiomer daily dose of from 0.375 mg to 45 mg of pramipexole dihydrochloride monohydrate.

For the treatment of a PMND, according to the above method (or use) the 5HT3-antagonist and/or NK1-antagonist, the 6-propylamino-4,5,6,7-tetrahydro-1,3-benzothiazole-2-amine, and fluoxetine, zonisamide, or statin, are each formulated in a pharmaceutical composition in admixture with a pharmaceutical carrier and concurrently or sequentially administered to a patient suffering from a PMND.

In addition, the 5HT3-antagonist and/or NK1-antagonist and the 6-propylamino-4,5,6,7-tetrahydro-1,3-benzothiazole-2-amine may be mixed together and formulated in a pharmaceutical composition (fixed-dose combination) in admixture with a pharmaceutical carrier or vehicle. This composition is for administration concurrently or sequentially to a patient suffering from a PMND, in combination with fluoxetine, zonisamide, or statin, also formulated in a pharmaceutical composition in admixture with a pharmaceutical carrier or vehicle. In order to allow flexibility in the prescription of 6-propylamino-4,5,6,7-tetrahydro-1,3-benzothiazole-2-amine, preferably pramipexole, the 5HT3-antagonist and/or NK1-antagonist and fluoxetine, zonisamide, or a statin, may be mixed together and formulated in a pharmaceutical composition (fixed-dose combination) in admixture with a pharmaceutical carrier or vehicle, to be administered to a patient suffering from a PMND, in combination with said 6-propylamino-4,5,6,7-tetrahydro-1,3-benzothiazole-2-amine, preferably pramipexole.

Thus, the invention provides a pharmaceutical composition for the treatment of protein misfolding neurodegenerative disorders in combination with propylamino-4,5,6,7-tetrahydro-1,3-benzothiazole-2-amine, in particular with pramipexole, comprising a pharmaceutical carrier or vehicle and a fixed-dose combination of a 5HT3-antagonist and/or NK1-antagonist with fluoxetine, zonisamide, or a statin. In addition, the 5HT3-antagonist and/or NK1-antagonist with the 6-propylamino-4,5,6,7-tetrahydro-1,3-benzothiazole-2-amine, preferably pramipexole, may be mixed together and formulated in a pharmaceutical composition (fixed-dose combination) in admixture with a pharmaceutical carrier or vehicle. This composition is concurrently or sequentially administered to a patient suffering from a PMND, in combination with fluoxetine, zonisamide, or statin, also formulated in a pharmaceutical composition in admixture with a pharmaceutical carrier or vehicle.

Moreover, the 5HT3-antagonist and/or NK1-antagonist may be formulated in a pharmaceutical composition in admixture with a pharmaceutical carrier or vehicle, to be administered to a patient suffering from a PMND, in combination with 6-propylamino-4,5,6,7-tetrahydro-1,3-benzothiazole-2-amine and with fluoxetine, zonisamide, or a statin, mixed together and formulated in a pharmaceutical composition (fixed-dose combination) in admixture with a pharmaceutical carrier. This composition is normally formulated in a dosage unit form.

Finally, the 5HT3-antagonist and/or NK1-antagonist, the 6-propylamino-4,5,6,7-tetrahydro-1,3-benzothiazole-2-amine and fluoxetine, zonisamide, or a statin, are mixed together and formulated in a pharmaceutical composition (fixed-dose combination) in admixture with a pharmaceutical carrier or vehicle, to be administered to a patient suffering from a PMND.

In one aspect, the present invention concerns a pharmaceutical combination comprising a 5HT3-antagonist, 6-propylamino-4,5,6,7-tetrahydro-1,3-benzothiazole-2-amine, and fluoxetine, and its use for the treatment of protein misfolding neurodegenerative diseases (or disorders) in humans.

The present invention also concerns a pharmaceutical combination comprising a NK1-antagonist, 6-propylamino-4,5,6,7-tetrahydro-1,3-benzothiazole-2-amine, and fluoxetine, and its use for the treatment of protein misfolding neurodegenerative diseases (or disorders) in humans.

A preferred embodiment of the present invention includes the use of a 5HT3-antagonist/fluoxetine combination or use of a NK1-antagonist/fluoxetine combination for augmenting the synucleinopathy-modifying potential of pramipexole in humans, thus inducing at least a slowing of disease progression at doses that are both safe and tolerable.

Another preferred embodiment of the invention includes the use of a combination of 5HT3-antagonist and a NK1-antagonist with fluoxetine for augmenting the synucleinopathy-modifying potential of pramipexole in humans.

In a second aspect, the present invention concerns a pharmaceutical combination comprising a 5HT3-antagonist, 6-propylamino-4,5,6,7-tetrahydro-1,3-benzothiazole-2-amine, and zonisamide, and its use for the treatment of protein misfolding neurodegenerative diseases (or disorders) in humans.

The present invention also concerns a pharmaceutical combination comprising a NK1-antagonist, 6-propylamino-4,5,6,7-tetrahydro-1,3-benzothiazole-2-amine, and zonisamide, and its use for the treatment of protein misfolding neurodegenerative diseases (or disorders) in humans.

A preferred embodiment of the present invention includes the use of a 5HT3-antagonist/zonisamide combination or use of a NK-1 antagonist/zonisamide combination for augmenting the synucleinopathy-modifying potential of pramipexole in humans, thus producing at least a slowing of disease progression at doses that are both safe and tolerable.

Another preferred embodiment of the invention includes the use of a combination of 5HT3-antagonist and a NK1-antagonist with zonisamide for augmenting the synucleinopathy-modifying potential of pramipexole in humans.

In a third aspect, the present invention concerns a pharmaceutical combination comprising a 5HT3-antagonist, 6-propylamino-4,5,6,7-tetrahydro-1,3-benzothiazole-2-amine, and a statin, and its use for the treatment of protein misfolding neurodegenerative diseases (or disorders) in humans.

The present invention also concerns a pharmaceutical combination comprising a NK1-antagonist, 6-propylamino-4,5,6,7-tetrahydro-1,3-benzothiazole-2-amine, and a statin, and its use for the treatment of protein misfolding neurodegenerative diseases (or disorders) in humans.

A preferred embodiment of the present invention includes the use of a 5HT3-antagonist/statin combination or use of a NK-1 antagonist/statin combination for augmenting the synucleinopathy-modifying potential of pramipexole in humans, thus producing at least a slowing of disease progression at doses that are both safe and tolerable.

Another preferred embodiment of the invention includes the use of a combination of 5HT3-antagonist and a NK1-antagonist with a statin for augmenting the synucleinopathy-modifying potential of pramipexole in humans.

DETAILED DESCRIPTION

The present invention is based on the discovery that fluoxetine, zonisamide, or a statin, synergistically and substantially improves the ability to provide safe and tolerable pramipexole doses to reduce the presence of toxic oligomers in neuronal proteins of patients suffering from a PMND, and thus benefit patients with such fatal disorders to a previously unrealized degree. The invention is also based on the discovery that a 5HT3-antagonist such as ondansetron or dolasetron and/or a NK1-antagonist such as aprepitant, acts by potentiating the neuroprotective effect of pramipexole and also by allowing the safe administration of pramipexole daily dose that are higher, and even much higher, than the pramipexole maximum recommended dose (4.5 mg/day).

As set forth above, these results are quite unexpected since

- the ability of fluoxetine, zonisamide, or a statin to augment the biomarker response to pramipexole to a degree that confers clinical patient benefit has never before been described, suggested or even anticipated in view of the lack of a rational basis and differences in the drugs' pharmacologic properties including their mechanisms of action;
- no drug or drug combination, let alone this particular combination, has ever been found to have convincing neuroprotective efficacy potential in humans with PMNDs; and
- no one, other than the present inventors, suspected that a 5HT3-antagonist and/or a NK1-antagonist would have enabled a safe increase of up to from more than 3.2 times to 10 times, normally from more than 3.2 times to 5 times, the pramipexole dihydrochloride monohydrate maximum amount per unit form and daily dose.

Thus, the present invention provides a pharmaceutical combination comprising a 5HT3-antagonist and/or a NK1-antagonist Component (a); a 6-propylamino-4,5,6,7-tetrahydro-1,3-benzothiazole-2-amine, in particular including pramipexole, Component (b); and fluoxetine, zonisamide, or a statin Component (c), for its use in the treatment of a PMND.

In this combination, the three components (a), (b), and (c) may be

- each in a pharmaceutical composition in dosage unit form comprising, respectively, said Component (a), (b) and (c), each in admixture with a pharmaceutical carrier or vehicle, herein below referred to as "combination (a/b/c)"; or
- a mixture of Component (a), Component (b), and a pharmaceutical carrier or vehicle, in a pharmaceutical composition in dosage unit form, herein below referred to as "Component (ab)"; and Component (c), in a pharmaceutical composition in dosage unit form in admixture with a pharmaceutical carrier or vehicle, the whole being herein below referred to as "combination (ab/c)"; or
- a mixture of Component (a), Component (c), and a pharmaceutical carrier or vehicle, in a pharmaceutical composition in dosage unit form, herein below referred to as "Component (ac)"; and Component (b), in a pharmaceutical composition in dosage unit form in admixture with a pharmaceutical carrier or vehicle, the whole being herein below referred to as "combination (ac/b)"; or
- a mixture of Component (b), Component (c), and a pharmaceutical carrier or vehicle, in a pharmaceutical composition in dosage unit form, herein below referred to as "Component (bc)"; and Component (a), in a pharmaceutical composition in dosage unit form in admixture with a pharmaceutical carrier or vehicle, the whole being herein below referred to as "combination (bc/a)"; or
- a mixture of Component (a), Component (b), Component (c), and a pharmaceutical carrier or vehicle, in a pharmaceutical composition in dosage unit form herein below referred to as fixed-dose "combination (abc)" or "fixed-dose combination (abc)".

Specifically, the present invention provides

- a method for the treatment of a PMND in a patient in need of said treatment, which comprises administering to said patient a 5HT3-antagonist and/or a NK1-antagonist in combination with an effective dose of a 6-propylamino-4,5,6,7-tetrahydro-1,3-benzothiazole-2-amine, in particular including pramipexole, and with an effective daily dose of fluoxetine, an effective daily dose of zonisamide, or an effective daily dose of a statin;
- a 5HT3-antagonist and/or a NK1-antagonist, for use in the treatment of a PMND in a patient in need of said treatment, in combination with an effective daily dose of 6-propylamino-4,5,6,7-tetrahydro-1,3-benzothiazole-2-amine, in particular including pramipexole, and with an effective daily dose of fluoxetine, an effective daily dose of zonisamide, or an effective daily dose of a statin; and
- the use of a 5HT3-antagonist and/or a NK1-antagonist for the preparation of a medicament for the treatment of patients suffering from a PMND, in combination with an effective daily dose of 6-propylamino-4,5,6,7-tetrahydro-1,3-benzothiazole-2-amine, in particular including pramipexole, and with an effective daily dose of fluoxetine, an effective daily dose of zonisamide, or an effective daily dose of a statin.

In the context of said method (or use), the present invention also provides

- a method for the treatment of a PMND in a patient in need of said treatment, which comprises administering to said patient a 5HT3-antagonist and/or NK1-antagonist in combination with an effective dose of a 6-propylamino-4,5,6,7-tetrahydro-1,3-benzothiazole-2-amine, in particular including pramipexole, and with an effective daily dose of fluoxetine, an effective daily dose of zonisamide, or an effective daily dose of a statin; and
- the use of a 5HT3-antagonist and/or NK1-antagonist for the preparation of a medicament (or a 5HT3-antagonist and/or NK1-antagonist for use) for the treatment of patients suffering from a PMND, in combination with an effective daily dose of 6-propylamino-4,5,6,7-tetrahydro-1,3-benzothiazole-2-amine, in particular including pramipexole, and with an effective daily dose of fluoxetine, an effective daily dose of zonisamide, or an effective daily dose of a statin.

In the context of said method (or use), the present invention also provides Component (ab) for the treatment of a PMND in combination with Component (c), Component (ac) for the treatment of a PMND in combination with Component (b), and Component (bc) for the treatment of a PMND in combination with Component (a).

In the context of said method (or use), the present invention also provides a pharmaceutical composition (abc) for use for the treatment of a PMND, comprising a pharmaceutical carrier and a fixed-dose combination of a 5HT3-antagonist and/or a NK1-antagonist Component (a), a 6-propylamino-4,5,6,7-tetrahydro-1,3-benzothiazole-2-amine Component (b) and fluoxetine, zonisamide, or a statin Component (c).

According to the present invention, due to the protective action of the 5HT3-antagonist or NK1-antagonist and the synergistic action of 5HT3-antagonist and/or NK1-antagonist and fluoxetine, zonisamide, or a statin, said method (or use) provides, at least, a safe increase of the 6-propylamino-4,5,6,7-tetrahydro-1,3-benzothiazole-2-amine (in particular of pramipexole) daily doses;

a better response to the therapy at the lower 6-propylamino-4,5,6,7-tetrahydro-1,3-benzothiazole-2-amine (in particular of pramipexole) daily doses, with the consequent ability of arresting or at least slowing the progression of said PMND in said patient.

The further benefit of early discovery of the disease condition derives from ongoing studies directed at the determination of, for example, misfolded exosomal α-Synuclein in the human peripheral blood.

The 5HT3-Antagonist and/or NK1-Antagonist Component (a)

Any of the 5HT3-antagonists disclosed in the literature may be used as Component (a) with or without a NK1-antagonist, in combination with a daily dose of the herein above defined 6-propylamino-4,5,6,7-tetrahydro-1,3-benzothiazole-2-amine and with fluoxetine, zonisamide, or a statin.

Any of the NK1-antagonists disclosed in the literature may be used as Component (a) with or without a 5HT3-antagonist, in combination with a daily dose of the herein above defined 6-propylamino-4,5,6,7-tetrahydro-1,3-benzothiazole-2-amine, preferably pramipexole, that is equivalent to up to 10 times the maximum pramipexole dihydrochloride monohydrate daily dose recommended for the relief of the motor symptoms of PD; and with fluoxetine, zonisamide, or a statin.

The 5HT3-antagonists and/or NK-1 antagonists may be safely used, as Component (a), in combination with a dose of 6-propylamino-4,5,6,7-tetrahydro-1,3-benzothiazole-2-amine, preferably pramipexole, Component (b) that is equivalent to up to 10 times the maximum pramipexole dihydrochloride monohydrate daily dose recommended for the relief of the motor symptoms of PD; and with a fluoxetine Component (c) daily dose equivalent to from 4 mg to 90 mg of fluoxetine base, or with a zonisamide Component (c) daily dose of from 25 mg to 600 mg, or with a statin Component (c) daily dose of from 0.5 mg to 80 mg.

The long-term use of a 5HT3-antagonist and/or a NK-1 antagonist Component (a) in combination with 6-propylamino-4,5,6,7-tetrahydro-1,3-benzothiazole-2-amine, preferably pramipexole, Component (b) and with fluoxetine, zonisamide, or a statin Component (c) slows the progression of a synucleinopathic disorder by mitigating or even eliminating the adverse effects induced by pramipexole, as such or as (S)-enantiomer in the racemate or in a (R)//S)-mixture, and thereby enabling the use of high doses and thus more neuroprotective doses of pramipexole.

Said 5HT3-antagonist is normally selected among those shown to be effective in or approved for the prevention or treatment of postoperative nausea and vomiting or for the prevention of the chemotherapy-induced nausea and vomiting.

The 5HT3-antagonist is preferably selected from the group consisting of 5-methyl-2-[(4-methyl-1H-imidazol-5-yl)methyl]-2,3,4,5-tetrahydro-1H-pyrido[4,3-b]indol-1-one (alosetron) and pharmaceutically acceptable salts and solvates thereof, especially its hydrochloride, disclosed in U.S. Pat. No. 5,360,800; N-(1-azabicyclo[2.2.2]octan-8-yl)-6-chloro-4-methyl-3-oxo-1,4-benzoxazine-8-carboxamide (azasetron) and pharmaceutically acceptable salts and solvates thereof, especially its hydrochloride, disclosed in U.S. Pat. No. 4,892,872; [(1S,5R)-8-methyl-8-azabicyclo[3.2.1]octan-3-yl] 3,5-dichlorobenzoate (bemesetron, CAS: 40796-97-2); (10R)-10-[(2-methyl-1H-imidazol-1-yl)methyl]-5,6,9,10-tetrahydro-4H-pyrido(3,2,1-jk)carbazol-11-one (cilansetron) and pharmaceutically acceptable salts and solvates thereof, especially its hydrochloride monohydrate, disclosed in U.S. Pat. No. 4,939,136; (3R)-10-oxo-8-azatricyclo[5.3.1.03,8]undec-5-yl 1H-indole-3-carboxylate (dolasetron) and pharmaceutically acceptable salts and solvates thereof, especially its monomethanesulfonate monohydrate, disclosed in U.S. Pat. No. 4,906,755; (+)-(R)-8,9-dihydro-10-methyl-7-[(5-methylimidazol-4-yl)methyl]pyrido[1,2-a]indol-6(7H)-one (fabesetron) and pharmaceutically acceptable salts and solvates thereof, especially its hydrochloride or maleate, disclosed in U.S. Pat. No. 5,141,945; 1-methyl-N-((1R,3r,5S)-9-methyl-9-azabicyclo[3.3.1]nonan-3-yl)-1H-indazole-3-carboxamide (granisetron) and pharmaceutically acceptable salts and solvates thereof, especially its hydrochloride, disclosed in U.S. Pat. No. 4,886,808; 2,3-dihydro-N-(8-methyl-8-azabicyclo[3.2.1]oct-3-yl)-2-oxo-1H-benzimidazole-1-carboxamide (itasetron) and pharmaceutically acceptable salts and solvates thereof, especially its hydrochloride, disclosed in U.S. Pat. No. 5,223,511; 1-phenylmethyl-2-(1-piperazinyl)-1H-benzimidazole (lerisetron) and pharmaceutically acceptable salts and solvates thereof, specially its hydrochloride, disclosed in U.S. Pat. No. 5,256,665 and, in a transdermal preparation, in U.S. Pat. No. 6,136,807; 6-fluoro-5-methyl-2-[(5-methyl-1H-imidazol-4-yl)methyl]-2,3,4,5-tetrahydro-1H-pyrido[4,3-b]indol-1-one (lurosetron, CAS 128486-54-4) and pharmaceutically acceptable salts and solvates thereof, especially its mesylate (GR 87442 N); (±) 1,2,3,9-tetrahydro-9-methyl-3-[(2-methyl-1H-imidazol-1-yl)methyl]-4H-carbazol-4-one (ondansetron) and pharmaceutically acceptable salts and solvates thereof, especially its hydrochloride dihydrate, disclosed in U.S. Pat. No. 4,695,578; (3aS)-2-[(S)-1-azabicyclo [2.2.2]oct-3-yl]-2,3,3a,4,5,6-hexahydro-1-oxo-1H-benz[de]isoquinoline (palonosetron) and pharmaceutically acceptable salts and solvates thereof, especially its hydrochloride, disclosed in U.S. Pat. No. 5,202,333; 1-methylindol-3-yl)-[(5R)-4,5,6,7-tetrahydro-3H-benzimidazol-5-yl] methanone (ramosetron) and pharmaceutically acceptable salts and solvates thereof, especially its fumarate, disclosed in U.S. Pat. No. 5,344,927; endo-N-(8-methyl-8-azabicyclo [3.2.1]oct-3-yl)-2,3-dihydro-3,3-dimethyl-indole-1-carboxamide (3,3-dimethyl-N-1αH,5αH-tropan-3α-yl-1-indolinecarboxamide, ricasetron, CAS 117086-68-7) and pharmaceutically acceptable salts and solvates thereof, especially its hydrochloride; the (3-endo)-8-methyl-8-azabicyclo [3.2.1]oct-3-yl ester of 1H-indole-3-carboxylic acid (3-tropanylindole-3-carboxylate, tropisetron) and pharmaceutically acceptable salts and solvates thereof, especially its hydrochloride, disclosed in U.S. Pat. No. 4,789,673; and 5-chloro-2,2-dimethyl-N-(8-methyl-8-azabicyclo [3.2.1]oct-3-yl)-2,3-dihydro-1-benzofuran-7-carboxamide (zatosetron) and pharmaceutically acceptable salts and solvates thereof, especially its maleate, disclosed in U.S. Pat. No. 5,563,148; the disclosures of all the US patents cited in this paragraph being incorporated herein in their entirety by reference in their entirety.

Advantageously, said 5HT3-antagonist is selected from the group consisting of azasetron and pharmaceutically salts and solvates thereof, dolasetron and pharmaceutically acceptable salts and solvates thereof, granisetron and pharmaceutically salts and solvates thereof, ondansetron and pharmaceutically salts and solvates thereof, palonosetron and pharmaceutically salts and solvates thereof, ramosetron and pharmaceutically acceptable salts and solvates thereof, and tropisetron and pharmaceutically salts and solvates thereof.

Illustrative examples of pharmaceutically acceptable salts of these advantageous 5HT3-antagonists include acid addition salts with mineral or organic acids such as hydrochloric acid, hydrobromic acid, sulfuric acid, sulfamic acid, phosphoric acid, nitric acid, acetic acid, propionic acid, stearic acid, glycolic acid, oxalic acid, succinic acid, lactic acid, maleic acid, hydroxymaleic acid, fumaric acid, malic acid, tartaric acid, citric acid, ascorbic acid, phenylacetic acid, glutamic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, and pamoic (embonic) acid. The solvation agent is generally water.

Antagonists of the 5HT3 receptor that are approved for the prevention or treatment of postoperative nausea and vomiting or for the prevention of the chemotherapy-induced nausea and vomiting are particularly useful according to the present invention. In particular, azasetron hydrochloride, commercially available in 10-mg tablets and in 10-mg vials for intravenous injection; dolasetron monomethanesulfonate monohydrate (also referred to as dolasetron mesylate), commercially available in 200-mg maximal dose tablets, and in 12.5 mg/0.625 ml vials; granisetron hydrochloride, commercially available in 2.24-mg maximal dose tablets; ondansetron hydrochloride dihydrate, commercially available in ondansetron hydrochloride dihydrate 10-mg (as maximal dose tablets), in 16-mg (in ondansetron base) suppositories, and in a 2 mg/ml (in ondansetron base) solution available in 4-mg vials, 8-mg vials and in 20-ml multidose vials; palonosetron hydrochloride, commercially available in 0.56-mg tablets and in 0.075 mg/1.5 ml or 0.25 mg/5 ml (in palonosetron base) vials; ramosetron hydrochloride, commercially available in 2.5-μg tablets, 5-μg tablets (Irribow®), 0.1 mg oral tablets (Nasea®), and in 0.3-mg vials (0.15 mg/ml) for injection (Nasea®); and tropisetron hydrochloride, commercially available in 5.64-mg capsules, in 2.256 mg/2 ml vials for intravenous injection, and in 5.64-mg vials for intravenous or subcutaneous injection; are particularly advantageous 5HT3-antagonists Component (a) for the combination with pramipexole Component (b) and with fluoxetine, zonisamide, or a statin Component (c) according to the present invention.

In the aforementioned method, use and combination, including fixed-dose combinations, said 5HT3-antagonist Component (a) is present in an amount per unit form of from 1 μg to 300 mg; and is administered at a daily dose of from 1 μg to 300 mg.

For its administration to a patient suffering from a PMND in combination with pramipexole Component (b) and fluoxetine, zonisamide, or a statin Component (c), each of the above 5HT3-antagonists is formulated in a pharmaceutical composition in dosage unit form comprising, as an active ingredient, said 5HT3-antagonist, in admixture with a pharmaceutical carrier or vehicle.

According to the present invention, the 5HT3-antagonist is used in a pharmaceutical composition comprising, as an active ingredient, said 5HT3-antagonist in an amount per unit form of from 1 μg to 300 mg, in admixture with a pharmaceutical carrier or vehicle, and is administered at a daily dose of from 1 μg to 300 mg, in combination with 6-propylamino-4,5,6,7-tetrahydro-1,3-benzothiazole-2-amine at a daily dose equivalent to from 0.375 mg to 3000 mg of pramipexole dihydrochloride monohydrate, in particular with pramipexole at a daily dose equivalent to from 0.375 mg to 45 mg, or from 0.375 mg to 42 mg of dihydrochloride monohydrate, and with fluoxetine at a daily dose equivalent to from 4 mg to 90 mg of fluoxetine base, or zonisamide at a daily dose of from 25 mg to 600 mg.

Thus, for example, a pharmaceutical composition according to the present invention to be chronically administered in combination with 6-propylamino-4,5,6,7-tetrahydro-1,3-benzothiazole-2-amine and fluoxetine, zonisamide or a statin, may comprise a 5HT3-antagonist selected from the group consisting of azasetron and pharmaceutically acceptable salts and solvates thereof, in an amount per unit form equivalent to from 5 mg to 10 mg of azasetron hydrochloride, to be administered at a daily dose equivalent to from 15 mg to 40 mg of azasetron hydrochloride; dolasetron and pharmaceutically acceptable salts and solvates thereof, in an amount per unit form equivalent to from 25 mg to 200 mg of dolasetron mesylate, to be administered at a daily dose equivalent to from 75 mg to 200 mg of dolasetron mesylate; granisetron and pharmaceutically acceptable salts and solvates thereof, in an amount per unit form equivalent to from 0.5 mg to 2 mg granisetron base, to be administered at a daily dose equivalent to from 1.5 mg to 8 mg of granisetron base; ondansetron and pharmaceutically acceptable salts and solvates thereof, in an amount per unit form equivalent to from 0.5 mg to 32 mg or from 0.5 mg to 16 mg, normally from 2 mg to 8 mg of ondansetron base, to be administered at a daily dose equivalent to from 6 mg to 64 mg, normally from 6 mg to 32 mg of ondansetron base; palonosetron and pharmaceutically acceptable salts and solvates thereof, in an amount per unit form equivalent to from 0.25 mg to 0.5 mg of palonosetron base, to be administered at a daily dose equivalent to from 0.75 mg to 2 mg of palonosetron base; ramosetron and pharmaceutically acceptable salts and solvates thereof, in an amount per unit form equivalent to from 0.05 mg to 0.5 mg of ramosetron hydrochloride, to be administered at a daily dose equivalent to from 0.05 mg to 1 mg of ramosetron hydrochloride; and tropisetron and pharmaceutically acceptable salts and solvates thereof, in an amount per unit form equivalent to from 2.5 mg to 5 mg of tropisetron base, to be administered at a daily dose equivalent to from 7.5 mg to 20 mg of tropisetron base. Each of these 5HT3-antagonists is a particularly advantageous 5HT3-antagonist Component (a) for the combination with pramipexole Component (b) and with fluoxetine, zonisamide, or a statin Component (c) according to the present invention.

Preferably, said 5HT3-antagonist is selected from the group consisting of azasetron hydrochloride, in an amount per unit form of from 5 mg to 10 mg to be administered at a daily dose of from 15 mg to 40 mg; dolasetron mesylate, in an amount per unit form of to from 25 mg to 200 mg, to be administered at a daily dose of from 75 mg to 200 mg; granisetron hydrochloride, in an amount per unit form equivalent to from 0.5 mg to 2 mg granisetron base, to be administered at a daily dose equivalent to from 1.5 mg to 16 mg, normally of from 2 mg to 8 mg of granisetron base; ondansetron hydrochloride dihydrate, in an amount equivalent to from 0.5 mg to 32 mg, normally from 2 mg to 32 mg, from 2 mg to 16 mg or from 2 mg to 8 mg ondansetron base, to be administered at a daily dose equivalent to from 6 mg to 64 mg, normally from 6 to 32 mg of ondansetron base; palonosetron hydrochloride, in an amount equivalent to from 0.25 mg to 0.5 mg palonosetron base, to be administered at a daily dose equivalent to from 0.75 mg to 2 mg of palonosetron base; ramosetron hydrochloride, in an amount per unit form of from 0.05 mg to 0.5 mg, to be administered at a daily dose of from 0.05 mg to 1 mg; and tropisetron hydrochloride, in an amount equivalent to from 2.5 mg to 5 mg of tropisetron base, to be administered at a daily dose equivalent to from 7.5 mg to 20 mg of tropisetron base.

A composition comprising a 5HT3-antagonist as illustrated above is administered to a patient suffering from a synucleinopathy, in combination with a composition comprising fluoxetine, zonisamide, or a statin, and with 6-propylamino-4,5,6,7-tetrahydro-1,3-benzothiazole-2-amine, also in a pharmaceutical composition in dosage unit form comprising said 6-propylamino-4,5,6,7-tetrahydro-1,3-benzothiazole-2-amine in an amount per unit form equivalent to from 0.125 mg to 3000 mg, in particular as a (R)/(S)-mixture, in an amount per unit form equivalent to from 50 mg to 3000 mg of pramipexole dihydrochloride monohydrate, said amount per unit form including a (S)-enantiomer amount equivalent to from 0.125 to 45 mg of pramipexole dihydrochloride monohydrate; as a racemate, in an amount equivalent to from 0.25 mg to 90 mg of pramipexole dihydrochloride monohydrate; or as pramipexole or a pharmaceutically acceptable salt thereof, in an amount equivalent to from 0.125 mg to 45 mg of pramipexole dihydrochloride monohydrate.

Advantageously, said NK1-antagonist Component (a) is selected from the group consisting of 5-[[(2R,3S)-2-[(1R)-1-[3,5-bis(trifluoromethyl)phenyl] ethoxy]-3-(4-fluorophenyl)-4-morpholinyl]methyl]-1,2-dihydro-3H-1,2,4-triazol-3-one (aprepitant), described in U.S. Pat. No. 5,719,147, US 2017/0035774 (in a liquid oral formulation), and available in an injectable emulsion in a single-dose vial for intravenous use containing 130 mg aprepitant in 18 ml of emulsion (Cinvanti®), described in U.S. Pat. No. 9,808,465 (the contents of each of which are incorporated herein in their entirety by reference);

[3-{[(2R,3S)-2-[(1R)-1-[3,5-bis(trifluoromethyl)phenyl] ethoxy]-3-(4-fluorophenyl)morpholin-4-yl]methyl}-5-oxo-2H-1,2,4-triazol-1-yl]phosphonic acid (fosaprepitant), disclosed, for example as meglumine salt in U.S. Pat. No. 5,691,336 and as di(cyclohexylamine) salt in US 2016/355533, the disclosures of which are incorporated herein in their entirety by reference;

(2S,4S)-4-(4-Acetyl-1-piperazinyl)-N-[(1R)-1-[3,5-bis (trifluoromethyl)phenyl]ethyl]-2-(4-fluoro-2-methylphenyl)-N-methyl-1-piperidinecarboxamide (casopitant) described in U.S. Pat. No. 7,294,630, the disclosure of which incorporated herein in its entirety by reference;

(2S)-1-[(3aS,4S,7aS)-4-hydroxy-4-(2-methoxyphenyl)-7,7-diphenyl-1,3,3a,5,6,7a-hexahydroisoindol-2-yl]-2-(2-methoxyphenyl)propan-1-one (INN: dapitant);

(2S,3S)—N-(5-tert-Butyl-2-methoxybenzyl)-2-(diphenylmethyl)-1-azabicyclo[2.2.2]octan-3-amine (maropitant), disclosed in U.S. Pat. No. 5,807,867, WO2005/082416 and EP 3173071 the contents of each of which are incorporated herein in their entirety by reference;

(2S,3S)-2-Diphenylmethyl-3-[(5-isopropyl-2-methoxybenzyl)amino]quinuclidine (ezlopitant), disclosed by Evangelista S (2001). "Ezlopitant Pfizer"; Current Opinion in Investigational Drugs: 2 (10): 1441-3; reviewed in Drugs: the Investigational Drugs Journal 6 (8): 758-72, the contents of each of which are incorporated herein in their entirety by reference;

(2S)—N-{2-[3,5-bis(trifluoromethyl)phenyl]ethyl}-2-[4-(cyclopropylmethyl)piperazin-1-yl]-N-methyl-2-phenylacetamide (INN figopitant);

N-[(2R)-1-[Acetyl-[(2-methoxyphenyl)methyl]amino]-3-(1H-indol-3-yl)propan-2-yl]-2-(4-piperidin-1-ylpiperidin-1-yl)acetamide (lanepitant);

2-[3,5-bis(trifluoromethyl)phenyl]-N,2-dimethyl-N-[4-(2-methylphenyl)-6-(4-methyl-1-piperazinyl)-3-pyridinyl]propanamide (netupitant), described in U.S. Pat. Nos. 6,297,375, 6,719,996, 6,593,472, and, in an oral composition comprising 300 mg of netupitant and palonosetron hydrochloride, in an amount equivalent to 0.5 mg of palonosetron base, herein below referred to as "netupitant-300/palonosetron-0.5", described in U.S. Pat. No. 8,951,969, the disclosures of which are incorporated herein in their entirety by reference;

{4-[5-{2-[3,5-bis(trifluoromethyl)phenyl]-N,2-dimethylpropanamido}-4-(2-methylphenyl)pyridin-2-yl]-1-methylpiperazin-1-ium-1-yl}methyl hydrogen phosphate (INN: fosnetupitant), described in WO 2013/082102 and, in a pure crystalline form, in US 2017/0096442, available in an injectable composition comprising fosnetupitant, in an amount of 235 mg, palonosetron hydrochloride, in an amount equivalent to 0.25 mg of palonosetron base (Akynzeo® for injection), herein below referred to as "fosnetupitant-235/palonosetron-0.25", the contents of each of which are incorporated herein in their entirety by reference;

(2R,4S)-4-[(8aS)-6-oxo-1,3,4,7,8,8a-hexahydropyrrolo [1,2-a]pyrazin-2-yl]-N-[(1R)-1-[3,5-bis(trifluoromethyl)phenyl]ethyl]-2-(4-fluoro-2-methylphenyl)-N-methylpiperidine-1-carboxamide maleate (orvepitant), described in U.S. Pat. Nos. 7,652,012 and 8,309,553, the disclosures of which are incorporated herein in their entirety by reference;

(5S,8S)-8-({(1R)-1-[3,5-bis(trifluoromethyl)phenyl] ethoxy}methyl)-8-phenyl-1,7-diazaspiro[4.5]decan-2-one (rolapitant), described in U.S. Pat. No. 7,049,320 and, for an injectable form thereof, in U.S. Pat. No. 9,101,615, the disclosures of which are incorporated herein in their entirety by reference;

3-((3aR,4R,5S,7aS)-5-[(1R)-1-[3,5-bis(trifluoromethylphenyl]ethoxy]-4-(4-fluorophenyl)-1,3,3a,4,5,6,7,7a-octahydroisoindol-2-ylcyclopent-2-en-1-one (serlopitant) described in U.S. Pat. Nos. 7,544,815 and 7,217,731, the disclosures of which are incorporated herein in their entirety by reference;

2-(S)-(4-Fluoro-2-methyl-phenyl)-piperazine-l-carboxylic acid [l-(R)-(3,5-bis-trifluoromethyl-phenyl)-ethyl]-methyl-amide (vestipitant), described in WO 2001/25219 and, in intravenous formulation having a reduced tendency to cause hemolysis, in WO 2012/175434, the disclosures of which are incorporated herein in their entirety by reference; and (2S,3S)—N-[(2-methoxy-5-[5-(trifluoromethyl)tetrazol-1-yl]phenylmethyl]-2-phenylpiperidin-3-amine (GR2015171, vofopitant), described in U.S. Pat. No. 5,703,240 (see also U.S. Pat. No. 8,093,268) and also disclosed by Gardner C J et al. Regul Pept. 1996 Aug. 27; 65(1):45-53, the contents of each of which are incorporated herein in their entirety by reference;

and pharmaceutically acceptable salts and solvates and prodrugs of each of said NK1-antagonists.

Illustrative examples of pharmaceutically acceptable salts of basic advantageous NK1-antagonists include acid addition salts with mineral or organic acids such as hydrochloric acid, hydrobromic acid, hydriodic acid, sulfuric acid, sulfamic acid, nitric acid, carbonic acid, phosphoric acid, formic acid, acetic acid, propionic acid, stearic acid, oxalic acid, malonic acid, succinic acid, fumaric acid, maleic acid, hydroxymaleic acid, lactic acid, malic acid, tartaric acid, citric acid, ascorbic acid, phenylacetic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, aspartic acid, glutamic acid and pamoic (embonic) acid. Said salt may be solvated with a solvent, said solvent normally being water.

Illustrative examples of pharmaceutically acceptable salts of acidic NK1-antagonists such as fosaprepitant include salts with inorganic bases such as alkaline metal or alkaline-earth metal salts, and salts with organic bases such as dicyclohexylamine salts, N-methyl-D-glucamine (meglumine) salts, and salts with amino acids, as described in U.S. Pat. No. 5,691,336, the contents of which are incorporated herein in their entirety by reference.

An advantageous NK1-antagonist to be used in combination with 6-propylamino-4,5,6,7-tetrahydro-1,3-benzothiazole-2-amine, in particular including pramipexole, and fluoxetine, zonisamide, or a statin, is selected from the group consisting of aprepitant and pharmaceutically acceptable salts and solvates thereof, fosaprepitant and pharmaceutically acceptable salts and solvates thereof, casopitant and pharmaceutically acceptable salts and solvates thereof, maropitant and pharmaceutically acceptable salts and solvates thereof, ezlopitant and pharmaceutically acceptable salts and solvates thereof, lanepitant and pharmaceutically acceptable salts and solvates thereof, netupitant and pharmaceutically acceptable salts and solvates thereof, orvapitant and pharmaceutically acceptable salts and solvates thereof, rolapitant and pharmaceutically acceptable salts and solvates thereof, serlopitant and pharmaceutically acceptable salts and solvates thereof, vestipitant and pharmaceutically acceptable salts and solvates thereof, vofopitant and pharmaceutically acceptable salts and solvates thereof, netupitant-300/palonosetron-0.5, and fosnetupitant-235/palonosetron-0.25. Each of these NK1-antagonists is a particularly advantageous NK1-antagonist Component (a) for the combination with pramipexole Component (b) and with fluoxetine, zonisamide, or a statin Component (c) according to the present invention.

Aprepitant, fosaprepitant meglumine, fosaprepitant di(cyclohexylamine), rolapitant, rolapitant hydrochloride, netupitant-300/palonosetron-0.5 and fosnetupitant-235/palonosetron-0.25 are particularly advantageous NK1-antagonists.

Fosaprepitant, fosaprepitant meglumine, and fosaprepitant di(cyclohexylamine), are prodrugs of aprepitant, and fosnetupitant is a prodrug of netupitant. Thus, the expressions "aprepitant and pharmaceutically acceptable salts and solvates and prodrugs thereof" and "netupitant and pharmaceutically acceptable salts and solvates and prodrugs thereof" include aprepitant, fosaprepitant, fosaprepitant meglumine, fosaprepitant di(cyclohexylamine), and other salts or solvates of aprepitant or fosaprepitant; and, respectively, netupitant, fosnetupitant, and salts or solvates of netupitant and fosnetupitant.

Antagonists of the NK1 receptor that are approved for the prevention or treatment of postoperative nausea and vomiting or for the prevention of chemotherapy-induced nausea and vomiting are particularly useful according to the present invention. In particular, aprepitant is commercially available (Emend®) in capsules containing 40 mg, 80 mg, or 125 mg aprepitant or, as fosaprepitant dimeglumine (Emend® Injection), in vials containing 115 mg or 150 mg fosaprepitant; rolapitant is available (Varubi®) in 90-mg tablets; netupitant is available (Akynzeo®) in a fixed-dose combination in capsules containing 300 mg of netupitant and 0.5 mg of the 5HT3-antagonist palonosetron (as hydrochloride), herein below referred to as "netupitant-300 mg/palonosetron-0.5 mg", and fosnetupitant is available (Akynzeo® for injection) in a fixed-dose combination in vials containing 235 mg of netupitant and 0.25 mg of the 5HT3-antagonist palonosetron (as hydrochloride), herein below referred to as "netupitant-235/palonosetron-0.25", in single-dose vial for reconstitution for intravenous injection. Each of these preparations is a particularly advantageous NK1-antagonist Component (a) for the combination with pramipexole Component (b) and with fluoxetine, zonisamide, or a statin Component (c) according to the present invention.

In the aforementioned method, use and combination, including fixed-dose combinations, said NK1-antagonist is present in an amount per unit form of from 1 μg to 600 mg, normally from 1 mg to 600 mg, or from 1 mg to 300 mg; and is administered at a daily dose of from 1 μg to 600 mg, normally from 1 mg to 600 mg, or from 1 mg to 300 mg.

In said combination, said NK1-antagonist is selected from the group consisting of aprepitant and pharmaceutically acceptable salts and solvates thereof, at a daily dose equivalent to from 10 mg to 250 mg of aprepitant; fosaprepitant and pharmaceutically acceptable salts and solvates thereof, at a daily dose equivalent to from 10 mg to 250 mg of aprepitant; rolapitant and pharmaceutically acceptable salts and solvates thereof, at a daily dose equivalent to from 15 mg to 270 mg of rolapitant, netupitant and pharmaceutically acceptable salts and solvates thereof, at a daily dose equivalent to from 150 mg to 600 mg of netupitant; NK-1 antagonist combination of netupitant-300/palonosetron-0.5; and NK-1 antagonist combination of fosnetupitant-235/palonosetron-0.25.

For its administration to a patient suffering from a PMND in combination with pramipexole and fluoxetine, zonisamide, or a statin, each of the above NK1-antagonists is formulated in a pharmaceutical composition in dosage unit form comprising, as an active ingredient, said NK1-antagonist, in admixture with a pharmaceutical carrier or vehicle.

In particular, said NK1-antagonist active ingredient of said pharmaceutical composition is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 150 mg to 600 mg of netupitant; fosnetupitant, in an amount, per unit form, equivalent to from 150 to 600 mg of netupitant; NK-1 antagonist combination of netupitant-300/palonosetron-0.5; and NK-1 antagonist combination of fosnetupitant-235/palonosetron-0.25.

Advantageously, said NK1-antagonist is aprepitant, in an amount per unit form of from 10 mg to 250 mg of aprepitant; fosaprepitant meglumine, in an amount per unit form equivalent to from 10 mg to 250 mg of aprepitant; or rolapitant, in an amount per unit form of from 15 mg to 270 mg or from 30 mg to 270 mg of rolapitant.

As set forth above, said pharmaceutical compositions comprises said NK1-antagonist in an amount per unit form of from 1 μg to 600 mg.

Aprepitant and pharmaceutically acceptable salts and solvates and prodrugs thereof, netupitant and pharmaceutically acceptable salts and solvates and prodrugs thereof and rolapitant and pharmaceutically acceptable salts and solvates and prodrugs thereof are particularly preferred NK1-antagonists of the invention.

More particularly, in said combination, said NK1-antagonist active ingredient of said pharmaceutical composition is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 150 mg to 600 mg of netupitant, fosnetupitant, in an amount, per unit form equivalent to from 150 to 600 mg of netupitant; NK-1 antagonist combination of netupitant-300/palonosetron-0.5; and NK-1 antagonist combination of fosnetupitant-235/palonosetron-0.25.

Advantageously, said NK1-antagonist is aprepitant, in an amount per unit form of from 10 mg to 250 mg of aprepitant; fosaprepitant meglumine, in an amount per unit form equivalent to from 10 mg to 250 mg of aprepitant; or rolapitant, in an amount per unit form of from 15 mg to 270 mg or from 30 mg to 270 mg of rolapitant.

A composition comprising a 5HT3-antagonist and/or NK1-antagonist as illustrated above, as Component (a) may be administered to a patient suffering from a PMND, in combination with 6-propylamino-4,5,6,7-tetrahydro-1,3-benzothiazole-2-amine, also in a pharmaceutical composition in dosage unit form, as Component (b), comprising said 6-propylamino-4,5,6,7-tetrahydro-1,3-benzothiazole-2-amine in an amount per unit form equivalent to from 0.125 mg to 3000 mg of pramipexole dihydrochloride monohydrate, inclusive of a (S)-enantiomer amount per unit form equivalent to from 0.125 mg to 45 mg of pramipexole dihydrochloride monohydrate, in particular

- as a (R)/(S)-mixture, in an amount per unit form equivalent to from 50 mg to 3000 mg of pramipexole dihydrochloride monohydrate, said amount per unit form including a (S)-enantiomer amount equivalent to from 0.125 to 45 mg of pramipexole dihydrochloride monohydrate;
- as a racemate, in an amount equivalent to from 0.25 mg to 90 mg of pramipexole dihydrochloride monohydrate; or
- as pramipexole or a pharmaceutically acceptable salt thereof, in an amount equivalent to from 0.125 mg to 45 mg of pramipexole dihydrochloride monohydrate; and with a statin, also in a pharmaceutical composition comprising said statin in an amount per unit form of from 0.5 mg to 80 mg, as Component (c).

Advantageously, said composition comprising said 5HT3-antagonist and/or NK1-antagonist as illustrated above, as Component (a) may be administered to a patient suffering from a PMND, in combination with 6-propylamino-4,5,6,7-tetrahydro-1,3-benzothiazole-2-amine, also in a pharmaceutical composition in dosage unit form, as Component (b), comprising said 6-propylamino-4,5,6,7-tetrahydro-1,3-benzothiazole-2-amine in an amount per unit form equivalent to from 0.125 mg to 3000 mg of pramipexole dihydrochloride monohydrate, inclusive of a (S)-enantiomer amount per unit form equivalent to from 15 mg to 25 mg or from more than 20 mg to 25 mg of pramipexole dihydrochloride monohydrate, in particular

- as a (R)/(S)-mixture, in an amount per unit form equivalent to from 50 mg to 3000 mg of pramipexole dihydrochloride monohydrate, said amount per unit form including a (S)-enantiomer amount equivalent to from 15 mg to 25 mg or from more than 20 mg to 25 mg of pramipexole dihydrochloride monohydrate;
- as a racemate, in an amount equivalent to from 30 mg to 50 mg or from more than 40 mg to 50 mg of pramipexole dihydrochloride monohydrate; or
- as pramipexole or a pharmaceutically acceptable salt thereof, in an amount equivalent to from 15 mg to 25 mg or from more than 20 mg to 25 mg of pramipexole dihydrochloride monohydrate; and with a statin, also in a pharmaceutical composition comprising said statin in an amount per unit form of from 0.5 mg to 80 mg, as Component (c).

In said combination with 6-propylamino-4,5,6,7-tetrahydro-1,3-benzothiazole-2-amine Component (b) and fluoxetine, zonisamide, or a statin Component (c), each of the above 5HT3-antagonists and/or NK-1 antagonists Component (a) may also be formulated in a fixed-dose combination (ab), (ac) or (abc), wherein the amount per unit form of each of said 5HT3-antagonist is, in particular, that indicated just above.

A fixed-dose combination (ab) comprises or consists of a pharmaceutical composition in dosage unit form comprising, as an active ingredient, each of said 5HT3-antagonist and/or NK-1 antagonist Component (a), in the above-illustrated amount per unit form; and, as a second active ingredient, 6-propylamino-4,5,6,7-tetrahydro-1,3-benzothiazole-2-amine Component (b), in particular pramipexole, in an effective amount per unit form as illustrated in "The 6-propylamino-4,5,6,7-tetrahydro-1,3-benzothiazole-2-amine Component (b)" section below, in admixture with a pharmaceutical carrier or vehicle. Said fixed-dose combination is administered to a patient suffering from a PMND in combination with fluoxetine, zonisamide, or a statin Component (c), also in a pharmaceutical composition in dosage unit form comprising said fluoxetine in an effective amount per unit form as illustrated in "The fluoxetine, zonisamide, or a statin Component (c)" section below, in admixture with a pharmaceutical carrier or vehicle.

In particular, as component (ab), the invention provides a pharmaceutical composition in dosage unit form comprising a 5HT3-antagonist, in an amount per unit form of from 1 μg to 300 mg and/or a NK1-antagonist, in an amount per unit form of from 1 μg to 600 mg, and a 6-propylamino-4,5,6,7-tetrahydro-1,3-benzothiazole-2-amine selected from the group consisting of pramipexole and pharmaceutically acceptable salts and solvates thereof, in an amount per unit form equivalent to from 14.5 mg to 45 mg or from 20.25 mg to 45 mg of pramipexole dihydrochloride monohydrate, in admixture with a pharmaceutical cater or vehicle.

Preferably, said 5HT3-antagonist Component (a) is selected from the group consisting of ondansetron, in an amount per unit form (in ondansetron base) of from 0.5 mg to 32 mg, and dolasetron, in an amount per unit form (in dolasetron mesylate) of from 25 mg to 200 mg.

Preferably, said NK1-antagonist Component (a) is selected from the group consisting of aprepitant, in an amount per unit form of from 10 mg to 250 mg of aprepitant, and rolapitant, in an amount per unit form of from 15 mg to 270 mg of rolapitant.

A fixed-dose combination (ac) comprises or consists of a pharmaceutical composition in dosage unit form comprising, as an active ingredient, each of said 5HT3-antagonists and/or NK-1 antagonists Component (a), in the above-illustrated amount per unit form; and as a second active ingredient, fluoxetine, zonisamide, or a statin Component (c), in an effective amount per unit form as illustrated in "The fluoxetine, zonisamide, or a statin Component (c)" section below, in admixture with a pharmaceutical carrier or vehicle. Said fixed-dose combination is administered to a patient suffering from a PMND in combination with 6-propylamino-4,5,6,7-tetrahydro-1,3-benzothiazole-2-amine, in particular pramipexole, also in a pharmaceutical composition in dosage unit form comprising said 6-propylamino-4,5,6,7-tetrahydro-1,3-benzothiazole-2-amine, in particular pramipexole Component (b), in an effective amount per unit form as illustrated in "The 6-propylamino-4,5,6,7-tetrahydro-1,3-benzothiazole-2-amine Component (b)" section below, in admixture with a pharmaceutical carrier or vehicle.

According to a specific embodiment, the invention provides a fixed-dose combination Component (ac), as a pharmaceutical composition comprising a 5HT3-antagonist, in an amount per unit form equivalent to from 1 μg to 300 mg and/or a NK1-antagonist, in an amount per unit form equivalent to from 1 μg to 600 mg, and fluoxetine or a pharmaceutically acceptable salt or solvate thereof, in an amount per unit form equivalent to from 2 mg to 90 mg of fluoxetine base, or zonisamide in an amount per unit form equivalent to from 25 mg to 600 mg of zonisamide free acid, for use in the treatment of a PMND in a patient in combination with Component (b), comprising a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg of pramipexole dihydrochloride monohydrate.

According to a specific embodiment, the present invention provides a pharmaceutical composition comprising a 5HT3-antagonist and/or NK1-antagonist, in an amount of from 1 μg to 600 mg, and a fluoxetine, in an amount of from 2 mg to 90 mg, zonisamide, in an amount of from 25 mg to 600 mg, or a statin, in an amount of from 0.5 mg to 80 mg, in admixture with a pharmaceutical carrier or vehicle. This composition is useful for the treatment of a patent suffering from a PMND in combination with, in particular, pramipexole and allows flexibility in the dosages of said pramipexole.

Normally, this composition is in dosage unit form and the above amounts are per unit form.

The invention also provides a pharmaceutical composition for use in the treatment of a PMND in a patient under pramipexole treatment, comprising a pharmaceutical carrier or vehicle and a fixed combination of a 5HT3-antagonist and/or NK1-antagonist, in an amount per unit form equivalent to from 1 μg to 600 mg, and a fluoxetine, in an amount per unit form of from 2 mg to 90 mg, zonisamide, in an amount per unit form of from 25 mg to 600 mg, or a statin, in an amount per unit form of from 0.5 mg to 80 mg.

In particular, according to this specific embodiment, the invention provides a pharmaceutical composition for the treatment of protein misfolding neurodegenerative disorders in a patient, in combination with a pramipexole daily dose equivalent to from 0.375 mg to 45 mg, up to from 14.5 mg to 45 mg or from more than 20 mg to 45 mg, normally from 15 mg to 25 mg, up to 20.25 mg to 25 mg, of pramipexole dihydrochloride monohydrate, comprising a pharmaceutical carrier or vehicle and a fixed-dose combination of a 5HT3-antagonist, in an amount per unit form of from 1 μg to 300 mg and/or a NK1-antagonist, in an amount per unit form of from 1 μg to 600 mg, and fluoxetine, in an amount per unit form equivalent to from 2 mg to 90 mg of fluoxetine base, or zonisamide, in an amount per unit form equivalent to from 25 mg to 600 mg of zonisamide free acid.

In said composition, said NK1-antagonist advantageously is aprepitant, in an amount per unit form of from 10 mg to 250 mg of aprepitant, and said statin is lovastatin, in an amount per unit form of from 5 mg to 80 mg. Preferably, said aprepitant, in said composition is in an unit form to be administered to a patient once a day, wherein said aprepitant is present in an amount of from 10 mg to 250 mg of aprepitant in an IR-form, and said lovastatin is present in an amount of from 5 mg to 80 mg or from 10 mg to 60 mg in an ER-form.

Alternatively, according to this specific embodiment the invention provides a pharmaceutical composition comprising a pharmaceutical carrier or vehicle and a fixed dose combination of a NK1-antagonist selected from the group consisting of aprepitant, in an amount per IR-unit form of from 10 mg to 250 mg of aprepitant, and rolapitant, in an amount per IR-unit form of from 15 mg to 270 mg of rolapitant; and rosuvastatin calcium, in an amount per IR-unit form of from 2.5 mg to 40 mg.

In combination with Component (ac), said pramipexole is advantageously administered to a patient at a daily dose equivalent to from more than 4.5 mg to 45 mg, from more than 6 mg to 45 mg, from 6.5 mg to 45 mg, from 14.5 mg to 45 mg or from more than 20 mg to 45 mg, normally from 15 mg to 25 mg or from 20.25 mg to 25 mg of pramipexole dihydrochloride monohydrate.

In said composition, said 5HT3-antagonist advantageously is ondansetron, in an amount per unit form equivalent to from 0.5 mg to 32 mg of ondansetron base, and said fluoxetine is in an amount per unit form equivalent to from 2 mg to 90 mg of fluoxetine base and/or said NK1-antagonist advantageously is aprepitant, in an amount per unit form of from 10 mg to 250 mg, and said zonisamide is zonisamide free acid, in an amount per unit form of from 25 mg to 600 mg. Preferably, said composition is in an IR-unit form, to be administered to a patient twice a day, wherein said ondansetron is present in an amount of from 0.5 mg to 16 mg (in ondansetron base) and/or said aprepitant is present in an amount of from 10 mg to 250 mg of aprepitant in an IR-form, and said fluoxetine is present in an amount of from 2 mg to 45 mg, normally from 2 mg to 40 mg (in fluoxetine base) or said zonisamide is zonisamide free acid present in an amount of from 200 mg to 600 mg of zonisamide free acid in an ER-form.

In said composition said 5HT3-antagonist, advantageously, may also be dolasetron, in an amount per unit form equivalent to from 25 mg to 200 mg, and/or said NK1-antagonist, advantageously, may also be rolapitant, in an amount per unit form of from 15 mg to 270 mg, and said zonisamide is zonisamide free acid, in an amount per unit form of from 25 mg to 600 mg. In said composition, said NK1-antagonist advantageously is rolapitant, in an amount per unit form of from 15 mg to 270 mg of rolapitant; and said fluoxetine is fluoxetine hydrochloride, in an amount per unit form equivalent to from 2 mg to 90 mg of fluoxetine base, or said zonisamide is zonisamide free acid, in an amount per unit form of from 25 mg to 600 mg of zonisamide free acid. Preferably, said composition is in an IR-unit form, to be administered to the patient twice a day, wherein said dolasetron is present in an amount of from 25 mg to 100 mg (in dolasetron mesylate) and/or said rolapitant is present in an amount of from 15 mg to 270 mg of rolapitant in an IR-form, and said fluoxetine is present in an amount of from 2 mg to 45 mg, normally from 2 mg to 40 mg (in fluoxetine base) or said zonisamide is zonisamide free acid present in an amount of from 200 mg to 600 mg of zonisamide free acid in an ER-form.

In said composition, said 5HT3-antagonist advantageously is ondansetron, in an amount per unit form equivalent to from 0.5 mg to 32 mg of ondansetron base, and said zonisamide is in an amount per unit form equivalent to from 25 mg to 600 mg of zonisamide free acid. Preferably, said composition Component (ac) is in an IR-unit form, to be administered to a patient twice a day, wherein said ondansetron is present in an amount of from 0.5 mg to 16 mg (in ondansetron base), and said zonisamide is present in an amount of from 25 mg to 600 mg (in zonisamide free acid).

In said composition said 5HT3-antagonist, advantageously, may also be dolasetron, in an amount per unit form equivalent to from 25 mg to 200 mg of dolasetron mesylate, and said zonisamide is in an amount per unit form equivalent to from 25 mg to 600 mg of zonisamide free acid. Preferably, said composition is in an IR-unit form, to be administered to the patient twice a day, wherein said dolasetron is present in an amount of from 25 mg to 100 mg (in dolasetron mesylate), and said zonisamide is present in an amount of from 2 mg to 45 mg, normally from 2 mg to 40 mg (in zonisamide free acid). In said composition, said 5HT3-antagonist is advantageously selected from the group consisting of ondansetron, in an amount per unit form equivalent to from 0.5 mg to 32 mg of ondansetron base, and dolasetron, in an amount per unit form equivalent to from 25 mg to 200 mg of dolasetron mesylate; said 6-propylamino-4,5,6,7-tetrahydro-1,3-benzothiazole-2-amine is selected from the group consisting of pramipexole and pharmaceutically acceptable salts and solvates thereof, in an amount per unit form equivalent to from 0.125 mg to 45 mg of pramipexole dihydrochloride monohydrate; and said zonisamide is in an amount per unit form equivalent to from 25 mg to 600 mg of zonisamide free acid.

In said combination, said pramipexole is advantageously administered to a patient at a daily dose equivalent to from more than 4.5 mg to 45 mg, from more than 6 mg to 45 mg, from 6.5 mg to 45 mg, from 14.5 mg to 45 mg or from more than 20 mg to 45 mg of pramipexole dihydrochloride monohydrate.

A fixed-dose combination (abc) comprises or consists of a pharmaceutical composition in dosage unit form comprising, as an active ingredient, each of said 5HT3-antagonist and/or NK1-antagonist Component (a), in the above-illustrated amount per unit form; as a second active ingredient, 6-propylamino-4,5,6,7-tetrahydro-1,3-benzothiazole-2-amine Component (b), preferably pramipexole, in an effective amount per unit form as illustrated in "The 6-propylamino-4,5,6,7-tetrahydro-1,3-benzothiazole-2-amine Component (b)" section below; and, as a third active ingredient, fluoxetine, zonisamide, or a statin Component (c), in an effective amount per unit form as described in "The fluoxetine, zonisamide, or a statin Component (c)" section below, in admixture with a pharmaceutical carrier or vehicle. This fixed-dose combination is destined to the treatment of a PMND in a patient in need of said treatment.

A specific fixed-dose combination (abc) comprises or consists of a pharmaceutical composition in a unit dosage form comprising (a) the 5HT3-antagonist in an amount per unit form of from 1 μg to 300 mg and/or the NK1-antagonist in an amount per unit form of from 1 μg to 600 mg;

(b) 6-propylamino-4,5,6,7-tetrahydro-1,3-benzothiazole-2-amine selected from the group consisting of the racemate or a pharmaceutically acceptable salt thereof, in an amount per unit form equivalent to from 0.25 mg to 90 mg, normally from 30 mg to 50 mg or from more than 20 mg to 50 mg of pramipexole dihydrochloride monohydrate, pramipexole or a pharmaceutically acceptable salt thereof, in an amount equivalent to from 0.125 mg to 45 mg, normally from 15 mg to 25 mg or from more than 20 mg to 25 mg of pramipexole dihydrochloride monohydrate, and a (R)/(S)-mixture, in an amount per unit form of from 50 mg to 3000 mg, inclusive of a (S)-enantiomer amount per unit form equivalent to from 0.125 mg to 45 mg, normally from 15 mg to 25 mg or from more than 20 mg to 25 mg of pramipexole dihydrochloride monohydrate; and (c) fluoxetine, in an amount per unit form equivalent to from 2 mg to 90 mg of fluoxetine base, or zonisamide, in an amount per unit form equivalent to from 25 mg to 600 mg of zonisamide free acid, or a statin, in an amount per unit form of from 0.5 mg to 80 mg;

and a pharmaceutical carrier or vehicle.

Accordingly, the invention provides a pharmaceutical composition for use in the treatment of a PMND, comprising a pharmaceutical carrier or vehicle and a fixed-dose combination of (a) a 5HT3-antagonist in an amount per unit form of from 1 μg to 300 mg and/or a NK1-antagonist in an amount per unit form of from 1 μg to 600 mg;

(b) 6-propylamino-4,5,6,7-tetrahydro-1,3-benzothiazole-2-amine selected from the group consisting of the racemate or a pharmaceutically acceptable salt thereof, in an amount per unit form equivalent to from 0.25 mg to 90 mg, normally from 30 mg to 50 mg or from more than 40 mg to 50 mg of pramipexole dihydrochloride monohydrate, pramipexole or a pharmaceutically acceptable salt thereof, in an amount equivalent to from 0.125 mg to 45 mg of pramipexole dihydrochloride monohydrate, and a (R)/(S)-mixture, in an amount per unit form of from 50 mg to 3000 mg, inclusive of a (S)-enantiomer amount per unit form equivalent to from 0.125 mg to 45 mg, normally from 15 mg to 25 mg or from more than 20 mg to 25 mg of pramipexole dihydrochloride monohydrate; and (c) fluoxetine, in an amount per unit form equivalent to from 2 mg to 90 mg of fluoxetine base, or zonisamide, in an amount per unit form equivalent to from 25 mg to 600 mg of zonisamide free acid, or a statin, in an amount per unit form of from 2.5 mg to 80 mg.

Preferably, in the above fixed-dose combination said 6-propylamino-4,5,6,7-tetrahydro-1,3-benzothiazole-2-amine is pramipexole or a pharmaceutically acceptable salt thereof, in an amount equivalent to from 0.125 mg to 45 mg, normally from 15 mg to 25 mg or from more than 20 mg to 25 mg of pramipexole dihydrochloride monohydrate.

The daily doses of the above Component (a) in said fixed dose combinations (ab), (ac), and (abc) are described above in this section.

The daily doses of the above Component (b) in said fixed dose combinations (ab), and (abc) are described below in the "6-propylamino-4,5,6,7-tetrahydro-1,3-benzothiazole-2-amine Component (b)" section.

The daily doses of the above Component (c) in said fixed dose combinations (ac), and (abc) when Component (c) is fluoxetine are from 4 mg to 90 mg.

The daily doses of the above Component (c) in said fixed dose combinations (ac), and (abc) when Component (c) is zonisamide are from 200 mg to 600 mg.

The daily doses of the above Component (c) in said fixed dose combinations (ac), and (abc) when Component (c) is statin are from 0.5 mg to 80 mg.

The 6-propylamino-4,5,6,7-tetrahydro-1,3-benzothiazole-2-amine Component (b)

As set forth in the above Definitions, the term "pramipexole" generally stands for (S)-6-propylamino-4,5,6,7-tetrahydro-1,3-benzothiazole-2-amine, as free base (pramipexole) or as pharmaceutically acceptable salts and solvates thereof, including pramipexole dihydrochloride monohydrate, their doses per unit form and their daily doses being expressed as equivalents of pramipexole dihydrochloride monohydrate, unless otherwise specified.

Specifically, the 6-propylamino-4,5,6,7-tetrahydro-1,3-benzothiazole-2-amine Component (b) is selected from the group consisting of

- pramipexole, i.e. (S)-6-propylamino-4,5,6,7-tetrahydro-1,3-benzothiazole-2-amine, and pharmaceutically acceptable salts and solvates thereof,
- the racemate, i.e. (R,S)-6-propylamino-4,5,6,7-tetrahydro-1,3-benzothiazole-2-amine, and pharmaceutically acceptable salts and solvates thereof; and
- a (S)/(R)-mixture, i.e. a mixture of (R)-6-propylamino-4,5,6,7-tetrahydro-1,3-benzothiazole-2-amine and (S)-6-propylamino-4,5,6,7-tetrahydro-1,3-benzothiazole-2-amine, normally in a pharmaceutical composition containing an effective amount of (S)-enantiomer, in admixture with a pharmaceutical carrier or vehicle.

Pharmaceutically acceptable salts or solvates of pramipexole are also included in the present invention.

Illustrative examples of pharmaceutically acceptable salts or solvates of 6-propylamino-4,5,6,7-tetrahydro-1,3-benzothiazole-2-amine are derived from inorganic or organic acids such as hydrochloric acid, hydrobromic acid, sulfuric acid, sulfamic acid, phosphoric acid, nitric acid, acetic acid, propionic acid, stearic acid, glycolic acid, oxalic acid, succinic acid, lactic acid, maleic acid, hydroxymaleic acid, fumaric acid, malic acid, tartaric acid, citric acid, ascorbic acid, phenylacetic acid, glutamic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, and pamoic (embonic) acid. The solvation solvent is normally water.

In the case of pramipexole or pharmaceutically acceptable salt or solvate thereof, pramipexole dihydrochloride monohydrate, commercially available, is the preferred 6-propylamino-4,5,6,7-tetrahydro-1,3-benzothiazole-2-amine Component (b). Pramipexole base may be preferably used in some circumstances, for example in transdermal drug delivery systems. For example, stable pharmaceutical compositions comprising pramipexole dihydrochloride monohydrate that are disclosed in WO 2012/0140604 and in WO 2008/122638, the contents of each of which are incorporated herein by reference in their entirety, and sustained release compositions comprising pramipexole dihydrochloride monohydrate that are disclosed in U.S. Pat. No. 8,399,016, the contents of which are incorporated herein by reference in their entirety, may be useful for use in combination with a 5HT3-antagonist and/or NK-1 antagonist and with fluoxetine, zonisamide, or a statin, for the treatment of a PMND.

The racemate and pramipexole, described in U.S. Pat. No. 4,886,812, the contents of which are incorporated herein in their entirety by reference, are each a useful 6-propylamino-4,5,6,7-tetrahydro-1,3-benzothiazole-2-amine for the treatment of a PMND in combination with a 5HT3-antagonist and/or NK-1 antagonist with fluoxetine, zonisamide, or a statin.

A (S)/(R)-mixture, i.e. a pharmaceutical composition comprising a therapeutically effective amount of (R)-6-propylamino-4,5,6,7-tetrahydro-1,3-benzothiazole-2-amine and a therapeutically effective amount of (S)-6-propylamino-4,5,6,7-tetrahydro-1,3-benzothiazole-2-amine, as disclosed in US 2008/0014259, the contents of which is incorporated herein in its entirety by reference, is also a useful Component (b) for the treatment of a PMND in combination with a 5HT3-antagonist and/or NK-1 antagonist Component (a) and with fluoxetine, zonisamide, or a statin Component (c).

For its administration to patients suffering from a PMND, including pediatric patients, in combination with an 5HT3-antagonist and/or NK-1 antagonist, as illustrated above in "The 5HT3-antagonist and/or NK-1 antagonist Component (a)" section, and with fluoxetine, zonisamide, or a statin, as illustrated in "The fluoxetine, zonisamide, or a statin Component (c)" below, the 6-propylamino-4,5,6,7-tetrahydro-1,3-benzothiazole-2-amine is formulated in a pharmaceutical composition in dosage unit form comprising, as an active ingredient, said 6-propylamino-4,5,6,7-tetrahydro-1,3-benzothiazole-2-amine, in admixture with a pharmaceutical carrier or vehicle.

For this administration the 6-propylamino-4,5,6,7-tetrahydro-1,3-benzothiazole-2-amine Component (b) is formulated in a pharmaceutical composition in dosage unit form comprising said 6-propylamino-4,5,6,7-tetrahydro-1,3-benzothiazole-2-amine in an amount equivalent to from 0.125 mg to 3000 mg of pramipexole dihydrochloride monohydrate, including a (S)-enantiomer amount equivalent to from 0.125 mg to 45 mg, normally from 15 mg to 25 mg or from more than 20 mg to 25 mg of pramipexole dihydrochloride monohydrate, in admixture with a pharmaceutical carrier or vehicle. Said composition is administered to a patient in need of said treatment at a daily dose equivalent to from 0.375 mg to 3000 mg of pramipexole dihydrochloride monohydrate including a (S)-enantiomer daily dose equivalent to from 0.375 mg to 45 mg, normally from 15 mg to 25 mg or from more than 20 mg to 25 mg of pramipexole dihydrochloride monohydrate, in combination with a 5HT3-antagonist and/or NK1-antagonist Component (a), at a daily dose of 1 μg to 600 mg, and with a statin Component (c), at a daily dose of from 0.5 mg to 80 mg of statin.

In particular, the 6-propylamino-4,5,6,7-tetrahydro-1,3-benzothiazole-2-amine is preferably selected from the group consisting of

- (S)-6-propylamino-4,5,6,7-tetrahydro-1,3-benzothiazole-2-amine (INN: pramipexole) and pharmaceutically acceptable salts and solvates thereof, in particular its dihydrochloride monohydrate (USAN: pramipexole hydrochloride), in an amount per unit form equivalent to from 0.125 mg to 45 mg, normally from 15 mg to 25 mg or from more than 20 mg to 25 mg of pramipexole dihydrochloride monohydrate;
- (R,S)-6-propylamino-4,5,6,7-tetrahydro-1,3-benzothiazole-2-amine (the racemate) and pharmaceutically acceptable salts an solvates thereof, in an amount per unit form equivalent to from 0.25 mg to 90 mg, normally from 30 mg to 50 mg or from more than 40 mg to 50 mg of pramipexole dihydrochloride monohydrate (thus, obviously, including an amount per unit form of (S)-6-propylamino-4,5,6,7-tetrahydro-1,3-benzothiazole-2-amine equivalent to from 0.125 mg to 45 mg, normally from 15 mg to 25 mg or from more than 20 mg to 25 mg of pramipexole dihydrochloride monohydrate, and an amount per unit form of (R)-6-propylamino-4,5,6,7-tetrahydro-1,3-benzothiazole-2-amine equivalent to from 0.125 mg to 45 mg, normally from 15 mg to 25 mg or from more than 20 mg to 25 mg of pramipexole dihydrochloride monohydrate); and a (R)/(S)-mixture, i.e. a pharmaceutical composition in dosage unit form comprising 6-propylamino-4,5,6,7-tetrahydro-1,3-benzothiazole-2-amine, in an amount per unit form equivalent to from 50 mg to 3000 mg, preferably to from 150 mg to 3000 mg, of pramipexole dihydrochloride monohydrate, said amount per unit form including a (S)-enantiomer amount equivalent to from 0.125 mg to 45 mg, normally from 15 mg to 25 mg or from more than 20 mg to 25 mg (thus, obviously, said amount per unit form being constituted by an amount of (S)-enantiomer equivalent to from 0.125 mg to 45 mg, normally from 15 mg to 25 mg or from more than 20 mg to 25 mg of pramipexole dihydrochloride monohydrate and by a (R)-6-propylamino-4,5,6,7-tetrahydro-1,3-benzothiazole-2-amine amount per unit form equivalent to from 50 mg, preferably from 150 mg, to 3000 mg (minus from 0.125 mg to 45 mg, normally minus from 15 mg to 25 mg or from more than 20 mg to 25 mg) of pramipexole dihydrochloride monohydrate.

In particular, said pharmaceutical composition in dosage unit form comprises said 6-propylamino-4,5,6,7-tetrahydro-1,3-benzothiazole-2-amine in an amount equivalent to from 0.125 mg to 3000 mg of pramipexole dihydrochloride monohydrate, including a (S)-enantiomer amount equivalent to from 0.125 mg to 45 mg of pramipexole dihydrochloride monohydrate, in admixture with a pharmaceutical carrier or vehicle.

In the above pharmaceutical composition, said 6-propylamino-4,5,6,7-tetrahydro-1,3-benzothiazole-2-amine is in an amount equivalent to from 0.125 mg to 1500 mg of pramipexole dihydrochloride monohydrate, including a (S)-enantiomer amount of from 0.125 mg to 22.5 mg, normally from 7.5 mg to 22.5 mg or from more than 10 mg to 22.5 mg in an IR-formulation, or in an amount equivalent to from 0.375 mg to 3000 mg of pramipexole dihydrochloride monohydrate, including a (S)-enantiomer amount of from 0.375 mg to 45 mg or from more than 20 mg to 45, normally from 15 mg to 25 mg or from more than 20 mg to 25 mg in an ER-formulation.

Said composition is administered to a patient in need of said treatment at a daily dose equivalent to from 0.375 mg to 3000 mg of pramipexole dihydrochloride monohydrate including a (S)-enantiomer daily dose equivalent to from 0.375 mg to 45 mg of pramipexole dihydrochloride monohydrate, in combination with a 5HT3-antagonist Component (a), at a daily dose of 1 μg to 300 mg and/or NK-1 antagonist Component (a), at a daily dose of 1 μg to 600 mg, and with fluoxetine Component (c), at a daily dose equivalent to from 4 mg to 90 mg of fluoxetine base, zonisamide Component (c), at a daily dose of from 25 mg to 600 mg, or a statin Component (c), at a daily dose of from 0.5 mg to 80 mg.

In the above pharmaceutical composition, said 6-propylamino-4,5,6,7-tetrahydro-1,3-benzothiazole-2-amine is in an amount equivalent to from 0.125 mg to 1500 mg of pramipexole dihydrochloride monohydrate, including a (S)-enantiomer amount of from 0.125 mg to 22.5 mg, in an IR-formulation, or in an amount equivalent to from 0.375 mg to 3000 mg of pramipexole dihydrochloride monohydrate, including a (S)-enantiomer amount of from 0.375 mg to 45 mg or from more than 20 mg to 45 mg, in an ER-formulation.

According to a specific embodiment, the invention provides a pharmaceutical composition in dosage unit form comprising a 6-propylamino-4,5,6,7-tetrahydro-1,3-benzothiazole-2-amine selected from the group consisting of pramipexole and pharmaceutically acceptable salts and solvates thereof in an amount per unit form equivalent to from 7.25 mg to 45 mg, normally from 7.5 mg to 25 mg, up to from more than 20 mg to 45 mg, normally from 20.25 mg to 25 mg, of pramipexole dihydrochloride monohydrate, in admixture with a pharmaceutical cater or vehicle.

More specifically, in the above composition, said pramipexole or pharmaceutically acceptable salt or solvate thereof is present either in an amount per unit form equivalent to from 7.25 mg to 22.5 mg, from 7.5 mg to 12.5 mg, or from more than 20 mg to 22.5 mg, normally from 20.25 mg to 22.5 mg of pramipexole dihydrochloride monohydrate in admixture with a pharmaceutical carrier or vehicle in an IR-formulation; or in an amount per unit form equivalent to from 15 mg to 45 mg, normally from 15 mg to 25 mg, or from more than 20 mg to 45 mg, normally from 20.25 mg to 25 mg of pramipexole dihydrochloride monohydrate in admixture with a pharmaceutical carrier or vehicle in an ER-formulation.

The effective daily dose of pramipexole, or of (S)-enantiomer, is a dose equivalent to at least the pramipexole dihydrochloride monohydrate approved daily dose for the treatment of PD. Said daily approved dose is from 0.375 mg to 4.5 mg. However, it is hereby specified that, according to the present invention, the combination of a 5HT3-antagonist and/or a NK1-antagonist and of fluoxetine, zonisamide, or a statin with 6-propylamino-4,5,6,7-tetrahydro-1,3-benzothiazole-2-amine allows the administration of 6-propylamino-4,5,6,7-tetrahydro-1,3-benzothiazole-2-amine, as pramipexole or as (S)-enantiomer component present in the racemate or in a (S/R)-mixture, at daily doses as high as the pramipexole doses approved for the treatment of Parkinson's disease without any adverse effect, but also at daily doses that are higher and also much higher than said approved doses.

For example, the daily dose of pramipexole or a pharmaceutically acceptable salt thereof may be a daily dose equivalent to from 1.1 times to 10 times, from 1.5 to 10 times, from 2.5 to 10 times, from 3 to 10 times, from more than 3.2 times to 10 times, from 4.5 times to 10 times, normally from more than 3.2 to 8 times, from more than 3.2 to 6 times, from more than 3.2 to 5 times, from 4.5 times to 10 times or from 4.5 to 5 times, higher than the maximum pramipexole dihydrochloride monohydrate recommended dose for the treatment of the symptoms of Parkinson's disease (such as motor symptoms).

For the treatment of a PMND in combination with a 5HT3-antagonist and/or a NK1-antagonist, as described in "The 5HT3-antagonist and/or a NK1-antagonist Component (a)" section above, and with fluoxetine, zonisamide, or a statin Component (c), as described in "The fluoxetine, zonisamide, or a statin component (c)" below, pramipexole is administered to a patient in need of said treatment at a daily dose equivalent to from 0.375 mg to 45 mg of pramipexole dihydrochloride monohydrate. Said daily dose-range includes pediatric doses and low daily doses used during the titration period.

In particular, pramipexole dihydrochloride monohydrate may be administered to a patient suffering from a PMND, including pediatric patients, at a daily dose equivalent to from 0.375 mg to 45 mg, from 1.5 mg to 45 mg, from more than 4.5 mg to 45 mg, from 5 mg to 45 mg, from more than 6 mg to 45 mg, from more than 10 mg to 45 mg, from 14.5 mg to 45 mg, from 15 mg to 45 mg, from 15 mg to 25 mg, normally from 0.375 mg to 20 mg, from more than 4.5 mg to 20 mg, from more than 6 mg to 20 mg, from 10 mg to 20 mg, from 13 mg to 20 mg, or from 15 mg to 20 mg of pramipexole dihydrochloride monohydrate-depending on the tolerability (in combination with the 5HT3-antagonist and/or NK-1 antagonist and fluoxetine, zonisamide, or statin).

As set forth above, with a 5HT3-antagonist and/or NK1-antagonist, in combination with 6-propylamino-4,5,6,7-tetrahydro-1,3-benzothiazole-2-amine and with fluoxetine, zonisamide, or a statin, it is possible to treat a patient suffering from a PMND by maintaining a therapeutically effective 6-propylamino-4,5,6,7-tetrahydro-1,3-benzothiazole-2-amine daily dose with minimal adverse effect.

In order to provide concurrent administration of said 5HT3-antagonist and/or NK1-antagonist and of said 6-propylamino-4,5,6,7-tetrahydro-1,3-benzothiazole-2-amine, the invention provides fixed-dose combinations, as pharmaceutical compositions in dosage unit form comprising, as active ingredients, a 5HT3-antagonist and/or a NK1-antagonist; and 6-propylamino-4,5,6,7-tetrahydro-1,3-benzothiazole-2-amine, and optionally a statin, in admixture with a pharmaceutical cater or vehicle.

The 5HT3-antagonist and/or NK1-antagonist/6-propylamino-4,5,6,7-tetrahydro-1,3-benzothiazole-2-amine/statin fixed-dose combinations are described in "The 5HT3-antagonist and/or NK1-antagonist" section above.

Thus, according to the present invention, 6-propylamino-4,5,6,7-tetrahydro-1,3-benzothiazole-2-amine Component (b), preferably pramipexole, is present in fixed-dose combinations, including, but not limited to:

in Component (ab) in a pharmaceutical composition comprising a 5HT3-antagonist and/or a NK1-antagonist Component (a), in an amount per unit form as illustrated in "The 5HT3-antagonist and/or NK1-antagonist Component (a)" section, and said 6-propylamino-4,5,6,7-tetrahydro-1,3-benzothiazole-2-amine Component (b), in a pharmaceutical composition comprising said 6-propylamino-4,5,6,7-tetrahydro-1,3-benzothiazole-2-amine Component (b), preferably pramipexole, in an amount per unit form as illustrated in this section, for the treatment of a PMND in combination with a fluoxetine, zonisamide, or statin Component (c), also in a pharmaceutical composition, in an amount per unit form as illustrated in "The fluoxetine, zonisamide, or statin Component (c)" section;

in Component (bc) in a pharmaceutical composition comprising said 6-propylamino-4,5,6,7-tetrahydro-1,3-benzothiazole-2-amine, preferably pramipexole, Component (b), in an amount per unit form as illustrated in this section, and a fluoxetine, zonisamide, or statin Component (c), in an amount per unit form as illustrated in "The fluoxetine, zonisamide, or statin Component (c)" section, for the treatment of a PMND in combination with a 5HT3-antagonist and/or NK1-antagonist Component (a), also in a pharmaceutical composition, in an amount per unit form as illustrated in "The NK1-antagonist Component (a)" section; or in a fixed dose combination (abc) including a pharmaceutical composition comprising a 5HT3-antagonist and/or NK1-antagonist Component (a), in an amount per unit form as illustrated in "The 5HT3-antagonist and/or NK1-antagonist Component (a)" section, a 6-propylamino-4,5,6,7-tetrahydro-1,3-benzothiazole-2-amine preferably pramipexole, Component (b), in an amount per unit form as illustrated in this section, and a fluoxetine, zonisamide, or statin Component (c), in an amount per unit form as illustrated in "The fluoxetine, zonisamide, or statin Component (c)" section.

In particular, in said combination, including fixed-dose combinations, with a 5HT3-antagonist and/or NK1-antagonist Component (a), and with fluoxetine, zonisamide, or statin Component (c), said 6-propylamino-4,5,6,7-tetrahydro-1,3-benzothiazole-2-amine Component (b) is pramipexole or a pharmaceutically acceptable salt thereof.

Among pramipexole and pharmaceutically acceptable salt or solvate thereof, pramipexole dihydrochloride monohydrate, commercially available, is preferred, but pramipexole base may be preferably used in some circumstances, for example in transdermal therapeutic systems. Stable pharmaceutical compositions comprising pramipexole dihydrochloride monohydrate are disclosed in WO 2012/0140604 and in WO 2008/122638, the contents of each of which are incorporated herein by reference in their entirety. Sustained release compositions comprising pramipexole dihydrochloride monohydrate, disclosed in U.S. Pat. No. 8,399,016, the contents of which are incorporated herein by reference in their entirety, may be useful for use in combination with a 5HT3-antagonist and/or NK1-antagonist Component (a) and with a fluoxetine, zonisamide, or statin Component (c) for the treatment of a PMND. For its use in combination, including fixed dose combinations, with a NK1-antagonist and with a statin, pramipexole Component (b) is formulated in a pharmaceutical composition in dosage unit form comprising said pramipexole in an amount per unit form equivalent to from 0.125 mg to 45 mg, advantageously from 15 mg to 25 mg or from more than 20 mg to 25 mg of pramipexole dihydrochloride monohydrate, in admixture with a pharmaceutical carrier or vehicle.

In particular, said pramipexole Component (b) is present in said composition in an amount per unit form equivalent to an amount-range per unit form selected from the group consisting of from 0.125 to 45 mg, from 1.5 mg to 45 mg, from 1.625 mg to 45 mg, from 3 mg to 45 mg, from more than 4.5 mg to 45 mg, from 4.8 mg to 45 mg, from more than 6 mg to 45 mg, from more than 10 mg to 45 mg, and from 20.25 mg to 45 mg of pramipexole dihydrochloride monohydrate.

Preferably, said pramipexole is present in said composition in an amount per unit form equivalent to a range selected from the group consisting of from 14.5 mg to 45 mg, from 15 mg to 45 mg, from 15 mg to 40 mg, from 15 mg to 35 mg, from 15 mg to 30 mg, from 15 mg to 25 mg and from 20.25 mg to 25 mg of pramipexole dihydrochloride monohydrate, in admixture with a pharmaceutical cater or vehicle.

According to the present invention, preferred embodiments of said pharmaceutical composition including Component (b) comprise, as an active ingredient, pramipexole or a pharmaceutically acceptable salt thereof in an amount per unit form equivalent to from 0.125 mg to 30 mg, from 0.125 mg to 22.5 mg, from 7.5 mg to 22.5 mg, from more than 20 mg to 22.5 mg, from 20.25 mg to 22.5 mg, normally from 1.5 mg to 10 mg of pramipexole dihydrochloride monohydrate, in an IR-formulation, or in an amount per unit form equivalent to from 0.375 mg to 45 mg, normally from 1.5 to 45 mg from 14.5 mg to 45 mg, from more than 20 mg to 45 mg or from 20.25 mg to 25 mg, of pramipexole dihydrochloride monohydrate, in an ER-formulation.

As set forth above in this section, according to the present invention, pramipexole may be administered to a patient, including pediatric patients, suffering from a PMND at a daily dose of from 0.375 mg to 45 mg, depending on the tolerability (in combination with the NK1-antagonist and statin). According to the present invention, the daily dose range of from 0.375 mg to 45 mg includes low doses to be administered to pediatric patient or during a titration period. More particularly, said daily dose range (in pramipexole dihydrochloride monohydrate) may be form 1.5 mg to 45 mg, from 1.6 mg to 45 mg, from 1.625 mg to 45 mg, from 3 mg to 45 mg, from more than 4.5 mg to 45 mg, from 4.8 to 45 mg, from more than 6 mg to 45 mg, and from 6.5 mg to 45 mg.

Preferably, said daily dose (in pramipexole dihydrochloride monohydrate) may be equivalent to a range selected from the group consisting of from more than 10 mg to 45 mg, from 14.5 mg to 45 mg, from 15 mg to 45 mg, from 15 mg to 35 mg, from 15 mg to 30 mg, from 15 mg to 25 mg and from 20.25 mg to 25 mg (in combination with the 5HT3-antagonist and/or NK1-antagonist and the fluoxetine, zonisamide, or statin).

More particularly, the 6-propylamino-4,5,6,7-tetrahydro-1,3-benzothiazole-2-amine is preferably selected from the group consisting of (S)-6-propylamino-4,5,6,7-tetrahydro-1,3-benzothiazole-2-amine (INN: pramipexole) and pharmaceutically acceptable salts and solvates thereof, in particular its dihydrochloride monohydrate (USAN: pramipexole hydrochloride), in an amount per unit form equivalent to from 0.125 mg to 45 mg, normally from 15 mg to 25 mg or from more than 20 mg to 25 mg of pramipexole dihydrochloride monohydrate;

(R,S)-6-propylamino-4,5,6,7-tetrahydro-1,3-benzothiazole-2-amine (the racemate) and pharmaceutically acceptable salts and solvates thereof, in an amount per unit form equivalent to from 0.25 mg to 90 mg, normally from 30 mg to 50 mg or from more than 40 mg to 50 mg of pramipexole dihydrochloride monohydrate (thus, obviously, including an amount per unit form of (S)-6-propylamino-4,5,6,7-tetrahydro-1,3-benzothiazole-2-amine equivalent to from 0.125 mg to 45 mg, normally from 15 mg to 25 mg or from more than 20 mg to 25 mg of pramipexole dihydrochloride monohydrate, and an amount per unit form of (R)-6-propylamino-4,5,6,7-tetrahydro-1,3-benzothiazole-2-amine equivalent to from 0.125 mg to 45 mg, normally from 15 mg to 25 mg or from more than 20 mg to 25 mg of pramipexole dihydrochloride monohydrate); and a (R)/(S)-mixture, i.e. a pharmaceutical composition in dosage unit form comprising 6-propylamino-4,5,6,7-tetrahydro-1,3-benzothiazole-2-amine, in an amount per unit form equivalent to from 50 mg to 3000 mg, preferably to from 150 mg to 3000 mg, of pramipexole dihydrochloride monohydrate, said amount per unit form including a (S)-enantiomer amount equivalent to from 0.125 mg to 45 mg, normally from 15 mg to 25 mg or from more than 20 mg to 25 mg (thus, obviously, said amount per unit form being constituted by an amount of (S)-enantiomer equivalent to from 0.125 mg to 45 mg, normally from 15 mg to 25 mg or from more than 20 mg to 25 mg of pramipexole dihydrochloride monohydrate and by a (R)-6-propylamino-4,5,6,7-tetrahydro-1,3-benzothiazole-2-amine amount per unit form equivalent to from 50 mg, preferably from 150 mg, to 3000 mg (minus from 0.125 mg to 45 mg, normally minus from 15 mg to 25 mg or from more than 20 mg to 25 mg) of pramipexole dihydrochloride monohydrate).

As set forth above, with a 5HT3-antagonist and/or a NK1-antagonist, in combination with 6-propylamino-4,5,6,7-tetrahydro-1,3-benzothiazole-2-amine and fluoxetine, it is possible to treat a patient suffering from a PMND by maintaining a therapeutically effective 6-propylamino-4,5,6,7-tetrahydro-1,3-benzothiazole-2-amine daily dose with minimal adverse effect.

In order to provide concurrent administration of said 5HT3-antagonist and/or a NK1-antagonist and of said 6-propylamino-4,5,6,7-tetrahydro-1,3-benzothiazole-2-amine, the invention provides fixed-dose combinations, as pharmaceutical compositions in dosage unit form comprising, as active ingredients, a 5HT3-antagonist and/or a NK1-antagonist; and 6-propylamino-4,5,6,7-tetrahydro-1,3-benzothiazole-2-amine, and optionally fluoxetine, zonisamide or a statin, in admixture with a pharmaceutical carrier or vehicle.

The 5HT3-antagonist and/or a NK1-antagonist/6-propylamino-4,5,6,7-tetrahydro-1,3-benzothiazole-2-amine/fluoxetine fixed-dose combinations are described in "The 5HT3-antagonist and/or a NK1-antagonist" section above.

Thus, according to the present invention, 6-propylamino-4,5,6,7-tetrahydro-1,3-benzothiazole-2-amine Component (b), preferably pramipexole, is present in fixed-dose combinations in particular but not limited to:

in Component (ab) in a pharmaceutical composition comprising a 5HT3-antagonist and/or a NK1-antagonist Component (a), in an amount per unit form as illustrated in "The 5HT3-antagonist and/or a NK1-antagonist Component (a)" section, and said 6-propylamino-4,5,6,7-tetrahydro-1,3-benzothiazole-2-amine Component (b), in a pharmaceutical composition comprising said 6-propylamino-4,5,6,7-tetrahydro-1,3-benzothiazole-2-amine Component (b), preferably pramipexole, in an amount per unit form as illustrated in this section, for the treatment of a PMND in combination with fluoxetine, zonisamide, or a statin Component (c), also in a pharmaceutical composition, in an amount per unit form as illustrated in "The fluoxetine, zonisamide, or a statin Component (c)" section;

in Component (bc) in a pharmaceutical composition comprising said 6-propylamino-4,5,6,7-tetrahydro-1,3-benzothiazole-2-amine, preferably pramipexole, Component (b), in an amount per unit form as illustrated in this section, and fluoxetine, zonisamide, or a statin Component (c), in an amount per unit form as illustrated in "The fluoxetine, zonisamide, or a statin Component (c)" section, for the treatment of a PMND in combination with a 5HT3-antagonist and/or a NK1-antagonist Component (a), also in a pharmaceutical composition, in an amount per unit form as illustrated in "The 5HT3-antagonist and/or a NK1-antagonist Component (a)" section; or in a fixed dose combination (abc) including a pharmaceutical composition comprising a 5HT3-antagonist and/or a NK1-antagonist Component (a), in an amount per unit form as illustrated in "The 5HT3-antagonist and/or a NK1-antagonist Component (a)" section, said 6-propylamino-4,5,6,7-tetrahydro-1,3-benzothiazole-2-amine preferably pramipexole, Component (b), in an amount per unit form as illustrated in this section, and fluoxetine, zonisamide, or a statin Component (c), in an amount per unit form as illustrated in "The fluoxetine, zonisamide, or a statin Component (c)" section.

In particular, in said combination, including fixed-dose combinations, with a 5HT3-antagonist and/or a NK1-antagonist Component (a), and with fluoxetine, zonisamide, or a statin Component (c), said 6-propylamino-4,5,6,7-tetrahydro-1,3-benzothiazole-2-amine Component (b) is pramipexole or a pharmaceutically acceptable salt thereof.

Among pramipexole and pharmaceutically acceptable salt or solvate thereof, pramipexole dihydrochloride monohydrate, commercially available, is preferred, but pramipexole base may be preferably used in some circumstances, for example in transdermal therapeutic systems. Stable pharmaceutical compositions comprising pramipexole dihydrochloride monohydrate are disclosed in WO 2012/0140604 and in WO 2008/122638, the contents of each of which are incorporated herein by reference in their entirety. Sustained release compositions comprising pramipexole dihydrochloride monohydrate, disclosed in U.S. Pat. No. 8,399,016, the contents of which are incorporated herein by reference in its entirety, may be useful for use in combination with a 5HT3-antagonist and/or a NK1-antagonist Component (a) and with fluoxetine, zonisamide, or a statin Component (c) for the treatment of a PMND.

For its use in combination, including fixed dose combinations, with a 5HT3-antagonist and/or a NK1-antagonist and fluoxetine, zonisamide, or a statin, pramipexole Component (b) is formulated in a pharmaceutical composition in dosage unit form comprising, as an active ingredient, said pramipexole in an amount per unit form equivalent to from 0.125 mg to 45 mg, normally from 15 mg to 25 mg or from more than 20 mg to 25 mg of pramipexole dihydrochloride monohydrate, in admixture with a pharmaceutical carrier or vehicle.

According to the present invention, preferred embodiments of said pharmaceutical composition including Component (b) comprise, as an active ingredient, pramipexole or a pharmaceutically acceptable salt thereof in an amount per unit form either

- equivalent to from 0.125 mg to 30 mg, from 0.125 mg to 22.5 mg, from 7.25 mg to 22.5 mg, from 7.5 mg to 22.5 mg, from 7.5 mg to 12.5 mg, from more than 20 mg to 22.5 mg, from 20.25 mg to 22.5 mg, normally from 1.5 mg to 22.5 mg of pramipexole dihydrochloride monohydrate, in an IR-formulation, or
- in an amount per unit form equivalent to from 0.375 mg to 45 mg or from 1.5 to 45 mg, from 14.5 mg to 45 mg, normally from 15 mg to 25 mg or from 20.25 mg to 25 mg, from more than 20 mg to 45 mg or from 20.25 mg of pramipexole dihydrochloride monohydrate, in an ER-formulation.

In particular, said pramipexole Component (b) is present in said composition in an amount per unit form equivalent to an amount-range per unit form selected from the group consisting of from 0.125 mg to 45 mg, from 1.5 mg to 45 mg, from 1.625 mg to 45 mg, from 3 mg to 45 mg, from more than 4.5 mg to 45 mg, from 4.8 mg to 45 mg, from more than 6 mg to 45 mg, from more than 10 mg to 45 mg and from 20.25 mg to 45 mg of pramipexole dihydrochloride monohydrate.

Preferably, said pramipexole is present in said composition in an amount per unit form equivalent to a range selected from the group consisting of from 14.5 mg to 45 mg, from 15 mg to 45 mg, from 15 mg to 40 mg, from 15 mg to 35 mg, from 15 mg to 30 mg, from 15 mg to 25 mg and from 20.25 mg to 25 mg of pramipexole dihydrochloride monohydrate, in admixture with a pharmaceutical cater or vehicle.

According to the present invention, advantageous embodiments of said pharmaceutical composition including Component (b) comprise, as an active ingredient, pramipexole or a pharmaceutically acceptable salt thereof in an amount per unit form equivalent to from 0.125 mg to 30 mg, from 0.125 mg to 22.5 mg, from 7.5 mg to 22.5 mg, from more than 20 mg to 22.5 mg, from 20.25 mg to 22.5 mg, normally from 1.5 mg to 10 mg of pramipexole dihydrochloride monohydrate, in an IR-formulation, or in an amount per unit form equivalent to from 0.375 mg to 45 mg, normally from 1.5 to 45 mg from 14.5 mg to 45 mg, from more than 20 mg to 45 mg or from 20.25 mg to 25 mg, of pramipexole dihydrochloride monohydrate, in an ER-formulation.

Preferred embodiments of said pharmaceutical composition including Component (b) comprise, as an active ingredient, pramipexole or a pharmaceutically acceptable salt thereof in an amount per unit form equivalent to from 7.5 mg to 12.5 or from more than 10 mg to 12.5 mg of pramipexole dihydrochloride monohydrate, in an IR-formulation, or in an amount per unit form equivalent to from 15 mg to 25 mg, normally from more than 20 mg to 25 mg, of pramipexole dihydrochloride monohydrate, in an ER-formulation.

As set forth above in this section, pramipexole may be administered to a patient, including pediatric patients, suffering from a PMND at a daily dose of from 0.375 mg to 45 mg, depending on the tolerability (in combination with the 5HT3-antagonist and fluoxetine). According to the present invention, the daily dose range of from 0.375 mg to 45 mg includes low doses to be administered to pediatric patients or during a titration period. More particularly, said daily dose range (in pramipexole dihydrochloride monohydrate) may be selected from the group consisting of form 1.5 mg to 45 mg, from 1.6 mg to 45 mg, from 1.625 mg to 45 mg, from 3 mg to 45 mg, from more than 4.5 mg to 45 mg, from 4.8 to 45 mg, from more than 6 mg to 45 mg, from 6.5 mg to 45 mg and from 20.25 to 45 mg.

Preferably, said daily dose (in pramipexole dihydrochloride monohydrate) may be equivalent to a range selected from the group consisting of from more than 10 mg to 45 mg, from 14.5 mg to 45 mg, from 15 mg to 45 mg, from 15 mg to 35 mg, from 15 mg to 30 mg, from 15 mg to 25 mg, from 20 mg to 25 mg, and from more than 20 mg to 25 mg (in combination with the 5HT3-antagonist and fluoxetine, zonisamide, or a statin).

For its administration to a patient suffering from PMND, including pediatric patients, in combination with a 5HT3-antagonist and/or NK1-antagonist, as described in "The 5HT3-antagonist and/or NK1-antagonist Component (a)" section above, and with fluoxetine, zonisamide, or a statin Component (c), the 6-propylamino-4,5,6,7-tetrahydro-1,3-benzothiazole-2-amine Component (b) is formulated in a pharmaceutical composition in dosage unit form comprising said 6-propylamino-4,5,6,7-tetrahydro-1,3-benzothiazole-2-amine in an amount equivalent to from 0.125 mg to 3000 mg of pramipexole dihydrochloride monohydrate, including a (S)-enantiomer amount equivalent to from 0.125 mg to 45 mg, normally from 15 mg to 25 mg or from more than 20 mg to 25 mg of pramipexole dihydrochloride monohydrate, in admixture with a pharmaceutical carrier or vehicle. Said composition is administered to a patient in need of said treatment at a daily dose equivalent to from 0.375 mg to 3000 mg of pramipexole dihydrochloride monohydrate including a (S)-enantiomer daily dose equivalent to from 0.375 mg to 45 mg, normally from 15 mg to 25 mg or from more than 20 mg to 25 mg of pramipexole dihydrochloride monohydrate, in combination with a 5HT3-antagonist and/or NK1-antagonist Component (a), at a daily dose of 1 μg to 600 mg, and with fluoxetine Component (c), at a daily dose equivalent to from 4 mg to 90 mg of fluoxetine base, zonisamide Component (c), at a daily dose equivalent to from 25 mg to 600 mg of zonisamide free acid, or a statin Component (c), at a daily dose of from 0.5 mg to 80 mg.

The daily doses of the above Component (a) in said fixed dose combinations (ab) and (abc) are described above in "The 5HT3-antagonist and/or a NK1-antagonist Component (a)" section.

The daily doses of the above Component (b) in said fixed dose combinations (ab), (bc), and (abc) are described above in this section.

The daily doses of the above Component (c) in said fixed dose combinations (bc) and (abc) when Component (c) is fluoxetine are from 4 mg to 90 mg.

The daily doses of the above Component (c) in said fixed dose combinations (ac), and (abc) when Component (c) is zonisamide are from 200 mg to 600 mg.

The daily doses of the above Component (c) in said fixed dose combinations (ac), and (abc) when Component (c) is a statin are from 0.5 mg to 80 mg.

The Fluoxetine, Zonisamide, or Statin Component (c)

Herein, "fluoxetine" stands for 1-methylamino-3-phenyl-3-[4-(trifluoromethyl)phenoxy]propane as the free base or a salt or solvate thereof. Preferably, fluoxetine may be used as free base or as its hydrochloride salt.

Fluoxetine is a selective serotonin reuptake inhibitor (SSRI) antidepressant. It is currently used in the treatment of major depressive disorder, obsessive-compulsive disorder (OCD), bulimia nervosa, panic disorder, and premenstrual dysphoric disorder. When taken by mouth at recommended maintenance IR-doses (20 mg to 80 mg daily in 1 to 2 divided doses), or ER-dose (90 mg once weekly) by patients with these disorders, fluoxetine typically evinces a high degree of efficacy.

The mechanism by which fluoxetine benefits patients with psycho-affective disorders is generally considered to be linked to the drug's ability to augment CNS serotonin-mediated transmission. In addition, however, large fluoxetine doses in rodents have been shown to induce a significant increase in extracellular concentrations of norepinephrine and dopamine after acute systemic administration (Bymaster et al. 2002).

Fluoxetine augments levels of neurotrophic factors such as glial-derived neurotrophic factor (GDNF) and brain-derived neurotrophic factor (BDNF) and, in addition, the effects of fluoxetine in in vivo transgenic models of alpha-synucleinopathy have received careful investigative attention.

It has also been extensively reported to exhibit neuroprotective activity in various cellular and animal models of neurodegenerative disease (Ubhi K et al. 2012). For example, a laboratory study examined the effect of fluoxetine in the MBP1-hα-syntg mice, a model of MSA (Shults, et al. 2005).

Fluoxetine can protect against 6-OHDA (6-hydroxydopamine) (Suzuki, et al. 2010) and MPTP (1-methyl-4-phenyl-1,2,3,6-tetrahydropyridine) (Chung, et al. 2011)-induced damage in toxin-induced models of PD.

The term "effective daily dose of fluoxetine", as used herein, refers to a daily dose of fluoxetine hydrochloride equivalent to from 4 mg to 90 mg of fluoxetine base. Said effective dose includes (a) low daily doses of from 4 mg to less than 20 mg (in fluoxetine base) for use, in combination with a 5HT3-antagonist and/or a NK1-antagonist and 6-propylamino-4,5,6,7-tetrahydro-1,3-benzothiazole-2-amine, in pediatric patients and during the titration period of said 6-propylamino-4,5,6,7-tetrahydro-1,3-benzothiazole-2-amine;

(b) daily doses of from 20 mg to 90 mg, normally from 20 mg to 80 mg (in fluoxetine base), in an IR or ER formulation; and (c) the fluoxetine daily dose released daily from the specific 90 mg ER-weekly preparation.

As set forth in the definitions, "fluoxetine" generally stands for the active principle per se, independently of the salt or solvate of said active principle, and "6-propylamino-4,5,6,7-tetrahydro-1,3-benzothiazole-2-amine" generally stands for the active principle per se, independently of the steric configuration and of the salt or solvate of said active principle.

In particular, the term "fluoxetine" includes the free base and pharmaceutically acceptable salts and solvates thereof, their doses per unit form or their daily doses being expressed as equivalents of fluoxetine base.

Pharmaceutically acceptable salts or solvates of fluoxetine are also included in the present invention. Illustrative examples of pharmaceutically acceptable salts of fluoxetine include acid addition salts with mineral or organic acids such as hydrochloric acid, hydrobromic acid, hydriodic acid, sulfuric acid, sulfamic acid, phosphoric acid, nitric acid, formic acid, acetic acid, propionic acid, stearic acid, glycolic acid, oxalic acid, malonic acid, succinic acid, lactic acid, maleic acid, hydroxymaleic acid, fumaric acid, malic acid, tartaric acid, citric acid, ascorbic acid, phenylacetic acid, carbonic acid, glutamic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, aspartic acid and pamoic (embonic) acid. The solvation agent is generally water.

For its use for the treatment of a PMND in combination with a 5HT3-antagonist and/or a NK1-antagonist Component (a) and with 6-propylamino-4,5,6,7-tetrahydro-1,3-benzothiazole-2-amine Component (b), fluoxetine Component (c) is formulated in a pharmaceutical composition in admixture with a pharmaceutical carrier or vehicle.

In the above composition, fluoxetine Component (c) is present in an amount equivalent to from 2 mg to 90 mg of fluoxetine hydrochloride.

In particular, the dose of fluoxetine per IR-unit form will be in an amount that is equivalent to from 2 mg to 45 mg or from 5 mg to 45 mg, normally from 2 mg to 40 mg or from 5 mg to 40 mg of fluoxetine base, depending on safety and tolerability, in combination with the 5HT3-antagonist and/or a NK1-antagonist Component (a) and the 6-propylamino-4,5,6,7-tetrahydro-1,3-benzothiazole-2-amine Component (b). Preferably, said fluoxetine pharmaceutically acceptable salt is fluoxetine hydrochloride in the above IR-dose per unit form.

The dose per unit form of fluoxetine, or of a pharmaceutically acceptable salt or solvate thereof, in an ER-formulation, including slow-release compositions and TTDS, such as transdermal patches, will be in an amount (in fluoxetine base) of from 4 mg to 90 mg, normally from 20 mg to 90 mg, depending on safety and tolerability, in combination with the 5HT3-antagonist and/or a NK1-antagonist Component (a) and the 6-propylamino-4,5,6,7-tetrahydro-1,3-benzothiazole-2-amine Component (b).

As set forth above, through the use of a 5HT3-antagonist and/or a NK1-antagonist, in combination with 6-propylamino-4,5,6,7-tetrahydro-1,3-benzothiazole-2-amine and fluoxetine, it is possible to treat a patient suffering from a PMND by maintaining a therapeutic 6-propylamino-4,5,6,7-tetrahydro-1,3-benzothiazole-2-amine daily dose with minimal adverse effect.

In order to provide concurrent administration of said 5HT3-antagonist and/or a NK1-antagonist and of said fluoxetine, the invention provides fixed-dose combinations, as pharmaceutical compositions in dosage unit form comprising, as active ingredients, a 5HT3-antagonist and/or a NK1-antagonist; and fluoxetine; and optionally 6-propylamino-4,5,6,7-tetrahydro-1,3-benzothiazole-2-amine, preferably pramipexole, in admixture with a pharmaceutical carrier or vehicle.

Thus, in said combination with the 5HT3-antagonist and/or a NK1-antagonist and 6-propylamino-4,5,6,7-tetrahydro-1,3-benzothiazole, preferably pramipexole, fluoxetine may also be formulated in a fixed-dose combination (ac), (bc) or (abc).

As stated in the definitions, zonisamide Component (c), is benzo[d]isoxazol-3-ylmethanesulfonamide

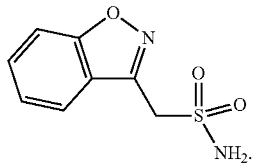 [SMILES: NS(=O)(=O)Cc1noc2ccccc12]

According to the present invention, zonisamide may be used, in the above acidic form or as an alkaline metal salt thereof, in particular as its sodium salt (zonisamide sodium), in combination with a 5HT3-antagonist and with 6-propylamino-4,5,6,7-tetrahydro-1,3-benzothiazole. Herein, unless otherwise specified, the term “zonisamide” includes its salts, but the doses per unit form and the daily doses refer to the free acid.

The effective daily dose of zonisamide is a dose at least as high as the zonisamide approved daily dose for its antiseizure indication. Said daily approved dose is from 200 mg to 600 mg.

For its use for the treatment of a PMND in combination with a 5HT3-antagonist and/or a NK1-antagonist Component (a) and with 6-propylamino-4,5,6,7-tetrahydro-1,3-benzothiazole Component (b), zonisamide Component (c) is formulated in a pharmaceutical composition in admixture with a pharmaceutical carrier or vehicle.

In the above composition, zonisamide Component (c) is present in an amount of from 25 mg to 600 mg.

In particular, the dose of zonisamide per IR-unit form will be in an amount of from 25 mg to 200 mg, depending on safety and tolerability, in combination with the 5HT3-antagonist and/or a NK1-antagonist Component (a) and pramipexole Component (b).

The dose of zonisamide per ER-unit form will be in an amount of from 25 mg to 600 mg, including low dose used in the pramipexole titration period, normally from 200 mg to 600 mg, depending on safety and 6-propylamino-4,5,6,7-tetrahydro-1,3-benzothiazole, in combination with the 5HT3-antagonist and/or a NK1-antagonist Component (a) and 6-propylamino-4,5,6,7-tetrahydro-1,3-benzothiazole Component (b).

As set forth above, through the use of a 5HT3-antagonist and/or NK-1 antagonist, in combination with 6-propylamino-4,5,6,7-tetrahydro-1,3-benzothiazole, preferably pramipexole, and zonisamide, it is possible to treat a patient suffering from a PMND by maintaining a therapeutically effective 6-propylamino-4,5,6,7-tetrahydro-1,3-benzothiazole daily dose with minimal adverse effect.

Prior to the present invention, the neuroprotective action of statins had not actually been evidenced in patients with a PMND and such action by statins alone would be expected to be minimal.

According to the present invention, a statin, in combination (including fixed-dose combinations) with a NK1-antagonist, assures a safe treatment of PMND in patients in need of said treatment, in combination with fa 6-propylamino-4,5,6,7-tetrahydro-1,3-benzothiazole-2-amine, in particular with pramipexole, with the intent of slowing or even arresting the progression of the disease.

Said statin may be selected from the group consisting of (3R,5R)-7-[2-(4-fluorophenyl)-3-phenyl-4-(phenylcarbamoyl)-5-propan-2-ylpyrrol-1-yl]-3,5-dihydroxyheptanoic acid (atorvastatin) and pharmaceutically acceptable salts and solvates thereof, disclosed in U.S. Pat. No. 4,681,893 and, as the calcium salt thereof, in U.S. Pat. No. 5,273,995, the contents of both of which are incorporated herein in their entirety by reference;

(3R,5S,6E)-7-[4-(4-Fluorophenyl)-5-(methoxymethyl)-2,6-bis(propan-2-yl)pyridin-3-yl]-3,5-dihydroxyhept-6-enoic acid (cerivastatin) and pharmaceutically acceptable salts and solvates thereof, described in U.S. Pat. Nos. 5,006,530, 5,177,080 and 5,502,199, the contents of which are incorporated herein in their entirety by reference;

(4S,6R)-6-[(E)-2-[2-(4-fluoro-3-methylphenyl)-4,4,6,6-tetramethylcyclohexen-1-yl]ethenyl]-4-hydroxyoxan-2-one (dalvastatin), described in U.S. Pat. No. 4,863,957 and in EP 738510, the contents of both of which are incorporated herein in their entirety by reference;

[R*,S*-(E)]-(±)-7-[3-(4-fluorophenyl)-1-(1-methylethyl)-1H-indol-2-yl]-3,5-dihydroxy-6-heptenoic acid (fluindostatin) disclosed in European Patent Application Publication No. 363934 and, in a fixed-dose combination with amlodipine, in US 2002/0025981, the contents of both of which are incorporated herein in their entirety by reference.

(3R,5S,6E)-7-[3-(4-Fluorophenyl)-1-(propan-2-yl)-1H-indol-2-yl]-3,5-dihydroxyhept-6-enoic acid (fluvastatin), described in U.S. Pat. No. 4,739,073, the contents of which are incorporated herein in their entirety by reference;

(1S,3R,7S,8S,8aR)-8-{2-[(2R,4R)-4-Hydroxy-6-oxooxan-2-yl]ethyl}-3,7-dimethyl-1,2,3,7,8,8a-hexahydronaphthalen-1-yl (2S)-2-methylbutanoate (lovastatin), described in U.S. Pat. No. 4,231,938, the contents of which are incorporated herein in their entirety by reference;

(3R,5S,6E)-7-[2-Cyclopropyl-4-(4-fluorophenyl)quinolin-3-yl]-3,5-dihydroxyhept-6-enoic acid (pitavastatin) and pharmaceutically acceptable salts and solvates thereof, described in U.S. Pat. No. 5,011,930, the contents of which are incorporated herein in their entirety by reference;

(1S,7S,8S,8aR)-8-{2-[(2R,4R)-4-Hydroxy-6-oxotetrahydro-2H-pyran-2-yl]ethyl}-7-methyl-1,2,3,7,8,8a-hexahydronaphthalen-1-yl (2S)-2-methylbutanoate (1S,7S,8S,8aR)-8-{2-[(2R,4R)-4-Hydroxy-6-oxotetrahydro-2H-pyran-2-yl]ethyl}-7-methyl-1,2,3,7,8,8a-hexahydronaphthalen-1-yl (2S)-2-methylbutanoate (mevastatin), disclosed in U.S. Pat. No. 3,983,140, the contents of which are incorporated herein in their entirety by reference;

(3R,5R)-3,5-dihydroxy-7-((1R,2S,6S,8R,8aR)-6-hydroxy-2-methyl-8-{[(2S)-2-methylbutanoyl]oxy}-1,2,6,7,8,8a-hexahydronaphthalen-1-yl)-heptanoic acid (pravastatin) and pharmaceutically acceptable salts and solvates thereof, described in U.S. Pat. No. 4,346,227, the contents of which are incorporated herein in their entirety by reference;

(1S,3R,7S,8S,8aR)-8-{2-[(2R,4R)-4-hydroxy-6-oxotetrahydro-2H-pyran-2-yl]ethyl}-3,7-dimethyl-1,2,3,7,8,8a-hexahydronaphthalen-1-yl 2,2-dimethylbutanoate; described in U.S. Pat. No. 4,444,784, the contents of which are incorporated herein in their entirety by reference;

(E,3R,5S)-7-[4-(4-fluorophenyl)-5-(methoxymethyl)-2,6-dipropan-2-yl-pyridin-3-yl]-3,5-dihydroxy-hept-6-enoic acid (rivastatin) and pharmaceutically acceptable salts and solvates thereof, (3R,5S,6E)-7-[4-(4-Fluorophenyl)-2-(N-methylmethanesulfonamido)-6-(propan-2-yl)pyrimidin-5-yl]-3,5-dihydroxyhept-6-enoic acid (rosuvastatin) and pharmaceutically acceptable salts and solvates thereof, described in U.S. Pat. No. 5,260,440, the contents of which are incorporated herein in their entirety by reference.

butanoic acid, 2,2-dimethyl-1,2,3,7,8,8a-hexahydro-3,7-dimethyl-8-[2-(tetrahydro-4-hydroxy-6-oxo-2H-pyran-2-yl)-ethyl]-1-naphthalenyl ester, [1S-[1α,3α,7β,8β(2S*,4S*)-8aβ]] (velostatin or synvinolin), disclosed in U.S. Pat. Nos. 4,448,784 and 4,450,171, both of which are incorporated herein by reference; and pharmaceutically acceptable salts and solvates and prodrugs of said statins. Esters of the above statins are also included in the context of the present invention.

According to the present invention, said statin is preferably selected from the group consisting of atorvastatin, available in 20 mg or 40 mg and 80 mg tablets;

fluvastatin, available in IR capsules containing an amount of fluvastatin sodium, equivalent to 20 mg, 40 mg of fluvastatin, and in 80 mg (in fluvastatin) ER tablets;

lovastatin, available in 20 mg and 40 mg IR and in 60 mg ER tablets;

pitavastatin, available in 1 mg, 2 mg and 4 mg tablets;

pravastatin, available in 10 mg, 20 mg, 40 mg, and 80 mg tablets;

rosuvastatin, available in 5 mg, 10 mg, 20 mg, and 40 mg tablets; and simvastatin, available in 5 mg, 10 mg, 20 mg, 40 mg and 80 mg tablets.

A particularly preferred statin is lovastatin.

Chemically, these statins are characterized by a 3,5-dihydroxyheptane or 3,5-dihydroxyhept-6-ene carboxylic acid linked, via its 7-position, to a carbocyclic or heterocyclic structure. Thus, they can be in form of a lactone formed by loss of a $H_2O$ between the carboxy group with the 5-hydroxy group of the 3,5-dihydroxyheptane carboxylic acid side-chain according to Scheme 1, wherein the steric configuration is not shown, and some of them are used in their lactone form.

Scheme 1

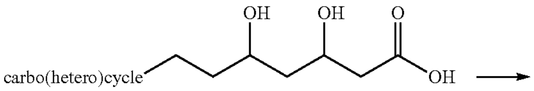

acidic form

-continued

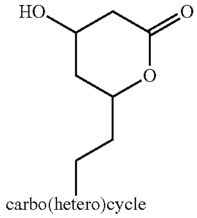

lactone form

Both the acid and lactone forms of these acids are included in the family of statins of the present invention.

Herein, the expressions "salt or solvate thereof", "salts or solvates thereof" and "salts and solvates thereof", in reference to a statin in acidic form, indicate that the salt of said statin may be solvated with a solvent, normally water. Said salt normally is an alkaline metal salt or alkaline-earth metal salt, preferably sodium or calcium salt.

According to the present method (or use), the statin is administered to said patient at a daily dose that is from the half of the aforementioned daily dose approved for the treatment of dyslipidemia, up to the maximum daily dose approved for the treatment of dyslipidemia Normally, said statin is administered at a daily dose of from 0.5 mg to 80 mg. Preferably, said daily dose is lower than the maximum approved daily dose of each of said statins.

Preferably, in the treatment of a patient suffering from a synucleinopathy, in combination with an effective daily dose of 6-propylamino-4,5,6,7-tetrahydro-1,3-benzothiazole-2-amine, a statin selected from the group consisting of atorvastatin calcium trihydrate, administered to said patient at a daily dose equivalent to from 5 mg to 80 mg, normally from 5 mg to 60 mg of atorvastatin free acid;

fluvastatin sodium, administered to said patient at a daily dose equivalent to from 10 mg to 80 mg, normally from 10 mg to 60 mg of fluvastatin free acid;

lovastatin, administered to said patient at a daily dose of from 5 mg to 80 mg, normally from 5 mg to 60 mg;

pitavastatin calcium, administered to said patient at a daily dose equivalent to from 0.5 mg to 4 mg, normally from 0.5 mg to 3 mg of pitavastatin free acid;

pravastatin sodium, administered to said patient at a daily dose of from 2.5 mg to 60 mg, normally from 2.5 mg to 40 mg;

simvastatin, administered to said patient at a daily dose of from 2.5 mg to 40 mg, normally from 2.5 mg to 30 mg; and rosuvastatin calcium, administered to said patient at a daily dose of from 2.5 mg to 40 mg, normally from 2.5 mg to 30 mg, is particularly advantageous.

In order to be administered to a patient suffering from a PMND, the above statin is formulated in a pharmaceutical composition in dosage unit form comprising said statin in an amount per unit form of from 0.5 mg to 80 mg, in admixture with a pharmaceutical carrier or vehicle.

Said statin is preferably selected from the group consisting of atorvastatine and pharmaceutically acceptable salts and solvates thereof, in an amount per unit form equivalent to from 5 mg to 80 mg, normally from 5 mg to 60 mg of atorvastatin free acid;

fluvastatin and pharmaceutically acceptable salts and solvates thereof, in an amount per unit form equivalent to from 10 mg to 80 mg, normally from 10 mg to 60 mg of fluvastatin free acid;

lovastatin, in an amount of from 5 mg to 80 mg, normally from 5 mg to 60 mg or from 10 mg to 60 mg;

pitavastatin and pharmaceutically acceptable salts and solvates thereof, in an amount per unit form equivalent to from 0.5 mg to 4 mg, normally from 0.5 mg to 3 mg of pitavastatin free acid;

pravastatin and pharmaceutically acceptable salts and solvates thereof, in an amount per unit form equivalent to from 2.5 mg to 60 mg, normally from 2.5 mg to 40 mg of pravastatin sodium;

rosuvastatin and pharmaceutically acceptable salts and solvates thereof, in an amount per unit form equivalent to from 2.5 mg to 40 mg, normally from 2.5 mg to 30 mg of rosuvastatin calcium; and simvastatin, in an amount per unit form of from 2.5 mg to 40 mg, normally from 2.5 mg to 30 mg.

As set forth above, through the use of a 5HT3-antagonist and/or NK1-antagonist, in combination with 6-propylamino-4,5,6,7-tetrahydro-1,3-benzothiazole-2-amine and a statin, it is possible to treat a patient suffering from a PMND by maintaining a therapeutically 6-propylamino-4,5,6,7-tetrahydro-1,3-benzothiazole-2-amine daily dose with minimal adverse effects.

In order to provide concurrent administration of said 5HT3-antagonist and/or a NK1-antagonist and of said statin, the invention provides fixed-dose combinations, as pharmaceutical compositions in dosage unit form comprising, as active ingredients, a 5HT3-antagonist and/or a NK1-antagonist and statin, and optionally 6-propylamino-4,5,6,7-tetrahydro-1,3-benzothiazole-2-amine, in admixture with a pharmaceutical carrier or vehicle.

Thus, in said combination with the 5HT3-antagonist and/or NK1-antagonist and 6-propylamino-4,5,6,7-tetrahydro-1,3-benzothiazole, preferably pramipexole, the statin may also be formulated in a fixed-dose combination (ac), (bc) or (abc).

According to an embodiment, said combination comprises or consists of a pharmaceutical composition comprising a pharmaceutically acceptable carrier or vehicle and a fixed-dose combination of a 5HT3-antagonist and/or NK1-antagonist and a statin. This composition is for use for the treatment of a PMND in a patient, in further combination with 6-propylamino-4,5,6,7-tetrahydro-1,3-benzothiazole-2-amine, normally with pramipexole.

A fixed-dose combination (ac) comprises or consists of a pharmaceutical composition in dosage unit form comprising a 5HT3-antagonist and/or a NK1-antagonist Component (a), in an effective amount per unit form as illustrated above in "The 5HT3-antagonist and/or a NK1-antagonist Component (a)" section; and fluoxetine, zonisamide, or a statin Component (c), in an amount per unit form as described above in this section, in admixture with a pharmaceutical carrier or vehicle. Said fixed-dose combination is administered to a patient suffering from a PMND in combination with 6-propylamino-4,5,6,7-tetrahydro-1,3-benzothiazole-2-amine Component (b), preferably pramipexole, also in a pharmaceutical composition in dosage unit form comprising an effective amount per unit form of said 6-propylamino-4,5,6,7-tetrahydro-1,3-benzothiazole-2-amine, preferably pramipexole, as described above in "The 6-propylamino-4,5,6,7-tetrahydro-1,3-benzothiazole-2-amine Component (b)" section, in admixture with a pharmaceutical carrier or vehicle. Said fixed-dose combination (ac), and its use in the treatment of a PMND are described in detail in "The 5HT3-antagonist and/or NK-1 antagonist Component (a) section above.

As mentioned above, this Component (ac) of a 5HT3-antagonist and/or NK1-antagonist/6-propylamino-4,5,6,7-tetrahydro-1,3-benzothiazole-2-amine/fluoxetine, zonisamide, or statin combination is particularly advantageous because it allows a flexibility in the dosage and in the mode of administration of the 6-propylamino-4,5,6,7-tetrahydro-1,3-benzothiazole-2-amine, Component (b), in particular of pramipexole.

A fixed-dose combination (bc) comprises or consists of a pharmaceutical composition in dosage unit form comprising said 6-propylamino-4,5,6,7-tetrahydro-1,3-benzothiazole-2-amine Component (b), preferably pramipexole, in an effective amount per unit form as illustrated above in "The 6-propylamino-4,5,6,7-tetrahydro-1,3-benzothiazole-2-amine Component (b)" section; and fluoxetine, zonisamide, or a statin Component (c), in an amount per unit form as illustrated above in this section, in admixture with a pharmaceutical carrier or vehicle. Said fixed-dose combination is administered to a patient suffering from a PMND in combination with a 5HT3-antagonist and/or a NK1-antagonist Component (a), also in a pharmaceutical composition in dosage unit form comprising said 5HT3-antagonist and/or a NK1-antagonist in an effective amount per unit form as described above in "The 5HT3-antagonist and/or a NK1-antagonist Component (a)" section, in admixture with a pharmaceutical carrier or vehicle.

In particular, as Component (bc), the invention provides a pharmaceutical composition in dosage unit form comprising a 6-propylamino-4,5,6,7-tetrahydro-1,3-benzothiazole-2-amine selected from the group consisting of pramipexole and pharmaceutically acceptable salts and solvates thereof, in an amount per unit form equivalent to from more than 20 mg to 45 mg, normally from 20.25 mg to 45 mg of pramipexole dihydrochloride monohydrate, and a fluoxetine selected from the group consisting of fluoxetine and pharmaceutically acceptable salts and solvates thereof, in an amount per unit form equivalent to from 2 mg to 90 mg of fluoxetine base in admixture with a pharmaceutical carrier or vehicle, or zonisamide, in an amount per unit form equivalent to from 25 mg to 600 mg of zonisamide free acid in admixture with a pharmaceutical carrier or vehicle, or a statin, in an amount per unit form of from 0.5 mg to 80 mg in admixture with a pharmaceutical carrier or vehicle.

More particularly, said statin is selected from the group consisting of lovastatin, in an amount per unit form of from 5 mg to 80 mg, normally from 10 mg to 60 mg, and rosuvastatin calcium, in an amount per unit form of from 2.5 mg to 40 mg.

According to another embodiment, said combination comprises or consists of a pharmaceutical composition comprising a pharmaceutically acceptable carrier or vehicle and a fixed-dose combination (abc) of a 5HT3-antagonist and/or NK1-antagonist, a 6-propylamino-4,5,6,7-tetrahydro-1,3-benzothiazole-2-amine, and a statin. This composition is for use for the treatment of a PMND in a patient. Said 6-propylamino-4,5,6,7-tetrahydro-1,3-benzothiazole-2-amine preferably is pramipexole.

A fixed-dose combination (abc) comprises or consists of a pharmaceutical composition in dosage unit form comprising a 5HT3-antagonist and/or a NK1-antagonist Component (a), in an effective amount per unit form as described above in "The 5HT3-antagonist and/or a NK1-antagonist Component (a)" section;

6-propylamino-4,5,6,7-tetrahydro-1,3-benzothiazole-2-amine preferably pramipexole, Component (b), in an effective amount per unit form as illustrated above in "The 6-propylamino-4,5,6,7-tetrahydro-1,3-benzothiazole-2-amine Component (b)" section; and fluoxetine, zonisamide, or a statin Component (c), in an effective amount per unit form as illustrated above in this section, in admixture with a pharmaceutical carrier or vehicle.

This fixed-dose combination is for the treatment of a PMND in a patient in need of said treatment.

A specific fixed-dose combination (abc) comprises or consists of a pharmaceutical composition in dosage unit form comprising a 5HT3-antagonist Component (a), in an amount per unit form of from 1 μg to 300 mg;

pramipexole Component (b), in an effective amount per unit form (in pramipexole dihydrochloride monohydrate) of from 7.5 mg to 25 mg; and fluoxetine, zonisamide, or a statin Component (c), in an effective amount per unit form as illustrated in this section, in admixture with a pharmaceutical carrier or vehicle.

The amounts per unit form and the daily doses of each of the above Component (a) and Component (b) in said fixed dose combinations (ac), (bc), and (abc) are illustrated in "The 5HT3-antagonist and/or NK1-antagonist Component (a)" and, respectively, in "The 6-propylamino-4,5,6,7-tetrahydro-1,3-benzothiazole-2-amine Component (b)" sections above.

The amount per unit form of fluoxetine Component (c) in said fixed dose combinations (ac), (bc), and (abc) is from 2 mg to 90 mg.

The amount per unit form of zonisamide Component (c) in said fixed dose combinations (ac), (bc), and (abc) is from 25 mg to 600 mg.

The amount per unit form of statin Component (c) in said fixed dose combinations (ac), (bc), and (abc) is from 0.5 mg to 80 mg or from 2.5 mg to 80 mg.

The daily doses of the above Component (a) in said fixed-dose combinations (ac), and (abc) are illustrated in "The 5HT3-antagonist and/or NK1-antagonist Component (a)" section.

The daily doses of the above Component (b) in said fixed dose combinations (bc), and (abc) are illustrated in "The 6-propylamino-4,5,6,7-tetrahydro-1,3-benzothiazole-2-amine Component (b)" section above.

The daily dose of the above fluoxetine Component (c) in said fixed dose combinations (ac), (bc), and (abc) is equivalent to from 4 mg to 90 mg or from 4 mg to 80 mg, normally from 20 mg to 80 mg of fluoxetine base. Said fluoxetine Component (c) daily doses include low doses for use in pediatric patients and during the titration period of 6-propylamino-4,5,6,7-tetrahydro-1,3-benzothiazole-2-amine, preferably pramipexole.

The daily dose of the above zonisamide Component (c) in said fixed-dose combinations (ac), (bc), and (abc) is from 25 mg to 600 mg. Said zonisamide Component (c) daily doses include low dose for use in pediatric patients, and, in combination with a 5HT3-antagonist and pramipexole low doses used in pediatric patients and during the titration period.

The daily dose of the above statin Component (c) in said fixed-dose combinations (ac), (bc), and (abc) is from 0.5 mg to 80 mg or from 2.5 mg to 80 mg. Said statin Component (c) daily doses include low dose for use in pediatric patients, and, in combination with a 5HT3-antagonist and pramipexole low doses used in pediatric patients and during the titration period.

In particular, for the treatment of a PMND in combination with a 5HT3-antagonist and/or a NK1-antagonist Component (a) and with 6-propylamino-4,5,6,7-tetrahydro-1,3-benzothiazole-2-amine Component (b), fluoxetine Component (c), in the above pharmaceutical compositions, is administered to a patient at daily IR-doses of from 4 mg to 90 mg, normally from 20 mg to 80 mg, or at a ER-dose of from 4 mg to 90 mg, normally from 20 mg to 90 mg once a day, or zonisamide Component (c), in the above pharmaceutical compositions, is administered to a patient at daily IR-doses/unit form of from 25 mg to 300 mg once or twice a day, or at a ER-dose of from 25 mg to 600 mg, normally from 200 mg to 600 mg, once a day, or statin Component (c), in a pharmaceutical composition as described above, is selected from the group consisting of lovastatin, in an amount per unit form of from 5 mg to 80 mg, normally from 5 mg to 60 mg or from 10 mg to 60 mg; and rosuvastatin, in an amount per unit form equivalent to from 2.5 mg to 60 mg, normally from 2.5 mg to 40 mg or from 2.5 mg to 30 mg, of rosuvastatin calcium. More particularly, for said treatment, the statin Component (c), in a pharmaceutical composition as described above, is selected from the group consisting of lovastatin, in an IR-dose/unit form of from 5 mg to 80 mg, normally from 20 mg to 40 mg, administered once or twice a day, or in an ER-dose/unit form of from 5 mg to 80 mg, normally from 20 mg to 60 mg, administered once a day; and rosuvastatin, in an IR-dose/unit form equivalent to from 2.5 mg to 40 mg or from 2.5 mg to 30 mg of rosuvastatin calcium, administered once a day.

In preferred embodiments, lovastatin or rosuvastatin calcium Component (c) may be administered to a patient suffering from a PMND, in the above doses per unit form, in combination with a 5HT3-antagonist and/or a NK1-antagonist Component (a) at a daily dose as described in "The 5HT3-antagonist and/or NK1-antagonist Component (a)" above section and with a 6-propylamino-4,5,6,7-tetrahydro-1,3-benzothiazole-2-amine, preferably pramipexole, daily dose as described in "The 6-propylamino-4,5,6,7-tetrahydro-1,3-benzothiazole-2-amine Component (b)" above section;

in combination with a fixed-dose combination Component (ab) comprising daily doses of the above Component (a) in said fixed dose combinations (ab) as described in "The 5HT3-antagonist and/or NK1-antagonist Component (a)" above section; and daily doses of the above Component (b) in said fixed dose combinations (ab), as described in "The 6-propylamino-4,5,6,7-tetrahydro-1,3-benzothiazole-2-amine Component (b)" above section; or in a fixed-dose combination (abc) with a 5HT3-antagonist and/or NK1-antagonist Component (a) at a daily dose as described in "The 5HT3-antagonist and/or NK1-antagonist Component (a)" above section; and with a 6-propylamino-4,5,6,7-tetrahydro-1,3-benzothiazole-2-amine, at a daily dose as described in "The 6-propylamino-4,5,6,7-tetrahydro-1,3-benzothiazole-2-amine Component (b)" above section.

A particularly preferred fixed-dose combination (abc) includes a pharmaceutical composition in dosage unit form wherein said NK1-antagonist is aprepitant, in an amount per unit from equivalent to from 10 mg to 250 mg of aprepitant, or rolapitant, in an amount of from equivalent to from 15 mg to 270 mg of rolapitant; said 6-propylamino-4,5,6,7-tetrahydro-1,3-benzothiazole-2-amine is pramipexole or a pharmaceutically acceptable salt or solvate thereof, in an amount per unit form equivalent to from 0.125 mg to 45 mg, normally from 7.5 mg to 25 mg, from 15 mg to 25 mg or from more than 20 mg to 25 mg of pramipexole dihydrochloride monohydrate; and said statin is lovastatin in an amount per unit form of from 5 mg to 80 mg (normally from 5 mg to 60 mg or from 10 mg to 60 mg), or rosuvastatin calcium in an amount per unit form of from 2.5 mg to 40 mg.

In preferred embodiments, fluoxetine, zonisamide, or a statin Component (c) may be administered to a patient suffering from a PMND as the specific 90 mg ER-weekly preparation,

- either in combination with a 5HT3-antagonist and/or a NK1-antagonist Component (a) at a daily dose as illustrated in "The 5HT3-antagonist and/or a NK1-antagonist Component (a)" section and with a 6-propylamino-4,5,6,7-tetrahydro-1,3-benzothiazole-2-amine, preferably pramipexole, daily dose as illustrated in "The 6-propylamino-4,5,6,7-tetrahydro-1,3-benzothiazole-2-amine Component (b)" above section;
- or in combination with a fixed-dose combination Component (ab) comprising daily doses of the above Component (a) in said fixed dose combinations (ab) as illustrated in "The 5HT3-antagonist and/or a NK1-antagonist Component (a)" above section; and daily doses of the above Component (b) in said fixed dose combinations (ab), as illustrated in "The 6-propylamino-4,5,6,7-tetrahydro-1,3-benzothiazole-2-amine Component (b)" above section.

First Aspect of the Invention

According to a first aspect, the present invention includes a method for safely treating a PMND in a patient suffering from this disorder with a 5HT3-antagonist and/or a NK1-antagonist and fluoxetine, zonisamide, or a statin, by concurrently or sequentially administering to said patient a 6-propylamino-4,5,6,7-tetrahydro-1,3-benzothiazole-2-amine, preferably pramipexole.

In particular, the present invention provides a method for safely treating a PMND in a patient in need of said treatment, which comprises administering to said patient an effective daily dose of a5HT3-antagonist and/or NK1-antagonist, in combination with an effective daily dose of 6-propylamino-4,5,6,7-tetrahydro-1,3-benzothiazole-2-amine or a pharmaceutically acceptable salt thereof and with an effective daily dose of fluoxetine, an effective daily dose of zonisamide, or an effective daily dose of a statin.

Herein, the expressions "salt or solvate thereof", "salts or solvates thereof" and "salts and solvates thereof", referred to 6-propylamino-4,5,6,7-tetrahydro-1,3-benzothiazole-2-amine, mean that said 6-propylamino-4,5,6,7-tetrahydro-1,3-benzothiazole-2-amine may be in the form of the free base or of a pharmaceutically acceptable acid addition salt thereof that may be solvated with a solvent, normally water.

In particular, the present invention provides a method for treating PMND in a patient in need of said treatment, which comprises administering to said patient an effective daily dose of a 5HT3-antagonist and/or an effective daily dose of a NK1-antagonist, in combination with an effective daily dose of 6-propylamino-4,5,6,7-tetrahydro-1,3-benzothiazole-2-amine or a pharmaceutically acceptable salt thereof and with an effective yet tolerable daily dose of fluoxetine or a pharmaceutically acceptable salt or solvate thereof, zonisamide or a pharmaceutically acceptable salt or solvate thereof, or a statin.

In said method, the 5HT3-antagonist and/or NK1-antagonist Component (a) is formulated in a pharmaceutical composition in dosage unit form comprising, as an active ingredient, said 5HT3-antagonist, in an amount per unit form of from 1 μg to 300 mg and/or said NK1-antagonist, in an amount per unit form of from 1 μg to 600 mg, in admixture with a pharmaceutical carrier or vehicle. Said composition is administered for the treatment of a PMND in a patient in combination with 6-propylamino-4,5,6,7-tetrahydro-1,3-benzothiazole-2-amine and with fluoxetine, each formulated in a pharmaceutical composition comprising, as an active ingredient, said with 6-propylamino-4,5,6,7-tetrahydro-1,3-benzothiazole-2-amine Component (b), in an amount per unit form equivalent to from 0.125 mg to 3000 mg of pramipexole dihydrochloride monohydrate, including an (S)-enantiomer amount per unit form equivalent to from 0.125 mg to 45 mg, normally from 15 mg to 25 mg or from more than 20 mg to 25 mg of pramipexole dihydrochloride monohydrate; and, respectively, said fluoxetine Component (c), in an amount per unit from equivalent to from 2 mg to 90 mg of fluoxetine base, in admixture with a pharmaceutical carrier or vehicle, said zonisamide Component (c), in an amount per unit from equivalent to from 25 mg to 600 mg of zonisamide free acid, in admixture with a pharmaceutical carrier or vehicle or said statin Component (c), in an amount per unit from equivalent to from 0.5 mg to 80 mg, in admixture with a pharmaceutical carrier or vehicle.

In particular, in said method, (a) the 5HT3-antagonist and/or the NK1-antagonist Component (a) is formulated in a pharmaceutical composition in dosage unit form comprising, as an active ingredient, said 5HT3-antagonist and/or said NK1-antagonist, each in an amount per unit form of from 1 μg to 600 mg, in admixture with a pharmaceutical carrier in IR- or ER-formulation;

(b) the 6-propylamino-4,5,6,7-tetrahydro-1,3-benzothiazole-2-amine Component (b) is formulated in a pharmaceutical composition in dosage unit form comprising, as an active ingredient, said 6-propylamino-4,5,6,7-tetrahydro-1,3-benzothiazole-2-amine
   - in an amount equivalent to from 0.125 mg to 1500 mg of pramipexole dihydrochloride monohydrate including a (S)-isomer amount equivalent to from 0.125 mg to 22.5 mg, normally from 7.5 mg to 12.5 mg or from more than 10 mg to 12.5 mg of pramipexole dihydrochloride monohydrate, in admixture with a pharmaceutical carrier in an IR-formulation; or
   - in an amount equivalent to from 0.375 mg to 3000 mg of pramipexole dihydrochloride monohydrate including a (S)-isomer amount equivalent to from 0.375 mg to 45 mg, normally from 15 mg to 25 mg or from more than 20 mg to 25 mg of pramipexole dihydrochloride monohydrate, in admixture with a pharmaceutical carrier in an ER-formulation; and (c) the fluoxetine Component (c) is formulated in a pharmaceutical composition in dosage unit form comprising, as an active ingredient, said fluoxetine
   - in an amount per unit form equivalent to from 2 mg to 45 mg, normally from 2 mg to 40 mg, of fluoxetine base, in admixture with a pharmaceutical carrier or vehicle in an IR-formulation; or
   - in an amount per unit form equivalent to from 4 mg to 90 mg, normally from 4 mg to 80 mg, of fluoxetine base in admixture with a pharmaceutical carrier or vehicle in an ER-formulation for a once a day administration; or in an amount of 90 mg, as the specific 90 mg ER-weekly preparation for once a week administration, or the zonisamide Component (c) is formulated in a pharmaceutical composition in dosage unit form comprising, as an active ingredient, said zonisamide in an amount per unit form of from 25 mg to 200 mg, normally from 25 mg to 100 mg, in admixture with a pharmaceutical carrier in admixture with a pharmaceutical carrier or vehicle in an IR-formulation; or in an amount per unit form of from 25 mg to 600 mg, normally from 200 mg to 600 mg, of zonisamide, in admixture with a pharmaceutical carrier or vehicle in an ER-formulation, or the statin Component (c) is formulated in a pharmaceutical composition in dosage unit form comprising, as an active ingredient, said statin, in an amount per unit form of from 0.5 mg to 80 mg in IR- or ER-formulation.

The 5HT3-antagonist active ingredient in said composition is advantageously selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base.

In particular, the 5HT3-antagonist Component (a) in said pharmaceutical composition is selected from the group consisting of azasetron hydrochloride, in an amount per unit form equivalent to from 5 mg to 10 mg to be administered at a daily dose of from 15 mg to 40 mg; dolasetron mesylate, in an amount per unit form of from 25 mg to 200 mg, to be administered at a daily dose of from 75 mg to 200 mg; granisetron hydrochloride, in an amount per unit form equivalent to from 0.5 mg to 2 mg granisetron base, to be administered at a daily dose equivalent to from 1.5 mg to 16 mg, normally of from 2 mg to 8 mg of granisetron base; ondansetron hydrochloride dihydrate, in an amount equivalent to from 0.5 mg to 32 mg, normally from 2 mg to 32 mg, from 2 mg to 16 mg or from 2 mg to 8 mg of ondansetron base, to be administered at a daily dose equivalent to from 6 mg to 32 mg of ondansetron base; palonosetron hydrochloride, in an amount equivalent to from 0.25 mg to 0.5 mg palonosetron base, to be administered at a daily dose equivalent to from 0.75 to 2 mg of palonosetron base; ramosetron hydrochloride, in an amount per unit form of from 0.05 mg to 0.5 mg, to be administered at a daily dose of from 0.05 mg to 1 mg; and tropisetron hydrochloride, in an amount equivalent to from 2.5 mg to 5 mg tropisetron base, to be administered at a daily dose equivalent to from 7.5 mg to 20 mg of tropisetron base.

The 5HT3-antagonist active ingredient in said composition is advantageously selected from the group consisting of ondansetron and pharmaceutically acceptable salts and solvates thereof, dolasetron and pharmaceutically acceptable salts and solvates thereof, and palonosetron and pharmaceutically acceptable salts and solvates thereof, each in the above amount per unit form and daily dose.

The NK1-antagonist active ingredient in said composition is advantageously selected from the group consisting of aprepitant and pharmaceutically acceptable salts and solvates and prodrugs thereof, netupitant and pharmaceutically acceptable salts and solvates and prodrugs thereof, and rolapitant and pharmaceutically acceptable salts and solvates and prodrugs thereof.

In particular, the NK1-antagonist Component (a) in said pharmaceutical composition is selected from the group consisting of aprepitant and pharmaceutically acceptable salts and solvates thereof, in an amount per unit form equivalent to from 10 mg to 250 mg of aprepitant; fosaprepitant and pharmaceutically acceptable salts and solvates thereof, in an amount per unit form equivalent to from 10 mg to 250 mg of aprepitant; rolapitant and pharmaceutically acceptable salts and solvates thereof, in an amount per unit form equivalent to from 15 mg to 270 mg of rolapitant; netupitant and pharmaceutically acceptable salts and solvates thereof, in an amount per unit form equivalent to from 150 mg to 600 mg of netupitant; fosnetupitant, in an amount per unit form equivalent to from 150 to 600 mg of netupitant; NK-1 antagonist combination of netupitant-300/palonosetron-0.5, and NK-1 antagonist combination of fosnetupitant-235/palonosetron-0.25.

Preferably said NK1-antagonist is aprepitant, in an amount per unit form and daily doses of from 10 mg to 250 mg of aprepitant, or rolapitant, in an amount of from 15 mg to 270 mg.

In said method, the 6-propylamino-4,5,6,7-tetrahydro-1,3-benzothiazole-2-amine Component (b) in said composition is present in an amount per unit form equivalent to from. 0.125 mg to 3000 mg of pramipexole dihydrochloride monohydrate, inclusive of a (S)-enantiomer amount per unit form equivalent to from 0.125 mg to 45 mg, normally from 7.5 mg to 25 mg, from 15 mg to 25 mg or from more than 20 mg to 25 mg of pramipexole dihydrochloride monohydrate.

The 6-propylamino-4,5,6,7-tetrahydro-1,3-benzothiazole-2-amine Component (b) in said composition is advantageously selected from the group consisting of pramipexole, in an amount per unit form equivalent to from 0.125 mg to 45 mg of pramipexole dihydrochloride monohydrate; racemic 6-propylamino-4,5,6,7-tetrahydro-1,3-benzothiazole-2-amine, in an amount per unit form equivalent to from 0.25 mg to 90 mg of pramipexole dihydrochloride monohydrate; and a (R/S)-mixture, in an amount per unit form equivalent to from 50 mg to 3000 mg of pramipexole dihydrochloride monohydrate, inclusive of a (S)-enantiomer amount per unit form equivalent to from 0.125 mg to 45 mg of pramipexole dihydrochloride monohydrate.

A specific combination of a NK1-antagonist and of a 5HT3-antagonist is selected from the group consisting of the fixed-dose combinations netupitant-300/palonosetron-0.5 and fosnetupitant-235/palonosetron-0.25.

In said above methods, the 6-propylamino-4,5,6,7-tetrahydro-1,3-benzothiazole-2-amine Component (b) in said composition is present in an amount per unit form equivalent to from 0.125 mg to 3000 mg of pramipexole dihydrochloride monohydrate, inclusive of a (S)-enantiomer amount per unit form equivalent to from 0.125 mg to 45 mg of pramipexole dihydrochloride monohydrate. The 6-propylamino-4,5,6,7-tetrahydro-1,3-benzothiazole-2-amine Component (b) in said composition is advantageously selected from the group consisting of pramipexole, in an amount per unit form equivalent to from 0.125 mg to 45 mg of pramipexole dihydrochloride monohydrate; racemic 6-propylamino-4,5,6,7-tetrahydro-1,3-benzothiazole-2-amine, in an amount per unit form equivalent to from 0.25 mg to 90 mg of pramipexole dihydrochloride monohydrate; and a (R/S)-mixture, in an amount per unit form equivalent to from 50 mg to 3000 mg of pramipexole dihydrochloride monohydrate, inclusive of a (S)-enantiomer amount per unit form equivalent to from 0.125 mg to 45 mg of pramipexole dihydrochloride monohydrate.

The statin Component (c) in said composition is in an amount per unit form of from 0.5 mg to 80 mg, normally from 2 mg to 80 mg.

The fluoxetine Component (c) in said composition normally is in an amount per unit form is equivalent to from 2 mg to 90 mg, normally from 2 mg to 80 mg, of fluoxetine base.

The zonisamide Component (c) active ingredient in said composition is in an amount per unit form of from 25 mg to 600 mg.

Preferably said 5HT3-antagonist is ondansetron, in an amount per unit form (in ondansetron base) of from 2 mg to 32 mg, or dolasetron, in an amount per unit form (in dolasetron mesylate) of from 25 mg to 200 mg.

The preferred 6-propylamino-4,5,6,7-tetrahydro-1,3-benzothiazole-2-amine Component (b) is pramipexole or a pharmaceutically acceptable salt or solvate thereof, in an amount per unit form (including low amounts per unit form used in pediatric patients and in the titration period) equivalent to a range selected from the group consisting of from 0.125 mg to 45 mg, from 1.5 mg to 45 mg, from 1.625 mg to 45 mg, from 3 mg to 45 mg, from more than 4.5 mg to 45 mg, from 4.8 mg to 45 mg, from more than 6 mg to 45 mg, from more than 10 mg to 45 mg, from 14.5 mg to 45 mg, from 15 mg to 45 mg, from 15 mg to 40 mg, from 15 mg to 35 mg, from 15 mg to 30 mg, from 15 mg to 25 mg, from more than 20 mg to 25 mg, and from 20.25 mg to 25 mg of pramipexole dihydrochloride monohydrate.

Specific pramipexole amounts per unit form are described above in "The 6-propylamino-4,5,6,7-tetrahydro-1,3-benzothiazole-2-amine Component (b)" section and below, in the "Specific embodiments" section.

In particular, this first aspect of the present invention provides a method for treating a PMND in a patient in need of said treatment, which comprises administering to said patient a 5HT3-antagonist and/or a NK1-antagonist Component (a), at a daily dose of from 1 μg to 300 mg of the 5HT3-antagonist and/or at a daily dose of from 1 μg to 600 mg of the NK1-antagonist, in combination with a daily dose of said 6-propylamino-4,5,6,7-tetrahydro-1,3-benzothiazole-2-amine Component (b) equivalent to from 0.375 mg to 3000 mg of pramipexole dihydrochloride monohydrate, including a (S)-enantiomer daily dose equivalent to from 0.375 mg to 45 mg, normally from 15 mg to 25 mg or from more than 20 mg to 25 mg of pramipexole dihydrochloride monohydrate; and with a daily dose of fluoxetine Component (c) equivalent to from 4 mg to 90 mg of fluoxetine base, or with a daily dose of zonisamide Component (c) of from 25 mg to 600 mg, or with a daily dose of statin Component (c) of from 0.5 mg to 80 mg.

More particularly, according to this first aspect, the invention provides a method for treating a PMND in a patient in need of said treatment, which comprises administering to said patient a 5HT3-antagonist and/or a NK1-antagonist Component (a), at a daily dose of from 1 μg to 300 mg of the 5HT3-antagonist and/or at a daily dose of from 1 μg to 600 mg of the NK1-antagonist, in combination with a pramipexole Component (b) daily dose equivalent to from 0.375 mg to 45 mg, from 14.5 mg to 45 mg, from more than 20 mg to 45 mg, normally from 15 mg to 25 mg or from 20.25 mg to 25 mg of pramipexole dihydrochloride monohydrate, and with a fluoxetine Component (c) daily dose equivalent to from 4 mg to 90 mg of fluoxetine base or with a zonisamide Component (c) daily dose of from 25 mg to 600 mg, or with a statin Component (c) daily dose of from 2.5 mg to 80 mg. In combination with the above daily doses of Component (a) and Component (b), the fluoxetine, zonisamide, or statin Component (c) may also be administered once a week in the specific 90 mg ER-weekly preparation. In the treatment of a PMND, a 5HT3-antagonist and/or a NK1-antagonist/pramipexole/fluoxetine combination may also be selected from the group consisting of

- a 5HT3-antagonist Component (a), in an amount per unit form of from 1 μg to 300 mg of the 5HT3-antagonist and/or a NK1-antagonist Component (a) in an amount per unit form of from 1 μg to 600 mg of the NK1-antagonist, for the treatment of a PMND in a patient in combination with a Component (bc) comprising 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount equivalent to from 0.125 mg to 45 mg, normally from 15 mg to 25 mg or from more than 20 mg to 25 mg of pramipexole dihydrochloride monohydrate and fluoxetine, in an amount per unit form equivalent to from 2 mg to 90 mg of fluoxetine base to be administered once or twice a day, or zonisamide, in an amount per unit form of from 25 mg to 600 mg to be administered once or twice a day, or a statin, in an amount per unit form of from 0.5 mg to 80 mg to be administered once or twice a day;
- a Component (ab), comprising a 5HT3-antagonist, in an amount per unit form of from 1 μg to 300 mg and/or a NK1-antagonist, in an amount per unit form of from 1 μg to 600 mg; and 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount equivalent to from 0.125 mg to 45 mg, normally from 15 mg to 25 mg or from more than 20 mg to 25 mg of pramipexole dihydrochloride monohydrate, for the treatment of a PMND in a patient in combination with Component (c), comprising fluoxetine, in an amount per unit form equivalent to from 2 mg to 90 mg of fluoxetine base, to be administered once or twice per day or once a week in the specific 90 mg ER-weekly preparation, or zonisamide, in an amount per unit form equivalent to from 25 mg to 600 mg, or a statin, in an amount per unit form equivalent to from 0.5 mg to 80 mg of statin, to be administered once or twice a day; and
- a Component (ac), comprising a 5HT3-antagonist, in an amount per unit form equivalent to from 1 μg to 300 mg and/or a NK1-antagonist, in an amount per unit form equivalent to from 1 μg to 600 mg; and fluoxetine, in an amount per unit form equivalent to from 2 mg to 90 mg of fluoxetine base, zonisamide, in an amount per unit form equivalent to from 25 mg to 600 mg, or a statin, in an amount per unit form equivalent to from 0.5 mg to 80 mg, for the treatment of a PMND in a patient in combination with Component (b), comprising 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount equivalent to from 0.125 mg to 45 mg of pramipexole dihydrochloride monohydrate, to from 0.125 mg to 22.5 mg, normally from 7.5 mg to 12.5 mg of pramipexole dihydrochloride monohydrate in IR-formulation to be administered twice a day, or from 0.375 mg to 45 mg, normally from 15 mg to 25 mg or from more than 20 mg to 25 mg of pramipexole dihydrochloride monohydrate in an ER-formulation to be administered once a day, each of said Component (a), Component (b), Component (c), Component (ab), Component (ac) and Component (bc) being or consisting of a pharmaceutical composition in dosage unit form wherein the active ingredients are in admixture with a pharmaceutical carrier or vehicle. Specific amounts per unit form and daily doses of the above 5HT3-antagonist and/or the above NK1-antagonist, 6-propylamino-4,5,6,7-tetrahydro-1,3-benzothiazole-2-amine, preferably pramipexole, and fluoxetine, zonisamide, or statin in the pharmaceutical composition Component (a), Component (b), Component (c), Component (ab), Component (ac) and Component (bc) are described in the "Specific embodiments" section below.

The fixed-dose combination (ac), and its use in the treatment of a PMND, as described in detail in "The 5HT3-antagonist and/or a NK1-antagonist Component (a) section above, is an advantageous embodiment of this first aspect of the invention.

Preferably, in said compositions, the 6-propylamino-4,5,6,7-tetrahydro-1,3-benzothiazole-2-amine is pramipexole or a pharmaceutically acceptable salt or solvate thereof, in an amount per unit form equivalent to from 0.125 mg to 45 mg, from 14.5 mg to 45 mg or from more than 20 mg to 45 mg, normally from 15 mg to 25 mg or from 20.25 mg to 25 mg of pramipexole dihydrochloride monohydrate.

Second Aspect of the Invention

According to a second aspect, the invention provides the use of a 5HT3-antagonist and/or NK1-antagonist for the preparation of a medicament (or a 5HT3-antagonist and/or NK1-antagonist for use) for the treatment of a PMND in a patient in need of said treatment, in combination with an effective daily dose of 6-propylamino-4,5,6,7-tetrahydro-1,3-benzothiazole-2-amine- and an effective daily dose of fluoxetin, an effective daily dose of zonisamide, or an effective daily dose of a statin.

According to an advantageous embodiment, the invention provides a pharmaceutical composition for use in treatment of a PMND in a patient, comprising a pharmaceutically acceptable carrier or vehicle and a fixed dose combination of a 5HT3-antagonist and/or NK1-antagonist, a 6-propylamino-4,5,6,7-tetrahydro-1,3-benzothiazole-2-amine and fluoxetine, zonisamide, or a statin.

According to a second aspect, the invention provides a pharmaceutical combination comprising (a) a 5HT3-antagonist and/or a NK1-antagonist;

(b) a 6-propylamino-4,5,6,7-tetrahydro-1,3-benzothiazole-2-amine or a pharmaceutically acceptable salt or solvate thereof, and (c) fluoxetine, at a dose per unit form that is equivalent to from 2 mg to 90 mg of fluoxetine base, or zonisamide, at a dose per unit form or daily dose that is at least as high as a dose approved for its antiseizure indication, or statin, in an amount per unit form equivalent to from 0.5 mg to 80 mg, for use for the treatment of a PMND.

For this use, said 5HT3-antagonist and/or NK1-antagonist is formulated in a pharmaceutical composition in dosage unit form comprising, as an active ingredient, said 5HT3-antagonist and/or NK1-antagonist in admixture with a pharmaceutical carrier or vehicle. This pharmaceutical composition is indicated for the treatment of a PMND in a patient in need of said treatment, in combination with 6-propylamino-4,5,6,7-tetrahydro-1,3-benzothiazole-2-amine and with fluxetine, zonisamide, or a statin, each at an effective daily dose.

In said pharmaceutical composition, said 5HT3-antagonist and/or NK1-antagonist is in admixture with a pharmaceutical carrier and formulated in unit forms for oral, intravenous, transcutaneous, and/or transdermal administration, as described in "The formulations" section below.

According to this second aspect of the present invention, any of the 5HT3-antagonists and/or NK1-antagonists described in "The 5HT3-antagonist and/or NK1-antagonist Component (a)" section may be used as an active ingredient of said pharmaceutical for the treatment of a PMND in combination with 6-propylamino-4,5,6,7-tetrahydro-1,3-benzothiazole-2-amine described in "The 6-propylamino-4,5,6,7-tetrahydro-1,3-benzothiazole-2-amine Component (b)" section and with a fluoxetine, zonisamide, or statin Component (c) described in "The fluoxetine, zonisamide, or statin" section.

In particular, the invention provides a 5HT3-antagonist and/or a NK1-antagonist for use in combination with 6-propylamino-4,5,6,7-tetrahydro-1,3-benzothiazole-2-amine, and fluoxetine, zonisamide, or a statin, in the treatment of a PMND in a patient in need of said treatment.

Said medicament is a pharmaceutical composition in dosage unit form comprising, as an active ingredient, said 5HT3-antagonist in an amount per unit form of from 1 μg to 300 mg and/or NK1-antagonist in an amount per unit form of from 1 μg to 600 mg, in admixture with a pharmaceutical carrier or vehicle. This medicament is indicated for the treatment of a PMND in a patient, in combination with 6-propylamino-4,5,6,7-tetrahydro-1,3-benzothiazole-2-amine daily dose equivalent to from 0.375 mg to 3000 mg of pramipexole dihydrochloride monohydrate, inclusive of a (S)-enantiomer daily dose equivalent to from 0.375 mg to 45 mg, normally from 15 mg to 25 mg or from more than 20 mg to 25 mg of pramipexole dihydrochloride monohydrate, and with a statin daily dose of from 0.5 mg to 80 mg.

More particularly, this second aspect of the present invention provides a 5HT3-antagonist and/or a NK1-antagonist Component (a), each at a daily dose of from 1 μg to 600 mg, for use for the treatment of a PMND in a patient in need of said treatment in combination with a daily dose of said 6-propylamino-4,5,6,7-tetrahydro-1,3-benzothiazole-2-amine Component (b) equivalent to from 0.375 mg to 3000 mg of pramipexole dihydrochloride monohydrate, inclusive of a (S)-enantiomer daily dose equivalent to from 0.375 mg to 45 mg, normally from 15 mg to 25 mg or from more than 20 mg to 25 mg of pramipexole dihydrochloride monohydrate; and with a daily dose of fluoxetine Component (c) of from 4 mg to 90 mg or in the specific 90 mg ER-weekly preparation or with a daily dose of from 25 mg to 600 mg of zonisamide Component (c) or with a statin daily dose of from 0.5 mg to 80 mg.

These daily doses of 6-propylamino-4,5,6,7-tetrahydro-1,3-benzothiazole-2-amine include low pramipexole daily doses useful for the administration, in combination with a 5HT3-antagonist and/or NK1-antagonist and fluoxetine, zonisamide, a statin, to pediatric patients or during the titration period. In the second case, at the end of said titration period, the medicament thus manufactured enables the safe intake of pramipexole daily doses never heretofore attained (without the combination with the NK1-antagonist and with the statin) as described in "The 6-propylamino-4,5,6,7-tetrahydro-1,3-benzothiazole-2-amine Component (b)" section.

Said 6-propylamino-4,5,6,7-tetrahydro-1,3-benzothiazole-2-amine may also be the racemate, at a daily dose equivalent to from 0.75 mg to 90 mg of pramipexole dihydrochloride monohydrate.

Preferably, said 6-propylamino-4,5,6,7-tetrahydro-1,3-benzothiazole-2-amine is pramipexole or pharmaceutically acceptable salt or solvate thereof, at a daily dose equivalent to from 0.375 mg to 45 mg or from more than 20 mg to 45 mg, normally from 20.25 mg to 25 mg of pramipexole dihydrochloride monohydrate.

Preferably, according to this second aspect, the present invention provides a pharmaceutical composition in dosage unit form comprising a 5HT3-antagonist Component (a), in an amount of from 1 μg to 600 mg and zonisamide Component (c), in an amount per unit form equivalent to from 25 mg to 600 mg, in admixture with a pharmaceutical carrier or vehicle.

Preferably, according to this second aspect, the present invention provides a pharmaceutical composition in dosage unit form comprising a 5HT3-antagonist in an amount of from 1 μg to 300 mg and/or a NK1-antagonist in an amount of from 1 μg to 600 mg Component (a), and fluoxetine Component (c), in an amount per unit form equivalent to from 2 mg to 90 mg of fluoxetine base or zonisamide Component (c), in an amount per unit form equivalent to from 25 mg to 600 mg of zonisamide free acid, or a statin Component (c) in an amount per unit form equivalent to from 0.5 mg to 80 mg, in admixture with a pharmaceutical carrier or vehicle. In said composition, said 5HT3-antagonist is advantageously selected from the group consisting of ondansetron and pharmaceutically acceptable salts and solvates thereof, in an amount per unit form equivalent to from 2 mg to 32 mg of ondansetron base; dolasetron and pharmaceutically acceptable salts and solvates thereof, in an amount per unit form equivalent to from 25 mg to 200 mg of dolasetron mesylate; and palonosetron and pharmaceutically acceptable salts and solvates thereof, in an amount per unit form equivalent to from 0.25 mg to 0.5 mg of palonosetron base.

In said composition, said 5HT3-antagonist is advantageously selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof.

Preferably, in said composition, said 5HT3-antagonist is ondansetron hydrochloride dihydrate, in an amount per unit form equivalent to from 2 mg to 32 mg of ondansetron base. In said composition, said NK1-antagonist is advantageously selected from the group consisting of aprepitant and pharmaceutically acceptable salts and solvates thereof, in an amount per unit form equivalent to from 10 mg to 250 mg of aprepitant; rolapitant and pharmaceutically acceptable salts and solvates thereof, in an amount per unit form equivalent to from 15 mg to 270 mg of rolapitant; and netupitant and pharmaceutically acceptable salts and solvates thereof, in an amount per unit form equivalent to from 150 mg to 600 mg of netupitant. Preferably, in said composition, said NK1-antagonist is aprepitant, in an amount per unit form of from 10 mg to 250 mg of aprepitant or rolapitant, in an amount per unit form of from 15 mg to 270 mg of rolapitant.

A specific combination of a NK1-antagonist and of a 5HT3-antagonist is selected from the group consisting of the fixed-dose combinations netupitant-300/palonosetron-0.5 and fosnetupitant-235/palonosetron-0.25.

According to an embodiment, said 5HT3-antagonist and/or a NK1-antagonist is for use in combination with 6-propylamino-4,5,6,7-tetrahydro-1,3-benzothiazole-2-amine, as a (R)/(S)-mixture, at a daily dose of from 50 to 3000 mg, including a (S)-enantiomer daily dose equivalent to from 0.375 mg to 45 mg of pramipexole dihydrochloride monohydrate, and with fluoxetine, at a daily dose equivalent to from 4 mg to 90 mg of fluoxetine base, or in the specific 90 mg ER-weekly preparation.

Said 6-propylamino-4,5,6,7-tetrahydro-1,3-benzothiazole-2-amine may also be the racemate, at a daily dose equivalent to from 0.75 mg to 90 mg, normally from 30 mg to 50 mg or from more than 40 mg to 50 mg of pramipexole dihydrochloride monohydrate.

Preferably, said 6-propylamino-4,5,6,7-tetrahydro-1,3-benzothiazole-2-amine is pramipexole or pharmaceutically acceptable salt or solvate thereof, at a daily dose equivalent to from 0.375 mg to 45 mg, normally from 15 mg to 25 mg, from 20.25 mg to 25 mg, or from more than 20 mg to 45 mg of pramipexole dihydrochloride monohydrate.

For the treatment of a PMND, the 5HT3-antagonist and/or the NK-1 antagonist, the 6-propylamino-4,5,6,7-tetrahydro-1,3-benzothiazole-2-amine and fluoxetine, zonisamide, or statin are each formulated in a pharmaceutical composition in dosage unit form comprising said 5HT3-antagonist and/or said NK-1 antagonist and, respectively, said 6-propylamino-4,5,6,7-tetrahydro-1,3-benzothiazole-2-amine and said fluoxetine, zonisamide, or statin, each in admixture with a pharmaceutical carrier or vehicle; and are concurrently or sequentially administered at the above daily doses to a patient in need of said treatment.

In general, said 5HT3-antagonist and/or said NK-1 antagonist, said 6-propylamino-4,5,6,7-tetrahydro-1,3-benzothiazole-2-amine and said fluoxetine, zonisamide, or statin, are each formulated in a pharmaceutical composition in dosage unit form comprising said 5HT3-antagonist in an amount per unit form of from 1 μg to 300 mg and/or said NK1-antagonist in an amount per unit form of from 1 μg to 600 mg;

said 6-propylamino-4,5,6,7-tetrahydro-1,3-benzothiazole-2-amine in an amount per unit form equivalent to from 0.125 mg to 3000 mg of pramipexole dihydrochloride monohydrate, including a (S)-enantiomer amount equivalent to from 0.125 mg to 45 mg, normally from 15 mg to 25 mg or from more than 20 mg to 25 mg of pramipexole dihydrochloride monohydrate; and respectively, said fluoxetine, in an amount per unit form equivalent to from 2 mg to 90 mg, normally from 2 mg to 80 mg, of fluoxetine base, zonisamide, in an amount per unit form equivalent to from 25 mg to 600 mg of zonisamide free acid, or a statin or a pharmaceutically acceptable salt or solvate thereof, in an amount per unit form of from 0.5 mg to 80 mg, each in admixture with a pharmaceutical carrier or vehicle.

Preferably, in the above combination, said 6-propylamino-4,5,6,7-tetrahydro-1,3-benzothiazole-2-amine is selected from the group consisting of pramipexole, in an amount per unit form equivalent to from 0.125 mg to 45 mg, normally from 15 mg to 25 mg or from more than 20 mg to 25 mg of pramipexole dihydrochloride monohydrate, racemic 6-propylamino-4,5,6,7-tetrahydro-1,3-benzothiazole-2-amine, in an amount per unit form equivalent to from 0.25 mg to 90 mg of pramipexole dihydrochloride monohydrate, and a (R)/(S)-mixture, in an amount per unit form of from equivalent to from 50 mg to 3000 mg of pramipexole dihydrochloride monohydrate, including a (S)-enantiomer amount of from 0.125 mg to 45 mg, normally from 15 mg to 25 mg or from more than 20 mg to 25 mg of pramipexole dihydrochloride monohydrate.

In particular, according to an embodiment of this second aspect, the invention also provides the use of a 5HT3-antagonist and/or NK1-antagonist Component (a) for the preparation of a medicament, as a pharmaceutical composition in dosage unit form comprising, as an active ingredient, said 5HT3-antagonist in an amount per unit form of from 1 μg to 300 mg and/or said NK1-antagonist in an amount per unit form of from 1 μg to 600 mg, in admixture with a pharmaceutical carrier or vehicle, in combination with a 6-propylamino-4,5,6,7-tetrahydro-1,3-benzothiazole-2-amine Component (b) selected from the group consisting of pramipexole and pharmaceutically acceptable salts thereof, at a daily dose equivalent to from 0.375 mg to 45 mg, normally from 15 mg to 25 mg or from more than 20 mg to 25 mg of pramipexole dihydrochloride monohydrate; and with fluoxetine Component (c), at a daily dose equivalent to from 4 mg to 90 mg of fluoxetine base, with zonisamide Component (c), at a daily dose equivalent to from 25 mg to to 600 mg, normally from 200 mg to 600 mg, or with a statin Component (c), at a daily dose equivalent to from 0.5 mg to 80 mg.

In particular, according to this second aspect, the invention provides a pharmaceutical combination selected from the group consisting of a 5HT3-antagonist and/or a NK-1 antagonist Component (a), in a pharmaceutical composition in dosage unit form comprising, as an active ingredient, said 5HT3-antagonist in an amount per unit form of from 1 μg to 300 mg and/or said NK1-antagonist in an amount per unit form of from 1 μg to 600 mg, in admixture with a pharmaceutical carrier or vehicle; in combination with a 6-propylamino-4,5,6,7-tetrahydro-1,3-benzothiazole-2-amine Component (b) selected from the group consisting of pramipexole and pharmaceutically acceptable salts thereof, at a daily dose equivalent to from 0.375 mg to 45 mg of pramipexole dihydrochloride monohydrate; and with fluoxetine Component (c), at a daily dose equivalent to from 4 mg to 90 mg of fluoxetine base, or in the specific 90 mg ER-weekly preparation, with zonisamide Component (c), at a daily dose equivalent to from 25 mg to to 600 mg, normally from 200 mg to 600 mg, or with a statin Component (c), at a daily dose of from 0.5 mg to 80 mg. According to this second aspect, the invention provides the use of a 5HT3-antagonist and/or NK1-antagonist for the preparation of a medicament (or a 5HT3-antagonist and/or NK1-antagonist for use) for the treatment of a PMND in combination, including fixed-dose combinations, with 6-propylamino-4,5,6,7-tetrahydro-1,3-benzothiazole-2-amine and with a statin. Said medicament comprises said 5HT3-antagonist and/or NK1-antagonist, alone or together with a 6-propylamino-4,5,6,7-tetrahydro-1,3-benzothiazole-2-amine or with a statin in a Component (ab) or Component (ac), respectively. Said combination comprises a Component selected from the group consisting of a 5HT3-antagonist in an amount of from 1 μg to 300 mg and/or a NK1-antagonist Component (a) in an amount per unit form of from 1 μg to 600 mg, for the treatment of a PMND in a patient in combination with a Component (bc) comprising 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, and fluoxetine or a pharmaceutically acceptable salt or solvate thereof, in an amount per unit form of from 4 mg to 90 mg, zonisamide or a pharmaceutically acceptable salt or solvate thereof, in an amount per unit form of from 25 mg to to 600 mg or a statin or a pharmaceutically acceptable salt or solvate thereof, in an amount per unit form of from 0.5 mg to 80 mg;

a Component (ab), comprising a 5HT3-antagonist in an amount of from 1 μg to 300 mg and/or a NK1-antagonist, in an amount per unit form of from 1 μg to 600 mg; and a 6-propylamino-4,5,6,7-tetrahydro-1,3-benzothiazole-2-amine, in an amount per unit form equivalent to from 0.125 mg to 3000 mg of pramipexole dihydrochloride monohydrate including a (S)-enantiomer amount per unit from equivalent to from 0.125 mg to 45 mg, normally from 15 mg to 25 mg or from more than 20 mg to 25 mg of pramipexole dihydrochloride monohydrate, for the treatment of a PMND in a patient, in combination with Component (c) comprising fluoxetine, in an amount per unit form of from 4 mg to 90 mg, zonisamide, in an amount per unit form of from 25 mg to to 600 mg, or a statin, in an amount per unit form of from 0.5 mg to 80 mg; and a Component (ac), comprising a 5HT3-antagonist in an amount of from 1 μg to 300 mg and/or a NK1-antagonist, in an amount per unit form of from 1 μg to 600 mg, and fluoxetine, in an amount per unit form of from 4 mg to 90 mg, zonisamide, in an amount per unit form of from 25 mg to to 600 mg, or a statin, in an amount per unit form of from 0.5 mg to 80 mg, for the treatment of a PMND in a patient in need of said treatment, in combination with Component (b), comprising a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, each of said Component (a), Component (b), Component (c), Component (ab), Component (ac) and Component (bc) being or consisting of a pharmaceutical composition in dosage unit form wherein the active ingredients are in admixture with a pharmaceutical carrier or vehicle.

Specific amounts per unit form and daily doses of the above 5HT3-antagonist and/or NK1-antagonist, 6-propylamino-4,5,6,7-tetrahydro-1,3-benzothiazole-2-amine and statin in the pharmaceutical compositions Component (a), Component (b), Component (c), Component (ab), Component (ac) and Component (bc) are described in the "Specific embodiments" section below.

According to this second aspect, the invention also provides a pharmaceutical composition for use in treatment of a PMND in a patient, comprising a pharmaceutically acceptable carrier or vehicle and a fixed-dose combination of a 5HT3-antagonist and/or NK1-antagonist, and fluoxetine, zonisamide, or a statin, Component (ac), to be administered to said patient in further combination with a 6-propylamino-4,5,6,7-tetrahydro-1,3-benzothiazole-2-amine Component (b).

More particularly, according to this second aspect, the invention provides a 5HT3-antagonist and/or NK-1 antagonist/6-propylamino-4,5,6,7-tetrahydro-1,3-benzothiazole-2-amine/fluoxetine combination, for use in treatment of a PMND, selected from the group consisting of a 5HT3-antagonist in an amount of from 1 μg to 300 mg and/or a NK1-antagonist Component (a) in an amount of from 1 μg to 600 mg Component (a), for use in the treatment of a PMND in a patient in combination with a Component (bc) comprising 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, and fluoxetine or a pharmaceutically acceptable salt or solvate thereof active ingredient, in an amount per unit form equivalent to from 2 mg to 90 mg of fluoxetine base;

a Component (ab), comprising a 5HT3-antagonist, in an amount per unit form of from 1 μg to 300 mg and/or a NK1-antagonist in an amount per unit form of from 1 μg to 600 mg; and a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit from equivalent to from 0.125 mg to 45 mg, normally from 15 mg to 25 mg or from more than 20 mg to 25 mg of pramipexole dihydrochloride monohydrate, for use in the treatment of a PMND in a patient in combination with Component (c), comprising fluoxetine or a pharmaceutically acceptable salt or solvate thereof active ingredient, in an amount per unit form equivalent to from 2 mg to 90 mg of fluoxetine base, to be administered at a daily dose equivalent to from 4 mg to 90 mg of fluoxetine base; and a Component (ac), comprising a 5HT3-antagonist, in an amount per unit form equivalent to from 1 μg to 300 mg and/or a NK1-antagonist in an amount per unit form of from 1 μg to 600 mg, and fluoxetine or a pharmaceutically acceptable salt or solvate thereof active ingredient, in an amount per unit form equivalent to from 2 mg to 90 mg of fluoxetine base, for use in the treatment of a PMND in a patient in combination with Component (b), comprising a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, each of said Component (a), Component (b), Component (c), Component (ab), Component (ac) and Component (bc) being or consisting of a pharmaceutical composition in dosage unit form wherein the active ingredients are in admixture with a pharmaceutical carrier or vehicle.

More particularly, according to this second aspect, the invention provides a 5HT3-antagonist and/or NK-1 antagonist/6-propylamino-4,5,6,7-tetrahydro-1,3-benzothiazole-2-amine/zonisamide combination, for use in treatment of a PMND, selected from the group consisting of a 5HT3-antagonist Component (a) in an amount of from 1 μg to 300 mg and/or a NK1-antagonist Component (a) in an amount of from 1 μg to 600 mg, for use in the treatment of a PMND in a patient in combination with a Component (bc) comprising 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, and zonisamide or a pharmaceutically acceptable salt or solvate thereof active ingredient, in an amount per unit form equivalent to from 25 mg to 600 mg of zonisamide free acid;

a Component (ab), comprising a 5HT3-antagonist, in an amount per unit form of from 1 μg to 300 mg and/or a NK1-antagonist Component (a) in an amount of from 1 μg to 600 mg; and 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit from equivalent to from 0.125 mg to 45 mg, normally from 15 mg to 25 mg or from more than 20 mg to 25 mg of pramipexole dihydrochloride monohydrate, for use in the treatment of a PMND in a patient in combination with Component (c), comprising zonisamide or a pharmaceutically acceptable salt or solvate thereof active ingredient, in an amount per unit form equivalent to from 25 mg to 600 mg of zonisamide free acid, to be administered at a daily dose equivalent to from 25 mg to 600 mg, normally from 200 mg to 600 mg of zonisamide free acid; and a Component (ac), comprising a 5HT3-antagonist, in an amount per unit form equivalent to from 1 μg to 300 mg and/or a NK1-antagonist Component (a) in an amount of from 1 μg to 600 mg, and zonisamide or a pharmaceutically acceptable salt or solvate thereof active ingredient, in an amount per unit form equivalent to from 25 mg to 600 mg of zonisamide free acid, for use in the treatment of a PMND in a patient in combination with Component (b), comprising a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45, normally from 15 mg to 25 mg or from more than 20 mg to 25 mg mg of pramipexole dihydrochloride monohydrate, each of said Component (a), Component (b), Component (c), Component (ab), Component (ac) and Component (bc) being or consisting of a pharmaceutical composition in dosage unit form wherein the active ingredients are in admixture with a pharmaceutical carrier or vehicle.

According to this second aspect, the invention provides the use of a NK1-antagonist for the preparation of a medicament (or a NK1-antagonist for use) for the treatment of a PMND in combination, including fixed-dose combinations, with 6-propylamino-4,5,6,7-tetrahydro-1,3-benzothiazole-2-amine and with a statin. Said medicament comprises said NK1-antagonist, alone or together with a 6-propylamino-4,5,6,7-tetrahydro-1,3-benzothiazole-2-amine or with a statin in a Component (ab) or Component (ac), respectively. Said combination comprises a Component selected from the group consisting of a NK1-antagonist Component (a) in an amount per unit form of from 1 μg to 600 mg, for the treatment of a PMND in a patient in combination with a Component (bc) comprising 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, and a statin or a pharmaceutically acceptable salt or solvate thereof, in an amount per unit form of from 0.5 mg to 80 mg;

a Component (ab), comprising a NK1-antagonist, in an amount per unit form of from 1 μg to 600 mg; and a 6-propylamino-4,5,6,7-tetrahydro-1,3-benzothiazole-2-amine, in an amount per unit form equivalent to from 0.125 mg to 3000 mg of pramipexole dihydrochloride monohydrate including a (S)-enantiomer amount per unit from equivalent to from 0.125 mg to 45 mg, normally from 15 mg to 25 mg or from more than 20 mg to 25 mg of pramipexole dihydrochloride monohydrate, for the treatment of a PMND in a patient, in combination with Component (c) comprising a statin, in an amount per unit form of from 0.5 mg to 80 mg; and a Component (ac), comprising a NK1-antagonist, in an amount per unit form of from 1 μg to 600 mg, and a statin, in an amount per unit form of from 0.5 mg to 80 mg, for the treatment of a PMND in a patient in need of said treatment, in combination with Component (b), comprising a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, each of said Component (a), Component (b), Component (c), Component (ab), Component (ac) and Component (bc) being or consisting of a pharmaceutical composition in dosage unit form wherein the active ingredients are in admixture with a pharmaceutical carrier or vehicle.

Specific amounts per unit form and daily doses of the above 5HT3-antagonist and/or NK-1 antagonist, 6-propylamino-4,5,6,7-tetrahydro-1,3-benzothiazole-2-amine and fluoxetine, zonisamide or a statin in the pharmaceutical composition Component (a), Component (b), Component (c), Component (ab), Component (ac) and Component (bc) are illustrated in the "Specific embodiments" section below.

According to an advantageous embodiment of this second aspect, the present invention provides a pharmaceutical composition for the treatment of a PMND in a patient, in combination with a 6-propylamino-4,5,6,7-tetrahydro-1,3-benzothiazole-2-amine (in particular with pramipexole), comprising a pharmaceutical carrier or vehicle and a fixed dose combination of a 5HT3-antagonist and/or a NK-1 antagonist with fluoxetine, zonisamide or a statin.

Normally, this pharmaceutical composition Component (ac) is in dosage unit form and comprises a 5HT3-antagonist Component (a), in an amount per unit form of from 1 μg to 300 mg and/or a NK1-antagonist Component (a) in an amount of from 1 μg to 600 mg and zonisamide Component (c), in an amount per unit form of from 25 mg to 600 mg, in admixture with a pharmaceutical carrier or vehicle.

Normally, this pharmaceutical composition Component (ac) is in dosage unit form and comprises a 5HT3-antagonist Component (a), in an amount of from 1 μg to 300 mg and/or a NK1-antagonist Component (a), in an amount per unit form of from 1 μg to 600 mg, and fluoxetine Component (c), in an amount per unit form equivalent to from 2 mg to 90 mg, in admixture with a pharmaceutical carrier or vehicle.

Among said components, an advantageous Component (ac) comprises or consists of a pharmaceutical composition in dosage unit form comprising (a) a 5HT3-antagonist Component (a), in an amount per unit form of from 1 μg to 300 mg and/or a NK1-antagonist, in an amount per unit form of from 1 μg to 600 mg; and (c) a statin selected from the group consisting of atorvastatine and pharmaceutically acceptable salts and solvates thereof, in an amount per unit form equivalent to from 5 mg to 80 mg of atorvastatin free acid; fluvastatin and pharmaceutically acceptable salts and solvates thereof, in an amount per unit form equivalent to from 10 mg to 80 mg of fluvastatin free acid; lovastatin, in an amount per unit form of from 5 mg to 80 mg; pitavastatin and pharmaceutically acceptable salts and solvates thereof, in an amount per unit form equivalent to from 0.5 mg to 4 mg of pitavastatin free acid; pravastatin and pharmaceutically acceptable salts and solvates thereof, in an amount per unit form equivalent to from 2.5 mg to 60 mg of pravastatin sodium; rosuvastatin and pharmaceutically acceptable salts and solvates thereof, in an amount per unit form equivalent to from 2.5 mg to 40 mg of rosuvastatin calcium; and simvastatin, in an amount per unit form of from 2.5 mg to 40 mg, in admixture with a pharmaceutical carrier or vehicle.

The advantage of this Component (ac) of a 5HT3-antagonist and/or NK1-antagonist/6-propylamino-4,5,6,7-tetrahydro-1,3-benzothiazole-2-amine/statin combination is the flexibility in the dosage and in the mode of administration of the 6-propylamino-4,5,6,7-tetrahydro-1,3-benzothiazole-2-amine, in particular of pramipexole.

In a particular advantageous Component (ac), said NK1-antagonist is selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; and netupitant and pharmaceutically acceptable salts and solvates and prodrugs thereof, in an amount per unit form equivalent to from 150 mg to 600 mg of netupitant; and said statin is selected from the group consisting of lovastatin, in an amount of from 5 mg to 80 mg; and rosuvastatin and pharmaceutically acceptable salts and solvates thereof, in an amount per unit form equivalent to from 2.5 mg to 40 mg of rosuvastatin calcium.

Preferably, in said Component (ac), said NK1-antagonist is aprepitant, in an amount per unit form of from 10 mg to 250 mg of aprepitant, or rolapitant, in an amount per unit form of from 15 mg to 270 mg of rolapitant; and said statin is lovastatin, in an amount of from 5 mg to 80 mg, normally from 5 mg to 60 mg.

The above Component (ac), administered to a patient suffering from a PMND, allows for the administration to said patient of a pramipexole daily dose, including pediatric doses and doses used in the titration period, equivalent to from 0.375 mg to 45 mg of pramipexole dihydrochloride monohydrate. Normally, the above Component (ac) allows for the administration of pramipexole daily dose equivalent to from more than 6 mg to 45 mg, from 14.5 mg to 45 mg, from more than 20 mg to 45 mg, normally from 15 mg to 25 mg or from 20.25 mg to 25 mg of pramipexole dihydrochloride monohydrate.

An advantageous Component (ab), to be used in combination with the statin Component (c) comprises or consists of a pharmaceutical composition in dosage unit form comprising (a) a 5HT3-antagonist Component (a), in an amount per unit form of from 1 μg to 300 mg and/or a NK1-antagonist, in an amount per unit form of from 1 μg to 600 mg; and (b) pramipexole or a pharmaceutically acceptable salt or solvate thereof, in an amount per unit form equivalent to from 14.5 mg to 45 mg or from more than 20.25 mg to, normally from 15 mg to 25 mg or from 20.25 mg to 25 mg, in admixture with a pharmaceutical carrier or vehicle.

An advantageous Component (bc), to be used in combination with the 5HT3-antagonist and/or NK1-antagonist Component (a) in the treatment of a patient suffering from a PMND, comprises or consists of a pharmaceutical composition in dosage unit form comprising (b) pramipexole or a pharmaceutically acceptable salt or solvate thereof, in an amount per unit form equivalent to from 14.5 mg to 45 mg or from more than 20.25 mg to 45 mg, normally from 15 mg to 25 mg or from 20.25 mg to 25 mg; and (c) a statin, in an amount per unit form of from 0.5 mg to 80 mg, in admixture with a pharmaceutical carrier or vehicle.

In particular, in said composition component (ab), said NK1-antagonist Component (a) is selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; and netupitant and pharmaceutically acceptable salts and solvates and prodrugs thereof, in an amount per unit form equivalent to from 150 mg to 600 mg of netupitant; and in said composition Component (bc), said statin Component (c) is selected from the group consisting of lovastatin, in an amount per unit form of from 5 mg to 80 mg or from 5 mg to 60 mg; and rosuvastatin calcium, in an amount per unit form of from 2.5 mg to 40 mg or from 2.5 mg to 30 mg.

According to a preferred embodiment, in the pharmaceutical compositions (b), (ab), and (bc) of the above 5HT3-antagonist and/or NK1-antagonist/6-propylamino-4,5,6,7-tetrahydro-1,3-benzothiazole-2-amine/statin combination, including fixed-dose combinations, the 6-propylamino-4,5,6,7-tetrahydro-1,3-benzothiazole-2-amine Component (b) is pramipexole or a pharmaceutically acceptable salt or solvate thereof, in an amount per unit form of from 0.125 mg to 45 mg, to be administered at a daily dose of from 0.375 mg to 45 mg. Sub-ranges of the above pramipexole amounts per unit form and daily doses are described in "The 6-propylamino-4,5,6,7-tetrahydro-1,3-benzothiazole-2-amine Component (b)" section and are also the object of this section.

In particular, in said composition, said 5HT3-antagonist is selected from the group consisting of azasetron hydrochloride, in an amount per unit form equivalent to from 5 mg to 10 mg to be administered at a daily dose of from 15 mg to 40 mg; dolasetron mesylate, in an amount per unit form of from 25 mg to 200 mg, to be administered at a daily dose of from 75 mg to 200 mg; granisetron hydrochloride, in an amount per unit form equivalent to from 0.5 mg to 2 mg of granisetron base, to be administered at a daily dose equivalent to from 1.5 mg to 16 mg, normally to from 2 mg to 8 mg of granisetron base; ondansetron hydrochloride dihydrate, in an amount equivalent to from 0.5 mg to 32 mg, normally from 2 mg to 32 mg, from 2 mg to 16 mg or from 2 mg to 8 mg of ondansetron base, to be administered at a daily dose equivalent to from 6 mg to 64 mg, normally from 6 to 32 mg of ondansetron base; palonosetron hydrochloride, in an amount equivalent to from 0.25 mg to 0.5 mg of palonosetron base, to be administered at a daily dose equivalent to from 0.75 to 2 mg of palonosetron base; ramosetron hydrochloride, in an amount per unit form of from 0.05 mg to 0.5 mg, to be administered at a daily dose of from 0.05 mg to 1 mg; and tropisetron hydrochloride, in an amount equivalent to from 2.5 mg to 5 mg tropisetron base, to be administered at a daily dose equivalent to from 7.5 mg to 20 mg of tropisetron base.

Preferably, in said composition, said 5HT3-antagonist is ondansetron, in an amount per unit form of from 2 mg to 32 mg, normally from 2 mg to 16 mg (in ondansetron base) and dolasetron mesylate, in an amount per unit form of from 25 mg to 200 mg.

In particular, in said composition, said NK1-antagonist is selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; netupitant and pharmaceutically acceptable salts and solvates and prodrugs thereof, in an amount per unit form equivalent to from 150 mg to 600 mg of netupitant.

Preferably, in said composition, said NK1-antagonist is aprepitant, in an amount per unit form of from 10 mg to 250 mg or rolapitant, in an amount per unit form of from 15 mg to 270 mg.

This pharmaceutical composition Component (ac) is administered to a patient suffering from a PMND in combination with a 6-propylamino-4,5,6,7-tetrahydro-1,3-benzothiazole-2-amine Component (b), in a pharmaceutical composition in dosage unit form comprising said 6-propylamino-4,5,6,7-tetrahydro-1,3-benzothiazole-2-amine an amount per unit form equivalent to from 0.125 mg to 3000 mg of pramipexole dihydrochloride monohydrate, including a (S)-enantiomer amount per unit form equivalent to from 0.125 to 45 mg, normally from 15 mg to 25 mg or from more than 20 mg to 25 mg of pramipexole dihydrochloride monohydrate, to be administered to said patient at a daily dose equivalent to from 0.375 mg to 3000 mg of pramipexole dihydrochloride monohydrate, including a (S)-enantiomer daily dose equivalent to from 0.375 mg to 45 mg, normally from 15 mg to 25 mg or from more than 20 mg to 25 mg of pramipexole dihydrochloride monohydrate.

Preferably, said 6-propylamino-4,5,6,7-tetrahydro-1,3-benzothiazole-2-amine is selected from the group consisting of pramipexole and pharmaceutically acceptable salt and solvates thereof, also in a pharmaceutical composition in dosage unit form comprising said pramipexole or pharmaceutically acceptable salt and solvates thereof in an amount per unit form equivalent to from 0.125 mg to 45 mg, normally from 15 mg to 25 mg or from more than 20 mg to 25 mg of pramipexole dihydrochloride monohydrate; and is administered to said patient at a daily dose equivalent to from 0.375 mg to 45 mg, normally from 15 mg to 25 mg or from more than 20 mg to 25 mg of pramipexole dihydrochloride monohydrate.

In the above compositions (b), (ab) and (bc), the 6-propylamino-4,5,6,7-tetrahydro-1,3-benzothiazole-2-amine advantageously is pramipexole or a pharmaceutically acceptable salt or solvate thereof, in an amount per unit form equivalent to from 0.125 mg to 45 mg of pramipexole dihydrochloride monohydrate, in particular in an amount-range (in pramipexole dihydrochloride monohydrate) of from 14.5 mg to 45 mg or from more than 20 mg to 45 mg.

Normally, said pramipexole amount-range in said compositions is equivalent to from 15 mg to 25 mg or from 20.25 mg to 25 mg of pramipexole dihydrochloride monohydrate.

Specific pramipexole amounts per unit form and daily doses of the above 5HT3-antagonist and/or NK1-antagonist, 6-propylamino-4,5,6,7-tetrahydro-1,3-benzothiazole-2-amine and fluoxetine, zonisamide, or statin, are described above in "The 5HT3-antagonist and/or NK1-antagonist Component (a)" section, "The 6-propylamino-4,5,6,7-tetrahydro-1,3-benzothiazole-2-amine Component (b)" section, and "The fluoxetine, zonisamide, or statin Component (c)" section; and below, in the "Specific embodiments" section.

As set forth above, in the treatment of a PMND, the 5HT3-antagonist and/or NK1-antagonist, the 6-propylamino-4,5,6,7-tetrahydro-1,3-benzothiazole-2-amine, and the fluoxetine, zonisamide, or statin are used in combination each other, and the three active components may be co-administered simultaneously or sequentially, or in a fixed dose combination including a pharmaceutical composition comprising the 5HT3-antagonist and/or NK1-antagonist, the 6-propylamino-4,5,6,7-tetrahydro-1,3-benzothiazole-2-amine, and the daily doses of the above 5HT3-antagonist and/or NK1-antagonist, 6-propylamino-4,5,6,7-tetrahydro-1,3-benzothiazole-2-amine and fluoxetine, zonisamide, or statin, in admixture with a pharmaceutically acceptable carrier or vehicle.

The 5HT3-antagonist and/or NK1-antagonist Component (a), the 6-propylamino-4,5,6,7-tetrahydro-1,3-benzothiazole-2-amine Component (b) and the fluoxetine, zonisamide, or statin Component (c) can be administered separately or together in any conventional oral or parenteral dosage unit form such as capsule, tablet, powder, cachet, suspension, solution, or transdermal drug delivery system.

In the case of separate (concurrent or sequential) administration, said 5HT3-antagonist and/or NK1-antagonist, in an effective amount per unit form, said 6-propylamino-4,5,6,7-tetrahydro-1,3-benzothiazole-2-amine, in an effective amount per unit form, and said fluoxetine, zonisamide, or statin, in an effective amount per unit form, can each be packaged in a kit comprising said 5HT3-antagonist and/or NK1-antagonist, in admixture with a pharmaceutical carrier or vehicle, said 6-propylamino-4,5,6,7-tetrahydro-1,3-benzothiazole-2-amine, preferably pramipexole, in admixture with a pharmaceutical carrier or vehicle, and said fluoxetine, zonisamide, or statin, in admixture with a pharmaceutical carrier or vehicle, in three separate containers.

Advantageously, said 5HT3-antagonist and/or NK1-antagonist and said statin, in a fixed-dose combination in admixture with a pharmaceutical carrier or vehicle, may be packaged in a container; and said 6-propylamino-4,5,6,7-tetrahydro-1,3-benzothiazole-2-amine, preferably pramipexole, and said fluoxetine, zonisamide, or statin, in a fixed-dose combination in admixture with a pharmaceutical carrier or vehicle, in another, separate container.

Alternatively, said 5HT3-antagonist and/or NK1-antagonist, in admixture with a pharmaceutical carrier or vehicle, may be packaged in a container; and said 6-propylamino-4,5,6,7-tetrahydro-1,3-benzothiazole-2-amine, preferably pramipexole, and said fluoxetine, zonisamide, or statin, in a fixed-dose combination in admixture with a pharmaceutical carrier or vehicle, in another, separate container.

For their concurrent administration for the treatment of synucleinopathies, said 5HT3-antagonist and/or NK1-antagonist, said 6-propylamino-4,5,6,7-tetrahydro-1,3-benzothiazole-2-amine or a pharmaceutically acceptable salt or solvate thereof, and said fluoxetine, zonisamide, or statin may also be formulated together in fixed-dose combination (abc) consisting of a pharmaceutical composition comprising said NK1-antagonist, said 6-propylamino-4,5,6,7-tetrahydro-1,3-benzothiazole-2-amine, and said statin, in admixture with a pharmaceutical carrier or vehicle.

The fixed-dose combinations, (ac) and (abc), assure the safe, concurrent administration of the 5HT3-antagonist and/or NK1-antagonist and of the fluoxetine, zonisamide, or statin, or of the NK1-antagonist, of the 6-propylamino-4,5,6,7-tetrahydro-1,3-benzothiazole-2-amine and of the fluoxetine, zonisamide, or statin.

The above Component (ac), administered to a patient suffering from a PMND, allows for the administration to said patient of a pramipexole daily dose, including pediatric doses and doses used in the titration period, equivalent to from 0.375 mg to 45 mg of pramipexole dihydrochloride monohydrate. Normally, the above Component (ac) allows for the administration of pramipexole daily dose equivalent to from more than 6 mg to 45 mg, from 14.5 mg to 45 mg, up to from more than 20 mg to 45 mg, normally from 15 mg to 25 mg or from 20.25 mg to 25 mg of pramipexole dihydrochloride monohydrate.

Third Aspect of the Invention

A third aspect of the present invention provides the use of a 5HT3-antagonist and/or a NK1-antagonist for the preparation of a medicament (or a 5HT3-antagonist and/or NK1-antagonist for use) for the treatment of a PMND in a patient in need of said treatment, said medicament comprising or consisting of a pharmaceutical composition comprising, as an active ingredient said 5HT3-antagonist and/or NK1-antagonist; as a second active ingredient said 6-propylamino-4,5,6,7-tetrahydro-1,3-benzothiazole-2-amine; and, as a third active ingredient, said fluoxetine, zonisamide, or statin, in admixture with a pharmaceutical carrier or vehicle.

According to a third aspect, the invention provides the use of a 5HT3-antagonist and/or a NK1-antagonist for the preparation of a medicament for the treatment of a PMND in a patient in need of said treatment, in combination with an effective daily dose of 6-propylamino-4,5,6,7-tetrahydro-1,3-benzothiazole-2-amine, preferably pramipexole, and an effective daily dose of fluoxetine, an effective daily dose of zonisamide, or an effective daily dose of a statin.

In particular, the invention provides a pharmaceutical composition for use in treatment of a PMND, comprising a pharmaceutically acceptable carrier and a fixed dose combination of a 5HT3-antagonist and/or NK1-antagonist, a 6-propylamino-4,5,6,7-tetrahydro-1,3-benzothiazole-2-amine; and fluoxetine, zonisamide, or a statin.

More particularly, the invention provides a pharmaceutical fixed-dose combination comprising or consisting of a pharmaceutical composition in dosage unit form comprising a 5HT3-antagonist and/or NK1-antagonist Component (a), a 6-propylamino-4,5,6,7-tetrahydro-1,3-benzothiazole-2-amine Component (b), fluoxetine, zonisamide, or a statin Component (c), and a pharmaceutical carrier or vehicle. In this fixed combination, said 6-propylamino-4,5,6,7-tetrahydro-1,3-benzothiazole-2-amine preferably is pramipexole.

Any of the 5HT3-antagonist and/or NK1-antagonists described in "The 5HT3-antagonist and/or NK1-antagonist Component (a)" section may be used as Component (a), in an amount per unit form as described in said section, in a fixed dose combination with said 6-propylamino-4,5,6,7-tetrahydro-1,3-benzothiazole-2-amine, preferably pramipexole, Component (b), in an amount per unit form as described above in "The 6-propylamino-4,5,6,7-tetrahydro-1,3-benzothiazole-2-amine Component (b)" section, with a fluoxetine, zonisamide, or statin Component (c), in an amount per unit form as described above in "The fluoxetine, zonisamide, or statin Component (c)" section, in admixture with a pharmaceutical carrier or vehicle.

According to this third aspect, the invention also provides a pharmaceutical composition comprising (a) a 5HT3-antagonist and/or NK1-antagonist;

(b) a 6-propylamino-4,5,6,7-tetrahydro-1,3-benzothiazole-2-amine or a pharmaceutically acceptable salt or solvate thereof; and (c) a fluoxetine, zonisamide, or statin or a pharmaceutically acceptable salt or solvate thereof;

in admixture with a pharmaceutical carrier or vehicle.

Preferably, in the above use and composition, said statin is selected from the group consisting of lovastatin and rosuvastatin.

The above pharmaceutical composition comprising said 5HT3-antagonist and/or NK1-antagonist, said 6-propylamino-4,5,6,7-tetrahydro-1,3-benzothiazole-2-amine or pharmaceutically acceptable salt or solvate thereof and said statin or pharmaceutically acceptable salt or solvate thereof normally is in a dosage unit form.

The invention further provides the use of a 5HT3-antagonist and/or NK1-antagonist for the preparation of a medicament (or a NK1-antagonist for use) for the treatment of PMND, and the medicament itself, said medicament being a pharmaceutical composition comprising (a) a 5HT3-antagonist, in an amount per unit form of from 1 μg to 300 mg and/or NK1-antagonist, in an amount per unit form of from 1 μg to 600 mg;

(b) a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to form 0.125 mg to 45 mg, normally from 15 mg to 25 mg or from more than 20 mg to 25 mg of pramipexole dihydrochloride monohydrate; and (c) fluoxetine, in an amount per unit form of from 2 mg to 90 mg, zonisamide, in an amount per unit form of from 25 mg to 600 mg, or a statin, in an amount per unit form of from 0.5 mg to 80 mg, in admixture with a pharmaceutical carrier or vehicle.

According to an embodiment, in this composition the 6-propylamino-4,5,6,7-tetrahydro-1,3-benzothiazole-2-amine is selected from the group consisting of the racemate or a pharmaceutically acceptable salt thereof, in an amount per unit form equivalent to from 0.25 mg to 90 mg of pramipexole dihydrochloride monohydrate; pramipexole or a pharmaceutically acceptable salt thereof, in an amount equivalent to from 0.125 mg to 45 mg, normally from 15 mg to 25 mg or from more than 20 mg to 25 mg of pramipexole dihydrochloride monohydrate; and a (R)/(S)-mixture, in an amount per unit form equivalent to from 50 mg to 3000 mg of pramipexole dihydrochloride monohydrate, inclusive of a (S)-enantiomer amount per unit form equivalent to from 0.125 mg to 45 mg, normally from 15 mg to 25 mg or from more than 20 mg to 25 mg of pramipexole dihydrochloride monohydrate.

In particular, according to this third aspect, the invention provides a pharmaceutical composition comprising a pharmaceutical carrier or vehicle and a fixed-dose combination of (a) a 5HT3-antagonist, in an amount per unit form of from 1 μg to 300 mg and/or NK1-antagonist, in an amount per unit form of from 1 μg to 600 mg;

(b) a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to form 0.125 mg to 45 mg, normally from 15 mg to 25 mg or from more than 20 mg to 25 mg of pramipexole dihydrochloride monohydrate;

(c) fluoxetine, in an amount per unit form of from 2 mg to 90 mg, zonisamide, in an amount per unit form of from 25 mg to 600 mg, or a statin, in an amount per unit form of from 0.5 mg to 80 mg.

For this use, said 5HT3-antagonist and/or said NK1-antagonist is formulated in a pharmaceutical composition in dosage unit form comprising, as an active ingredient, said 5HT3-antagonist and/or said NK1-antagonist, in admixture with a pharmaceutical carrier or vehicle. This pharmaceutical composition is indicated for the treatment of a PMND in a patient in need of said treatment, in combination with 6-propylamino-4,5,6,7-tetrahydro-1,3-benzothiazole-2-amine and with fluoxetine, each at an effective daily dose, an effective daily dose of zonisamide, or an effective daily dose of a statin.

In said pharmaceutical composition, said 5HT3-antagonist and/or said NK1-antagonist is in admixture with a pharmaceutical carrier and formulated in unit form, for example for oral, intravenous, transcutaneous, and/or transdermal administration, as described in "The formulations" section below.

Any of the 5HT3-antagonists and/or the NK1-antagonist described in "The 5HT3-antagonist and/or NK1-antagonist Component (a)" section may be used as an active ingredient of said pharmaceutical composition for the treatment of a PMND in combination with 6-propylamino-4,5,6,7-tetrahydro-1,3-benzothiazole-2-amine described in "The 6-propylamino-4,5,6,7-tetrahydro-1,3-benzothiazole-2-amine Component (b)" section and with "The fluoxetine, zonisamide, or a statin Component (c)" section, according to this third aspect of the present invention.

According to an embodiment of this third aspect, said medicament is a pharmaceutical composition in dosage unit form comprising, as an active ingredient, said 5HT3-antagonist in an amount per unit form of from 1 μg to 300 mg and/or said NK1-antagonist in an amount per unit form of from 1 μg to 600 mg, in admixture with a pharmaceutical carrier or vehicle. This medicament is indicated for the treatment of a PMND in a patient, in combination with 6-propylamino-4,5,6,7-tetrahydro-1,3-benzothiazole-2-amine daily dose equivalent to from 0.375 mg to 3000 mg of pramipexole dihydrochloride monohydrate, inclusive of a (S)-enantiomer daily dose equivalent to from 0.375 mg to 45 mg, normally from 15 mg to 25 mg or from more than 20 mg to 25 mg of pramipexole dihydrochloride monohydrate, and with fluoxetine, at a daily dose equivalent to from 4 mg to 90 mg of fluoxetine base or in the specific 90 mg ER-weekly preparation, with a zonisamide daily dose of from 25 mg to 600 mg of zonisamide free acid, or with a daily dose of from 0.5 mg to 80 mg of a statin.

These daily doses of 6-propylamino-4,5,6,7-tetrahydro-1,3-benzothiazole-2-amine include low pramipexole daily doses useful for the administration, in combination with the 5HT3-antagonist and/or NK1-antagonist with fluoxetine, zonisamide, or a statin, to pediatric patients or during the titration period. In the second case, at the end of said titration period, the medicament thus manufactured enables the safe intake of pramipexole daily doses never heretofore attained (without the combination with the 5HT3-antagonist and/or NK1-antagonist) as described above in "The 6-propylamino-4,5,6,7-tetrahydro-1,3-benzothiazole-2-amine Component (b)" section.

Said 6-propylamino-4,5,6,7-tetrahydro-1,3-benzothiazole-2-amine may also be the racemate, at a daily dose equivalent to from 0.75 mg to 90 mg of pramipexole dihydrochloride monohydrate.

Preferably, said 6-propylamino-4,5,6,7-tetrahydro-1,3-benzothiazole-2-amine is pramipexole or pharmaceutically acceptable salt or solvate thereof, at a daily dose equivalent to from 0.375 mg to 45 mg, normally from 15 mg to 25 mg or from more than 20 mg to 25 mg of pramipexole dihydrochloride monohydrate.

For the treatment of a PMND at the aforementioned respective daily doses, the 5HT3-antagonist and/or the NK1-antagonist, the 6-propylamino-4,5,6,7-tetrahydro-1,3-benzothiazole-2-amine and fluoxetine are each formulated in a pharmaceutical composition in dosage unit form comprising said 5HT3-antagonist and/or NK1-antagonist and, respectively, said 6-propylamino-4,5,6,7-tetrahydro-1,3-benzothiazole-2-amine and said fluoxetine, each in admixture with a pharmaceutical carrier or vehicle.

In general, said 5HT3-antagonist and/or said NK1-antagonist, said 6-propylamino-4,5,6,7-tetrahydro-1,3-benzothiazole-2-amine and said fluoxetine, zonisamide, or statin, are each formulated in said pharmaceutical composition in dosage unit form comprising

- said 5HT3-antagonist in an amount per unit form of from 1 μg to 300 mg and/or said NK1-antagonist in an amount per unit form of from 1 μg to 600 mg;
- said 6-propylamino-4,5,6,7-tetrahydro-1,3-benzothiazole-2-amine in an amount per unit of from equivalent to from 0.125 mg to 3000 mg of pramipexole dihydrochloride monohydrate, including an (S)-enantiomer amount per unit form equivalent to from 0.125 mg to 45 mg, normally from 15 mg to 25 mg or from more than 20 mg to 25 mg of pramipexole dihydrochloride monohydrate and, respectively,
- said fluoxetine, in an amount per unit form equivalent to from 2 mg to 90 mg, normally from 2 mg to 80 mg, of fluoxetine base, zonisamide, in an amount per unit form of from 25 mg to 600 mg, or statin, in an amount per unit form of from 0.5 mg to 80 mg, each in admixture with a pharmaceutical carrier or vehicle. Preferably, in the above combination, said 6-propylamino-4,5,6,7-tetrahydro-1,3-benzothiazole-2-amine is selected from the group consisting of pramipexole, in an amount per unit form equivalent to from 0.125 mg to 45 mg of pramipexole dihydrochloride monohydrate, racemic 6-propylamino-4,5,6,7-tetrahydro-1,3-benzothiazole-2-amine, in an amount per unit form equivalent to from 0.25 mg to 90 mg of pramipexole dihydrochloride monohydrate, and a (R)/(S)-mixture, in an amount per unit form of from equivalent to from 50 mg to 3000 mg of pramipexole dihydrochloride monohydrate, including a (S)-enantiomer amount of from 0.125 mg to 45 mg, normally from 15 mg to 25 mg or from more than 20 mg to 25 mg of pramipexole dihydrochloride monohydrate.

Preferably, in the above use and composition, said statin is selected from the group consisting of lovastatin and rosuvastatin.

In particular, according to an embodiment of this third aspect, the invention also provides the use of a 5HT3-antagonist and/or NK1-antagonist Component (a) for the preparation of a medicament, as a pharmaceutical composition in dosage unit form comprising, as an active ingredient, said 5HT3-antagonist in an amount per unit form of from 1 μg to 300 mg and/or said NK1-antagonist in an amount per unit form of from 1 μg to 600 mg, in admixture with a pharmaceutical carrier or vehicle, in combination with a 6-propylamino-4,5,6,7-tetrahydro-1,3-benzothiazole-2-amine Component (b) selected from the group consisting of pramipexole and pharmaceutically acceptable salts thereof, at a daily dose equivalent to from 0.375 mg to 45 mg, normally from 15 mg to 25 mg or from more than 20 mg to 25 mg of pramipexole dihydrochloride monohydrate; and with fluoxetine Component (c), at a daily dose equivalent to from 4 mg to 90 mg of fluoxetine base, or in the specific 90 mg ER-weekly preparation, or with zonisamide Component (c), at a daily dose of from 25 mg to 600 mg or from 200 mg to 600 mg. Said 5HT3-antagonist is preferably selected from the group consisting of ondansetron and pharmaceutically salts and solvates thereof, in an amount per unit form equivalent to from 2 mg to 32 mg of ondansetron base, dolasetron and pharmaceutically acceptable salts and solvates thereof, in an amount per unit form equivalent to from 25 mg to 200 mg of dolasetron mesylate, and palonosetron and pharmaceutically salts and solvates thereof, in an amount per unit form equivalent to from 0.25 mg to 0.5 mg of palonosetron base.

Said NK1-antagonist is preferably selected from the group consisting of aprepitant and pharmaceutically acceptable salts and solvates and prodrugs thereof; rolapitant and pharmaceutically acceptable salts and solvates and prodrugs thereof; netupitant and pharmaceutically acceptable salts and solvates and prodrugs thereof.

More particularly, according to this third aspect, the invention, provides the use of a 5HT3-antagonist and/or NK1-antagonist for the preparation of a medicament selected from the group consisting of

- a 5HT3-antagonist Component (a) in an amount of from 1 μg to 300 mg and/or a NK1-antagonist in an amount of from 1 μg to 600 mg, for the treatment of a PMND in a patient in combination with a Component (bc) comprising 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, and fluoxetine or a pharmaceutically acceptable salt or solvate thereof active ingredient, in an amount per unit form equivalent to from 2 mg to 90 mg of fluoxetine base, zonisamide or a pharmaceutically acceptable salt or solvate thereof, in an amount per unit form equivalent to from 25 mg to 600 mg, or a statin, in an amount per unit form of from 0.5 mg to 80 mg;

a Component (ab), comprising a 5HT3-antagonist, in an amount per unit form of from 1 μg to 300 mg and/or a NK1-antagonist in an amount per unit form of from 1 μg to 600 mg; and a 6-propylamino-4,5,6,7-tetrahydro-1,3-benzothiazole-2-amine, in an amount per unit form equivalent to from 0.125 mg to 3000 mg of pramipexole dihydrochloride monohydrate including a (S)-enantiomer amount per unit from equivalent to from 0.125 mg to 45 mg, normally from 15 mg to 25 mg or from more than 20 mg to 25 mg of pramipexole dihydrochloride monohydrate, for the treatment of a PMND in a patient, in combination with Component (c) comprising fluoxetine or a pharmaceutically acceptable salt or solvate thereof active ingredient, in an amount per unit form equivalent to from 2 mg to 90 mg of fluoxetine base, zonisamide or a pharmaceutically acceptable salt or solvate thereof, in an amount per unit form equivalent to from 25 mg to 600 mg, or a statin, in an amount per unit form of from 0.5 mg to 80 mg;

a Component (ac), comprising a 5HT3-antagonist, in an amount per unit form of from 1 μg to 300 mg and/or a NK1-antagonist in an amount per unit form of from 1 μg to 600 mg, and fluoxetine or a pharmaceutically acceptable salt or solvate thereof active ingredient, in an amount per unit form equivalent to from 2 mg to 90 mg of fluoxetine base, for the treatment of a PMND in a patient in combination with Component (b), comprising a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, a 5HT3-antagonist Component (a), in an amount per unit form of from 1 μg to 300 mg and/or a NK1-antagonist in an amount per unit form of from 1 μg to 600 mg, for the treatment of a PMND in a patient in combination with a Component (bc), comprising 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate; and fluoxetine, in an amount per unit form of from 2 mg to 90 mg, zonisamide, in an amount per unit form of from 25 mg to 600 mg, or a statin, in an amount per unit form of from 0.5 mg to 80 mg;

a Component (ab) comprising a 5HT3-antagonist, in an amount per unit form of from 1 μg to 300 mg and/or a NK1-antagonist in an amount per unit form of from 1 μg to 600 mg and a 6-propylamino-4,5,6,7-tetrahydro-1,3-benzothiazole-2-amine, in an amount per unit form equivalent to from 0.125 mg to 3000 mg of pramipexole dihydrochloride monohydrate including a (S)-enantiomer amount per unit from equivalent to from 0.125 mg to 45 mg, normally from 15 mg to 25 mg or from more than 20 mg to 25 mg of pramipexole dihydrochloride monohydrate, for the treatment of a PMND in a patient, in combination with Component (c) comprising fluoxetine, in an amount per unit form equivalent to from 2 mg to 90 mg of fluoxetine base, zonisamide, in an amount per unit form equivalent to from 25 mg to 600 mg, or a statin, in an amount per unit form equivalent to from 0.5 mg to 80 mg; and a Component (ac) comprising a 5HT3-antagonist in an amount per unit form of from 1 μg to 300 mg and/or a NK1-antagonist in an amount per unit form of from 1 μg to 600 mg; and fluoxetine, in an amount per unit form of from 2 mg to 90 mg, zonisamide, in an amount per unit form of from 25 mg to 600 mg, or a statin, in an amount per unit form of from 0.5 mg to 80 mg, for the treatment of a PMND in a patient in combination with Component (b), comprising a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit from equivalent to from 0.125 mg to 45 mg, normally from 15 mg to 25 mg or from more than 20 mg to 25 mg of pramipexole dihydrochloride monohydrate, each of said Component (a), Component (b), Component (c), Component (ab), Component (ac) and Component (bc) being or consisting of a pharmaceutical composition, normally in dosage unit form wherein the active ingredients, normally in the above amount per unit form, are in admixture with a pharmaceutical carrier or vehicle.

In particular, according to this third aspect, the invention provides a pharmaceutical composition comprising a pharmaceutical carrier or vehicle and a fixed-dose combination of (a) a NK1-antagonist, in an amount per unit form of from 1 μg to 600 mg;

(b) a 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to form 0.125 mg to 45 mg, normally from 15 mg to 25 mg or from more than 20 mg to 25 mg of pramipexole dihydrochloride monohydrate;

(c) a statin, in an amount per unit form of from 0.5 mg to 80 mg.

More particularly, according to this third aspect, as fixed-dose combination (abc) the invention provides a pharmaceutical composition comprising (a) a 5HT3-antagonist, in an amount per unit form of from 1 μg to 300 mg and/or a NK1-antagonist, in an amount per unit form of from 1 μg to 600 mg;

(b) a 6-propylamino-4,5,6,7-tetrahydro-1,3-benzothiazole-2-amine selected from the group consisting of pramipexole and pharmaceutically acceptable salts and solvates thereof, in an amount per unit form equivalent to from more than 20 mg to 45 mg, normally from 20.25 mg to 25 mg of pramipexole dihydrochloride monohydrate; and (c) a statin, in an amount per unit form of from 0.5 mg to 80 mg, in admixture with a pharmaceutical carrier or vehicle.

Preferably, said NK1-antagonist Component (a) is selected from the group consisting of aprepitant, in an amount per unit form of from 10 mg to 250 mg of aprepitant, and rolapitant, in an amount per unit form of from 15 mg to 270 mg of rolapitant.

This pharmaceutical composition is useful for the treatment of a PMND in a patient in need of said treatment.

According to an advantageous embodiment, in this fixed-dose combination, said NK1-antagonist Component (a) is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; and netupitant and pharmaceutically acceptable salts and solvates thereof, in an amount, per unit form, equivalent to from 150 mg to 600 mg of netupitant;

said 6-propylamino-4,5,6,7-tetrahydro-1,3-benzothiazole-2-amine Component (b) is selected from the group consisting of the racemate or a pharmaceutically acceptable salt thereof, in an amount per unit form equivalent to from 0.25 mg to 90 mg, normally from 30 mg to 50 mg or from more than 30 mg to 50 mg of pramipexole dihydrochloride monohydrate, pramipexole or a pharmaceutically acceptable salt thereof, in an amount equivalent to from 0.125 mg to 45 mg, normally from 15 mg to 25 mg or from more than 20 mg to 25 mg of pramipexole dihydrochloride monohydrate, and a (R)/(S)-mixture, in an amount per unit form equivalent to from 50 mg to 3000 mg of pramipexole dihydrochloride monohydrate, inclusive of a (S)-enantiomer amount per unit form equivalent to from 0.125 mg to 45 mg, normally from 15 mg to 25 mg or from more than 20 mg to 25 mg of pramipexole dihydrochloride monohydrate; and said statin is selected from the group consisting of atorvastatine and pharmaceutically acceptable salts and solvates thereof, in an amount per unit form equivalent to from 5 mg to 80 mg, normally from 5 mg to 60 mg of atorvastatin free acid; fluvastatin and pharmaceutically acceptable salts and solvates thereof, in an amount per unit form equivalent to from 10 mg to 80 mg, normally from 10 mg to 60 mg of fluvastatin free acid; lovastatin, in an amount of from 5 mg to 80 mg, normally from 5 mg to 60 mg; pitavastatin and pharmaceutically acceptable salts and solvates thereof, in an amount per unit form equivalent to from 0.5 mg to 4 mg, normally from 0.5 mg to 3 mg of pitavastatin free acid; pravastatin and pharmaceutically acceptable salts and solvates thereof, in an amount per unit form equivalent to from 2.5 mg to 60 mg, normally from 2.5 mg to 40 mg of pravastatin sodium; rosuvastatin and pharmaceutically acceptable salts and solvates thereof, in an amount per unit form equivalent to from 2.5 mg to 40 mg, normally from 2.5 mg to 30 mg of rosuvastatin calcium; and simvastatin, in an amount per unit form of from 2.5 mg to 40 mg, normally from 2.5 mg to 30 mg.

According to a particularly advantageous embodiment, the invention provides a pharmaceutical composition comprising a pharmaceutical carrier or vehicle and a fixed-dose combination of aprepitant Component (a), in an amount from 10 mg to 250 mg; a 6-propylamino-4,5,6,7-tetrahydro-1,3-benzothiazole-2-amine Component (b) selected from the group consisting of pramipexole and pharmaceutically acceptable salts and solvates thereof, in an amount equivalent to from 0.125 mg to 45 mg, normally from 15 mg to 25 mg or from more than 20 mg to 25 mg of pramipexole dihydrochloride monohydrate; and a statin Component (c) selected from the group consisting of rosuvastatin and pharmaceutically acceptable salts and solvates thereof, in an amount equivalent to from 2.5 mg to 40 mg of rosuvastatin calcium, and lovastatin, in an amount of from 5 mg to 80 mg.

In said pharmaceutical composition, useful or for use for the treatment of a PMND, said pramipexole may be present in an amount per unit form of from more than 4.5 mg to 45 mg, from more than 6 mg to 45 mg and even from 6.5 mg to 45 mg, normally from 15 mg to 25 mg or from more than 20 mg to 25 mg of pramipexole dihydrochloride monohydrate.

A specific, preferred fixed-dose combination (abc) comprises aprepitant, in an amount of from 10 mg to 250 mg or rolapitant in an amount of from 15 mg to 270 mg;

pramipexole or a pharmaceutically acceptable salt or solvate thereof, in an amount equivalent to of from 0.125 mg to 45 mg, normally from 15 mg to 25 mg or from more than 20 mg to 25 mg of pramipexole dihydrochloride monohydrate; and lovastatin, in an amount of from 5 mg to 80 mg, from 5 mg to 60 mg or from 10 mg to 60 mg.

In this specific, preferred fixed-dose combination (abc), pramipexole or a pharmaceutically acceptable salt or solvate thereof may be present in an amount equivalent to from 15 mg to 25 mg or from 20.25 mg to 25 mg of pramipexole dihydrochloride monohydrate.

Specific amounts per unit form of the 5HT3-antagonist and/or NK1-antagonist Component (a), of the 6-propylamino-4,5,6,7-tetrahydro-1,3-benzothiazole-2-amine Component (b), and of the statin Component (c) active ingredients, in particular the amounts per unit form sub-ranges of said Component (a), of said Component (b) and, respectively, of said Component (c), are described above in "The 5HT3-antagonist and/or NK1-antagonist Component (a)", and in "The 6-propylamino-4,5,6,7-tetrahydro-1,3-benzothiazole-2-amine Component (b)", and, respectively, in "The fluoxetine, zonisamide, or statin Component (c)" sections.

As set forth above, in the treatment of a PMND, the 5HT3-antagonist and/or the NK1-antagonist, the 6-propylamino-4,5,6,7-tetrahydro-1,3-benzothiazole-2-amine and fluoxetine are used in combination with each other, and the three active components may be co-administered simultaneously or sequentially, or in a fixed dose combination including a pharmaceutical composition comprising the 5HT3-antagonist and/or the NK1-antagonist, the 6-propylamino-4,5,6,7-tetrahydro-1,3-benzothiazole-2-amine and the fluoxetine, in admixture with a pharmaceutically acceptable carrier or vehicle.

According to a preferred embodiment, Component (b) in the pharmaceutical compositions (b), (ab), and (bc) of the above combinations, including fixed-dose combination, the 6-propylamino-4,5,6,7-tetrahydro-1,3-benzothiazole-2-amine is pramipexole or a pharmaceutically acceptable salt or solvate thereof, in an amount per unit form of from 0.125 mg to 45 mg, to be administered at a daily dose of from 0.375 mg to 45 mg. sub-ranges of the above pramipexole amounts per unit form and daily doses are described in "The 6-propylamino-4,5,6,7-tetrahydro-1,3-benzothiazole-2-amine Component (b)" section and are also the object of this section.

In this specific, preferred fixed-dose combination (abc), pramipexole or a pharmaceutically acceptable salt or solvate thereof may be present in an amount equivalent to from 15 mg to 25 mg or from 20.25 mg to 25 mg of pramipexole dihydrochloride monohydrate.

Specific amounts per unit form and daily doses of the above 5HT3-antagonist and/or the above NK1-antagonist, pramipexole and fluoxetine, zonisamide, or statin in the pharmaceutical compositions Component (a), Component (b), Component (c), Component (ab), Component (ac) and Component (bc) are described in the "Specific embodiments" section below.

The 5HT3-antagonist and/or the NK1-antagonist Component (a), the 6-propylamino-4,5,6,7-tetrahydro-1,3-benzothiazole-2-amine Component (b) and the fluoxetine, zonisamide, or statin Component (c) can be administered separately or together in any conventional oral or parenteral dosage unit form such as capsule, tablet, powder, cachet, suspension, solution, or transdermal drug delivery system.

In the case of separate (concurrent or sequential) administration of said 5HT3-antagonist and/or said NK1-antagonist, in an effective amount per unit form, of said 6-propylamino-4,5,6,7-tetrahydro-1,3-benzothiazole-2-amine, in an effective amount per unit form, and of said fluoxetine, zonisamide, or a statin, in an effective amount per unit form, each of them can be packaged in a kit comprising said 5HT3-antagonist and/or said NK1-antagonist, in admixture with a pharmaceutical carrier or vehicle, said 6-propylamino-4,5,6,7-tetrahydro-1,3-benzothiazole-2-amine, preferably pramipexole, in admixture with a pharmaceutical carrier or vehicle, and said fluoxetine, zonisamide, or statin, in admixture with a pharmaceutical carrier or vehicle, in three separate containers.

Advantageously, said 5HT3-antagonist and/or said NK1-antagonist and said fluoxetine, zonisamide, or a statin, in a fixed-dose combination in admixture with a pharmaceutical carrier or vehicle, may be packaged in a container; and said 6-propylamino-4,5,6,7-tetrahydro-1,3-benzothiazole-2-amine, preferably pramipexole, in admixture with a pharmaceutical carrier or vehicle, in another, separate container.

Alternatively, said 5HT3-antagonist and/or said NK1-antagonist, in admixture with a pharmaceutical carrier or vehicle, may be packaged in a container; and said 6-propylamino-4,5,6,7-tetrahydro-1,3-benzothiazole-2-amine, preferably pramipexole, and said fluoxetine, zonisamide, or a statin, in a fixed-dose combination in admixture with a pharmaceutical carrier or vehicle, in another, separate container.

For their concurrent administration for the treatment of synucleinopathies, said 5HT3-antagonist and/or said NK1-antagonist, said 6-propylamino-4,5,6,7-tetrahydro-1,3-benzothiazole-2-amine or a pharmaceutically acceptable salt or solvate thereof, preferably pramipexole, and said fluoxetine or a pharmaceutically acceptable salt or solvate thereof, said zonisamide, in admixture with a pharmaceutical carrier or vehicle, or said statin, may also be formulated together in fixed-dose combination (abc) consisting of a pharmaceutical composition comprising said 5HT3-antagonist and/or said NK1-antagonist, said 6-propylamino-4,5,6,7-tetrahydro-1,3-benzothiazole-2-amine, preferably pramipexole or pharmaceutically acceptable salt or solvate thereof, and said fluoxetine, zonisamide, or a statin, in admixture with a pharmaceutical carrier or vehicle.

The fixed-dose combination (abc) assure the safe, concurrent administration of the 5HT3-antagonist and/or the NK1-antagonist, of the 6-propylamino-4,5,6,7-tetrahydro-1,3-benzothiazole-2-amine and of fluoxetine, zonisamide, or a statin.

Fourth Aspect of the Invention

A fourth aspect of the present invention provides the use of a 5HT3-antagonist and/or a NK1-antagonist for the preparation of a medicament for the treatment of a PMND in a patient in need of said treatment, said medicament comprising or consisting of a pharmaceutical composition in dosage unit form comprising, as an active ingredient said 5HT3-antagonist and/or said NK1-antagonist; as a second active ingredient 6-propylamino-4,5,6,7-tetrahydro-1,3-benzothiazole-2-amine; and, as a third active ingredient, fluoxetine, zonisamide, or a statin, in admixture with a pharmaceutical carrier or vehicle.

In particular, the invention provides a pharmaceutical fixed-dose combination comprising or consisting of a pharmaceutical composition in dosage unit form comprising a 5HT3-antagonist and/or a NK1-antagonist Component (a), a 6-propylamino-4,5,6,7-tetrahydro-1,3-benzothiazole-2-amine Component (b), and fluoxetine, zonisamide, or a statin Component (c), in admixture with a pharmaceutical carrier or vehicle. In this fixed combination, said 6-propylamino-4,5,6,7-tetrahydro-1,3-benzothiazole-2-amine preferably is pramipexole.

Any of the 5HT3-antagonists and/or the NK1-antagonist described in "The 5HT3-antagonist and/or NK1-antagonist Component (a)" section may be used as Component (a) of said pharmaceutical composition, in an amount per unit form as described in said section, in a fixed dose combination with said 6-propylamino-4,5,6,7-tetrahydro-1,3-benzothiazole-2-amine, preferably pramipexole, Component (b), in an amount per unit form as described above in "The 6-propylamino-4,5,6,7-tetrahydro-1,3-benzothiazole-2-amine Component (b)" section, and with fluoxetine, zonisamide, or a statin Component (c), in an amount per unit form as described above in "The fluoxetine, zonisamide, or a statin Component (c)" section, in admixture with a pharmaceutical carrier or vehicle.

According to this fourth aspect, the invention provides the use of 5HT3-antagonist and/or NK1-antagonist for the preparation of a medicament for the treatment of PMND, said medicament being a pharmaceutical composition comprising (a) a 5HT3-antagonist, in an amount per unit form of from 1 μg to 300 mg and/or a NK1-antagonist, in an amount per unit form of from 1 μg to 600 mg;

(b) 6-propylamino-4,5,6,7-tetrahydro-1,3-benzothiazole-2-amine, in an amount per unit form equivalent to from 0.125 mg to 3000 mg of pramipexole dihydrochloride monohydrate, including a (S)-enantiomer amount per unit form equivalent to form 0.125 mg to 45 mg of pramipexole dihydrochloride monohydrate; and (c) fluoxetine or a pharmaceutically acceptable salt or solvate thereof, in an amount per unit form (in fluoxetine base) of from 2 mg to 90 mg, or
   zonisamide or a pharmaceutically acceptable salt or solvate thereof, in an amount per unit form in an amount per unit form of from 25 mg to 600 mg, or
   a statin or a pharmaceutically acceptable salt or solvate thereof, in an amount per unit form of from 0.5 mg to 80 mg;

in admixture with a pharmaceutical carrier or vehicle.

Preferably, in the above use and composition, said fluoxetine or pharmaceutically acceptable salt or solvate thereof is fluoxetine hydrochloride.

The present invention also provides a fixed-dose combination comprising or consisting of a pharmaceutical composition in dosage unit form comprising (a) a 5HT3-antagonist, in an amount per unit form of from 1 μg to 300 mg and/or a NK1-antagonist, in an amount per unit form of from 1 μg to 600 mg;

(b) a 6-propylamino-4,5,6,7-tetrahydro-1,3-benzothiazole-2-amine selected from the group consisting of the racemate, in an amount per unit form equivalent to from 0.25 mg to 90 mg, normally from 30 mg to 50 mg or from more than 40 mg to 50 mg of pramipexole dihydrochloride monohydrate; pramipexole, in an amount equivalent to from 0.125 mg to 45 mg, normally from 15 mg to 25 mg or from more than 20 mg to 25 mg of pramipexole dihydrochloride monohydrate; and a (R)/(S)-mixture, in an amount per unit form of from 50 mg to 3000 mg of pramipexole dihydrochloride monohydrate, inclusive of a (S)-enantiomer amount per unit form equivalent to form 0.125 mg to 45 mg, normally from 15 mg to 25 mg or from more than 20 mg to 25 mg of pramipexole dihydrochloride monohydrate; and (c) fluoxetine, in an amount per unit form (in fluoxetine base) of from 2 mg to 90 mg, zonisamide, in an amount per unit form of from 25 mg to 600 mg, or statin, in an amount per unit form of from 0.5 mg to 80 mg;

in admixture with a pharmaceutical carrier or vehicle.

Thus, the present invention provides a fixed-dose combination (abc) comprising or consisting of a pharmaceutical composition comprising:

(a) a 5HT3-antagonist and/or a NK1-antagonist;

(b) a 6-propylamino-4,5,6,7-tetrahydro-1,3-benzothiazole-2-amine or a pharmaceutically acceptable salt or solvate thereof; and (c) fluoxetine or a pharmaceutically acceptable salt or solvate thereof, zonisamide or a pharmaceutically acceptable salt or solvate thereof, or fluoxetine, zonisamide, or a statin, in admixture with a pharmaceutical carrier or vehicle.

Normally, said pharmaceutical composition comprising said active ingredients (a), (b) and (c) is in dosage unit form.

In particular, according to this fourth aspect, as fixed-dose combination (abc), the invention provides a pharmaceutical composition in dosage unit form comprising (a) a 5HT3-antagonist, in an amount per unit form of from 1 μg to 300 mg and/or a NK1-antagonist, in an amount per unit form of from 1 μg to 600 mg;

(b) a 6-propylamino-4,5,6,7-tetrahydro-1,3-benzothiazole-2-amine selected from the group consisting of pramipexole and pharmaceutically acceptable salts and solvates thereof, in an amount per unit form equivalent to from more than 20 mg to 45 mg, normally from 20.25 mg to 45 mg, normally from 15 mg to 25 mg or from more than 20 mg to 25 mg of pramipexole dihydrochloride monohydrate; and (c) a fluoxetine selected from the group consisting of fluoxetine and pharmaceutically acceptable salts and solvates thereof, in an amount per unit form equivalent to from 2 mg to 90 mg of fluoxetine base, or zonisamide, in an amount per unit form of from 25 mg to 600 mg, or a statin, in an amount per unit form of from 0.5 mg to 80 mg;

in admixture with a pharmaceutical carrier or vehicle.

Preferably, said 5HT3-antagonist is preferably selected from the group consisting of ondansetron and pharmaceutically salts and solvates thereof, in an amount per unit form equivalent to from 2 mg to 32 mg of ondansetron base, dolasetron and pharmaceutically acceptable salts and solvates thereof, in an amount per unit form equivalent to from 25 mg to 200 mg of dolasetron mesylate, and palonosetron and pharmaceutically salts and solvates thereof, in an amount per unit form equivalent to from 0.25 mg to 0.5 mg of palonosetron base.

Preferably, said NK1-antagonist Component (a) is selected from the group consisting of aprepitant, in an amount per unit form of from 10 mg to 250 mg of aprepitant, and rolapitant, in an amount per unit form of from 15 mg to 270 mg of rolapitant.

A specific combination of a NK1-antagonist and of a 5HT3-antagonist is selected from the group consisting of the fixed-dose combinations netupitant-300/palonosetron-0.5 and fosnetupitant-235/palonosetron-0.25.

This pharmaceutical composition is useful for the treatment of a PMND in a patient in need of said treatment.

Specific amounts per unit form of the 5HT3-antagonist and/or the NK1-antagonist, of the 6-propylamino-4,5,6,7-tetrahydro-1,3-benzothiazole-2-amine and, of the fluoxetine active ingredients, in particular the amounts per unit form sub-ranges of said Component (a), of said Component (b) and, respectively, of said Component (c), are described in "The 5HT3-antagonist and/or NK1-antagonist Component (a)", and in "The 6-propylamino-4,5,6,7-tetrahydro-1,3-benzothiazole-2-amine Component (b)", and, respectively, in "The fluoxetine, zonisamide or statin Component (c)" sections.

SPECIFIC EMBODIMENTS

As mentioned above, for the treatment of a PMND, the 5HT3-antagonist and/or the NK1-antagonist Component (a), the 6-propylamino-4,5,6,7-tetrahydro-1,3-benzothiazole-2-amine Component (b) and the fluoxetine, zonisamide, or statin Component (c) are formulated, separately or in fixed-dose combinations, in a pharmaceutical composition in dosage unit form, each in admixture with a pharmaceutical carrier.

Thus, for the above method (or use), each of Component (a), Component (b), Component (c), fixed-dose combination (ab), fixed-dose combination (ac), fixed-dose combination (bc) and fixed-dose combination (abc) is formulated in a pharmaceutical composition in dosage unit form in admixture with a pharmaceutical carrier or vehicle, herein below referred to as "Unit Form". In the Unit Form, each of the Component (a), Component (b) and Component (c) may also be formulated separately, each in admixture with a pharmaceutical carrier or vehicle.

As also set forth above, for said use in the combination of the present invention, the 5HT3-antagonist is present in a Unit Form in an amount per unit form of from 1 μg to 300 mg, and is administered at a daily dose of from 1 μg to 300 mg; and/or the NK1-antagonist is present in a Unit Form in an amount per unit form of from 1 μg to 600 mg, and is administered at a daily dose of from 1 μg to 600 mg.

In the Unit Form, the 5HT3-antagonist Component (a) active ingredient is advantageously selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base.

In the Unit Form, the NK1-antagonist Component (a) active ingredient is advantageously selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; and netupitant and pharmaceutically acceptable salts and solvates and prodrugs thereof, in an amount per unit form equivalent to from 150 mg to 600 mg of netupitant.

In the Unit form, a specific Component (a) is selected from the group consisting of the fixed-dose combinations netupitant-300/palonosetron-0.5 and fosnetupitant-235/palonosetron-0.25.

In particular, for its use in combination with 6-propylamino-4,5,6,7-tetrahydro-1,3-benzothiazole-2-amine Component (b) and with fluoxetine, zonisamide, or a statin Component (c) for the treatment of a PMND, the 5HT3-antagonist of a 5HT3-antagonist and/or NK1-antagonist Component (a) of the Unit Form is selected from the group consisting of azasetron hydrochloride, at a daily dose of from 15 mg to 20 mg; dolasetron mesylate monohydrate, at a daily dose equivalent to from 75 mg to 200 mg of dolasetron mesylate; granisetron hydrochloride, at a daily dose equivalent to from 1.5 mg to 8 mg of granisetron base; ondansetron hydrochloride dihydrate, at a daily dose equivalent to from 6 mg to 32 mg of ondansetron base; palonosetron hydrochloride, at a daily dose of from 0.1 mg to 2 mg, preferably from 0.25 mg to 0.5 mg of palonosetron base; ramosetron hydrochloride, at a daily dose of from 0.075 mg to 0.1 mg; and tropisetron hydrochloride, at a daily dose equivalent to from 7.5 mg to 20 mg of tropisetron base.

Ondansetron hydrochloride dihydrate, in an amount per unit form equivalent to from 2 mg to 16 mg of ondansetron base. is the preferred 5HT3-antagonist of the of 5HT3-antagonist and/or NK1-antagonist Component (a) of the Unit Form, and is administered at a daily dose equivalent to from 4 mg to 32 mg of ondansetron base.

In particular, for its use in combination with 6-propylamino-4,5,6,7-tetrahydro-1,3-benzothiazole-2-amine Component (b) and with fluoxetine, zonisamide, or a statin Component (c) for the treatment of a PMND, the NK1-antagonist of a 5HT3-antagonist and/or NK1-antagonist Component (a) of the Unit Form is selected from the group consisting of aprepitant and pharmaceutically acceptable salts and solvates thereof, in an amount equivalent to from 10 mg to 250 mg of aprepitant; fosaprepitant and pharmaceutically acceptable salts and solvates thereof, in an amount equivalent to from 10 mg to 250 mg of aprepitant; rolapitant and pharmaceutically acceptable salts and solvates thereof, in an amount equivalent to from 15 mg to 270 mg of rolapitant; netupitant and pharmaceutically acceptable salts and solvates thereof, in an amount equivalent to from 150 mg to 600 mg of netupitant; fosnetupitant, in an amount equivalent to from 150 mg to 600 mg of netupitant; NK-1 antagonist combination of netupitant-300/palonosetron-0.5; and NK-1 antagonist combination of fosnetupitant-235/palonosetron-0.25.

Aprepitant, in an amount per unit form of from 10 mg to 250 mg, administered at a daily dose of from 10 mg to 250 mg, or rolapitant, in an amount per unit form of from 15 mg to 270 mg, administered at a daily dose of from 15 mg to 270 mg, is the preferred NK1-antagonist of a 5HT3-antagonist and/or NK1-antagonist Component (a) of the Unit Form.

In the combination with a 5HT3-antagonist and/or NK1-antagonist and with fluoxetine, zonisamide, or a statin, the 6-propylamino-4,5,6,7-tetrahydro-1,3-benzothiazole-2-amine Component (b) is present in the Unit Form in an amount equivalent to from 0.125 mg to 3000 mg of pramipexole dihydrochloride monohydrate, including a (S) enantiomer amount equivalent to from 0.125 mg to 45 mg, normally from 15 mg to 25 mg or from more than 20 mg to 25 mg of pramipexole dihydrochloride monohydrate.

The amount per unit form of the 6-propylamino-4,5,6,7-tetrahydro-1,3-benzothiazole-2-amine Component (b) in a Unit Form in IR-formulation normally is equivalent to from 0.125 mg to 1500 mg, advantageously from 1.6 mg to 1500 mg preferably from 1.625 mg to 1500 mg of pramipexole dihydrochloride monohydrate, including a (S)-enantiomer amount equivalent to from 0.125 mg to 22.5 mg, advantageously from 1.6 mg to 22.5 mg preferably from 1.625 mg to 22.5 mg, normally from 7.5 mg to 12.5 mg or from more than 10 mg to 12.5 mg of pramipexole dihydrochloride monohydrate, depending on safety and tolerability, in combination with the 5HT3-antagonist and/or NK1-antagonist Component (a) and with fluoxetine, zonisamide, or a statin Component (c).

The amount of 6-propylamino-4,5,6,7-tetrahydro-1,3-benzothiazole-2-amine in a Unit Form in ER-formulation will normally be equivalent to from 0.375 mg to 3000 mg of pramipexole dihydrochloride monohydrate, including a (S)-enantiomer amount equivalent to from 0.375 mg to 45 mg, advantageously from more than 4.5 mg to 45 mg, preferably from more than 6 mg to 45 mg, from 14.5 mg to 45 mg, normally from 15 mg to 25 mg or from more than 20 mg to 25 mg, of pramipexole dihydrochloride monohydrate, depending on safety and tolerability, in combination with the 5HT3-antagonist and/or NK1-antagonist Component (a) and with fluoxetine, zonisamide, or a statin Component (c).

In the Unit Form, the 6-propylamino-4,5,6,7-tetrahydro-1,3-benzothiazole-2-amine Component (b) active ingredient is selected from the group consisting of

- (S)-6-propylamino-4,5,6,7-tetrahydro-1,3-benzothiazole-2-amine (pramipexole) and pharmaceutically acceptable salts and solvates thereof, in an amount equivalent to from 0.125 mg to 45 mg, normally from 15 mg to 25 mg or from more than 20 mg to 25 mg of pramipexole dihydrochloride monohydrate;
- (R,S)-6-propylamino-4,5,6,7-tetrahydro-1,3-benzothiazole-2-amine (the racemate) and pharmaceutically acceptable salts and solvates thereof, in an amount equivalent to from 0.25 mg to 90 mg, normally from 30 mg to 50 mg or from more than 40 mg to 50 mg of pramipexole dihydrochloride monohydrate; and
- a (R)/(S)-mixture, comprising 6-propylamino-4,5,6,7-tetrahydro-1,3-benzothiazole-2-amine, in an amount equivalent to from 50 mg to 3000 mg of pramipexole dihydrochloride monohydrate, including a (S)-enantiomer amount equivalent to from 0.125 mg to 45 mg, normally from 15 mg to 25 mg or from more than 20 mg to 25 mg of pramipexole dihydrochloride monohydrate.

In the Unit Form, said 6-propylamino-4,5,6,7-tetrahydro-1,3-benzothiazole-2-amine Component (b) may be pramipexole or a pharmaceutically acceptable salt or solvate thereof, in an amount per IR-unit form equivalent to from 0.125 mg to 30 mg or from 0.125 mg to 22.5 mg, up to from 7.25 mg to 22.5 mg or from 20.25 mg to 22.5 mg of pramipexole dihydrochloride monohydrate, normally equivalent to a range selected from the group consisting of from 0.125 mg to 30 mg, from 0.125 mg to 22.5 mg, from 0.125 mg to 11.25 mg, 0.125 mg to 15 mg, and from 0.125 mg to 10 mg of pramipexole dihydrochloride monohydrate, depending on safety and tolerability, in combination with the 5HT3-antagonist Component (a) and with fluoxetine, zonisamide, or a statin Component (c).

Advantageously, said pramipexole or a pharmaceutically acceptable salt or solvate thereof, is in an amount in IR-formulation equivalent to a range selected from the group consisting of from 3 mg to 22.5 mg, from more than 4.5 mg to 22.5 mg, from 4.8 mg to 22.5 mg, from more than 6 mg to 22.5 mg, from 7.25 mg to 22.5 mg, from more than 10 mg to 22.5 mg, and from 20.25 mg to 22.5 mg of pramipexole dihydrochloride monohydrate.

Preferably, said pramipexole or pharmaceutically acceptable salt or solvate thereof active ingredient is in an amount in IR-formulation equivalent to a range selected from the group consisting of from more than 10 mg to 22.5 mg, from 14.5 mg to 22.5 mg, from 15 mg to 22.5 mg, from 17.5 mg to 22.5 mg, and from 20 mg to 22.5 mg and from 20.25 mg to 22.5 mg of pramipexole dihydrochloride monohydrate.

Normally, in this Unit Form, said pramipexole or pharmaceutically acceptable salt thereof is present in an amount per IR-unit form in an amount equivalent to from 7.5 mg or 12.5 mg or from more than 10 mg to 12.5 mg of pramipexole dihydrochloride monohydrate.

According to a particular embodiment, as described in "The formulations" section below, said 6-propylamino-4,5,6,7-tetrahydro-1,3-benzothiazole-2-amine is pramipexole or a pharmaceutically acceptable salt or solvate thereof, in an ER-formulation, in an amount equivalent to a range selected from the group consisting of from more than 4.5 mg to 45 mg, from 4.8 mg to 45 mg, from more than 6 mg to 45 mg, and from more than 10 mg to 45 mg of pramipexole dihydrochloride monohydrate.

Said pramipexole or pharmaceutically acceptable salt or solvate thereof active ingredient in ER-formulation may also be present in an amount equivalent to a range selected from the group consisting of from more than 10 mg to 45 mg, from 14.5 mg to 45 mg, from 15 mg to 45 mg, from 20.25 mg to 45 mg, from 20.25 mg to 40 mg, from 20.25 mg to 35 mg, from 20.25 mg to 30 mg and from 20.25 mg to 25 mg of pramipexole dihydrochloride monohydrate.

Preferably, said pramipexole or pharmaceutically acceptable salt or solvate thereof active ingredient in ER-formulation is be present in an amount equivalent to from 15 mg to 25 mg or from more than 20 mg to 25 mg of pramipexole dihydrochloride monohydrate.

In the combination with a 5HT3-antagonist and/or a NK1-antagonist and with 6-propylamino-4,5,6,7-tetrahydro-1,3-benzothiazole-2-amine, the fluoxetine Component (c) is present in the Unit Form in an amount equivalent to from 2 mg to 90 mg of fluoxetine base or the zonisamide Component (c) is present in the Unit Form in an amount of from 25 mg to 600 mg or the statin Component (c) is present in the Unit Form in an amount of from 0.5 mg to 80 mg.

When fluoxetine Component (c) is not formulated in a fixed-dose combination, the Unit Form may also be the specific 90 mg ER-weekly preparation, to be administered once a week, in combination either with Component (a) and with Component (b), or with Component (ab). According to a specific embodiment of the fourth aspect of the invention, the 5HT3-antagonist and/or NK1-antagonist/6-propylamino-4,5,6,7-tetrahydro-1,3-benzothiazole-2-amine/fluoxetine combination is selected from the group consisting of 5HT3-antagonist Component (a), in a pharmaceutical composition comprising an active ingredient selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base, in admixture with a pharmaceutical carrier or vehicle, for the treatment of a PMND in a patient in combination with Component (bc) in a pharmaceutical composition in dosage unit form comprising pramipexole or pharmaceutically acceptable salt or solvate thereof active ingredient, in an amount per unit form equivalent to from 0.125 mg to 22.5 mg, normally from 7.5 mg to 12.5 mg or from more than 10 mg to 12.5 mg of pramipexole dihydrochloride monohydrate; and fluoxetine or a pharmaceutically acceptable salt or solvate thereof active ingredient, in an amount per unit form equivalent to from 2 mg to 40 mg of fluoxetine base, in admixture with a pharmaceutical carrier or vehicle in IR-formulation;

a 5HT3-antagonist Component (a), in a pharmaceutical composition comprising an active ingredient selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base, in admixture with a pharmaceutical carrier or vehicle, for the treatment of a PMND in a patient in combination with Component (bc) in a pharmaceutical composition in dosage unit form comprising pramipexole or pharmaceutically acceptable salt or solvate thereof active ingredient, in an amount per unit form equivalent to from 0.375 mg to 45 mg, normally from 15 mg to 25 mg or from more than 20 mg to 25 mg of pramipexole dihydrochloride monohydrate; and fluoxetine or a pharmaceutically acceptable salt or solvate thereof active ingredient, in an amount per unit form equivalent to from 4 mg to 90 mg of fluoxetine base, in admixture with a pharmaceutical carrier or vehicle in ER-formulation to be administered once a day;

a Component (ab), as a pharmaceutical composition comprising a 5HT3-antagonist active ingredient (a) selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base; and pramipexole or pharmaceutically acceptable salt or solvate thereof Component (b) active ingredient, in an amount per unit form equivalent to from 0.125 mg to 45 mg, normally from 15 mg to 25 mg or from more than 20 mg to 25 mg of pramipexole dihydrochloride monohydrate in admixture with a pharmaceutical carrier or vehicle;

for the treatment of a PMND in combination with Component (c), as a pharmaceutical composition comprising fluoxetine or a pharmaceutically acceptable salt or solvate thereof active ingredient, in an amount per unit form equivalent to from 2 mg to 90 mg of fluoxetine base, in admixture with a pharmaceutical carrier or vehicle;

a Component (ac), as a pharmaceutical composition in dosage unit form comprising a 5HT3-antagonist active ingredient (a) selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base; and fluoxetine or pharmaceutically acceptable salt or solvate thereof Component (c) active ingredient, in an amount per unit form equivalent to from 2 mg to 90 mg of fluoxetine base, in admixture with a pharmaceutical carrier or vehicle in an IR or ER formulation to be administered once or twice a day;

for the treatment of a PMND in combination with Component (b), as a pharmaceutical composition comprising 6-propylamino-4,5,6,7-tetrahydro-1,3-benzothiazole-2-amine active ingredient, in an amount per unit form equivalent to from 0.125 mg to 3000 mg of pramipexole dihydrochloride monohydrate, including a (S)-enantiomer amount per unit form equivalent to from 0.125 mg to 45 mg of pramipexole dihydrochloride monohydrate, in particular pramipexole or a pharmaceutically acceptable salt or solvate thereof, amount per unit form equivalent to from 0.125 mg to 45 mg, up to from 20.25 mg to 45 mg, normally from 15 mg to 25 mg or from more than 20 mg to 25 mg of pramipexole dihydrochloride monohydrate, in admixture with a pharmaceutical carrier or vehicle;

a NK1-antagonist Component (a), in a pharmaceutical composition comprising an active ingredient selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; and netupitant and pharmaceutically acceptable salts and solvates and prodrugs thereof, in an amount per unit form equivalent to from 150 mg to 600 mg of netupitant; in admixture with a pharmaceutical carrier or vehicle, in an IR formulation to be administered once a day, for the treatment of a PMND in a patient in combination with Component (bc) in a pharmaceutical composition in dosage unit form comprising pramipexole or pharmaceutically acceptable salt or solvate thereof active ingredient (b), in an amount per unit form equivalent to from 0.125 mg to 22.5 mg, normally from 7.5 mg to 12.5 mg or from more than 10 mg to 12.5 mg of pramipexole dihydrochloride dihydrate; and fluoxetine or a pharmaceutically acceptable salt or solvate thereof active ingredient (c), in an amount per unit form equivalent to from 2 mg to 40 mg of fluoxetine base, in admixture with a pharmaceutical carrier or vehicle in IR-formulation to be administered twice a day;

a NK1-antagonist Component (a), in a pharmaceutical composition comprising an active ingredient selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; and netupitant and pharmaceutically acceptable salts and solvates and prodrugs thereof, in an amount per unit form equivalent to from 150 mg to 600 mg of netupitant; in admixture with a pharmaceutical carrier or vehicle in an IR formulation to be administered once a day, for the treatment of a PMND in a patient in combination with Component (bc) in a pharmaceutical composition in dosage unit form comprising pramipexole or pharmaceutically acceptable salt or solvate thereof active ingredient (b), in an amount per unit form equivalent to from 0.375 mg to 45 mg of pramipexole dihydrochloride dihydrate; and fluoxetine or a pharmaceutically acceptable salt or solvate thereof active ingredient (c), in an amount per unit form equivalent to from 4 mg to 90 mg of fluoxetine base, in admixture with a pharmaceutical carrier or vehicle in ER-formulation to be administered once a day;

a Component (ab), as a pharmaceutical composition comprising a NK1-antagonist active ingredient (a) selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; and netupitant and pharmaceutically acceptable salts and solvates and prodrugs thereof, in an amount per unit form equivalent to from 150 mg to 600 mg of netupitant; and pramipexole or a pharmaceutically acceptable salt or solvate thereof active ingredient (b), in an amount per unit form equivalent to from 0.375 mg to 45 mg, or from 14.5 mg to 45 mg, normally from 15 mg to 25 mg or from more than 20 mg to 25 mg of pramipexole dihydrochloride monohydrate in admixture with a pharmaceutical carrier or vehicle;

for the treatment of a PMND in combination with Component (c), as a pharmaceutical composition comprising fluoxetine or a pharmaceutically acceptable salt or solvate thereof active ingredient, in an amount per unit form equivalent to from 2 mg to 90 mg of fluoxetine base, in admixture with a pharmaceutical carrier or vehicle; and a Component (ac), as a pharmaceutical composition in dosage unit form comprising a NK1-antagonist active ingredient (a) selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; and netupitant and pharmaceutically acceptable salts and solvates and prodrugs thereof, in an amount per unit form equivalent to from 150 mg to 600 mg of netupitant; and fluoxetine active ingredient (c), in an amount per unit form equivalent to from 2 mg to 90 mg, in admixture with a pharmaceutical carrier or vehicle;

for the treatment of a PMND in combination with Component (b), as a pharmaceutical composition comprising 6-propylamino-4,5,6,7-tetrahydro-1,3-benzothiazole-2-amine active ingredient, in an amount per unit form equivalent to from 0.125 mg to 3000 mg of pramipexole dihydrochloride monohydrate, including a (S)-enantiomer amount per unit form equivalent to from 0.125 mg to 45 mg, normally from 15 mg to 25 mg or from more than 20 mg to 25 mg of pramipexole dihydrochloride monohydrate, in particular pramipexole or a pharmaceutically acceptable salt or solvate thereof, amount per unit form equivalent to from 0.125 mg to 45 mg, up to from more than 20 mg to 45 mg or from 20.25 mg to 25 mg, of pramipexole dihydrochloride monohydrate, in admixture with a pharmaceutical carrier or vehicle.

According to a specific embodiment of the fourth aspect of the invention, the 5HT3-antagonist/6-propylamino-4,5,6,7-tetrahydro-1,3-benzothiazole-2-amine/zonisamide combination is selected from the group consisting of a 5HT3-antagonist Component (a), in a pharmaceutical composition comprising an active ingredient selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base, in admixture with a pharmaceutical carrier or vehicle, for the treatment of a PMND in a patient in combination with Component (bc), in a pharmaceutical composition in dosage unit form comprising pramipexole or pharmaceutically acceptable salt or solvate thereof active ingredient (b), in an amount per unit form equivalent to from 0.125 mg to 22.5 mg, normally from 7.5 mg to 12.5 mg or from more than 10 mg to 12.5 mg of pramipexole dihydrochloride monohydrate; and zonisamide, in an amount per unit form of from 25 mg to 200 mg, in admixture with a pharmaceutical carrier or vehicle in IR-formulation;

a 5HT3-antagonist Component (a), in a pharmaceutical composition comprising an active ingredient selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base, in admixture with a pharmaceutical carrier or vehicle;

for the treatment of a PMND in a patient in combination with Component (bc) in a pharmaceutical composition in dosage unit form comprising pramipexole or pharmaceutically acceptable salt or solvate thereof active ingredient, in an amount per unit form equivalent to from 0.375 mg to 45 mg, normally from 15 mg to 25 mg or from more than 20 mg to 25 mg of pramipexole dihydrochloride monohydrate; and zonisamide active ingredient, in an amount per unit form of from 25 mg to 600 mg, in admixture with a pharmaceutical carrier or vehicle in IR- or ER-formulation; and a Component (ab), as a pharmaceutical composition comprising a 5HT3-antagonist active ingredient (a) selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base; and pramipexole or pharmaceutically acceptable salt or solvate thereof Component (b) active ingredient, in an amount per unit form equivalent to from 0.125 mg to 45 mg, normally from 7.5 mg (or more than 7.5 mg) to 25 mg or from 15 mg to 25 mg of pramipexole dihydrochloride monohydrate, in admixture with a pharmaceutical carrier or vehicle;

for the treatment of a PMND in combination with Component (c), as a pharmaceutical composition comprising zonisamide active ingredient in an amount per unit form of from 25 mg to 600 mg, in admixture with a pharmaceutical carrier or vehicle; and a Component (ac), as a pharmaceutical composition in dosage unit form comprising a 5HT3-antagonist active ingredient (a) selected from the group consisting of azasetron and pharmaceutically acceptable salt and solvate thereof, in an amount per unit form equivalent to from 5 mg to 10 mg of azasetron hydrochloride; dolasetron and pharmaceutically acceptable salt and solvate thereof, in an amount per unit form equivalent to from 25 mg to 200 mg of dolasetron mesylate; granisetron and pharmaceutically acceptable salt and solvate thereof, in an amount per unit form equivalent to from 0.5 mg to 2 mg granisetron base; ondansetron and pharmaceutically acceptable salt and solvate thereof, in an amount per unit form equivalent to from 0.5 mg to 32 mg, normally from 2 mg to 32 mg, from 2 mg to 16 mg or from 2 mg to 8 mg ondansetron base; palonosetron and pharmaceutically acceptable salt and solvate thereof, in an amount per unit form equivalent to from 0.25 mg to 0.5 mg palonosetron base; ramosetron and pharmaceutically acceptable salt and solvate thereof, in an amount per unit form equivalent to from 0.05 mg to 0.5 mg of ramosetron hydrochloride; and tropisetron and pharmaceutically acceptable salt and solvate thereof, in an amount per unit form equivalent to from 2.5 mg to 5 mg tropisetron base; and zonisamide active ingredient (c), in an amount per unit form of from 25 mg to 600 mg, in admixture with a pharmaceutical carrier or vehicle in an IR or ER formulation to be administered once or twice a day;

for the treatment of a PMND in combination with Component (b), as a pharmaceutical composition comprising 6-propylamino-4,5,6,7-tetrahydro-1,3-benzothiazole-2-amine active ingredient in an amount per unit form equivalent to from 0.125 mg to 3000 mg of pramipexole dihydrochloride monohydrate, including a (S)-enantiomer amount per unit form equivalent to from 0.125 mg to 45 mg, normally from 7.5 mg (or more than 7.5 mg) to 25 mg or from 15 mg to 25 mg, of pramipexole dihydrochloride monohydrate, in admixture with a pharmaceutical carrier or vehicle.

According to a specific embodiment of the three aspects of the invention, the NK1-antagonist/6-propylamino-4,5,6,7-tetrahydro-1,3-benzothiazole-2-amine/statin combination is selected from the group consisting of a NK1-antagonist Component (a), in a pharmaceutical composition comprising an active ingredient selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; netupitant and pharmaceutically acceptable salts and solvates and prodrugs thereof, in an amount per unit form equivalent to from 150 mg to 600 mg of netupitant, in admixture with a pharmaceutical carrier or vehicle, in an IR formulation to be administered once a day, for the treatment of a PMND in a patient in combination with Component (bc) in a pharmaceutical composition in dosage unit form comprising pramipexole or pharmaceutically acceptable salt or solvate thereof active ingredient (b), in an amount per unit form equivalent to from 0.125 mg to 22.5 mg, normally from 7.5 mg to 12.5 mg or more than 10 mg to 12.5 mg of pramipexole dihydrochloride monohydrate; and a statin active ingredient (c) selected from the group consisting of fluvastatin in an amount per unit form of from 20 mg to 40 mg; and lovastatin, in an amount per unit form of from 20 mg to 40 mg, in admixture with a pharmaceutical carrier or vehicle in IR-formulation, to be administered twice a day;

a NK1-antagonist Component (a), in a pharmaceutical composition comprising an active ingredient selected from the group consisting of aprepitant and pharmaceutically acceptable salts and solvates and prodrugs thereof, in an amount per unit form equivalent to from 10 mg to 250 mg of aprepitant; rolapitant and pharmaceutically acceptable salts and solvates and prodrugs thereof, in an amount per unit form equivalent to from 15 mg to 270 mg of rolapitant; netupitant and pharmaceutically acceptable salts and solvates and prodrugs thereof, in an amount per unit form equivalent to from 150 mg to 600 mg of netupitant, in admixture with a pharmaceutical carrier or vehicle in an IR formulation, to be administered once a day, for the treatment of a PMND in a patient in combination with Component (bc) in a pharmaceutical composition in dosage unit form comprising pramipexole or pharmaceutically acceptable salt or solvate thereof active ingredient, in an amount per unit form equivalent to from 0.375 mg to 45 mg, normally from 15 mg to 25 mg or from more than 20 mg to 25 mg of pramipexole dihydrochloride monohydrate; and a statin selected from the group consisting of fluvastatin in an amount per unit form of from 20 mg to 80 mg; and lovastatin, in an amount per unit form of from 20 mg to 80 mg, normally from 20 mg to 60 mg, in admixture with a pharmaceutical carrier or vehicle in ER-formulation, to be administered once a day;

a Component (ab), as a Unit Form comprising a NK1-antagonist active ingredient (a) selected from the group consisting of aprepitant and pharmaceutically acceptable salts and solvates and prodrugs thereof, in an amount equivalent to from 10 mg to 250 mg of aprepitant; rolapitant and pharmaceutically acceptable salts and solvates and prodrugs thereof, in an amount equivalent to from 15 mg to 270 mg of rolapitant; and netupitant and pharmaceutically acceptable salts and solvates and prodrugs thereof, in an amount equivalent to from 150 mg to 600 mg of netupitant, in an IR-formulation; and pramipexole or a pharmaceutically acceptable salt or solvate thereof active ingredient (b), in an amount equivalent to from 0.375 mg to 45 mg, from 14.5 mg to 45 mg, normally from 15 mg to 25 mg or from more than 20 mg to 25 mg, of pramipexole dihydrochloride monohydrate, in an ER-formulation;

for the treatment of a PMND in combination with Component (c), as a pharmaceutical composition comprising a statin, in an amount per unit form of from 0.5 mg to 80 mg, in admixture with a pharmaceutical carrier or vehicle; and a Component (ac), as an Unit Form comprising a NK1-antagonist active ingredient (a) selected from the group consisting of aprepitant and pharmaceutically acceptable salts and solvates and prodrugs thereof, in an amount equivalent to from 10 mg to 250 mg of aprepitant; rolapitant and pharmaceutically acceptable salts and solvates and prodrugs thereof, in an amount equivalent to from 15 mg to 270 mg of rolapitant; and netupitant and pharmaceutically acceptable salts and solvates and prodrugs thereof, in an amount equivalent to from 150 mg to 600 mg of netupitant; and a statin active ingredient (c) selected from the group consisting of atorvastatin, in an amount of from 10 mg to 80 mg, lovastatin, in an amount of from 20 mg to 60 mg; pravastatin, in an amount of from 10 mg to 80 mg; rosuvastatin, in an amount of from 10 mg to 40 mg; and simvastatin, in an amount of from 5 mg to 80 mg, in admixture with a pharmaceutical carrier or vehicle;

for the treatment of a PMND in combination with Component (b), as a pharmaceutical composition in dosage unit form comprising 6-propylamino-4,5,6,7-tetrahydro-1,3-benzothiazole-2-amine active ingredient, in an amount per unit form equivalent to from 0.125 mg to 3000 mg of pramipexole dihydrochloride monohydrate, including a (S)-enantiomer amount per unit form equivalent to from 0.125 mg to 45 mg of pramipexole dihydrochloride monohydrate, in particular pramipexole or a pharmaceutically acceptable salt or solvate thereof amount per unit form equivalent to from 0.125 mg to 45 mg, up to from more than 20 mg to 45 mg or from 20.25 mg to 25 mg, normally equivalent to from 15 mg to 25 mg or from more than 20 mg to 25 mg of pramipexole dihydrochloride monohydrate, in admixture with a pharmaceutical carrier or vehicle.

Preferably, said 6-propylamino-4,5,6,7-tetrahydro-1,3-benzothiazole-2-amine Component (b) comprises pramipexole or a pharmaceutically acceptable salt thereof, in an amount per unit form as illustrated in the "The 6-propylamino-4,5,6,7-tetrahydro-1,3-benzothiazole-2-amine Component (b)" section in admixture with a pharmaceutical carrier or vehicle, in an IR or ER formulation.

As Component (a), for the treatment of a PMND in a patient in combination with Component (bc) as described above, said aprepitant or pharmaceutically acceptable salt or solvate or prodrug thereof active ingredient may be fosaprepitant dimeglumine injectable for intravenous administration containing 188 mg of fosaprepitant dimeglumine equivalent to 115 mg of fosaprepitant; and said netupitant or pharmaceutically acceptable salt or solvate or prodrug thereof active ingredient may be netupitant-300/palonosetron-0.5, in an oral formulation, or fosnetupitant-235/palonosetron-0.25, in an injectable formulation.

A typical composition (abc) comprises or consists of a Unit Form comprising (a) a NK1-antagonist in an amount of from 1 μg to 600 mg;

(b) 6-propylamino-4,5,6,7-tetrahydro-1,3-benzothiazole-2-amine selected from the group consisting of the racemate or a pharmaceutically acceptable salt thereof, in an amount equivalent to from 0.25 mg to 90 mg, normally from 30 mg to 50 mg or from more than 40 mg to 50 mg of pramipexole dihydrochloride monohydrate, pramipexole or a pharmaceutically acceptable salt thereof, in an amount equivalent to from 0.125 mg to 45 mg, normally from 15 mg to 25 mg or from more than 20 mg to 25 mg of pramipexole dihydrochloride monohydrate, and a (R)/(S)-mixture, in an amount equivalent to from 50 mg to 3000 mg, inclusive of a (S)-enantiomer amount equivalent to from 0.125 mg to 45 mg, normally from 15 mg to 25 mg or from more than 20 mg to 25 mg of pramipexole dihydrochloride monohydrate;

(c) a statin, in an amount of from 0.5 mg to 80 mg; and a pharmaceutical carrier or vehicle.

Preferably, said 6-propylamino-4,5,6,7-tetrahydro-1,3-benzothiazole-2-amine Component (b) comprises pramipexole or a pharmaceutically acceptable salt thereof, in an amount per unit form as illustrated in the "The 6-propylamino-4,5,6,7-tetrahydro-1,3-benzothiazole-2-amine Component (b)" section in admixture with a pharmaceutical cater or vehicle, in an IR or ER formulation.

According to a further specific embodiment, Component (ab), Component (ac), Component (bc) and the fixed-dose combination (abc) may be in a Unit Form wherein the 5HT3-antagonist and/or NK-1 antagonist, the 6-propylamino-4,5,6,7-tetrahydro-1,3-benzothiazole-2-amine (preferably pramipexole) and the fluoxetine, zonisamide, or statin, are each in admixture with a pharmaceutical carrier or vehicle, in different formulations.

Normally, the 5HT3-antagonist and/or NK-1 antagonist, the 6-propylamino-4,5,6,7-tetrahydro-1,3-benzothiazole-2-amine (preferably pramipexole) and the fluoxetine, zonisamide, or statin, may be each in an IR-formulation or ER-formulation. In said ER-formulation, zonisamide, in the above components (ac), (bc) and (abc) is present in an amount of from 25 mg to 600 mg, in an Unit Form to be administered once a day.

According to a preferred embodiment, the aforementioned Unit Form Component (bc), administered in combination with the 5HT3-antagonist and/or NK-1 antagonist Component (a), comprises or consists of a pharmaceutical composition comprising pramipexole or a pharmaceutically acceptable salt or solvate thereof in an amount per unit form equivalent to from 7.5 mg to 25 mg of pramipexole dihydrochloride monohydrate; and zonisamide free acid, in an amount of from 25 mg to 600 mg, in admixture with a pharmaceutical carrier or vehicle.

In particular, according to this preferred embodiment, the aforementioned Unit Form Component (bc), administered in combination with the 5HT3-antagonist and/or NK-1 antagonist Component (a), comprises or consists of a pharmaceutical composition comprising pramipexole or a pharmaceutically acceptable salt or solvate thereof in an amount per unit form equivalent to from 7.5 mg (or from more than 7.5 mg) to 12.5 mg of pramipexole dihydrochloride monohydrate; and zonisamide free acid, in an amount of from 25 mg to 200 mg, in admixture with a pharmaceutical carrier or vehicle in IR-formulation.

Alternatively, according to this preferred embodiment, the aforementioned Unit Form Component (bc), administered in combination with the 5HT3-antagonist and/or NK-1 antagonist Component (a), comprises or consists of a pharmaceutical composition comprising pramipexole or a pharmaceutically acceptable salt or solvate thereof in an amount per unit form equivalent to from 15 mg (or from more than 15 mg) to 25 mg of pramipexole dihydrochloride monohydrate; and zonisamide free acid, in an amount of from 200 mg to 600 mg, in admixture with a pharmaceutical carrier or vehicle in ER-formulation.

As Component (a), for the treatment of a PMND in a patient in combination with Component (bc) as described above, said aprepitant or pharmaceutically acceptable salt or solvate or prodrug thereof active ingredient may be a fosaprepitant dimeglumine injectable for intravenous administration containing 188 mg of fosaprepitant dimeglumine equivalent to 115 mg of fosaprepitant; and said netupitant or pharmaceutically acceptable salt or solvate or prodrug thereof active ingredient may be netupitant-300/palonosetron-0.5, in an oral formulation, or fosnetupitant-235/palonosetron-0.25, in an injectable formulation.

A fixed-dose combination (abc) comprises or consists of an Unit Form comprising (a) a 5HT3-antagonist in an amount per unit form of from 1 μg to 300 mg and/or a NK1-antagonist in an amount per unit form of from 1 μg to 600 mg;

(b) a 6-propylamino-4,5,6,7-tetrahydro-1,3-benzothiazole-2-amine selected from the group consisting of the racemate or a pharmaceutically acceptable salt thereof, in an amount per unit form equivalent to from 0.25 mg to 90 mg, normally from 30 mg to 50 mg or from more than 40 mg to 50 mg of pramipexole dihydrochloride monohydrate, pramipexole or a pharmaceutically acceptable salt thereof, in an amount equivalent to from 0.125 mg to 45 mg, normally from 15 mg to 25 mg or from more than 20 mg to 25 mg of pramipexole dihydrochloride monohydrate, and a (R)/(S)-mixture, in an amount per unit form of from 50 mg to 3000 mg, inclusive of a (S)-enantiomer amount per unit form equivalent to from 0.125 mg to 45 mg, normally from 15 mg to 25 mg or from more than 20 mg to 25 mg of pramipexole dihydrochloride monohydrate;

(c) fluoxetine, in an amount per unit form of from 2 mg to 90 mg, or zonisamide, in an amount per unit form of from 25 mg to 600 mg;

and a pharmaceutical carrier or vehicle.

A typical composition (abc) comprises or consists of a Unit Form comprising (a) a NK1-antagonist in an amount of from 1 μg to 600 mg;

(b) 6-propylamino-4,5,6,7-tetrahydro-1,3-benzothiazole-2-amine selected from the group consisting of the racemate or a pharmaceutically acceptable salt thereof, in an amount equivalent to from 0.25 mg to 90 mg, normally from 30 mg to 50 mg or from more than 40 mg to 50 mg of pramipexole dihydrochloride monohydrate, pramipexole or a pharmaceutically acceptable salt thereof, in an amount equivalent to from 0.125 mg to 45 mg, normally from 15 mg to 25 mg or from more than 20 mg to 25 mg of pramipexole dihydrochloride monohydrate, and a (R)/(S)-mixture, in an amount equivalent to from 50 mg to 3000 mg, inclusive of a (S)-enantiomer amount equivalent to from 0.125 mg to 45 mg, normally from 15 mg to 25 mg or from more than 20 mg to 25 mg of pramipexole dihydrochloride monohydrate;

(c) a statin, in an amount of from 0.5 mg to 80 mg; and a pharmaceutical carrier or vehicle.

According to an advantageous embodiment, said fixed-dose combination (abc) Unit Form comprises pramipexole or a pharmaceutically acceptable salt or solvate thereof in an amount per unit form (in pramipexole dihydrochloride monohydrate) in a range selected from the group consisting of from more than 4.5 mg to 45 mg, from 7.5 mg to 45 mg, from 10 mg to 45 mg, from 14.5 mg to 45 mg, from more than 20 mg to 45 mg, and from 20.25 mg to 45 mg, normally from 7.5 mg to 25 mg or from 15 mg to 25 mg, of pramipexole dihydrochloride monohydrate; and a pharmaceutical carrier or vehicle.

In particular, as fixed-dose combination (abc), the invention provides a pharmaceutical composition in dosage unit form comprising a 5HT3-antagonist, in an amount per unit form of from 1 μg to 300 mg and/or a NK1-antagonist, in an amount per unit form of from 1 μg to 600 mg; a 6-propylamino-4,5,6,7-tetrahydro-1,3-benzothiazole-2-amine selected from the group consisting of pramipexole and pharmaceutically acceptable salts and solvates thereof, in an amount per unit form equivalent to from 7.5 mg to 45 mg, up to from 20.25 mg to 45 mg, normally from 7.5 mg to 25 mg, from 15 mg to 25 mg, or from 20.25 mg to 25 mg of pramipexole dihydrochloride monohydrate; and fluoxetine, in an amount per unit form of from 2 mg to 90 mg of fluoxetine base, or zonisamide, in an amount per unit form of from 25 mg to 600 mg of zonisamide free acid, or a statin, in an amount per unit form of from 0.5 mg to 80 mg, in admixture with a pharmaceutical carrier or vehicle.

Preferably, said NK1-antagonist Component (a) is selected from the group consisting of aprepitant, in an amount per unit form of from 10 mg to 250 mg, and rolapitant, in an amount per unit form of from 15 mg to 270 mg.

A specific fixed-dose combination (abc) comprises or consists of a Unit Form comprising (a) a 5HT3-antagonist selected from the group consisting of ondansetron and pharmaceutically acceptable salts and solvates thereof, in an amount per unit form equivalent to from 2 mg to 32 mg of ondansetron base, and dolasetron and pharmaceutically acceptable salts and solvates thereof, in an amount per unit form equivalent to from 20 mg to 200 mg of dolasetron mesylate;

(b) pramipexole or a pharmaceutically acceptable salt or solvate thereof in an amount per unit form equivalent to from 7.5 mg (or from more than 7.5 mg) to 25 mg of pramipexole dihydrochloride monohydrate; and (c) zonisamide free acid, in an amount of from 25 mg to 600 mg, in admixture with a pharmaceutical carrier or vehicle.

In the case of separate (concurrent or sequential) administration of, for example, a 5HT3-antagonist and/or NK-1 antagonist/pramipexole/zonisamide combination, said 5HT3-antagonist and/or NK-1 antagonist Component (a), in an effective amount per unit form, said pramipexole Component (b), in an effective amount per unit form, and said zonisamide Component (c), in an effective amount per unit form, the components can each be packaged in a kit comprising said 5HT3-antagonist and/or NK-1 antagonist, in admixture with a pharmaceutical carrier or vehicle, in a container; said pramipexole, in admixture with a pharmaceutical carrier or vehicle, in another, separate container, and said zonisamide, in admixture with a pharmaceutical carrier or vehicle, in a third, separate container.

Similarly, an ondansetron/pramipexole/zonisamide combination may be packaged for example in kit wherein a pharmaceutical composition comprising ondansetron Component (a), in an amount per unit form of from 2 mg to 16 mg in an IR oral formulation, is in a container; a pharmaceutical composition comprising pramipexole dihydrochloride monohydrate Component (b), in an amount per unit form of from 0.375 mg to 45 mg in an ER oral formulation, is in another container; and a pharmaceutical composition comprising zonisamide Component (c), in an amount per unit form of from 25 mg to 200 mg in an IR oral formulation is in third, separate container.

Preferably, said 5HT3-antagonist of a 5HT3-antagonist and/or NK-1 antagonist Component (a) is selected from the group consisting of ondansetron and pharmaceutically salts and solvates thereof, in an amount per unit form equivalent to from 2 mg to 32 mg of ondansetron base, dolasetron and pharmaceutically acceptable salts and solvates thereof, in an amount per unit form equivalent to from 25 mg to 200 mg of dolasetron mesylate, and palonosetron and pharmaceutically salts and solvates thereof, in an amount per unit form equivalent to from 0.25 mg to 0.5 mg of palonosetron base.

Preferably, said NK1-antagonist of a 5HT3-antagonist and/or NK-1 antagonist Component (a) is selected from the group consisting of aprepitant, in an amount per unit form of from 10 mg to 250 mg, and rolapitant, in an amount per unit form of from 15 mg to 270 mg.

According to a further specific embodiment, Component (ab), Component (ac), Component (bc) and the fixed-dose combination (abc) may be in a Unit Form wherein the 5HT3-antagonist and/or the NK1-antagonist, the 6-propylamino-4,5,6,7-tetrahydro-1,3-benzothiazole-2-amine (preferably pramipexole) and the fluoxetine, zonisamide, or statin, are each in admixture with a pharmaceutical carrier or vehicle, in different formulations.

Normally, the NK1-antagonist is in an IR-formulation, in an amount of from 1 µg to 600, and the 6-propylamino-4,5,6,7-tetrahydro-1,3-benzothiazole-2-amine (preferably pramipexole) and zonisamide are each in an ER-formulation, each in an Unit Form to be administered once a day. In said ER-formulation, pramipexole is present in the above Components (ac), (bc) and (abc) in an amount (in pramipexole dihydrochloride monohydrate) of from 0.375 mg to 45 mg or from 20.25 mg to 45 mg normally from 7.5 mg to 25 mg, from 15 mg to 25 mg, or from 20.25 mg to 25 mg, and, respectively, zonisamide, is present in the above components (ac), (bc) and (abc) in an amount of from 25 mg to 600 mg, in an Unit Form to be administered once a day.

Preferably, in said Component (ac), zonisamide active ingredient (c) in said ER-formulation, is an amount per unit form of from 200 mg to 600 mg.

According to further specific embodiments, Component (ab), Component (ac), Component (bc) and the fixed-dose combination (abc) may be in a Unit Form wherein the NK1-antagonist, the 6-propylamino-4,5,6,7-tetrahydro-1,3-benzothiazole-2-amine (preferably pramipexole) and the statin are each in admixture with a pharmaceutical carrier or vehicle, in different formulations.

Normally, the NK1-antagonist is in an IR-formulation, in an amount of from 1 µg to 600 mg and the 6-propylamino-4,5,6,7-tetrahydro-1,3-benzothiazole-2-amine (preferably pramipexole) and the statin may be in an IR or ER formulation.

As Component (a), in certain embodiments, netupitant or pharmaceutically acceptable salt or solvate or prodrug thereof active ingredient may be netupitant-300/palonosetron-0.5, in an oral formulation, or fosnetupitant-235/palonosetron-0.25, in an injectable formulation.

As Component (b), in certain embodiments, pramipexole is present in the above Components (ac), (bc) and (abc) in an amount (in pramipexole dihydrochloride monohydrate) of from 0.375 mg to 45 mg, from 14.5 mg to 45 mg, normally from 15 mg to 25 mg or from 20.25 mg to 25 mg in an ER-formulation.

Preferably, as Component (c) in the above Components (ac), (bc) and (abc), the statin is present in an amount per IR unit form of from 0.5 mg to 80 mg or in an amount per ER unit form of from 4 mg to 80 mg.

In Component (ac), the NK1-antagonist Component (a), preferably, is selected from the group consisting of aprepitant, in an amount per unit form of from 10 mg to 250 mg, and rolapitant, in an amount per unit form of from 15 mg to 270 mg; and the statin Component (c), preferably, is selected from the group consisting of lovastatin, in an amount per unit form of from 5 mg to 60 mg or from 5 mg to 40 mg, normally from 20 mg to 40 mg, in IR-formulation, or 10 mg to 60 mg, normally from 20 mg to 60 mg in an ER-formulation; and rosuvastatin calcium, in an amount per unit form of from 2.5 mg to 40 mg or from 5 mg to 40 mg, normally from 2.5 mg to 30 mg or from 5 mg to 30 mg in IR-formulation.

In the case of separate (concurrent or sequential) administration of, for example, a 5HT3-antagonist/pramipexole/fluoxetine combination, said 5HT3-antagonist of a 5HT3-antagonist and/or NK-1 antagonist Component (a), in an effective amount per unit form, said pramipexole Component (b), in an effective amount per unit form, and said fluoxetine, zonisamide, or statin Component (c), in an effective amount per unit form, each of the components can be packaged in a kit comprising said 5HT3-antagonist, in admixture with a pharmaceutical carrier or vehicle, in a container; said pramipexole, in admixture with a pharmaceutical carrier or vehicle, in another, separate container, and said fluoxetine, zonisamide, or statin, in admixture with a pharmaceutical carrier or vehicle, in a third, separate container.

In the case of separate (concurrent or sequential) administration of, for example, a NK1-antagonist/pramipexole/ fluoxetine combination, said NK1-antagonist of a 5HT3-antagonist and/or NK-1 antagonist Component (a), in an effective amount per unit form, said pramipexole Component (b), in an effective amount per unit form, and said fluoxetine, zonisamide, or statin Component (c), in an effective amount per unit form, can each be packaged in a kit comprising said NK1-antagonist, in admixture with a pharmaceutical carrier or vehicle, in a container; said pramipexole, in admixture with a pharmaceutical carrier or vehicle, in another, separate container, and said fluoxetine, zonisamide, or statin, in admixture with a pharmaceutical carrier or vehicle, in a third, separate container.

Similarly, an ondansetron/pramipexole/fluoxetine combination may be packaged for example in kit wherein a pharmaceutical composition comprising ondansetron as the 5HT3-antagonist of a 5HT3-antagonist and/or NK-1 antagonist Component (a), in an amount per unit form of from 2 mg to 16 mg in an IR oral formulation is in a container, a pharmaceutical composition comprising pramipexole dihydrochloride monohydrate Component (b), in an amount per unit form of from 0.375 mg to 45 mg, normally from 15 mg to 25 mg, from more than 20 mg to 25 mg or from 20.25 mg to 25 mg, in an ER oral formulation is in another container; and a pharmaceutical composition comprising fluoxetine hydrochloride Component (c), in an amount per unit form equivalent to from 2 mg to 40 mg or from 2 mg to 45 mg of fluoxetine base in an IR oral formulation is in third, separate container.

Similarly, an aprepitant/pramipexole/zonisamide combination may be packaged for example in kit wherein a pharmaceutical composition comprising aprepitant Component (a), in an amount per unit form of from 10 mg to 250 mg in an IR oral formulation, is in a container; a pharmaceutical composition comprising pramipexole dihydrochloride monohydrate Component (b), in an amount per unit form of from 0.375 mg to 45 mg, normally from 15 mg to 25 mg, from more than 20 mg to 25 mg or from 20.25 mg to 25 mg in an ER oral formulation, is in another container; and a pharmaceutical composition comprising zonisamide Component (c), in an amount per unit form of from 25 mg to 200 mg in an IR oral formulation is in third, separate container.

Similarly, an aprepitant/pramipexole/statin combination may be packaged for example in kit wherein a pharmaceutical composition comprising aprepitant Component (a), in an amount per unit form of from 10 mg to 250 mg in an IR oral formulation is in a container, a pharmaceutical composition comprising pramipexole dihydrochloride monohydrate Component (b), in an amount per unit form of from 0.375 mg to 45 mg, normally from 15 mg to 25 mg, from more than 20 mg to 25 mg or from 20.25 mg to 25 mg in an ER oral formulation is in another container; and a pharmaceutical composition comprising rosuvastatin Component (c), in an amount per unit form of from 2 mg to 40 mg in an IR oral formulation is in third, separate container.

The Formulations

For the treatment of a PMND in combination with 6-propylamino-4,5,6,7-tetrahydro-1,3-benzothiazole-2-amine and fluoxetine, zonisamide, or statin, the 5HT3-antagonist and/or the NK1-antagonist Component (a) is formulated in a pharmaceutical composition in dosage unit form, wherein said 5HT3-antagonist and/or a NK1-antagonist is in admixture with a pharmaceutical carrier or vehicle. For said treatment, also the 6-propylamino-4,5,6,7-tetrahydro-1,3-benzothiazole-2-amine Component (b) is formulated in a pharmaceutical composition in dosage unit form, wherein said 6-propylamino-4,5,6,7-tetrahydro-1,3-benzothiazole-2-amine is in admixture with a pharmaceutical carrier or vehicle. Similarly, for said treatment, fluoxetine, zonisamide, or statin Component (c) is formulated in a pharmaceutical composition in dosage unit form in admixture with a pharmaceutical carrier or vehicle.

The dosage, i.e. the amount of active ingredient in a single dose (amount per unit form) to be administered to the patient, can vary widely depending on the age, weight, and the health condition of the patient. This dosage includes the administration of a 5HT3-antagonist in an amount from 1 μg to 300 mg, according to the potency of each 5HT3-antagonist and the age of the patient and/or administration of a NK1-antagonist in an amount from 1 μg to 600 mg, according to the potency of each NK1-antagonist and the age of the patient, an effective amount of 6-propylamino-4,5,6,7-tetrahydro-1,3-benzothiazole-2-amine, preferably a pramipexole amount equivalent to from 0.125 mg to 45 mg of pramipexole dihydrochloride monohydrate, according to the age of the patient, and an amount of fluoxetine equivalent to from 2 mg to 80 mg of fluoxetine base, zonisamide amount of from 25 mg to 600 mg, or a statin amount of from 0.5 mg to 80 mg, according to the age of the patient, from one to two times a day by intravenous, subcutaneous, oral, or transcutaneous administration, according to the strength of the doses of the each of the active ingredients.

The above pharmaceutical compositions are formulated in admixture with a pharmaceutical carrier or vehicle for any administration route. For example, said pharmaceutical compositions are in a pharmaceutical dosage unit form for oral, intravenous (including infusion), intramuscular, intranasal, intraperitoneal, subcutaneous, transdermal, or rectal administration.

In the pharmaceutical compositions of the present invention for oral, subcutaneous, intravenous, transdermal or topical administration, the active ingredients are preferably administered in the form of dosage units, comprising a predetermined amount of active ingredient per unit form, in admixture with the classic excipients suitable for different ways of administration, as described above.

These unit forms are manufactured according to conventional technologies. Particularly advantageous are the formulations in the form of tablets, multi-score tablets, multilayer tablets, coated tables, orally disintegrating tablets, extended release tablets, hard or soft capsules, multi-compartment capsules, extended-release capsules, suppositories for rectal administration, patches for transdermal administration, liquid oral solutions, syrups or suspensions in a predetermined unit form, apparatus for intravenous infusion, and vials for the intravenous or subcutaneous administration.

For example, ondansetron may be formulated in a coated tablet, in an orally disintegrable tablet, in a syrup, in injectable solution for intravenous, subcutaneous or intramuscular use, or in a suppository for rectal use.

For example, aprepitant or a pharmaceutically acceptable salt or solvate or prodrug thereof may be formulated in a coated tablet, in an orally disintegrable tablet, in a syrup, in injectable solution for intravenous, subcutaneous or intramuscular use, or in a suppository for rectal use.

The pharmaceutical compositions may be formulated in oral unit forms such as tablets or gelatin capsules wherein the 5HT3-antagonist and/or the NK1-antagonist Component (a), the 6-propylamino-4,5,6,7-tetrahydro-1,3-benzothiazole-2-amine Component (b), the fluoxetine, zonisamide, or statin Component (c), the Component (ab), the Component (ac), the Component (bc) and the Component (abc) active ingredients are in admixture with a carrier or vehicle that may include a diluent, such as cellulose, microcrystalline cellulose, a starch such as maize or corn starch, dextrose, lactose, mannitol, sorbitol or sucrose; a lubricant, such as stearic acid, calcium stearate, magnesium stearate, polyethylene glycol, silica, colloidal silicon dioxide or talc; an emulsifying agent such as silicone, sorbitan monooleate, glyceryl monostearate or sodium lauryl sulfate; and if needed, a binder such as magnesium aluminum silicate, gelatin, methylcellulose, sodium carboxymethylcellulose, a pregelatinized starch such as pregelatinized potato starch, or polyvinylpyrrolidone.

Said oral unit forms may be tablets coated with sucrose, iron oxide, titanium dioxide or with various polymers for an immediate release.

Alternatively, the tablets can be manufactured by using carriers such as acrylic and methacrylic acid polymers and copolymers; cellulose derivatives such as hydroxypropylethylcellulose; or other appropriate materials, to have a prolonged or delayed activity by progressively releasing a predetermined quantity of active ingredient.

For example, the unit forms may be formulated in tablets in which each of the Components (a), (b), (c), (ab), (ac), (bc) and, respectively, the fixed-dose combination (abc) is in ER-formulation, for example in admixture with hydroxypropyl methyl cellulose or in a film-coated microgranule. Carriers and vehicles for ER tablets include retardant materials such as the aforementioned acrylic and methacrylic acid polymers and copolymers; the aforementioned cellulose derivatives such as hydroxypropylmethylcellulose (hypromellose), hydroxyethylcellulose, hydroxypropylethylcellulose, hydroxypropylcellulose, methylcellulose, ethylcellulose, or sodium carboxymethylcellulose; gums; waxes; glycerides or aliphatic alcohols or a mixture thereof.

Said unit forms may also be manufactured according to conventional technologies allowing, for example, the formulation of the 5HT3-antagonist and/or the NK1-antagonist Component (a) in an IR-form and of pramipexole dihydrochloride monohydrate Component (b), in ER-form in the same unit-form and fluoxetine, zonisamide, or statin Component (c) in a separate unit form, in a IR-formulation or in an ER-formulation.

These unit forms may also be manufactured according to conventional technologies allowing, for example, an IR-formulation of the 5HT3-antagonist and/or NK1-antagonist Component (a) and an ER-formulation of lovastatin Component (c) in the same unit-form.

Said unit forms also allow, for example, the formulation of the 5HT3-antagonist and/or NK1-antagonist Component (a) in an IR-form and of pramipexole dihydrochloride monohydrate Component (b), in ER-form in the same unit-form and lovastatin Component (c) in a separate unit form, in an IR-formulation or in an ER-formulation.

Syrups and orally dispersible tablets may also comprise sweeteners, lubricants, taste-masking agents, binders, and coloring agents.

Suppositories are manufactured by using a suppository base such as cocoa butter, poloxamers combined with solvents such as. polyethylene glycols (for example PEG 3350), propylene glycol, or triglycerides according to conventional technologies.

A Transdermal Drug Delivery System (TDDS) provides transdermal delivery using transdermal drug formulations and transdermal patches incorporating such transdermal drug formulations. A transdermal drug delivery system may include a composition in form of a patch, a cream, a gel, a lotion or a paste comprising a 5HT3-antagonist and/or a NK1-antagonist, pramipexole or both the active ingredients; a 5HT3-antagonist and/or a NK1-antagonist, fluoxetine or both the active ingredients, or a 5HT3-antagonist and/or a NK1-antagonist, pramipexole and fluoxetine altogether. Likewise, a transdermal drug delivery system may include a composition in form of a patch, a cream, a gel, a lotion or a paste comprising a 5HT3-antagonist, pramipexole or both the active ingredients; a 5HT3-antagonist, zonisamide or both the active ingredients, or a 5HT3-antagonist, pramipexole and zonisamide altogether.

Typical TDDS is a patch formulation wherein the active ingredient or the mixture of the active ingredients may comprise adjuvants such as D-sorbitol, gelatin, kaolin, methyl paraben, polysorbate 80, propylene glycol, propyl paraben, povidone, sodium carboxymethylcellulose, sodium polyacrylate, tartaric acid, titanium dioxide, and purified water. A patch formulation may also contain skin permeability enhancer such as lactate esters (e.g., lauryl lactate), triacetin or diethylene glycol monoethyl ether.

"Transdermal drug delivery system" provides transdermal delivery using transdermal drug formulations and transdermal patches incorporating such transdermal drug formulations. For example, the transdermal drug delivery system may include a composition in form of a patch, a cream, a gel, a lotion or a paste comprising a 5HT3-antagonist (such as ondansetron). Examples of transdermal formulations may include, but are not limited, to those as described in U.S. Pat. No. 6,562,368, a transdermal gel formulation as described in U.S. Pat. Nos. 7,029,694; 7,179,483; 8,241,662 and US 2009/0018190, a transdermal or transmucosal pharmaceutical formulation, that can be utilized for topical or transdermal application, such that solutions, creams, lotions, sprays, ointment, gels, aerosols and patch drug deliveries as described in WO 2005/039531, US2007/022379, US 2010/0216880, US 2014/0037713 and U.S. Pat. No. 8,652,491, a transdermal absorption preparation as described in WO2013/061969 and US 2014/0271796, the disclosures of which are herein incorporated by reference in their entirety. The transdermal patches may also include, but are not limited to, a patch pump having an in-dwelling rigid catheter with flexible features and/or a flexible catheter attachment as described in U.S. Pat. No. 9,782,536, a selectively activatable patch pump as described in U.S. Pat. No. 9,724,462, a patch pump attached to a wireless communication system as described in U.S. Pat. No. 9,623,173, a conformable patch pump as described in U.S. Pat. No. 9,616,171, an infusion pump as described in U.S. Pat. No. 8,915,879, a portable infusion drug delivery as described in U.S. Pat. No. 8,480,649, a micropump as described in U.S. Pat. No. 8,282,366, and a patch pump as described in U.S. Pat. No. 7,828,771; the disclosures of which are herein incorporated by reference in their entirety. Other transdermal patches may include, but are not limited to, a patch in which oxybutynin is incorporated in an adhesive agent layer composition comprises the acrylic-based polymer as the adhesive base agent, and the acrylic-based polymer is a copolymer of polymethyl methacrylate with a polyacrylate as described in U.S. Pat. No. 8,802,134, a patch consisting of a support layer and of an adhesive agent layer arranged on the at least one surface of the support layer as described in U.S. Pat. No. 8,877,235, a patch using a monoglyceride or a mixture of monoglycerides of fatty acids as skin permeation-enhancer as described in U.S. Pat. Nos. 5,441,740 and 5,500,222, a patch for using a monoglyceride or a mixture of monoglycerides plus a lactate ester as skin permeation-enhancer as described in U.S. Pat. Nos. 5,686,097; 5,747,065; 5,750,137 and 5,900,250, a patch with a non-rate controlling tie layer on the skin-proximal surface of the reservoir, not affecting the drug release as described in U.S. Pat. Nos. 5,614,211 and 5,635,203, a patch using triacetin as permeation enhancer as described in U.S. Pat. Nos. 5,212,199, 5,227,169, 5,601,839 and 5,834,010, a patch with a matrix mass in the form of a layer which is self-adhesive, and in which the matrix mass consists of ammonium-group-containing (meth)acrylate copolymers as described in U.S. Pat. No. 6,555,129, a transdermal patch as described in U.S. Pat. Nos. 6,743,441; 7,081,249; 7,081,250; 7,081,251; 7,081,252 and 7,087,241; the disclosures of which are herein incorporated by reference in their entirety. Preferably, the transdermal drug delivery system is a patch, a patch pump, an infusion pump, or a micropump.

Unit forms may be formulated in tablets in which Component (b) and Component (c) are each in ER-formulation, for example each in admixture with hydroxypropyl methyl cellulose or in a film-coated microgranule. These unit forms (b) and (c) are destined to be concurrently or sequentially administered to a patient suffering from a PMND in combination with an oral unit form such as a tablet or gelatin capsule wherein Component (a) is formulated with a diluent and a lubricant in an IR- or ER-formulation.

Unit forms may be formulated in tablets in which Component (b) and Component (c) each in ER-formulation, for example pramipexole and lovastatin, each in admixture with hydroxypropyl methyl cellulose or in a film-coated microgranule. These unit forms (b) and (c) are concurrently or sequentially administered to a patient suffering from a PMND in combination with an oral unit form such as a tablet or gelatin capsule wherein Component (a) is formulated with a diluent and a lubricant in an IR-formulation, or in a tablet or capsule for extended release.

The above Component (ab), Component (ac) and Component (bc), may be formulated in a two-layer tablet or in a two-compartment capsule wherein, in each of the layers or compartments, each of the (a), (b) and (c) components is in admixture with a pharmaceutical carrier for an IR formulation, or in admixture with a pharmaceutical carrier for an ER formulation.

As set forth above, said oral unit forms may also be tablets or capsules wherein one of the active ingredient is in an IR-formulation and another one is in an ER-formulation.

For example a Component (ab) is a unit form comprising ondansetron or dolasetron in an IR-formulation and pramipexole dihydrochloride monohydrate also in ER-formulation, each at the amount per unit form as described above, to be administered in combination with fluoxetine, zonisamide or a statin, in IR-formulation or ER-formulation. As another example, a Component (ab) is a unit form comprising aprepitant or rolapitant in an IR-formulation and pramipexole dihydrochloride monohydrate in an ER-formulation, each at the amount per unit form as described above, in a Component (ab) fixed dose combination to be administered in combination, including fixed-dose combinations (abc), with fluoxetine, zonisamide or a statin, in IR-formulation or ER-formulation.

In particular, in said Component (ab) pramipexole dihydrochloride monohydrate is in IR-formulation comprising said pramipexole dihydrochloride monohydrate in an amount of from 0.125 mg to 22.5 mg, normally from 7.5 mg to 12.5 mg, from more than 10 mg to 12.5 mg or from 10.125 mg to 12.5 mg. Said Component (ab) is administered to a patient suffering from a PMND in combination with fluoxetine, zonisamide or a statin Component (c), or in an ER-formulation comprising said pramipexole dihydrochloride monohydrate in an amount of from 0.375 mg to 45 mg, normally from 15 mg to 25 mg, from more than 20 mg to 25 mg or from 20.25 mg to 25 mg. Said Component (ab) is administered to a patient suffering from a PMND in combination with fluoxetine, zonisamide or a statin Component (c). Said Component (c) IR-formulation may comprise fluoxetine, in an amount equivalent to from 2 mg to 40 mg or from 2 mg to 45 mg, to be administered once or twice a day. Said Component (c) ER-formulation may comprise fluoxetine, in an amount equivalent to from 20 mg to 90 mg of fluoxetine base, to be administered once a day, or may be in the specific 90 mg ER-weekly preparation to be administered once a week. Said Component (c) IR-formulation may also comprise zonisamide, in an amount of from 25 mg to 200 mg to be administered once to three times per day. Said Component (c) ER-formulation may comprise zonisamide, in an amount of from 25 mg to 600 mg, normally from 200 mg to 600 mg, to be administered once a day.

Similarly, said unit form may comprise ondansetron or dolasetron in an IR- or ER-formulation and fluoxetine hydrochloride also in an IR- or ER-formulation, each in the amount per unit form as described above, in a Component (ac) fixed dose combination, to be administered in combination with pramipexole Component (b), in IR-formulation or ER-formulation; and/or said unit form may comprise aprepitant or rolapitant in an IR-formulation and fluoxetine hydrochloride in an ER-formulation, each in the amount per unit form as described above, in a Component (ac) fixed dose combination, to be administered in combination with pramipexole Component (b), in IR-formulation or ER-formulation.

Similarly, a unit form may comprise aprepitant, in an amount per unit form of from 10 mg to 250 mg of aprepitant, or rolapitant, in an amount per unit form of from 15 mg to 270 mg of rolapitant in an IR-formulation and lovastatin, in an amount per unit form of from 5 mg to 60 mg, in an ER-formulation, in a Component (ac) fixed dose combination, to be administered in combination with pramipexole, in IR-formulation of ER-formulation.

Analogously, a unit form may comprise pramipexole hydrochloride monohydrate, in an amount per unit form of from 0.375 mg to 45 mg, normally from 15 mg to 25 mg, from more than 20 mg to 25 mg or from 20.25 mg to 25 mg in an ER-formulation; and rosuvastatin, in an amount per unit form of from 2.5 mg to 40 mg, in an IR-formulation in a Component (bc) fixed dose combination, to be administered to a patient in combination with aprepitant, in an amount per unit form of from 10 mg to 250 mg of aprepitant, in an IR-formulation, or with rolapitant, in an amount per unit form of from 150 mg to 270 mg of rolapitant, in an IR-formulation.

In the above unit forms Components (ab) and (bc), pramipexole or a pharmaceutically acceptable salt or solvate thereof Component (b) is present in an amount per unit form (in pramipexole dihydrochloride monohydrate)

either in a range selected from the group consisting of from 0.125 mg to 30 mg, from 0.125 mg to 22.5 mg, from 0.125 mg to 20 mg, from 0.125 mg to 15 mg, from 0.125 mg to 11.25 mg, and from 0.125 mg to 10 mg, advantageously from 3 mg to 22.5 mg, from more than 4.5 mg to 22.5 mg, from 4.8 mg to 22.5 mg, from more than 6 mg to 22.5 mg, from more than 10 mg to 22.5 mg, from 14.5 mg to 22.5 mg, from 15 mg to 22.5 mg, from 17.5 mg to 22.5 mg and from more than 20 mg to 22.5 mg, normally in a range of from 7.5 mg to 12.5 mg, from more than 10 mg to 12.5 mg or from 10.125 mg to 25 mg, in admixture with a pharmaceutical carrier comprising corn or maize starch and magnesium stearate, in an IR-formulation;

or in a range selected from the group consisting of from 0.375 mg to 45 mg, from 0.375 mg to 40 mg, from 0.375 mg to 30 mg, from 0.375 mg to 25 mg, and from 0.375 mg to 20 mg, advantageously from more than 4.5 mg to 45 mg, from 4.8 mg to 45 mg, from more than 6 mg to 45 mg, from more than 10 mg to 45 mg, from 14.5 mg to 45 mg, from 15 mg to 45 mg, from 17.5 mg to 45 mg, from more than 20 mg to 45 mg and from 20.25 mg to 25 mg, normally in a range of from 15 mg to 25 mg, from mare than 20 mg to 25 mg or from 20.25 mg to 25 mg, in admixture with a pharmaceutical carrier comprising corn or maize starch, magnesium stearate and hypromellose, in an ER-formulation.

In the case of pediatric or obese patients, the NK1-antagonist daily dose may be decided on the basis of the body weight. Thus, for example, aprepitant may be administered at a daily dose of 0.16 mg/kg to 4.2 mg/kg and rolapitant may be administered at a daily dose of 0.25 mg/kg to 4.5 mg/kg.

Preferably, in this unit form, the NK1-antagonist is selected from the group consisting of aprepitant, in an amount of from 10 mg to 250 mg of aprepitant and rolapitant, in an amount of from 15 mg to 270 mg of rolapitant, in an IR-formulation; and fluoxetine or a pharmaceutically acceptable salt or solvate thereof Component (b) is present in an amount per unit form equivalent to a range selected from the group consisting of from 4 mg to 90 mg, from 4 mg to 80 mg, from 4 mg to 60 mg, from 4 mg to 50 mg, from 4 mg to 40 mg, from 4 mg to 30 mg, and from 4 mg to 20 mg of fluoxetine base, advantageously from 10 mg to 90 mg, from 10 mg to 80 mg, from 10 mg to 60 mg, from 10 mg to 50 mg, from 10 mg to 40 mg, and from 10 mg to 30 mg of fluoxetine base, in admixture with a pharmaceutical carrier comprising corn or maize starch, magnesium stearate and hypromellose for an ER-formulation, or zonisamide is present in an amount of from 25 mg to 600 mg, normally from 200 mg to 600 mg in ER-formulation.

An advantageous Component (bc) to be administered once a day, comprises pramipexole dihydrochloride monohydrate in an amount of from 0.375 mg to 45 mg in ER-formulation, and fluoxetine hydrochloride comprising a fluoxetine hydrochloride in an amount equivalent to from 20 mg to 90 mg of fluoxetine base in ER-formulation. and pramipexole dihydrochloride monohydrate in an amount of from 0.375 mg to 45 mg in ER-formulation.

Another advantageous Component (bc) to be administered once a day, comprises pramipexole dihydrochloride monohydrate in an amount of from 0.375 mg to 45 mg, normally from 15 mg to 25 mg, from more than 20 mg to 25 mg or from 20.25 mg to 25 mg in ER-formulation, and zonisamide in ER-formulation, in an amount of from 25 mg to 600 mg, normally from 200 mg to 600 mg.

The above Component (ab) and Component (bc) may be formulated in a two-layer tablet or in a two-compartment capsule wherein, in each of the layers or compartments, each of the (a), (b) and (c) components is in admixture with a pharmaceutical carrier for an IR formulation, or in admixture with a pharmaceutical carrier for an ER formulation.

In the above unit forms Components (ab) and (bc), pramipexole or a pharmaceutically acceptable salt or solvate thereof Component (b) is present in an amount per unit form (in pramipexole dihydrochloride monohydrate)

either in a range selected from the group consisting of from 0.125 mg to 30 mg, from 0.125 mg to 22.5 mg, from 0.125 mg to 20 mg, from 0.125 mg to 15 mg, from 0.125 mg to 11.25 mg, and from 0.125 mg to 10 mg, advantageously from 3 mg to 22.5 mg, from more than 4.5 mg to 22.5 mg, from 4.8 mg to 22.5 mg, from more than 6 mg to 22.5 mg, from more than 10 mg to 22.5 mg, from 14.5 mg to 22.5 mg, from 15 mg to 22.5 mg, from 17.5 mg to 22.5 mg and from more than 20 mg to 22.5 mg, normally in a range from 7.5 mg to 12.5 mg, from more than 10 mg to 12.5 mg or from 10.125 mg to 12.5 mg, in admixture with a pharmaceutical carrier comprising corn or maize starch and magnesium stearate, in an IR-formulation;

or in a range selected from the group consisting of from 0.375 mg to 45 mg, from 0.375 mg to 40 mg, from 0.375 mg to 30 mg, from 0.375 mg to 25 mg, and from 0.375 mg to 20 mg, advantageously from more than 4.5 mg to 45 mg, from 4.8 mg to 45 mg, from more than 6 mg to 45 mg, from more than 10 mg to 45 mg, from 14.5 mg to 45 mg, from 15 mg to 45 mg, from 17.5 mg to 45 mg, and from more than 20 mg to 45 mg, normally in a range from 15 mg to 25 mg, from more than 20 mg to 25 mg or from 20.25 mg to 25 mg of pramipexole dihydrochloride monohydrate, in admixture with a pharmaceutical carrier comprising corn or maize starch, magnesium stearate and hypromellose, in an ER-formulation.

In the above pharmaceutical compositions, the preferred 5HT3-antagonist active ingredient is selected from the group consisting of ondansetron base, ondansetron hydrochloride dihydrate, dolasetron base and dolasetron hydrochloride; the preferred 6-propylamino-4,5,6,7-tetrahydro-1,3-benzothiazole-2-amine active ingredient is pramipexole base or its dihydrochloride monohydrate; and the preferred fluoxetine is fluoxetine base or its hydrochloride or zonisamide is zonisamide free acid.

In the above pharmaceutical compositions, the preferred NK1-antagonist active ingredient is aprepitant, fosaprepitant, rolapitant, netupitant-300/palonosetron-0.5, or fosnetupitant-235/palonosetron-0.25, the preferred 6-propylamino-4,5,6,7-tetrahydro-1,3-benzothiazole-2-amine active ingredient is pramipexole base or its dihydrochloride monohydrate and the preferred fluoxetine is fluoxetine base or its hydrochloride or zonisamide is zonisamide free acid.

In these formulations, pramipexole or a pharmaceutically acceptable salt or solvate thereof Component (b) is present in an amount per unit form equivalent to a range selected from the group consisting of from 0.125 mg to 45 mg, from 0.125 mg to 30 mg, from 0.125 mg to 22.5 mg, from 0.125 mg to 20 mg, from 0.125 mg to 15 mg, from 0.125 mg to 11.25 mg, and from 0.125 mg to 10 mg, advantageously from 3 mg to 22.5 mg, from more than 4.5 mg to 22.5 mg, from 4.8 mg to 22.5 mg, from more than 6 mg to 22.5 mg, from more than 10 mg to 22.5 mg, from 14.5 mg to 22.5 mg, from 15 mg to 22.5 mg, from 17.5 mg to 22.5 mg and from more than 20 mg to 22.5 mg, normally in an amount of from 7.5 mg to 12.5 mg, from more than 10 mg to 12.5 mg or from 10.125 mg to 12.5 mg of pramipexole dihydrochloride monohydrate, in admixture with a pharmaceutical carrier comprising corn or maize starch and magnesium stearate for an IR-formulation; or in an amount equivalent to a range selected from the group consisting of from 0.375 mg to 45 mg, from 0.375 mg to 40 mg, from 0.375 mg to 30 mg, from 0.375 mg to 25 mg, and from 0.375 mg to 20 mg, advantageously from more than 4.5 mg to 45 mg, from 4.8 mg to 45 mg, from more than 6 mg to 45 mg, from more than 10 mg to 45 mg, from 14.5 mg to 45 mg, from 15 mg to 45 mg, from 17.5 mg to 45 mg and from more than 20 mg to 45 mg and from 20.25 mg to 25 mg, normally from 15 mg to 25 mg, from more than 20 mg to 25 mg or from 20.25 mg to 25 mg of pramipexole dihydrochloride monohydrate, in admixture with a pharmaceutical carrier comprising corn or maize starch, magnesium stearate and hypromellose for an ER-formulation.

In the case of pediatric or obese patients, the 5HT3-antagonist daily dose and/or the NK1-antagonist daily dose may be decided on the basis of the body weight. Thus, for example, azasetron hydrochloride may be administered at a daily dose of 0.4-0.5 mg/kg, dolasetron mesylate may be administered at a daily dose of 9-9.5 mg/kg, granisetron hydrochloride may be administered at a daily dose of 0.09-0.11 mg/kg, ondansetron hydrochloride dihydrate may be administered at a daily dose of 0.45-0.55 mg/kg, palonosetron hydrochloride may be administered at a daily dose of 0.03 mg/kg and tropisetron hydrochloride may be administered at a daily dose of 0.5-0.6 mg/kg. Likewise, for example, aprepitant may be administered at a daily dose of 0.16 mg/kg to 4.2 mg/kg and rolapitant may be administered at a daily dose of 0.25 mg/kg to 4.5 mg/kg.

Kits

The present invention also provides a kit or package containing a medicament, a pharmaceutical combination, or a pharmaceutical composition as described herein, accompanied by instructions for use of the same in the treatment of a PMND in a patient in need thereof.

In one embodiment, a kit of the present invention is a kit comprising Unit Form Component (ac), wherein a 5HT3-antagonist and/or a NK1-antagonist with fluoxetine, zonisamide, or a statin, are in admixture with a pharmaceutical carrier or vehicle; and instructions for use of the same for treatment of a synucleinopathy in a patient in need thereof, in combination with 6-propylamino-4,5,6,7-tetrahydro-1,3-benzothiazole-2-amine, preferably pramipexole.

In another embodiment, a kit of the present invention is a kit comprising pharmaceutical composition (a) comprising a 5HT3-antagonist and/or a NK1-antagonist, a pharmaceutical composition (b) comprising 6-propylamino-4,5,6,7-tetrahydro-1,3-benzothiazole-2-amine, preferably pramipexole, and a pharmaceutical composition (c) comprising fluoxetine, zonisamide, or a statin; and instructions for use of the same for treatment of a PMND in a patient in need thereof.

EXAMPLES

Example 1

A Phase I-II clinical study conducted in parkinsonian subjects receiving oral doses of pramipexole or fluoxetine, alone and in combination. The trial was designed as a single-blind, placebo-controlled study.

The objective of the study was to demonstrate that pramipexole and fluoxetine, when administered together at their standard therapeutic doses, can safely normalize concentrations of synuclein species in peripheral blood exosomes.

To be enrolled in the study, male or female participants (40 to 89 years of age) were required to carry the diagnosis of Parkinson's disease or a related synucleinopathic disorder. Additionally, they had to agree to refrain from other antiparkinsonian (excepting levodopa-carbidopa) or antidepressant drugs, and to avoid prolonged intensive physical exercise during the conduct of this study. All subjects signed an informed consent form indicating that they understood the purpose of and procedures required for the study and that they were willing to participate in the study and comply with all study procedures and restrictions. Key criteria for exclusion of a subject from enrollment in the study were as follows:

1. Any clinically relevant acute or chronic disease which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study medications;
3. History of substance abuse, known drug addiction, or positive test for drugs of abuse or alcohol.
4. History of drug or other significant allergy.
5. Congenital long QT syndrome; a previous history of QT prolongation; a family history of long QT syndrome or sudden cardiac death; and other conditions that predispose to QT prolongation and ventricular arrhythmia
6. Treatment with centrally active drugs except for levodopa-carbidopa given at a stable dose for at least 3 months.
7. Excessive daily consumption of xanthines containing drinks (i.e. >500 mg/day of caffeine).
8. Hospitalization or intake of an investigational drug within 30 days of study entry.

Following baseline clinical and laboratory evaluations, consenting individuals meeting accession criteria were first randomized to either pramipexole or fluoxetine treatment. In either case, dosage of the initial drug was gradually increased over the ensuing 6-8 weeks in accordance with current recommendations to each patient's maximum tolerated dose (MTD) or the maximum recommended dose, whichever is lower, and stably maintained for approximately 6 weeks. Patients then entered the next study phase, lasting about 6-8 weeks when the second study medication was added to their ongoing treatment regimen, in accordance with its recommended titration schedules to their MTD or the maximum recommended dose. Once safe and tolerable doses of the drug combination were achieved, it was stably maintained for approximately 6 weeks. Doses of both drugs were then be tapered in accordance with current recommendations and patients were returned to their pre-admission regimen pending discharge from the study.

Drug safety-tolerability was monitored by means of standard clinical and laboratory tests on a weekly basis during dose titration, and otherwise at intervals not exceeding every 4 weeks. Weekly telephone interviews were generally conducted on those not scheduled for a clinic visit. A final safety check was performed approximately one month after withdrawal of all study medications.

Additionally, venous blood for synuclein and drug assays was collected on the same schedule.

Example 2

A Phase I-II clinical study as described in EXAMPLE 1 is conducted in Parkinsonian subjects receiving oral doses of pramipexole or zonisamide, alone and in combination.

The objective of the study is to demonstrate that pramipexole and zonisamide, when administered together at their standard therapeutic doses, can safely tend to normalize the characteristic alterations in synuclein and synuclein congener concentrations in exosomes collected from peripheral venous blood samples from patients who safely tolerated their therapeutic regimens.

To be enrolled in the study, male or female participants (40 to 89 years of age) are required to carry the diagnosis of Parkinson's disease or a related synucleinopathic disorder. All subjects signed an informed consent form indicating that they understood the purpose of and procedures required for the study and that they are willing to participate in the study and comply with all study procedures and restrictions. Key criteria for exclusion of a subject from enrollment in the study are as follows:

1. Any clinically relevant acute or chronic disease which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study medications;
3. History of substance abuse, known drug addiction, or positive test for drugs of abuse or alcohol.
4. History of drug or other significant allergy.
5. Excessive daily consumption of xanthines containing drinks (i.e. >500 mg/day of caffeine).
6. Hospitalization or intake of an investigational drug within 30 days of study entry.

Following baseline clinical and laboratory evaluations, consenting individuals meeting accession criteria are first randomized to either pramipexole or zonisamide treatment. In either case, dosage of the initial drug is gradually increased over the ensuing 6-12 weeks in accordance with current recommendations to each patient's maximum tolerated dose (MTD) or the maximum recommended dose, whichever is lower, and is stably maintained for approximately 6 weeks.

Patients then enter the next study phase, lasting about 6-12 weeks when the second study medication is added to their ongoing treatment regimen, in accordance with its recommended titration schedules to their MTD or the maximum recommended dose, whichever is lower. Once safe and tolerable doses of the drug combination are achieved, this is stably maintained for approximately 6 to 12 weeks. Doses of both drugs are then tapered in accordance with current recommendations and patients are returned to their pre-admission regimen pending discharge from the study.

Drug safety-tolerability is monitored by means of standard clinical and laboratory tests during dose titration, and otherwise at regular intervals throughout the trial. Weekly telephone interviews are generally conducted on those not scheduled for a clinic visit. A final safety check is performed approximately one month after withdrawal of all study medications.

Additionally, venous blood for synuclein and drug assays is collected at baseline and periodically throughout the trial.

Example 3

A Phase I-II clinical study is conducted in Parkinsonian subjects receiving oral high doses of pramipexole ER with aprepitant with or without lovastatin in patients with moderately advanced PD.

The objective of the study is to demonstrate that high doses of pramipexole ER co-administered with approved therapeutic doses of aprepitant co-administered together with approved therapeutic doses of lovastatin, tend to safely normalize concentrations of synuclein species in brain-derived exosomes found in peripheral blood.

To be enrolled in the study, male and female participants (40 to 89 years of age) are required to carry the diagnosis of Parkinson's disease or a related synucleinopathic disorder. All subjects sign an informed consent form indicating that they understood the purpose of and procedures required for the study and that they are willing to participate in the study and comply with all study procedures and restrictions. Key criteria for exclusion of a subject from enrollment in the study are as follows:

1. Any clinically relevant acute or chronic disease which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study medications;
3. History of substance abuse, known drug addiction, or positive test for drugs of abuse or alcohol.
4. History of drug or other significant allergy.
6. Hospitalization or intake of an investigational drug within 30 days of study entry.

Following baseline clinical and laboratory evaluations, consenting individuals meeting accession criteria are treated with aprepitant plus pramipexole ER titrated up to maximum tolerated dose (MTD), or up to a maximum dose of 40 mg/day, whichever came first. Patients are then maintained on aprepitant plus pramipexole ER at their MTD or at 40 mg/day for up to 12 weeks. At the end of the maintenance period, venous blood for synuclein and drug assays is collected and standard doses of lovastatin are added to the therapeutic regimen for up to 12 weeks. At the end of this triple combination treatment period venous blood for synuclein and drug assays is collected. Doses of both drugs are then tapered in accordance with current recommendations and patients are returned to their pre-admission regimen pending discharge from the study.

Drug safety-tolerability is monitored throughout the trial by means of standard clinical and laboratory tests. Weekly telephone interviews are generally conducted on those not scheduled for a clinic visit. A final safety check is performed approximately one month after withdrawal of all study medications.

Additionally, venous blood for the measurement in brain-derived exosomes levels of synuclein and oligomers. Drug plasma concentrations are also measured during the study.

Example 4

A Phase I-II clinical study is conducted in Parkinsonian subjects receiving oral high doses of pramipexole dihydrochloride monohydrate IR ("pramipexole") with ondansetron hydrochloride dihydrate ("ondansetron") IR with or without lovastatin IR in patients with moderately advanced PD.

The objective of the study, is to demonstrate that high doses of pramipexole IR co-administered with approved therapeutic doses of IR ondansetron (ranging from 6 to 24 mg per day) co-administered together with approved therapeutic doses of IR lovastatin, tend to safely normalize concentrations of synuclein species in brain-derived exosomes found in peripheral blood.

To be enrolled in the study, male or female participants (40 to 89 years of age) are required to carry the diagnosis of Parkinson's disease or a related synucleinopathic disorder. All subjects sign an informed consent form indicating that they understood the purpose of and procedures required for the study and that they were willing to participate in the study and comply with all study procedures and restrictions. Key criteria for exclusion of a subject from enrollment in the study are as follows:

1. Any clinically relevant acute or chronic disease which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study medications;
3. History of substance abuse, known drug addiction, or positive test for drugs of abuse or alcohol.
4. History of drug or other significant allergy.
5. Excessive daily consumption of xanthines containing drinks (i.e. >500 mg/day of caffeine).
6. Hospitalization or intake of an investigational drug within 30 days of study entry.

Following baseline clinical and laboratory evaluations, consenting individuals meeting accession criteria are first randomized to treatment with pramipexole titrated up to maximum tolerated dose (MTD), or up to a maximum dose of 5 mg/day, whichever came first. Patients are then maintained on pramipexole at their MTD or at 5 mg/day for 2 to 4 weeks. At the end of the maintenance period, venous blood for synuclein and drug assays is collected and patients are randomized lovastatin treatment (starting with 20 mg/day for approximately 2 weeks. If 20 mg/day is tolerated the dose of lovastatin is then to be increased to 40 mg/day (maximum recommended dose)) or placebo added on to pramipexole treatment. Patients are stably maintained on pramipexole and lovastatin (or placebo) treatment for 6 to 12 weeks. At the end of this combination treatment period venous blood for synuclein and drug assays is collected. Doses of both drugs are then tapered in accordance with current recommendations and patients are returned to their pre-admission regimen pending discharge from the study.

Drug safety-tolerability is monitored throughout the trial by means of standard clinical and laboratory tests. Weekly telephone interviews are generally conducted on those not scheduled for a clinic visit. A final safety check is performed approximately one month after withdrawal of all study medications.

Additionally, venous blood for synuclein and drug assays are collected during the study.

Example 5

A Phase I study was conducted in subjects receiving a single oral dose of pramipexole dihydrochloride monohydrate ("pramipexole") with or without a single oral dose of aprepitant. The study was a single center, single-blind study.

The objective of the study was to demonstrate that aprepitant could safely attenuate the gastro-intestinal side effects of pramipexole given in doses equivalent or higher than those approved in the treatment of Parkinson's Disease or shown in clinical trials to be effective in the treatment of depression.

To be enrolled in the study, participants the following inclusion/exclusion key criteria:

Key Inclusion Criteria

1. Male and female subjects aged 20-45 years old, both limit ages included.
2. Females of childbearing potential must agree to be abstinent or else use any two of the following medically acceptable forms of contraception from the Screening Period through 14 days after the study Exit Visit: condom with spermicidal jelly, diaphragm or cervical cap with spermicidal jelly, or intrauterine device (IUD). A female whose male partner has had a vasectomy must agree to use one additional form of medically acceptable contraception. Subjects must agree to practice the above birth control methods for 14 days after the final visit as a safety precaution.
3. Females of non-childbearing potential, defined as surgically sterile (status post-hysterectomy, bilateral oophorectomy, or bilateral tubal ligation) or post-menopausal for at least 12 months, do not require contraception during the study. The reason must be documented in the source documents.
4. Males with female partners of childbearing potential must agree to use a highly effective, medically acceptable form of contraception from the Screening Period through 14 days after the study Exit Visit. Males with female partners of childbearing potential who themselves are surgically sterile (status post vasectomy) must agree to use condoms with spermicide over the same period of time. Male subjects must agree to practice the above birth control methods for 14 days after the final visit as a safety precaution.
5. Subjects must be in good health as determined by their medical history including personal and family psychiatric history and results of physical examination, electrocardiogram (ECG), vital signs, and laboratory tests. A subject with a medical abnormality may be included only if the investigator or designee considers that the abnormality will not introduce significant additional risk to the subject's health or interfere with study objectives.
6. Subjects must be able to clearly and reliably communicate changes in their medical condition.
7. Subjects with a body mass index (BMI) between 19.0 and 32.0 $kg/m^2$ (both inclusive).
8. Subjects able to swallow multiple pills or capsules simultaneously.
9. Subjects must have signed an informed consent form indicating that they understand the purpose of and procedures required for the study and are willing to participate in the study and comply with the study procedures and restrictions.

Key Exclusion Criteria:

The criteria for exclusion of a subject from enrollment in the study were as follows:

1. Any clinically relevant acute or chronic diseases which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study drugs.
3. History of substance abuse, known drug addiction, or positive test for drugs of abuse or alcohol.
4. History of drug or other significant allergy.
5. Known hypersensitivity to pramipexole, or to ondansetron or similar serotonin receptor antagonists, or to aprepitant or similar Substance P/NK1 receptor antagonists.
5. History of and/or current QT interval prolongation, congenital long QT syndrome, electrolyte abnormalities (e.g., hypokalemia or hypomagnesemia), congestive heart failure, bradyarrhythmias or other medicinal products that lead to QT prolongation or 1st degree AV block at Screening, Day −1, or pre-dose, ≥450 QTcF for males and ≥470 QTcF for females.

7. Treatment with centrally active drugs or antiemetics, within 1 months of study entry.
8. Tobacco or nicotine users (except subjects who stopped using tobacco or nicotine 1 year or more before enrollment in the study).
9. Excessive daily consumption of xanthines containing drinks (i.e. >500 mg/day of caffeine).
10. Subjects unwilling to curtail prolonged intensive physical exercise during the study conduct (from the Screening visit until the last dose of study drug).
11. Positive test result for hepatitis B surface antigen, hepatitis C antibody.
12. Positive test result for HIV 1 or 2 serology.
13. Likely to need any medical or dental treatment during the study period.
14. Use of any prescription or over-the-counter medication within 14 days prior to admission on Day −1. In addition any medications with central effects are prohibited for a period equal to 5 times the drug half-life prior to admission (Day −1), should this period be longer than 14 days.
15. Subjects unlikely to co-operate during the study, and/or be questionably compliant in the opinion of the investigator.
16. Subjects unable to be contacted in case of an emergency.
17. Intake of an investigational drug within 30 days of study entry.
18. Show evidence of suicidal ideation within the last 6 months as assessed by the C-SSRS (Columbia Suicide Severity Rating Scale) at Screening.

Following enrollment in the study, participants received single increasing oral doses of pramipexole given once daily in the morning (Period 1 of the study). The starting dose of pramipexole was 0.5 mg and the dose was increased daily by 0.5 mg increments. Once a subject had reached his/her first intolerable dose (FID-1), upward dose escalation was discontinued. First intolerable dose (FID) was defined as:

One (1) episode of vomiting; or

Two (2) episodes of retching, or

One (1) episode of severe nausea (Grade 3; defined as nausea interfering with activities of daily living or inadequate oral caloric or fluid intake; tube feeding, total parenteral nutrition or hospitalization indicated) lasting more than 1 hour, or Three (3) consecutive episodes at every 4 hour ratings of moderate nausea (Grade 2; defined as subjectively symptomatic, but not interfering with activities of daily living), or One (1) episode of moderate diarrhea (Grade 2; defined as 4-6 stools more than at baseline).

When a subject reached FID-1 on pramipexole alone, the subject was washed out for at least 5 days, and then entered Period 2 of the study during which the subject received single daily oral doses of pramipexole starting at 0.5 mg and titrated upward by 0.5 mg increments, together with oral aprepitant (80 mg) until subjects again reached an intolerable dose defined as above. The FID on oral pramipexole plus oral aprepitant was referred to as FID-2.

If a subject reached FID-2 during Period 2 at the same or lower dose than FID-1, and providing the investigator judged there were no safety issues and the subject was consenting, the subject received the same dose of pramipexole as the FID-2 dose together with a higher dose of oral aprepitant (120 mg) on the next day and the protocol specified that said subject should continue with the remainder of the dose titration with the higher dose of oral aprepitant (120 mg) until they reach the intolerable dose (FID2+). All other provisions of the protocol remained unchanged. Assessments were the same as those planned for the dose escalation day.

On each study day, subjects were followed up for up to 8 hours following drug administration for AEs, vital signs, ECGs. In addition, a laboratory panel was taken at screening and at the end of the study.

Four subjects were enrolled in the study. The following Table 1 summarizes the demographic characteristics of the subjects.

TABLE 1

Demographic Characteristics of Subjects Enrolled in the Study

| Subject ID | Gender | Age (years) | Baseline Weight (kg) |
|---|---|---|---|
| 1001 (019) | Female | 40 | 76.4 kg |
| 1006 (001) | Male | 41 | 99.1 kg |
| 1007 (004) | Male | 38 | 64.9 kg |
| 1008 (008) | Male | 40 | 81.8 kg |

All subjects reached FID-1 (pramipexole alone) during the study. The dose limiting toxicity was gastro-intestinal adverse events in all 4 subjects. During Period 2 of the study, all 4 subjects tolerated the maximum pramipexole dose allowed by the protocol of 6 mg and therefore none of them reached FID-2 (pramipexole with aprepitant). In other words, concomitant administration of aprepitant with pramipexole prevented the occurrence of dose-limiting gastro-intestinal adverse events associated with high doses of pramipexole. Table 2 lists for each subject the values for FID-1 (on pramipexole alone) and FID-2 (on pramipexole+ aprepitant).

TABLE 2

Listing of First Intolerable Doses (FID) values

| Subject ID | FID-1 (Pramipexole alone) | FID-1 Dose Limiting Adverse Event | FID-2 Pramipexole + Aprepitant |
|---|---|---|---|
| 1001 | 2.5 mg | GI issues | >6.0 mg |
| 1006 | 0.5 mg | Moderate nausea | >6.0 mg |
| 1007 | 4.5 mg | Severe nausea | >6.0 mg |
| 1008 | 1.5 mg | Vomiting | >6.0 mg |

As shown in the following Table 3, the Maximum Tolerated Dose (MTD) during Period 2 was higher than MTD during Period 1 in all subjects, and in 3 subjects MTD-2 was increased by more than 3-fold.

TABLE 3

Listing of Maximum Tolerated Doses (MTD)

| Subject ID | MTD-1 (Pramipexole alone) | Maximal Tolerated Dose Pramipexole + Aprepitant | MTD2/ MTD1 |
|---|---|---|---|
| 1001 | 2.0 mg | ≥6.0 mg | ≥3.0 |
| 1006 | <0.5 mg | ≥6.0 mg | ≥12.0 |

TABLE 3-continued

| Listing of Maximum Tolerated Doses (MTD) | | | |
|---|---|---|---|
| Subject ID | MTD-1 (Pramipexole alone) | Maximal Tolerated Dose Pramipexole + Aprepitant | MTD2/ MTD1 |
| 1007 | 4.0 mg | ≥6.0 mg | ≥1.5 |
| 1008 | 1.0 mg | ≥6.0 mg | ≥6.0 |

MTD: Maximum Tolerated Dose

Taken together, results showed that the co-administration of aprepitant with pramipexole attenuated dose-limiting gastro-intestinal adverse effects reported with pramipexole alone, thus showing that a NK1-antagonist enables the administration to a human being of pramipexole in doses otherwise non-tolerated when administering pramipexole alone.

In conclusion, the co-administration of aprepitant with pramipexole inhibited the occurrence of gastro-intestinal AEs associated with pramipexole given alone, thus enabling doses of pramipexole to be safely and tolerably raised by more than 2-fold, thereby allowing a far greater efficacy of this drug. In particular, these results show that the protective action of a NK1-antagonist allows the safe treatment of a human with pramipexole not only within the pramipexole approved dose range but also at doses that are higher than its maximum recommended dose.

REFERENCES

Al-Mansoori et al. 2013: Al-Mansoori K M, Hasan M Y, Al-Hayani A, El-Agnaf M, "*The role of α-synuclein in neurodegenerative diseases: from molecular pathways in disease to therapeutic approaches*"; Curr. Alzheimer Res. 2013 July; 10(6): 559-568.

Braak et al. 2003: Braak H, Del Tredici K, Rüb U, de Vos R A, Jansen Steur E N, Braak E. "*Staging of brain pathology related to sporadic Parkinson's disease*". Neurobiol Aging. 2003 March-April; 24(2):197-211.

Bymaster et al. 2002: Bymaster F, Zhang W, Carter P, Shaw J, Chernet E, Phebus L, Wong D, Perry K; "*Fluoxetine, but not other selective serotonin uptake inhibitors, increases norepinephrine and dopamine extracellular levels in prefrontal cortex via serotonin type 2C antagonism*". Psychopharmacology 2002160 (4): 353-61.

Castillo-Carranza et al. 2018: Castillo-Carranza D L, Marcos J. Guerrero-Muñoz M J, Sengupta U, Gerson J E, Kayed R; "*α-Synuclein Oligomers Induce a Unique Toxic Tau Strain*", Biol. Psychiatry, pii: 50006-3223(18) 30034-9 (January 2018).

Chen et al. 2016: Chen M, Weiwei Yang W, Li Xin, X, Li Xuran, Wang P, Feng Yue F, Yang H, Chan P, and Yu S; "*Age- and brain region-dependent α-synuclein oligomerization is attributed to alterations in intrinsic enzymes regulating α-synuclein phosphorylation in aging monkey brains*"; Oncotarget. 2016 Feb. 23; 7(8): 8466-8480.

Choi and Gandhi 2018: Choi M L, Gandhi S. "*Crucial role of protein oligomerization in the pathogenesis of Alzheimer's and Parkinson's diseases*". FEBS J. 2018 Jun. 20).

Choksi et al. 2014: Choksi D K, Roy B, Chatterjee S, Yusuff T, Bakhoum M. F, Sengupta U, Ambegaokar S, Kayed R, Jackson G R. "*TDP-43 phosphorylation by casein kinase Iepsilon promotes oligomerization and enhances toxicity in vivo*". Hum Mol Genet 2014, 23, 1025-1035.

Chow et al. 2010: Chow V W, Savonenko A V, Melnikova T, Kim H, Price D L, Li T, Wong P C. "*Modeling an anti-amyloid combination therapy for Alzheimer's disease*". Sci Transl Med. 2010 Jan. 6; 2(13):13ra1. PubMed. 8 Jan. 2010.

Chung et al. 2011: Chung Y C, Kim S R, Park J Y, Chung E S, Park K W, Yoon S H, Ko H W, Kim Y S, Jin B K. "*Fluoxetine prevents MPTP-induced loss of dopaminergic neurons by inhibiting microglial activation*". Neuropharmacology. 2011 May; 60(6):963-74, doi: 10.1016/j.neuropharm.2011.01.043. Epub 2011 Feb. 1.

Cline et al. 2018: Cline E N, Bicca M A, Viola K L, Klein W L "*The Amyloid-β Oligomer Hypothesis: Beginning of the Third Decade*". J Alzheimer Dis. 2018; 64(s1):S567-S610.

Connolly and Lang 2014: Connolly B S, Lang A E, "*Pharmacological treatment of Parkinson disease: a review*". JAMA. 2014 Apr. 23-30; 311(16):1670-83).

Corrigan et al. 2000: Corrigan M H, Denahan A Q, Wright C E, Ragual R J, Evans D L; Corrigan M H, Denahan A Q, Wright C E, Ragual R J, Evans D; "*Comparison of pramipexole, fluoxetine, and placebo in patients with major depression*"; Depress Anxiety. 2000; 11(2):58-65.

Erro Aguirre et al. 2015: Erro Aguirre M E, Zelaya M V, Sánchez Ruiz de Gordoa J, Tuñón M T, Lanciego J L; "*Midbrain catecholaminergic neurons co-express α-synuclein and tau in progressive supranuclear palsy*"; Front Neuroanat. 2015 Mar. 11; 9:25. doi: 10.3389/fnana.2015.00025. eCollection 2015 (March 2105).

Fang et al. 2014: Fang Y S, Tsai K J, Chang Y J, Kao P, Woods R, Kuo, P H, Wu C C, Liao J Y, Chou S C, Lin V, Jin L W, Yuan H S, Cheng I H, Tu P H, Chen Y R. "*Full-length TDP-43 forms toxic amyloid oligomers that are present in frontotemporal lobar dementia-TDP patients*". Nat Commun 2014, 5, 4824.

Gandy et al. 2010: Gandy S, Simon A J, Steele J W, Lublin, A L, Lah, J J, Walker L C, Levey A I, Krafft G A, Levy E, Checler F, Glabe C, Bilker W., Abel T. Schmeidler J., Ehrlich M E. "*Days-to-criterion as an indicator of toxicity associated with human Alzheimer amyloid-β oligomers*". Ann Neurol. 2010, 68, 220-230.

Gerson and Kayed 2013: Gerson J E, Kayed R. "*Formation and propagation of tau oligomeric seeds*". Front Neurol 2013, 4, 93.

Glabe 2016: Glabe C G, 2006. "*Common mechanisms of amyloid oligomer pathogenesis in degenerative disease*". Neurobiol. Aging 27, 570-575.

Hoffner and Djian 2014: Hoffner G., Djian P. "*Monomeric, oligomeric and polymeric proteins in huntington disease and other diseases of polyglutamine expansion*". Brain Sci. 2014 Mar. 3; 4(1):91-122.

Inden et al. 2009: Inden M, Kitamura Y, Tamaki A, Yanagida T, Shibaike T, Yamamoto A, Takata K, Yasui H, Taira T, Ariga H, Taniguchi T; "*Neuroprotective effect of the antiparkinsonian drug pramipexole against nigrostriatal dopaminergic degeneration in rotenone-treated mice*"; Neurochem Int. 2009 December; 55(8):760-7.

Jellinger 2008a: Jellinger K A, "*A critical reappraisal of current staging of Lewy-related pathology in human brain*"; Acta Neuropathol. 2008 July; 116(1): 1-16.

Jellinger 2008b: Jellinger K A, "*Neuropathological aspects of Alzheimer disease, Parkinson disease and frontotemporal dementia*"; Neurodegener. Dis. 2008; 5(3-4): 118-121

Kakimura et al. 2001: Kakimura J, Kitamura Y, Takata K, Kohno Y, Nomura Y, Taniguchi T; "*Release and aggregation of cytochrome c and alpha-synuclein are inhibited*

*by the antiparkinsonian drugs, talipexole and pramipexole*"; Eur J Pharmacol. 2001 Apr. 6; 417(1-2):59-67.

Keowkase et al. 2010: Keowkase R, Aboukhatwa M, Luo Y. "*Fluoxetine protects against amyloid-beta toxicity, in part via daf-16 mediated cell signaling pathway, in Caenorhabditis elegans*". Neuropharmacology. 2010 September-October; 59(4-5):358-65.

Kim et al. 2004: Kim S, Seo J H, Suh Y H, "*Alpha-synuclein, Parkinson's disease, and Alzheimer's disease*"; Parkinsonism Relat. Disord. 2004 May; 10 Suppl. 1: S9-13.

Luo et al. 2016: Luo H T, Zhang J P, Miao F; "*Effects of pramipexole treatment on the α-synuclein content in serum exosomes of Parkinson's disease patients*"; Exp Ther Med. 2016 September; 12(3):1373-1376.

Marques and Outeiro 2012: Marques O, Outeiro T F; "*Alpha-synuclein: from secretion to dysfunction and death*"; Cell Death Dis. 2012 Jul. 19; 3:e350. doi: 10.1038/cddis.2012.94.

Mitchell Sontag et al. 2012: Mitchel Sontag E, Sontag C, Cumming B J, Muchowski P J (+4); "*Detection of Mutant Huntingtin Aggregation Conformers and Modulation of SDS-Soluble Fibrillar Oligomers by Small Molecules*"; Journal of Huntington's Disease (June 2012).

Nilson et al. 2017: Nilson A N, English K C, Gerson J E, Barton Whittle T, Nicolas Crain C, Xue J, Sengupta U, Castillo-Carranza D L, Zhang W, Gupta P, Kayed R, Tau Oligomers Associate with Inflammation in the Brain and Retina of Tauopathy Mice and in Neurodegenerative Diseases, J. Alzheimers Dis., 55(3): 1083-1099 (2017).

Ono et al. 2013: Ono K, Takasaki J, Takahashi R, Ikeda T, Yamada M; "*Effects of antiparkinsonian agents on β-amyloid and α-synuclein oligomer formation in vitro*"; J Neurosci Res; 2013 October; 91(10):1371-81).

O'Regan et al. 2017: O'Regan G, DeSouza R M, Balestrino R, "*Glucocerebrosidase Mutations in Parkinson Disease*". J Parkinson's Dis 7 (2017) 411-422—DOI 10.3233/JPD-171092.

Petersen et al. 2013: Petersen R C, Aisen P, Boeve B F, Geda Y E, Ivnik R J, Knopman D S, Mielke M, Pankratz V S, Roberts R, Rocca W A, Weigand S, Weiner M, Wiste H, Jack C R. "*Criteria for mild cognitive impairment due to Alzheimer's disease in the community*". Ann. Neurol. 2013, 74, 199-208.

Poewe et al. 2017: Poewe W, Seppi K, Tanner C M, Halliday G M, Brundin P, Volkmann J, Schrag A E, Lang A E. "*Parkinson disease*". Nat Rev Dis Primers. 2017 Mar. 23; 3:17013.

Prusiner et al. 2015: Prusiner SB[1], Woerman AL[2], Mordes DA[3], WaTDDS JC[4], Rampersaud R[2], Berry DB[2], Patel S[2], Oehler A[5], Lowe JK[6], Kravitz SN[6], Geschwind DH[7], Glidden DV[8], Halliday GM[9], Middleton LT[10], Gentleman SM[11], Grinberg LT[12], Giles K[4], "*Evidence for α-synuclein prions causing multiple system atrophy in humans with parkinsonism*" Proc Natl Acad Sci USA; 2015 Sep. 22; 112(38):E5308-17.

Reich and Grill 2009: Reich S G, Grill S E. "*Corticobasal degeneration*" Curr Treat Options Neurol. 2009 May; 11(3):179-85.

Rogóz and Skuza 2006: Rogóz Z and Skuza G. "*Mechanism of synergistic action following co-treatment with pramipexole and fluoxetine or sertraline in the forced swimming test in rats*", Pharmacol Rep 2006 58(4):493-500.

Sangwan et al. 2017: Sangwan S, Zhao A, Adams K L, Jayson C K, Sawaya M R, Guenther E L, Pan A C, Ngo J, Moore D M, Soriaga A B, Do T D, Goldschmidt L, Nelson R, Bowers M T, Koehler C M, Shaw D E, Novitch B G, Eisenberg D S. "*Atomic structure of a toxic, oligomeric segment of SOD1 linked to amyotrophic lateral sclerosis (ALS)*". Proc Natl Acad Sci USA. 2017 Aug. 15; 114(33):8770-8775).

Schapira et al. 2013: Schapira A H, McDermott M P, Barone P, Comella C L, Albrecht S, Hsu H H, Massey D H, Mizuno Y, Poewe W, Rascol O, Marek K. "Pramipexole in patients with early Parkinson's disease (PROUD): a randomised delayed-start trial"; Lancet Neurol. 2013 August; 12(8):747-55).

Schneider and Mierau 1987: Schneider C S, Mierau J "Dopamine autoreceptor agonists: resolution and pharmacological activity of 2,6-diaminotetrahydrobenzothiazole and an aminothiazole analogue of apomorphine"; J. Med Chem. 1987 March; 30(3):494-8.

Sengupta et al. 2016: Sengupta U, Nilson A, Kayed R. "*The Role of Amyloid-β Oligomers in Toxicity, Propagation, and Immunotherapy*". EBioMedicine 6, April 2016. DOI: 10.1016/j.ebiom.2016.03.035.

Sengupta et al. 2017: Sengupta U, Portelius E, Hansson O, Farmer K, Castillo-Carranza D, Woltjer R, Zetterberg H, Galasko D, Blennow K, Kayed; "*Tau oligomers in cerebrospinal fluid in Alzheimer's disease*". Ann Clin Transl Neurol. 2017 April; 4(4): 226-235.

Shi et al. 2014: Shi M, Liu C, Cook T J, Bullock K M, Zhao Y, Ginghina C, Li Y, Aro P, Dator R, He C, Hipp M J, Zabetian C P, Peskind E R, Hu S C, Quinn J F, Galasko D R, Banks W A, Zhang J; "*Plasma exosomal α-synuclein is likely CNS-derived and increased in Parkinson's disease*"; Acta Neuropathol. 2014 November; 128(5):639-50. doi: 10.1007/s00401-014-1314-y. Epub 2014 Jul. 6.

Shults et al. 2005: Shults C W, Rockenstein E, Crews L, Adame A, Mante M, Larrea G, Hashimoto M, Song D, Iwatsubo T, Tsuboi K, Masliah E.; "*Neurological and neurodegenerative alterations in a transgenic mouse model expressing human alpha-synuclein under oligodendrocyte promoter: implications for multiple system atrophy*"; J Neurosci 2005 Nov. 16; 25(46):10689-99.

Soria et al. 2017: Soria F N, Engeln M, Martinez-Vicente M, Glangetas C, Lopez-Gonzales J, Dovero S, Dehay B, Normand E, Vila M, Lopez-Gonzales M J, Favereaux A, Georges F, Lo Bianco C, Bezard E, Fernagut; "Glucocerebrosidase deficiency in dopaminergic neurons induces microglial activation without neurodegeneration"; Hum Mol Genet 2017 July; 26(14):2603-2615.

Stuendl et al. 2016: Stuendl A, Kunadt M, Kruse N, Bartels C, Moebius W, Danzer K M, Mollenhauer B, Schneider A; "*Induction of alpha-synuclein in aggregate formation by CSF exosomes from patients with Parkinson's disease and dementia with Lewy bodies*" Brain 2016, 139; 481-494

Suzuki et al. 2010: PLoS One. 2010 Feb. 17; 5(2):e9260. doi: 10.1371/journal.pone.0009260.

Sweeney et al. 2017: Sweeney P, Park H, Baumann M, Dunlop J, Frydman J, Kopito R, McCampbell A, Leblanc G, Venkateswaran A, Nurmi A, Hodgson R. "*Protein misfolding in neurodegenerative diseases: implications and strategies*". Transl Neurodegener. 2017 Mar. 13; 6:6. doi: 10.1186/s40035-017-0077-5. eCollection 2017.

Ubhi et al. 2012: Ubhi K, Inglis C, Mante M, Patrick C, Adame A, Spencer B, Rockenstein E, May V, Winkler J, Masliah; "*Fluoxetine ameliorates behavioral and neuropathological deficits in a transgenic model mouse of α-synucleinopathy*"; E. Exp Neurol. 2012 April; 234(2): 405-16.

Visanji et al. 2016: Visanji N P, Brotchie J M, Kalia L V, Koprich J B, Tandon A, WaTDDS J C, Lang A E;

"α-*Synuclein-Based Animal Models of Parkinson's Disease: Challenges and Opportunities in a New Era*"; Trends Neurosci. 2016 November; 39(11):750-762.

The invention claimed is:

1. A method for treating a protein misfolding neurodegenerative disease ("PMND") in a patient by administering to said patient in need of said treatment a pharmaceutical combination comprising active ingredients consisting of 5HT3-antagonist and/or a NK-1 antagonist, in combination with 6-propylamino-4,5,6,7-tetrahydro-1,3-benzothiazole-2-amine and with fluoxetine, zonisamide, or a statin.

2. The method of claim 1, wherein said 5HT3-antagonist is selected from the group consisting of ondansetron or a pharmaceutically acceptable salt or solvate thereof, at a daily dose equivalent to from 4 mg to 32 mg of ondansetron base, and dolasetron or a pharmaceutically acceptable salt or solvate thereof, at a daily dose equivalent to from 75 mg to 200 mg of dolasetron mesylate;

said NK1-antagonist is selected from the group consisting of aprepitant or a pharmaceutically acceptable salt, solvate or prodrug thereof, at daily dose equivalent to from 10 mg to 250 mg of aprepitant; netupitant or a pharmaceutically acceptable salt, solvate or prodrug thereof, at daily dose equivalent to from 150 mg to 600 mg of netupitant; and rolapitant or a pharmaceutically acceptable salt, solvate or prodrug thereof, at daily dose equivalent to from 15 mg to 270 mg of rolapitant;

said 6-propylamino-4,5,6,7-tetrahydro-1,3-benzothiazole-2-amine is pramipexole or a pharmaceutically acceptable salt or solvate thereof, at a daily dose equivalent to from 0.375 mg to 45 mg of pramipexole dihydrochloride; and said fluoxetine is fluoxetine base or a pharmaceutically acceptable salt or solvate thereof, at a daily dose equivalent to from 4 mg to 90 mg of fluoxetine base; or said zonisamide is selected from the group consisting of zonisamide base or a pharmaceutically acceptable salt or solvate thereof, at a daily dose equivalent to from 25 mg to 600 mg of zonisamide free acid, and zonisamide free acid, at a daily dose of from 25 mg to 600 mg; or said statin is selected from the group consisting of rosuvastatin or a pharmaceutically acceptable salt or solvate thereof, at a daily dose equivalent to from 2.5 mg to 40 mg of rosuvastatin calcium, and lovastatin, at a daily dose of from 2.5 mg to 80 mg.

3. The method of claim 2, wherein said 6-propylamino-4,5,6,7-tetrahydro-1,3-benzothiazole-2-amine is pramipexole or a pharmaceutically acceptable salt or solvate thereof at a daily dose equivalent to from more than 20 mg to 45 mg of pramipexole dihydrochloride monohydrate.

4. The method of claim 1, wherein said fluoxetine is in the specific 90 mg ER-weekly preparation.

5. The method of claim 1, wherein said 5HT3-antagonist and/or NK-1 antagonist and said fluoxetine are administered to said patient in a fixed dose combination.

6. The method of claim 1, wherein said 5HT3-antagonist and/or NK1-antagonist and said zonisamide are administered to said patient in a fixed dose combination.

7. The method of claim 1, wherein said 5HT3-antagonist and/or NK1-antagonist and said statin are administered to said patient in a fixed dose combination.

8. The method of claim 1, wherein said PMND is selected from the group consisting of Alzheimer's disease, Parkinson's disease, Lewy body dementia, dementia with Lewy bodies, the Lewy body variant of Alzheimer's disease, multiple system atrophy, neurodegeneration with brain iron accumulation, Parkinsonian disorders associated with glucocerebrosidase mutations, Huntington's Disease, corticobasal degeneration, frontotemporal dementia with parkinsonism-linked to chromosome 17, Pick's Disease, Multiple Tauopathies, Amyotrophic Lateral Sclerosis, Spongiform encephalopathies, and Familial Amyloidotic Polyneuropathy.

9. The method of claim 1, wherein said NK1-antagonist is selected from the group consisting of aprepitant or a pharmaceutically acceptable salt, solvate or prodrug thereof, at daily dose equivalent to from 10 mg to 250 mg of aprepitant; netupitant or a pharmaceutically acceptable salt, solvate or prodrug thereof, at daily dose equivalent to from 150 mg to 600 mg of netupitant; and rolapitant or a pharmaceutically acceptable salt, solvate or prodrug thereof, at daily dose equivalent to from 15 mg to 270 mg of rolapitant;

said 6-propylamino-4,5,6,7-tetrahydro-1,3-benzothiazole-2-amine is pramipexole or a pharmaceutically acceptable salt or solvate thereof at a daily dose equivalent to from 0.375 mg to 45 mg of pramipexole dihydrochloride monohydrate; and said fluoxetine is fluoxetine base or a pharmaceutically acceptable salt or solvate thereof, at a daily dose equivalent to from 4 mg to 90 mg of fluoxetine base; or said zonisamide is zonisamide base or a pharmaceutically acceptable salt or solvate thereof, at a daily dose equivalent to from 25 mg to 600 mg of zonisamide free acid, and zonisamide free acid, at a daily dose of from 25 mg to 600 mg; or said statin is selected from the group consisting of rosuvastatin or a pharmaceutically acceptable salt or solvate thereof, at a daily dose equivalent to from 2.5 mg to 40 mg of rosuvastatin calcium, and lovastatin, at a daily dose of from 2.5 mg to 80 mg.

10. The method of claim 9, wherein said 6-propylamino-4,5,6,7-tetrahydro-1,3-benzothiazole-2-amine is pramipexole or a pharmaceutically acceptable salt or solvate thereof at a daily dose equivalent to from more than 20 mg to 45 mg of pramipexole dihydrochloride monohydrate.

11. A pharmaceutical composition comprising:

(A) active ingredients consisting of:

(a) a 5HT3-antagonist and/or a NK-1 antagonist;

(b) a 6-propylamino-4,5,6,7-tetrahydro-1,3-benzothiazole-2-amine or a pharmaceutically acceptable salt or solvate thereof; and (c) fluoxetine or a pharmaceutically acceptable salt or solvate thereof, zonisamide or a pharmaceutically acceptable salt or solvate thereof, or a statin;

in admixture with (B) a pharmaceutical carrier or vehicle.

12. The pharmaceutical composition of claim 11, wherein said pharmaceutical composition is in a dosage unit form wherein (a) said 5HT3-antagonist is in an amount per unit form of from 1 μg to 300 mg and/or said NK1-antagonist is an amount of from 1 μg to 600 mg;

(b) said 6-propylamino-4,5,6,7-tetrahydro-1,3-benzothiazole-2-amine is selected from the group consisting of (i) the racemate or a pharmaceutically acceptable salt or solvate thereof, in an amount per unit form equivalent to from 0.25 mg to 90 mg of pramipexole dihydrochloride monohydrate, (ii) pramipexole or a pharmaceutically acceptable salt or solvate thereof, in an amount equivalent to from 0.125 mg to 45 mg of pramipexole dihydrochloride monohydrate, and (iii) a (R)/(S)-mixture or a pharmaceutically acceptable salt or solvate thereof, in an amount per unit form of from 50 mg to 3000 mg, inclusive of a(S)-enantiomer or a pharmaceutically acceptable salt or solvate thereof amount per unit form equivalent to from 0.125 mg to 45 mg of pramipexole dihydrochloride monohydrate; and (c) said fluoxetine is in an amount per unit form of from 2 mg to 90 mg, said zonisamide is in an amount per unit form of from 25 mg to 600 mg, or said statin is in an amount of from 2.5 mg to 80 mg.

13. The pharmaceutical composition of claim 12, wherein said 6-propylamino-4,5,6,7-tetrahydro-1,3-benzothiazole-2-amine is pramipexole or a pharmaceutically acceptable salt or solvate thereof, in an amount per unit form selected from the group consisting of an amount per unit form equivalent to from more than 4.5 mg to 45 mg of pramipexole dihydrochloride monohydrate, an amount per unit form equivalent to from more than 6 mg to 45 mg of pramipexole dihydrochloride monohydrate, an amount per unit form equivalent to from 6.5 mg to 45 mg of pramipexole dihydrochloride monohydrate, an amount per unit form equivalent to from 7.5 mg to 25 mg of pramipexole dihydrochloride monohydrate, an amount per unit form equivalent to from 15 mg to 25 mg of pramipexole dihydrochloride monohydrate, and an amount per unit form equivalent to from 20.25 mg to 25 mg of pramipexole dihydrochloride monohydrate.

14. The pharmaceutical composition of claim 12, wherein said 5HT3-antagonist is ondansetron hydrochloride dihydrate, in an amount per unit form equivalent to from 2 mg to 32 mg of ondansetron base and said 6-propylamino-4,5,6,7-tetrahydro-1,3-benzothiazole-2-amine is pramipexole dihydrochloride monohydrate, in an amount per unit form of from 0.125 mg to 45 mg.

15. The pharmaceutical composition of claim 12, wherein said NK1-antagonist is aprepitant, in an amount per unit of from 10 mg to 250 mg; and said 6-propylamino-4,5,6,7-tetrahydro-1,3-benzothiazole-2-amine is pramipexole dihydrochloride monohydrate, in an amount per unit form of from 0.125 mg to 45 mg.

16. A fixed-dose combination consisting of the pharmaceutical composition of claim 11.

17. A kit comprising the pharmaceutical composition according to claim 11, and instructions for use for the treatment of a PMND in a patient in need of said treatment.

* * * * *